(12) United States Patent
Skiadopoulos et al.

(10) Patent No.: US 7,622,123 B2
(45) Date of Patent: Nov. 24, 2009

(54) ATTENUATED HUMAN-BOVINE CHIMERIC PARAINFLUENZA VIRUS (PIV) VACCINES

(75) Inventors: Mario H. Skiadopoulos, Potomac, MD (US); Peter L. Collins, Kensington, MD (US); Brian R. Murphy, Bethesda, MD (US); Alexander C. Schmidt, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/982,223

(22) Filed: Nov. 4, 2004

(65) Prior Publication Data

US 2007/0134271 A1    Jun. 14, 2007

Related U.S. Application Data

(63) Continuation of application No. 09/900,112, filed on Jul. 5, 2001, now abandoned, and a continuation-in-part of application No. 09/458,813, filed on Dec. 10, 1999, now Pat. No. 7,314,631, which is a continuation-in-part of application No. 09/083,793, filed on May 22, 1998, now Pat. No. 7,208,161, application No. 10/982,223, which is a continuation-in-part of application No. 09/459,062, filed on Dec. 10, 1999, now Pat. No. 7,250,171, which is a continuation-in-part of application No. 09/083,793, application No. 10/982,223, which is a continuation-in-part of application No. 09/586,479, filed on Jun. 1, 2000, now Pat. No. 7,201,907, which is a continuation-in-part of application No. 09/083,793.

(60) Provisional application No. 60/215,809, filed on Jul. 5, 2000, provisional application No. 60/059,385, filed on Sep. 19, 1997, provisional application No. 60/047,575, filed on May 23, 1997, provisional application No. 60/143,134, filed on Jul. 9, 1999.

(51) Int. Cl.
*A61K 39/155* (2006.01)

(52) U.S. Cl. .................. 424/199.1; 424/211.1

(58) Field of Classification Search ........................ None
See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 5,716,821 A | 2/1998 | Wertz et al. | |
| 5,789,229 A | 8/1998 | Wertz et al. | |
| 5,869,036 A | 2/1999 | Belshe et al. | |
| 6,033,886 A | 3/2000 | Conzelmann | |
| 6,136,585 A * | 10/2000 | Ball et al. | ........... 435/236 |
| 6,264,957 B1 | 7/2001 | Collins | |

FOREIGN PATENT DOCUMENTS

| | | |
|---|---|---|
| EP | 0 440 219 A1 | 8/1991 |
| EP | 0 702 085 A1 | 3/1996 |
| WO | WO 92/01471 | 2/1992 |
| WO | WO 93/14207 | 7/1993 |
| WO | WO 93/21310 | 10/1993 |
| WO | WO 97/06270 | 2/1997 |
| WO | WO 97/11093 | 3/1997 |
| WO | WO 97/12032 | 4/1997 |
| WO | WO 97/20468 | 6/1997 |
| WO | WO 98/02530 | 1/1998 |
| WO | WO 98/43668 | 10/1998 |
| WO | WO 98/53078 | 11/1998 |
| WO | WO 99/02657 | 1/1999 |
| WO | WO 99/15631 | 4/1999 |
| WO | WO 99/24564 | 5/1999 |
| WO | WO 00/61611 | 10/2000 |
| WO | WO 00/61737 | 10/2000 |
| WO | WO 01/04271 | 1/2001 |
| WO | WO 01/04321 | 1/2001 |
| WO | WO 01/04335 | 1/2001 |

OTHER PUBLICATIONS

Bailly et al., "A Recombinant Human Parainfluenza Virus Type 3 (PIV3) In Which the Nucleocapsid N Protein Has Been Replaced", Journal Virology, vol. 74, No. 7, 3188-3195 (2000).

(Continued)

*Primary Examiner*—Stacy B Chen
(74) *Attorney, Agent, or Firm*—Woodcock Washburn LLP

(57) ABSTRACT

Chimeric human-bovine parainfluenza viruses (PIVs) are infectious and attenuated in humans and other mammals and useful individually or in combination in vaccine formulations for eliciting an anti-PIV immune response. Also provided are isolated polynucleotide molecules and vectors incorporating a chimeric PIV genome or antigenome which includes a partial or complete human or bovine PIV "background" genome or antigenome combined or integrated with one or more heterologous gene(s) or genome segment(s) of a different PIV. Chimeric human-bovine PIV of the invention include a partial or complete "background" PIV genome or antigenome derived from or patterned after a human or bovine PIV virus combined with one or more heterologous gene(s) or genome segment(s) of a different PIV virus to form the human-bovine chimeric PIV genome or antigenome.

36 Claims, 27 Drawing Sheets

OTHER PUBLICATIONS

Baron et al., "Rescue of Rinderpest Virus From Cloned Cdna", Journal Virology, vol. 71, No. 2, 1265-1271 (1997).
Bellini et al., "Measles Virus P Gene Codes for Two Proteins", Journal Virology, vol. 53, No. 3, 908-919 (1985).
Belshe et al., "Cold Adaptation of Parainfluenza Virus Type 3", Journal Medical Virology, vol. 10(4), 235-242 (1982).
Belshe et al., "Comparison of Enzyme-Linked Immunosorbent Assay and Neutralization Techniques for Measurement of Antibody", Infect And Immun. vol. 37, 160-165 (1982).
Blumberg et al., "Measles Virus L Protein Evidences Elements of Ancestral RNA Polymerase," Virology, 164:487-497, 1988.
Buchholz et al., "Chimeric Bovine Respiratory Syncytial Virus With Glycoprotein Gene Substitutions," Journal Virology, vol. 74, No. 3, 1187-1199 (2000).
Buchholz et al., "Generation of Bovine Respiratory Syncytial Virus (BRSV) from cDNA," Journal Virology, vol. 73, No. 1, 251-259 (1999).
Bukreyev et al., "Recombinant Respiratory Syncytial virus from which the Entire SH Gene has been Deleted Grows Efficiently in Cell Culture and Exhibits Site-Specific Attenuation in the Respiratory Tract of the Mouse," J. Virol. 71:8973-8982, 1977.
Bukreyev et al., "Interferon Gamma Expressed By A Recombinant Respiratory Syncytial Virus Attenuates Virus Replication In Mice," Proc. Natl. Acad. Sci. USA, vol. 96, 2367-2372 (1999).
Bukreyev et al., "Recovery of Infectious Respiratory Syncytial Virus Expressing An Additional, Foreign Gene," Journal Virology, vol. 70, No. 10, 6634-6641 (1996).
Cadd et al., "The Sendai Paramyxiovirus Accessory C Proteins Inhibit Viral Genome Amplification in Promoter-Specific Fashion," J. Virol 70: 5067-74, 1996.
Cahour et al., "Growth-Restricted Dengue Virus Mutants Containing Deletions in the 5 Noncoding Region of the RNA Genome," Virology, vol. 207, 68-76 (1995).
Cattaneo et al., "Measles Virus Editing Provides Additional Cytosine-Rich Protein," Cell, vol. 56, 759-764, (1989).
Cheng et al., "Effective Amplification of Long Targets From Cloned Inserts," Proc. Natl. Acad. Sci. USA, vol. 91, 5695-5699 (1994).
Clarke et al., "Rescue of Mumps Virus From cDNA," J Virology, vol. 74, No. 10, 4831-4838 (2000).
Clements et al., "Comparison of Virologic—Immunologic Resp. of Volunteers To Live Avian-Human Influenza A H3N2 Reassortant," Journal Clinical Microbiology, vol. 27, No. 1, 219-222 (1989).
Clements et al., "Evaluation of Bovine Cold-Adapted Human, and Wild Type Human Parainfluenza Type 3 Viruses in Adult Volunteers," J. Clinical Microbiology, vol. 29, 1175-1182 (1991).
Clements et al., "Use of Single-Gene Reassortant Viruses to Study Role of Anain Influenza A Virus," Journal Clinical Microbiology, vol. 30, No. 3, 655-662 (1992).
Clements-Mann et al., "Safety and Immunogenicity of Live Attenuated Human-Bovine (UK) Reassortant Rotavirus Vaccines VP7 Specificity," Vaccine vol. 17, 2715-2725 (1999).
Collins et al., "Parainfluenza Viruses," Fields Virology 3rd ed., Lippincott-Raven Publishers, Philadelphia 1205-1241, (1996).
Collins et al., "Rescue of a 7502-Nucleotide (49.3% of Full-Length) Synthetic Analog of Respiratory Syncytial Virus Genomic RNA," Virology 195:252-256, 1993.
Collins et al., "Rescue of Synthetic Analogs of Respiratory Syncytial Virus Genomic RNA and Effect of Truncations and Mutations on the Expression of a Foreign Reporter Gene," Proc. Natl. Acad. Sci. USA, 88:9663-9667, 1991.
Collins et al., "Production of Infectious Human Respiratory Syncytial Virus From Cloned cDNA," Pro. Natl. Acad. Sci., vol. 92, 11563-11567 (1995).
Connors et al., "A Cold-Passaged Attenuated Strain of Human Respiratory Syncytial Virus Contains Mutations in the F and L Genes," Virology 208:478-484, 1995.
Conzelmann et al., "Rescue of Synthetic Genomic RNA Analogs of Rabies Virus by Plasmid-Encoded Proteins," J. Virol. 68: 713-719, 1994.
Conzelmann et al., "Genetic Manipulation of Non-Segmented Negative-Strand RNA Viruses," Journal General Virology, vol. 77, 381-389 (1996).
Cook et al., "Antigenic Relationships Among the "Newer" Myxoviruses (Parainfluenza)," Amer. Jour. Hyq. 69:250, 1959.
Cook et al., "In Vivo Antigenic Studies of Parainfluenza Viruses," American Journal of Hygiene, vol. 77, 150-159 (1962).
Corsoro and Pearson, "Enhancing the Efficiency of DNA Mediated Gene Transfer In Mammalian Cells," Somatic Cell Genetics, vol. 7, No. 5, 603-616 (1981).
Crookshanks et al., "Evaluation of Cold-Adapted And Temperature-Sensitive Mutants Of Parainfluenza Virus Type 3," Journal Medical Virology, vol. 13, 243-249 (1984).
Crowe et al., "A Further Attenuated Derivative of a Cold-Passaged Temperature-Sensitive Mutant of Human Respiratory Syncytial Virus Retains Immunogenicity and Protective Efficacy Against Wild-Type Challenge in Seronegative Chimpanzees," Vaccine 12:783-790, 1994.
Crowe et al., "Acquisition of the $ts$ Phenotype by a Chemically Mutagenized Cold-Passaged Human Respiratory Syncytial Virus Vaccine Candidate Results from the Acquisition of a Single Mutation in the Polymerase (L) Gene," Virus Genes 13: 269-273, 1996.
Crowe et al., "Cold-Passaged, Temperature-Sensitive Mutants of Human Respiratory Syncytial Virus (RSV)," Vaccine, vol. 13, No. 9, 847-855 (1995).
Curran et al., "The Sendai Virus Nonstructural C Proteins Specifically Inhibit Viral mRNA Synthesis," Virology 189: 647-656, 1992.
Curran et al., "Sendai Virus P Gene Produces Multiple Proteins From Overlapping Open Reading Frames, Enzyme," vol. 44, 244-249 (1990).
Delenda et al., "Normal Cellular Replication of Sendai Virus Without Trans-Frame, Nonstructural V Protein," Virology, vol. 228, 55-62 (1997).
Delenda et al., "Sendai Viruses With Altered P, V, and W Protein Expression," Virology, vol. 242, 327-337 (1998).
Deng et al, "Localization of a Domain on the Paramyxovirus Attachment Protein Required for the Promotion of Cellular Fusion," Virology, vol. 209, 457-469 (1995).
Dimock et al., "Rescue of Synthetic analogs of Genomic RNA and Replicative-Intermediate RNA of Human Parainfluenza Virus Type 3," Journal Virology, vol. 67, No. 5, 2772-2778 (1993).
Durbin et al., "Mini. Protein Requirements for Transcription, RNA Replication of Minigenome of Human Parainfluenza Virus Type 3 and Evaluation of the Rule of Six," Virology, vol. 234, 74-83 (1997).
Durbin et al., "Mutations In C, D, and V Open Reading Frames of Human Parainfluenza Virus Type 3 Attenuate Replication In Rodents and Primates," Virology, vol. 261, 319-330 (1999).
Durbin et al., "Recovery of Infections Human Parainfluenza Virus Type 3 from cDNA," Virology, vol. 235, 323-332 (1997).
Emerson et al., "A Simian Strain of Hepatitis A Virus, AGM-27, Functions As An Attenuated Vaccine for Chimpanzees," Journal Infectious Diseases, vol. 173, 592-597 (1996).
Escoffier et al., "Nonstructural C Protein is Required for Efficient Measles Virus Replication in Human Peripheral Blood Cells," J Virol. 73:1695-8, 1999.
Finke et al. "Ambisense Gene Expression for Recombinant Rabies Virus: Random Packaging of Positive- and Negative-Strand Ribonucleoprotein Complexes into Rabies Virions," J. Virol. 71:7281-7288, 1997.
Firestone et al., "Nucleotide Sequence Analysis of the Respiratory Syncytial Virus Subgroup A Cold-Passaged ($cp$) Temperature Sensitive ($ts$) $cpts$-248/404 Live Attenuated Virus Vaccine Candidate," Virology 225:419-422, 1996.
Flexner et al., "Prevention of vaccinia virus infection in immunodeficient mice by vector-directed IL-2 expression," Nature 33:259-262,1987.
Frank et al. "Comparison of Different Tissue Cultures for Isolation and Quantitation of Influenza and Parainfluenza Viruses," J. Clin. Microbiol. 10:32-6(1979).
Fuerst et al., "Eukaryotic transient-expression system based on recombinant vaccinia virus that synthesizes bacteriophage T7 RNA polymerase," Proc. Natl. Acad. Sci. USA 83:8122-8126, 1986.

Galinski et al., "Molecular Cloning and Sequence Analysis of Human Parainfluenza 3 Virus mRNA Encoding the P and C Proteins," Virology 155:46-60, 1986.

Galinski et al., "Molecular Cloning and Sequence Analysis of Human Parainfluenza 3 Virus mRNA Encoding the L Protein," Virology 165:499-510, 1988.

Galinski et al., "RNA Editing in the Phosphoprotein Gene of the Human Parainfluenza Virus Type 3," Virology 186:543-550, 1992.

Galinski, "Annotated Nucleotide and Protein Sequences for Selected Paramyxoviridae," In The Paramyxoviruses, Kingsbury D.W., Ed., 537-568, Plenum Press, New York, 1991.

Garcin et al., "A Point Mutation in the Sendai Virus Accessory C Proteins Attenuates Virulence for Mice, but Not Virus Growth in Cell Culture," Virology 238:424-431, 1997.

Garcin et al., "A Highly Recombinogenic System For Recovery of Infectious Sendai Paramyxovirus for cDNA," EMBO Journal, vol. 14, No. 24, 6087-6094 (1995).

Graham et al., "A New Technique for The Assay of Infectivity of Human Adenovirus 5 DNA, Virology," vol. 52, 456-467 (1973).

Gromeier et al., "Dual Stem Loops within the Poliovirus Internal Ribosomal Entry Site Control Neurovirulence," Journal of Virology, vol. 73, No. 2, 958-964 (1999).

Grosfeld et al., "RNA Replication by Respiratory Syncytial Virus (RSV) Is Directed by N, P, and L Proteins," Journal of Virology, vol. 69, No. 9, 5677-5686 (1995).

Haas et al., "Codon Usage Limitation In The Expression Of HIV-1 Envelope Glycoprotein," Current Biology, vol. 6, No. 3, 315-324 (1996).

Hall et al., "Cold Passaged Human Parainfluenza Type 3 Viruses Contain ts and Non ts Mutations Leading To Attenuation In Rhesus Monkeys," Virus Research, vol. 22, 173-184 (1992).

Hasan et al., "Creation of an Infectious Recombinant Sendai Virus Expressing the Firefly Luciferase Gene from the 3' Proximal First Locus," J. Gen. Virol. 78:2813-20, 1997.

Hawley-Nelson et al., "A New Higher Efficiency Polyatomic Liposome Transfection Reagent," Focus, vol. 15, No. 3, 73-79 (1993).

He et al., "Recovery of Infectious SV5 From Cloned DNA and Expression of A Foreign Gene," Virology, vol. 237, 249-260 (1997).

He et al., "The Paramyxovirus SV5 Small Hydrophobic (SH) Protein Is Not Essential For virus Growth In Tissue Culture Cells," Virol. vol. 250 30-40 (1998).

Heikkinen et al., "Prevalence of Various Respiratory Viruses In The Middle Ear During Acute Otitis Media," New England Journal of Medicine, vol. 340, 260-264 (1999).

Hoffman et al., "An Infectious Clone of Human Parainfluenza Virus Type 3," Journal Virology, vol. 71, No. 6, 4272-4277 (1997).

Hurwitz et al., "Intranasal Sendai Virus Vaccine Protects African Green Monkeys From Infection With Human Parainfluenza Virus Type One," Vaccine, vol. 15, No. 5, 533-540 (1997).

Itoh et al., "Isolation of an Avirulent Mutant of Sendai Virus with Two Amino Acid Mutations from a Highly Virulent Field Strain Through Adaptation to LLC-MK$_2$ Cells," J. Gen Virol. 78:3207-3215, 1997.

Jin et al., "Recombinant Human Respiratory Syncytial Virus (RSV) from cDNA and Construction of Subgroup A and B Chimeric RSV," Virology, vol. 251, 206-214 (1998).

Johnson et al., "Specific Targeting to CD4+ Cells of Recombinant Vesicular Stomatitis Viruses Encoding Human Immunodeficiency Virus Envelope Proteins," J. Virol. 71:5060-5068, 1997.

Juhasz et al., "The Temperature-Sensitive (ts) Phenotype of a Cold-Passaged (cp) Live Attenuated Respiratory Syncytial Virus," Journal of Virology, vol. 71, No. 8, 5814-5819 (1997).

Kahn et al., "Recombinant Vesicular Stomatitis Virus Expressing Respiratory Syncytial Virus (RSV) Glycoproteins: RSV Fusion Protein Can Mediate Infection and Cell Fusion," Virology 254:81-91, 1999.

Kapikian et al., "Update On Jennerian And Modified Jennerian Approach To Vaccination Of Infants And Young Children . . . ," Genetically Engineered Vaccines, vol. 327, 59-69 (1992).

Karron et al., "A Live Human Parainfluenza Type 3 Virus Vaccine is Attenuated and Immunogenic in Healthy Infants and Children," J. Inf. Dis. 172:1445-1450, 1995b.-yes.

Karron et al., "A. Live Attenuated Bovine Parainfluenza Virus Type 3 Vaccine Is Safe, Infectious, Immunogenic, and Phenotypically Stable In Infants And Children," Journal of Infectious Diseases, vol. 171, 1107-1104 (1995).

Karron et al., "Evaluation of a Live Attenuated Bovine Parainfluenza Type 3 Vaccine In Two To Six Month Old Infants," Pediatric Infectious Diseases Journal, vol. 15, 650-654 (1996).

Kast et al., "Protection against lethal Sendai virus infection by in vivo priming of virus-specific cytotoxic T lymphocytes with a free synthetic peptide," Proc. Natl. Acad.Sci.USA 88:2283-2287,1991.

Kato et al., "Importance of Cysteine Rich Carboxyl Terminal Half of V Protein for Sendai Virus Pathogenesis," Journal Virology, vol. 71, No. 10, 7266-7272 (1997).

Kato et al., "Initiation of Sendai Virus Multiplication From Transfected cDNA or RNA with Negative or Positive Sense," Genes To Cells, vol. 1, 569-579 (1996).

Kato et al., "The Paramyxovirus Sendai Virus V Protein Encodes A Luxury Function Required For Viral Pathogenesis," EMBO Journal, vol. 16, No. 3, 578-587 (1997).

Kozak et al, "At Least Six Nucleotides Preceding the AUG Initiator Codon Enhance Translation in Mammalian Cells," Journal Molecular Biology, vol. 196, 947-950 (1987).

Kretzschmar et al., "Normal Replication of Vesicular Stomatitis Virus Without C Proteins," Virology, vol. 216, 309-316 (1996).

Kunkel et al., "Rapid and Efficient Site-Specific Mutagenesis Without Phenotypic Selection," Proc. Natl. Acad. Sci., vol. 82, 488-492 (1985).

Kuo et al., "Effect of Mutations in the Gene-Start and Gene-End Sequence Motifs on Transcription of Monocistronic and Dicistronic Minigenomes of Respiratory Syncytial Virus," J. Virol. 70:6892-6901, 1996.

Kurotani et al., "Sendai Virus C Proteins are Categorically Nonessential Gene Products but Silencing Their Expression Severely Impairs Viral Replication and Pathogenesis," Genes to Cells 3:111-124, 1998.

Lamb et al., "In The Paramyxoviruses," D. Kingsbury, ed., 181-214, Plenum Press, New York, 1991.

Latorre et al., The Various Sendai Virus C Proteins are Not Functionally Equivalent and Exert both Positive and Negative Effects on Viral FNA Accumulation During the Course of Infection, J. Virol. 72:5984-5993, 1998.

Lawson et al., "Recombinant Vesicular Stomatitis Viruses From DNA," Proc. Natl. Acad. Sci., vol. 92, 4477-4481 (1995).

Liston et al., "Ribosomal Frameshifting During Translation of Measles Virus P Protein mRNA Is Capable of Directing Synthesis," Journal Virology, vol. 69, No. 11, 6742-6750 (1995).

Mallipeddi et al., "Sequence Comparison Between the Phosphoprotein mRNAs of Human and Bovine Respiratory Syncytial Viruses Identifies a Divergent Domain in the Predicted Protein," J. Gen. Virol. 73:2441-2444, 1992.

Mallipeddi et al., "Sequence Variability of the Glycoprotein Gene of Bovine Respiratory Syncytial Virus," J. Gen. Virol. 74:2001-2004, 1993.

Marx et al., "Pediatric Hospitalizations for Croup," Journal Infectious Diseases, vol. 176, 1423-1427 (1997).

Matsuoka et al., "The P Gene of Human Parainfluenza Virus Type 1 Encodes P And C Proteins But Not a Cysteine Rich V Protein," Journal Virology, vol. 65, No. 6, 3406-3410 (1991).

Mebatsion et al., "Highly Stable Expression of a Foreign Gene from Rabies Virus Vectors," Proc. Natl. Acad. Sci. U S A 93:7310-7314,1996.

Men et al., "Dengue Type 4 Virus Mutants Containing Deletions in the 3 Noncoding Region of the RNA," Journal of Virology, vol. 70, No. 6, 3930-3937 (1996).

Mink et al., "Nucleotide Sequences of the 3' Leader and 5' Trailer Regions of Human Respiratory Syncytial Virus Genomic RNA," Virology 185:615-624, 1991.

Moriya et al., "Large Quantity Production with Extreme Convenience of Human SDF-Ia by a Sendai Virus Vector," FEBS Lett. 425:105-111, 1998.

Murphy et al., "Enhanced pulmonary histopathology is observed in cotton rats immunized with formalin-inactivated respiratory syncytial virus (RSV) or purified F glycoprotein and challenged with RSV 3-6 months after immunization," Vaccine 8(5):497-502, 1990.
Murphy et al., "Failure of Attenuated Temperature-Sensitive Influenza A (H3N2) Virus to Induce Heterologous Interference in Humans to Parainfluenza Type 1 Virus," Infect.Immun.12:62-8,1975.
Murphy et al., "Current Approaches to the Development of Vaccines Effective Against Parainfluenza," Virus Research, vol. 11, 1-15 (1988).
Murphy et al., "Dose Response of Influenza A Washington 897 80 (H3N2) Avian-Human Reassortant Virus In Adult Volunteers," Journal Infectious Diseases, vol. 152, No. 1, 225-229 (1985).
Muster et al., "An Influenza A Virus Containing Influenza B Virus 5 and 3 Noncoding Regions on the Neuraminidase Gene Is Attenuated In Mice," Proc. Natl. Acad. Sci., vol. 88, 5177-5181 (1991).
Needleman and Wunsch, "A General Method Applicable To The Search For Similarities In The Amino Acid Sequence Of Two Proteins," Journal of Molecular Biology, vol. 48 (1970).
Neumann et al., "Gene Transfer Into Mouse Lymoa Cells By Electroporation In High Electric Fields," EMBO J. vol. 1, No. 7, 841-845 (1982).
Palese et al., "Negative Strand RNA Viruses Genetic Engineering and Applications," Proc. Natl. Acad. Sci., vol. 93, 11354-11358 (1996).
Park et al., "In Vivo Model for Pseudo-Templated Transcription in Sendai Virus," Journal Virology, vol. 66, No. 12, 7033-7039 (1992).
Pastey et al., "Nucleotide Sequence Analysis of the Non-Structural NS1(1C) and NS2 (1B) Protein Genes of Bovine Respiratory Syncytial Virus," J. of Gen. Virol. 76:193-197, 1995.
Pastey et al., "Structure and Sequence Comparison of Bovine Respiratory Syncytial Virus Fusion Protein," Virus Res. 29: 195-202, 1993.
Pearson et al., "Improved Tools For Biological Sequence Comparison," Proc. Natl. Acad. Sci. USA, vol. 85, 2444-2448 (1988).
Peeters et al., "Rescue of Newcastle Disease Virus From Cloned cDNA . . . ," Journal of Virology, vol. 73 (1999).
Pelet et al., "The P Gene of Bovine Parainfluenza Virus 3 Expresses All Three Reading Frames from A Single MRNA Edition Site," EMBO Journal, vol. 10, No. 2, 443-448 (1991).
Perez-Schael et al., "Efficacy of Rhesus Rotavirus Based Quadrivalent Vaccine In Infants and Young Children In Venezuela," New England of Journal Medicine, vol. 337, No. 17, 1181-1187 (1997).
Perrotta et al., "A Pseudoknot-Like Structure Required For Efficient Self-Cleavage Of Hepatitis Delta Virus RNA," Nature, vol. 350, 434-436 (1991).
Radecke (Radicle) et al., "The Nonstructural C Protein Is Not Essential For Multiplication of Edmonston B Strain Measles Virus In Cultured Cells," Virology, vol. 217, 418-421 (1996).
Radecke et al., "Rescue of Measles Viruses from Cloned DNA," EMBO Journal, vol. 14, 5773-5784 (1995).
Randhawa et al., "Nucleotide Sequences of Genes Encoding the Putative Attachment Glycoprotein (G) of Mouse and Tissue Culture Passaged Strains of Pneumonia," Virology, vol. 207 240-245 (1995).
Ray et al., "Temperature-Sensitive Phenotype of Human Parainfluenza Virus Type 3 Candidate Vaccine Strain (cp45) Correlates with a Defect in the L Gene," J. Virol. 70:580-584, 1996.
Ray et al., "Human Parainfluenza Virus Induces A Type Specific Protective Immune Response, Journal Infectious Diseases," vol. 162, 746-749 (1990).
Roberts et al., "Recovery of Negative Strand RNA Viruses From Plasmid DNAs," Virology 247, 1-6 (1998).
Roberts et al., "Attenuated Vesicular Stomatitis Viruses as Vaccine Vectors," J. Virol. 73:3723-3732, 1999.
Roberts et al., "Vaccination with a Recombinant Vesicular Stomatitis Virus Expressing an Influenza Virus Hamagglutinin Provides Complete Protection from Influenza Virus Challenge," J. Virol. 72:4704-4711, 1998.
Sakaguchi et al., "Expression of the HN, F, NP and M Proteins of Sendai Virus by Recombinant Vaccinia Viruses and Their Contribution to Protective Immunity Against Sendai Virus Infections in Mice," J. Gen. Virol. 74:479-484, 1993.
Sakai et al., "Accommodation of Foreign Genes into the Sendai Virus Genome: Sizes of Inserted Genes and Viral Replication," FEBS Letters 456:221-226, 1999.

Sanchez et al., "Cloning and Gene Assignment of mRNAs of Human Parainfluenza Virus 3," Virology, vol. 147, 177-186 (1985).
Schnell et al., "Foreign Glycoproteins Expressed from Recombinant Vesicular Stomatitis Viruses are Incorporated Efficiently into Virus Particles," Proc. Natl. Acad. Sci. USA 93:11359-11365, 1996.
Schneider et al., "Recombinant Measles Viruses Defective for RNA Editing," Virology, vol. 227, 314-322 (1997).
Schnell et al., "Construction of a Novel Virus that Targets HIV-1-Infected Cells and Controls HIV-1 Infection," Cell 90:849-857, 1997.
Schnell et al., "The Minimal Conserved Transcription Stop-Start Signal Promotes Stable Expression of a Foreign Gene in Vesicular Stomatitis Virus," J. Virol. 70:2318-2323, 1996.
Schnell et al., "Infectious Rabies Viruses from Cloned cDNA," EMBO Journal, vol. 13, No. 18, 4195-4203 (1994).
Singh et al., "A Recombinant Measles Virus Expressing Biologically Active Human Interleukin-12," J. Gen. Virol. 80:101-106, 1999.
Singh et al., "A Recombinant Measles Virus expressing Hepatitis B Virus Surface Antigen Induces Humoral Immune Responses in Genetically Modified Mice," J. Virol. 73:4823-4828, 1999.
Skiadopoulos et al., "Generation of Parainfluenza Virus Type 1 Vaccine Candidate By Replacing HN and F Glycoproteins . . . ," Vaccine, vol. 18, 503-510 (1999).
Skiadopoulos et al., "Identification of Mutations Contributing to Temperature Sensitive Cold Adapted . . . ," Journal Virology, vol. 73, No. 2, 1374-1381 (1999).
Skiadopoulos et al., "Three Amino Acid Substitutions In L Protein of Human Parainfluenza Virus Type 3 cp45 Live Attenuated Vaccine . . . ," Journal Virology, vol. 72, No. 3, 1762-1768 (1998).
Smith & Waterman, "Comparison of Biosequences," Advanced Applied Mathematics, vol. 2, 482-489 (1981).
Snyder et al., "Evaluation of Live Avian Human Reassortant Influenza A H2N2 and H1N1 Virus Vaccines," Journal Clinical Micro., vol. 23, No. 5, 852-857 (1986).
Spielhofer et al., "Chimeric Measles Viruses with a Foreign Envelope," J. Virol. 72:2150-2159, 1998.
Sprent et al., "Generalization Of The Sign Test, Applied Nonparametric Statistical Method," 123-126, Chapman and Hall, London, 1989.
Spriggs et al., "Sequence Analysis of P and C Protein Genes of Human Parainfluenza Virus Type 3," Journal General Virology, vol. 67, 2705-2719 (1986).
Steinhoff et al., "A Mallard 6750 78 Avian Human By Not A Ann Arbor 6 60 Cold Adapted Influenza," Journal Infectious Diseases, vol. 163, 1023-1028 (1991).
Stokes et al., "The Complete Nucleotide Sequence of Two Cold-Adapted, Temperature-Sensitive Attenuated Mutant Vaccine Viruses (cp12 and cp45) Derived from the JS Strain and Human Parainfluenza Virus Type 3 (PIV3)," Virus Res. 30:43-52, 1993.
Stokes et al., "The Complete Nucleotide Sequence of JS Strain of Human Parainfluenza Virus Type 3," Virus Research, vol. 25, 91-103 (1992).
Suzu et al., "Nucleotide Sequence of Bovine Parainfluenza 3 Virus Genome, Nucleic Acids Research," vol. 15, No. 7, 2945-2958 (1987).
Tanabayashi et al., "Functional Interaction of Paramyxovirus Glycoproteins," Journal Virology, vol. 70, No. 9, 6112-6118 (1996).
Tao et al., "A Live Attenuated Chimeric Recombinant Parainfluenza Virus (PIV) Encoding the Internal Proteins of PIV Type 3 . . . ," Vaccine, vol. 17, 1100-1108 (1999).
Tao et al., "Recovery of A Fully Viable Chimeric Human Parainfluenza Virus (PIV) Type 3 . . . ," Journal Virology, vol. 72, No. 4, 2955-2961 (1998).
Teng et al., "Altered Growth Characteristics of Recombinant Respiratory Syncytial Viruses," Journal Virology, vol. 73, No. 1, 466-473 (1999).
Teng et al., "Identification of Respiratory Syncytial virus Proteins Required for Formation and Passage," Journal Virology, vol. 72, No. 7, 5707-5716 (1998).
Thomas et al., "Two mRNAs That Differ by Two Nontemplated Nucleotides," Cell, vol. 54, 891-902 (1988).
Thomson et al., "Recombinant Polyepitope Vaccines for the Delivery of Multiple CD8 Cytotoxic T Cell Epitopes," J. Immunol. 157:822,1996.

Valsamakis et al., "Recombinant Measles Viruses with Mutations in the C, V, or F Gene Have Altered Growth Phenotypes In Vivo," Journal Virology, vol. 72, No. 10, 7754-7761 (1998).

van Wyke Coelingh et al., "Antigenic Variation in the Hemagglutinin-Neuraminidase Protein of Human Parainfluenza Type 3 Virus," Virology 143(2):569-582,1985.

Van Wyke Coelingh et al., "Antigenic and Structural Properties of Hemagglutinin-Neuraminidase Glycoprotein of Human Parainfluenza Virus Type 3: Sequence Analysis of Variants Selected with Monoclonal Antibodies which Inhibit Infectivity, Hemagglutination, and Neuraminidase Activities," J. Virol. 61:1473-1477, 1987.

van Wyke Coelingh et al., "Antibody Responses of Humans and Nonhuman Primates to Individual Antigenic Sites," Journal Virology, vol. 64, No. 8, 3833-3843 (1990).

Van Wyke Coelingh et al., "Attenuation of Bovine Parainfluenza Virus Type 3 in Nonhuman Primates, Journal Infectious Diseases," vol. 157, No. 4, 655-662 (1988).

van Wyke Coelingh et al., "Conserved Epitopes On Hemagglutinin-Neuraminidase Proteins of Human and Bovine Parainfluenza Type 3 Viruses," Journal Virology, vol. 60, No. 1, 90-96 (1986).

Vidal et al., "Editing of Sendai Virus PC mRNA by G Insertion Occurs During mRNA Synthesis Via A Virus Encoded Activity," Journal Virology, vol. 64, No. 1, 239-246 (1990).

Wathen et al., "Characterization of a Novel Human Respiratory Syncytial Virus Chimeric FG Glycoprotein Expressed Using a Baculovirus Vector," J. Gen. Virol. 70:2625-2635, 1989.

Whelan et al., "Efficient Recovery of Infectious Vesicular Stomatitis Virus Entirely from cDNA Clones," Proc. Natl. Acad. Sci., vol. 92, 8388-8392 (1995).

Whitehead et al., "A Single Nucleotide Substitution In Transcription Start Signal of M2 Gene . . . ," Virology, vol. 247, 232-239 (1998).

Whitehead et al., "Recombinant Respiratory Syncytial Virus (RSV) Bearing A Set of Mutations . . . ," Journal Virology, vol. 72, No. 5, 4467-4471 (1998).

Whitehead et al., "Recombinant Respiratory Syncytial Virus Bearing A Deletion of Either the NS2 or SH Gene . . . ," Journal Virology, vol. 73, No. 4, 3438-3442 (1999).
Wigler et al., "Biochemical Transfer of Single Copy Eukaryotic Genes Using Total Cellular DNA As Donor," Cell, vol. 14, 725-731 (1978).
Wyatt et al., "Replication Deficient Vaccinia Virus Encoding Bacteriophage T7 RNA, Virology," vol. 210, 202-205 (1995).
Yu et al., "Sendai Virus-Based Expression of HIV-1 gp 120: Reinforcement by the V(−) Version," Genes to Cells 2:457-466, 1997.
Zamora et al., "Gene Junction Sequences of Bovine Respiratory Syncytial Virus," Virus Res. 24:115-121, 1992.
Zamora et al., "Sequence Analysis of M2 mRNA of Bovine Respiratory Syncytial Virus Obtained from an F-M2 Dicistronic mRNA Suggests Structural Homology with that of Human Respiratory Syncytial Virus," J. Gen Virol. 73:737-741, 1992.
Zimmerman et al., "The Poly(C) Region Affects Progression of Encephalomyocarditis Virus," Journal Virology, vol. 71, No. 5, 4145-4149 (1997).
Crowe et al, "Current Approaches to the Development of Vaccines Against Disease Caused by Respiratory Syncytial Virus," Vaccine vol. 13 No. 4 415-421 (1995).
Kunkel et al., "Rapid and Efficient Site-Specific Mutagenesis Without Phenotypic Selection," Methods Enzymol. vol. 154 367-383 (1987).
Kretzschmar et al., "High-Efficiency Incorporaion of Functional Influenza Virus Glycoproteins into Recombinant Vesicular Stomatitis Viruses," J. Virol. vol. 71, pp. 5982-5989 (1997).

* cited by examiner

| | | | | | | |
|---|---|---|---|---|---|---|
|ACCAAACAAG|AGAAGAGACT|TGCTTGGGAA|TATTAATTCA|AATAAAAATT|AACTTAGGAT|60|
|TAAAGAACTT|TACCGAAAGG|TAAGGGAAA|GAAATCCTAA|GACTGTAATC|ATGTTGAGTC|120|
|TATTCGACAC|ATTCAGTGCG|CGTAGGCAGG|AGAACATAAC|GAAATCAGCT|GGTGGGGCTG|180|
|TTATTCCCGG|GCAAAAAAAC|ACTGTGTCTA|TATTTGCTCT|TGGACCATCA|ATAACAGATG|240|
|ACAATGATAA|AATGACATTG|GCTCTTCTCT|TTTTGTCTCA|TTCTTTAGAC|AATGAAAAGC|300|
|AGCATGCGCA|AAGAGCTGGA|TTTTTAGTTT|CTCTGTTATC|AATGGCTTAT|GCCAACCCAG|360|
|AATTATATTT|AACATCAAAT|GGTAGTAATG|CAGATGTTAA|ATATGTTATC|TACATGATAG|420|
|AGAAAGACCC|AGGAAGACAG|AAATATGGTG|GGTTTGTCGT|CAAGACTAGA|GAGATGGTTT|480|
|ATGAAAAGAC|AACTGATTGG|ATGTTCGGGA|GTGATCTTGA|GTATGATCAA|GACAATATGT|540|
|TGCAAAATGG|TAGAAGCACT|TCTACAATCG|AGGATCTTGT|TCATACTTTT|GGATATCCAT|600|
|CGTGTCTTGG|AGCCCTTATA|ATCCAAGTTT|GGATAATACT|TGTTAAGGCT|ATAACCAGTA|660|
|TATCAGGATT|GAGGAAAGGA|TTCTTTACTC|GGTTAGAAGC|ATTTCGACAA|GATGGAACAG|720|
|TTAAATCCAG|TCTAGTGTTG|AGCGGTGATG|CAGTAGAACA|AATTGGATCA|ATTATGAGGT|780|
|CCCAACAGAG|CTTGGTAACA|CTCATGGTTG|AAACACTGAT|AACAATGAAC|ACAGGCAGGA|840|
|ATGATCTGAC|AACAATAGAA|AAGAATATAC|AGATTGTAGG|AAACTACATC|AGAGATGCAG|900|
|GTCTTGCTTC|ATTTTTCAAC|ACAATCAGAT|ATGGCATTGA|GACTAGAATG|GCAGCTCTAA|960|
|CTCTGTCTAC|CCTTAGACCG|GATATCAACA|GACTCAAGGC|ACTGATCGAG|TTATATCTAT|1020|
|CAAAGGGGCC|ACGTGCTCCT|TTTATATGCA|TTTTGAGAGA|TCCCGTGCAT|GGTGAGTTTG|1080|
|CACCAGGCAA|CTATCCTGCC|CTCTGGAGTT|ATGCGATGGG|TGTAGCAGTT|GTACAAAACA|1140|
|AGGCCATGCA|ACAGTATGTA|ACAGGAAGGT|CTTATCTGGA|TATTGAAATG|TTCCAACTTG|1200|
|GTCAAGCAGT|GGCACGTGAT|GCCGAGTCGC|AGATGAGTTC|AATATTAGAG|GATGAACTGG|1260|
|GGGTCACACA|AGAAGCCAAG|CAAAGCTTGA|AGAAACACAT|GAAGAACATC|AGCAGTTCAG|1320|
|ATACAACCTT|TCATAAGCCT|ACAGGGGGAT|CAGCCATAGA|AATGGCGATA|GATGAAGAAG|1380|
|CAGGGCAGCC|TGAATCCAGA|GGAGATCAGG|ATCAAGGAGA|TGAGCCTCGG|TCATCCATAG|1440|
|TTCCTTATGC|ATGGGCAGAC|GAAACCGGGA|ATGACAATCA|AACTGAATCA|ACTACAGAAA|1500|
|TTGACAGCAT|CAAAACTGAA|CAAAGAAACA|TCAGAGACAG|GCTGAACAAA|AGACTCAACG|1560|
|AGAAAAGGAA|ACAGAGTGAC|CCGAGATCAA|CTGACATCAC|AAACAACACA|AATCAAACTG|1620|
|AAATAGATGA|TTTGTTCAGT|GCATTCGGAA|GCAACTAGTC|ACAAAGAGAT|GACCACTATC|1680|
|ACCAGCAACA|AGTAAGAAAA|ACTTAGGATT|AATGGAAATT|ATCCAATCCA|GAGACGGAAG|1740|
|GACAAATCCA|GAATCCAACC|ACAACTCAAT|CAACCAAAGA|TTCATGGAAG|ACAATGTTCA|1800|
|AAACAATCAA|ATCATGGATT|CTTGGGAAGA|GGGATCAGGA|GATAAATCAT|CTGACATCTC|1860|
|ATCGGCCCTC|GACATCATTG|AATTCATACT|CAGCACCGAC|TCCCAAGAAA|ACACGGCAGA|1920|
|CAGCAATGAA|ATCAACACAG|GAACCACAAG|ACTTAGCACG|ACAATCTACC|AACCTGAATC|1980|
|CAAAACAACA|GAAACAAGCA|AGGAAAATAG|TGGACCAGCT|AACAAAAATC|GACAGTTTGG|2040|
|GGCATCACAC|GAACGTGCCA|CAGAGACAAA|AGATAGAAAT|GTTAATCAGG|AGACTGTACA|2100|
|GGGAGGATAT|AGGAGAGGAA|GCAGCCCAGA|TAGTAGAACT|GAGACTATGG|TCACTCGAAG|2160|
|AATCTCCAGA|AGCAGCCCAG|ATCCTAACAA|TGGAACCCAA|ATCCAGGAAG|ATATTGATTA|2220|
|CAATGAAGTT|GGAGAGATGG|ATAAGGACTC|TACTAAGAGG|GAAATGCGAC|AATTTAAAGA|2280|
|TGTTCCAGTC|AAGGTATCAG|GAAGTGATGC|CATTCCTCCA|ACAAAACAAG|ATGGAGACGG|2340|
|TGATGATGGA| | | | | |2350|

FIGURE 1A

```
AGAGGCCTGG AATCTATCAG TACATTTGAT TCAGGATATA CCAGTATAGT GACTGCCGCA    2410
ACACTAGATG ACGAAGAAGA ACTCCTTATG AAGAACAACA GGCCAAGAAA GTATCAATCA    2470
ACACCCCAGA ACAGTGACAA GGGAATTAAA AAAGGGGTTG GAAGGCCAAA AGACACAGAC    2530
AAACAATCAT CAATATTGGA CTACGAACTC AACTTCAAAG GATCGAAGAA GAGCCAGAAA    2590
ATCCTCAAAG CCAGCACGAA TACAGGAGAA CCAACAAGAC CACAGAATGG ATCCCAGGGG    2650
AAGAGAATCA CATCCTGGAA CATCCTCAAC AGCGAGAGCG GCAATCGAAC AGAATCAACA    2710
AACCAAACCC ATCAGACATC AACCTCGGGA CAGAACCACA CAATGGGACC AAGCAGAACA    2770
ACCTCCGAAC CAAGGATCAA GACACAAAAG ACGGATGGAA AGGAAAGAGA GGACACAGAA    2830
GAGAGCACTC GATTTACAGA AAGGGCGATT ACATTATTAC AGAATCTTGG TGTAATCCAA    2890
TCTGCAGCAA AATTAGACCT ATACCAAGAC AAGAGAGTTG TGTGTGTGGC GAATGTCCTA    2950
AACAATGCAG ATACTGCATC AAAGATAGAC TTCCTAGCAG GTTTGATGAT AGGAGTGTCA    3010
ATGGATCATG ATACCAAATT AAATCAGATT CAGAACGAGA TATTAAGTTT GAAAACTGAT    3070
CTTAAAAAGA TGGATGAATC ACATAGAAGA CTAATTGAGA ATCAAAAAGA ACAATTATCA    3130
CTGATCACAT CATTAATCTC AAATCTTAAA ATTATGACAG AGAGAGGAGG GAAGAAGGAC    3190
CAACCAGAAC CTAGCGGGAG GACATCCATG ATCAAGACAA AAGCAAAAGA AGAGAAAATA    3250
AAGAAAGTCA GGTTTGACCC TCTTATGGAA ACACAGGGCA TCGAGAAAAA CATCCCTGAC    3310
CTCTATAGAT CAATAGAGAA AACACCAGAA AACGACACAC AGATCAAATC AGAAATAAAC    3370
AGATTGAATG ATGAATCCAA TGCCACTAGA TTAGTACCTA GAAGAATAAG CAGTACAATG    3430
AGATCATTAA TAATAATCAT TAACAACAGC AATTTATCAT CAAAAGCAAA GCAATCATAC    3490
ATCAACGAAC TCAAGCTCTG CAAGAGTGAC GAGGAAGTGT CTGAGTTGAT GGACATGTTC    3550
AATGAGGATG TCAGCTCCCA GTAAACCGCC AACCAAGGGT CAACACCAAG AAAACCAATA    3610
GCACAAAACA GCCAATCAGA GACCACCCCA ATACACCAAA CCAATCAACA CATAACAAAG    3670
ATCTCCAGAT CATAGATGAT TAAGAAAAAC TTAGGATGAA AGGACTAATC AATCCTCCGA    3730
AACAATGAGC ATCACCAACT CCACAATCTA CACATTCCCA GAATCCTCTT TCTCCGAGAA    3790
TGGCAACATA GAGCCGTTAC CACTCAAGGT CAATGAACAG AGAAAGGCCA TACCTCATAT    3850
TAGGGTTGTC AAGATAGGAG ATCCGCCCAA ACATGGATCC AGATATCTGG ATGTCTTTTT    3910
ACTGGGCTTC TTTGAGATGG AAAGGTCAAA AGACAGGTAT GGGAGCATAA GTGATCTAGA    3970
TGATGATCCA AGTTACAAGG TTTGTGGCTC TGGATCATTG CCACTTGGGT TGGCTAGATA    4030
CACCGGAAAT GATCAGGAAC TCCTACAGGC TGCAACCAAG CTCGATATAG AAGTAAGAAG    4090
AACTGTAAAG GCTACGGAGA TGATAGTTTA CACTGTACAA AACATCAAAC CTGAACTATA    4150
TCCATGGTCC AGTAGATTAA GAAAAGGGAT GTTATTTGAC GCTAATAAGG TTGCACTTGC    4210
TCCTCAATGT CTTCCACTAG ATAGAGGGAT AAAATTCAGG GTGATATTTG TGAACTGCAC    4270
AGCAATTGGA TCAATAACTC TATTCAAAAT CCCTAAGTCC ATGGCATTGT TATCATTGCC    4330
TAATACAATA TCAATAAATC TACAAGTACA TATCAAAACA GGAGTTCAGA CAGATTCCAA    4390
AGGAGTAGTT CAGATTCTAG ATGAAAAAGG TGAAAAATCA CTAAATTTCA TGGTTCATCT    4450
CGGGTTGATC AAAAGGAAGA TGGGCAGAAT GTACTCAGTT GAATATTGTA AGCAGAAGAT    4510
CGAGAAGATG AGATTATTAT TCTCATTGGG ATTAGTTGGA GGGATCAGCT TCCACGTCAA    4570
CGCAACTGGC TCTATATCAA AGACATTAGC AAGTCAATTA GCATTCAAAA GAGAAATCTG    4630
CTATCCCCTA ATGGATCTGA ATCCACACTT AAATTCAGTT ATATGGGCAT CATCAGTTGA    4690
AATTACAAGG                                                          4700
```

FIGURE 1B

```
GTAGATGCAG TTCTCCAGCC TTCATTACCT GGCGAATTCA GATACTACCC AAACATCATA    4750
GCAAAGGGG  TCGGGAAAAT CAGACAGTAA AATCAACAAC CCTGATATCC AACATTGCAA    4820
ATCAGGCTAC CCACAGGAGA AAAATCAAAA ACTTAGGATC AAAGGGATCA CCACGAACCC    4880
CGGAAAACAG CCAAACAAAC CAACACACAA ATCACAGACA AAAAGGAGAA GGCACTGCAA    4940
AGACCGAGAA AAAACAGAAC GCACACAACC AAGCAGAGAA AAGCCAAAGC CCGCCATTCA    5000
CAAACACACC AACAATCCTG CAAACAAGCA CCAAAACAGA GGTCAAAAGA CAAAGAGCAC    5060
CAGATATGAC CATCACAACC ACAATCATAG CCATATTACT AATACCCCCA TCATTTTGTC    5120
AAATAGACAT AACAAAACTG CAACGTGTAG GTGTGTTAGT CAACAATCCT AAAGGCATGA    5180
AGATTTCACA AAATTTCGAA ACGAGATACC TGATATTAAG TTTGATACCC AAAATAGAGA    5240
ATTCACACTC ATGTGGGGAT CAACAGATAA ACCAATACAA GAAGTTATTG GATAGATTGA    5300
TAATTCCTCT ATATGATGGA TTAAAATTAC AAAAAGATGT AATAGTAGTA AGTCATGAAA    5360
CCCACAACAA TACTAATCTT AGGACAAAAC GATTCTTTGG AGAGATAATT GGGACAATTG    5420
CGATAGGGAT AGCCACTTCA GCACAAATCA CCGCAGCAGT CGCTCTTGTC GAAGCTAAAC    5480
AGGCAAAGTC AGACATAGAA AAACTCAAAG AGGCTATAAG AGACACAAAC AAGGCAGTAC    5540
AATCGATTCA AAGTTCTGTA GGTAACCTAA TTGTTGCAGT TAAATCAGTT CAAGACTATG    5600
TCAACAATGA AATTATACCT TCAATCACAA GATTAGGCTG TGAAGCAGCA GGGTTACAAT    5660
TGGGAATTGC ATTGACACAA CATTACTCAG AATTAACAAA TATATTTGGT GATAATATAG    5720
GAACACTGAA AGAAAAGGG  ATAAAATTAC AAGGGATAGC ATCATTATAT CACACAAACA    5780
TAACGGAAAT ATTTACTACT TCAACAGTTG ACCAATATGA TATTTATGAC CTATTATTCA    5840
CTGAGTCAAT CAAGATGAGA GTGATAGATG TTGATTTGAG TGATTACTCA ATTACTCTTC    5900
AAGTTAGACT TCCTTTATTA ACTAAACTAT CAAATACTCA AATTTATAAA GTAGATTCTA    5960
TATCATACAA CATCCAGGGC AAAGAGTGGT ATATTCCTCT TCCCAATCAC ATCATGACAA    6020
AAGGGGCTTT TCTAGGTGGT GCTGATATTA AGAATGCAT  AGAGGCATTC AGCAGTTATA    6080
TATGTCCTTC TGATCCAGGT TACATATTAA ATCACGAGAT AGAGAATTGT TTATCAGGGA    6140
ACATAACACA GTGTCCTAAG ACTGTTGTTA CATCAGATGT GGTACCACGA TACGCGTTTG    6200
TGAATGGTGG ATTAATTGCA AACTGCATAA CAACTACATG TACATGCAAT GGAATTGACA    6260
ATAGAATTAA TCAATCACCT GATCAAGGAA TTAAGATCAT AACACATAAA GAATGCCAGG    6320
TAATAGGTAT AAACGGAATG TTATTCAATA CTAATAGAGA AGGGACATTA GCAACTTATA    6380
CATTTGATGA CATCATATTA AATAACTCTG TTGCACTTAA TCCAATTGAT ATATCTATGG    6440
AACTCAACAA GGCAAAACTA GAATTAGAAG AATCGAAGGA ATGGATAAAG AAATCAAATC    6500
AAAAGTTAGA TTCCGTTGGA AGTTGGTATC AATCTAGTGC AACAATCACC ATAATCATAG    6560
TGATGATAAT AATTCTAGTT ATAATCAATA TAACAATTAT TGTAGTCATA ATCAAATTCC    6620
ATAGAATTCA GGGGAAAGAT CAAAACGACA AAAACAGTGA GCCGTATATA CTGACAAATA    6680
GACAATAAGA CTATACACGA TCAAATATAA AAAGTACAAA AAACTTAGGA ACAAAGTTGT    6740
TCAACACAGC AGCACCGAAT AGACCAAAAG GCAGCGCAGA GGCGACACCA AACTCAAAAA    6800
TGGAATATTG AAACACACA  AACAGCATAA ATAACACCAA CAATGAAACC GAAACAGCCA    6860
GAGGCAAACA TAGTAGCAAG GTTACAAATA TCATAATGTA CACCTTCTGG ACAATAACAT    6920
TAACAATATT ATCAGTCATT TTTATAATGA TATTGACAAA CTTAATTCAA GAGAACAATC    6980
ATAATAAATT AATGTTGCAG GAAATAAGAA AAGAATTCGC GGCAATAGAC ACCAAGATTC    7040
AGAGGACTTC                                                          7050
```

*FIGURE 1C*

```
GGATGACATT GGAACCTCAA TACAGTCAGG AATAAATACA AGACTTCTCA CAATTCAGAG    7110
TCATGTTCAA AACTATATCC CACTATCATT AACACAACAA ATGTCAGATC TCAGAAAATT    7170
TATCAATGAT CTAACAAATA AAAGAGAACA TCAAGAAGTG CCAATACAGA GAATGACTCA    7230
TGATAGAGGT ATAGAACCCC TAAATCCAAA CAAGTTCTGG AGGTGTACAT CTGGTAACCC    7290
ATCTCTAACA AGTAGTCCTA AGATAAGGTT AATACCAGGA CCAGGTTTAT TAGCAACATC    7350
TACTACAGTA AATGGCTGTA TTAGAATTCC ATCGTTAGTA ATCAATCATC TAATCTATGC    7410
TTACACCTCT AATCTTATTA CCCAGGGCTG TCAAGATATA GGGAAATCTT ACCAAGTACT    7470
ACAAATAGGG ATAATTACTA TAAATTCGGA CCTAGTACCT GATTTAAACC CCAGAGTCAC    7530
ACATACATTT AATATTGATG ATAATAGAAG ATCTTGCTCT CTGGCACTAT TGAATACAGA    7590
TGTTTATCAG TTATGCTCAA CACCAAAAGT TGATGAAAGA TCCGATTATG CATCAACAGG    7650
TATTGAGGAT ATTGTACTTG ACATTGTCAC TAATAATGGA TTAATTATAA CAACAAGGTT    7710
TACAAATAAT AATATAACTT TTGATAAACC GTATGCAGCA TTGTATCCAT CAGTGGGACC    7770
AGGAATCTAT TATAAGGATA AAGTTATATT TCTCGGATAT GGAGGTCTAG AGCATGAAGA    7830
AAACGGAGAC GTAATATGTA ATACAACTGG TTGTCCTGGC AAAACACAGA GAGACTGTAA    7890
TCAGGCTTCT TATAGCCCAT GGTTCTCAAA TAGGAGAATG GTAAACTCTA TTATTGTTGT    7950
TGATAAAGGC ATAGATGCAA CTTTTAGCTT GAGGGTGTGG ACTATTCCAA TGAGCCAAAA    8010
TTATTGGGGA TCAGAAGGAA GATTACTTTT ATTAGGTGAC AGAATATACA TATATACTAG    8070
ATCCACAAGT TGGCACAGTA AATTACAGTT AGGGGTAATT GATATTTCTG ATTATACTAA    8130
TATAAGAATA AATTGGACTT GGCATAATGT ACTATCACGG CCAGGGAATG ATGAATGTCC    8190
ATGGGGTCAT TCATGCCCAG ACGGATGTAT AACAGGAGTT TACACTGATG CATATCCGCT    8250
AAACCCATCG GGGAGTGTTG TATCATCAGT AATTCTTGAT TCACAAAAGT CTAGAGAAAA    8310
CCCAATCATT ACTTACTCAA CAGCTACAAA TAGAATAAAT GAATTAGCTA TATATAACAG    8370
AACACTTCCA GCTGCATATA CAACAACAAA TTGTATCACA CATTATGATA AAGGGTATTG    8430
TTTTCATATA GTAGAAATAA ATCACAGAAG TTTGAATACG TTTCAACCTA TGTTATTCAA    8490
AACAGAAGTT CCAAAAAACT GCAGCTAAAT TGATCATCGC ATATCGGATG CAAGATGACA    8550
TTAAAAGAGA CCACCAGACA GACAACACAG GAGACGATGC AAGATATAAA GAAATAATAA    8610
AAAACTTAGG AGAAAAGTGT GCAAGAAAAA TGGACACCGA GTCCCACAGC GGCACAACAT    8670
CTGACATTCT GTACCCTGAA TGTCACCTCA ATTCTCCTAT AGTTAAAGGA AAGATAGCAC    8730
AACTGCATAC AATAATGAGT TTGCCTCAGC CCTACGATAT GGATGATGAT TCAATACTGA    8790
TTATTACTAG ACAAAAAATT AAACTCAATA AATTAGATAA AAGACAACGG TCAATTAGGA    8850
AATTAAGATC AGTCTTAATG GAAAGAGTAA GTGATCTAGG TAAATATACC TTTATCAGAT    8910
ATCCAGAGAT GTCTAGTGAA ATGTTCCAAT TATGTATACC CGGAATTAAT AATAAAATAA    8970
ATGAATTGCT AAGTAAAGCA AGTAAAACAT ATAATCAAAT GACTGATGGA TTAAGAGATC    9030
TATGGGTTAC TATACTATCG AAGTTAGCAT CGAAAAATGA TGGAAGTAAT TATGATATCA    9090
ATGAAGATAT TAGCAATATA TCAAATGTTC ACATGACTTA TCAATCAGAC AAATGGTATA    9150
ATCCATTCAA GACATGGTTT ACTATTAAGT ATGACATGAG AAGATTACAA AAAGCCAAAA    9210
ATGAGATTAC ATTCAATAGG CATAAAGATT ATAATCTATT AGAAGACCAA AAGAATATAT    9270
TGCTGATACA TCCAGAACTC GTCTTAATAT TAGATAAACA AAATTACAAT GGGTATATAA    9330
TGACTCCTGA ATTGGTACTA ATGTATTGTG ATGTAGTTGA AGGGAGGTGG AATATAAGTT    9390
CATGTGCAAA                                                          9400
```

FIGURE 1D

```
ATTGGATCCT AAGTTACAAT CAATGTATTA TAAGGGTAAC AATTTATGGG AAATAATAGA    9460
TGGACTATTC TCGACCTTAG GAGAAAGAAC ATTTGACATA ATATCACTAT TAGAACCACT    9520
TGCATTATCG CTCATTCAAA CTTATGACCC GGTTAAACAG CTCAGGGGGG CTTTTTTAAA    9580
TCACGTGTTA TCAGAAATGG AATTAATATT TGCAGCTGAG TGTACAACAG AGGAAATACC    9640
TAATGTGGAT TATATAGATA AAATTTTAGA TGTGTTCAAA GAATCAACAA TAGATGAAAT    9700
AGCAGAAATT TTCTCTTTCT TCCGAACTTT TGGACACCCT CCATTAGAGG CGAGTATAGC    9760
AGCAGAGAAA GTTAGAAAGT ATATGTATAC TGAGAAATGC TTGAAATTTG ATACTATCAA    9820
TAAATGTCAT GCTATTTTTT GTACAATAAT TATAAATGGA TATAGAGAAA GACATGGTGG    9880
TCAATGGCCT CCAGTTACAT TACCTGTCCA TGCACATGAA TTTATCATAA ATGCATACGG    9940
ATCAAATTCT GCCATATCAT ATGAGAATGC TGTAGATTAT TATAAGAGCT TCATAGGAAT   10000
AAAATTTGAC AAGTTTATAG AGCCTCAATT GGATGAAGAC TTAACTATTT ATATGAAAGA   10060
TAAAGCATTA TCCCCAAAGA AATCAAACTG GACACAGTC TATCCAGCTT CAAACCTGTT    10120
ATACCGCACT AATGTGTCTC ATGATTCACG AAGATTGGTT GAAGTATTTA TAGCAGATAG   10180
TAAATTTGAT CCCCACCAAG TATTAGATTA CGTAGAATCA GGATATTGGC TGGATGATCC   10240
TGAATTTAAT ATCTCATATA GTTAAAAGA GAAAGAAATA AAACAAGAAG GTAGACTTTT    10300
TGCAAAAATG ACATACAAGA TGAGGGCTAC ACAAGTATTA TCAGAAACAT TATTGGCGAA   10360
TAATATAGGG AAATTCTTCC AAGAGAATGG GATGGTTAAA GGAGAAATTG AATTACTCAA   10420
GAGACTAACA ACAATATCTA TGTCTGGAGT TCCGCGGTAT AATGAGGTAT ACAATAATTC   10480
AAAAAGTCAC ACAGAAGAAC TTCAAGCTTA TAATGCAATT AGCAGTTCCA ATTTATCTTC   10540
TAATCAGAAG TCAAAGAAGT TTGAATTTAA ATCTACAGAT ATATACAATG ATGGATACGA   10600
AACCGTAAGC TGCTTCTTAA CGACAGATCT TAAAAAATAT TGTTTAAATT GGAGGTATGA   10660
ATCAACAGCT TTATTCGGTG ATACTTGTAA TCAGATATTT GGGTTAAAGG AATTATTTAA   10720
TTGGCTGCAC CCTCGCCTTG AAAAGAGTAC AATATATGTT GGAGATCCTT ATTGCCCGCC   10780
ATCAGATATT GAACATTTAC CACTTGATGA CCATCCTGAT TCAGGATTTT ATGTTCATAA   10840
TCCTAAAGGA GGAATAGAAG GGTTTTGCCA AAAGTTATGG ACACTCATAT CTATCAGTGC   10900
AATACATTTA GCAGCTGTCA AAATCGGTGT AAGAGTTACT GCAATGGTTC AAGGGGATAA   10960
TCAAGCCATA GCTGTTACCA CAAGAGTACC TAATAATTAT GATTATAAAG TTAAGAAAGA   11020
GATTGTTTAT AAAGATGTGG TAAGATTTTT TGATTCCTTG AGAGAGGTGA TGGATGATCT   11080
GGGTCATGAG CTCAAACTAA ATGAAACTAT AATAAGTAGT AAAATGTTTA TATATAGCAA   11140
AAGGATATAC TATGACGGAA GAATCCTTCC TCAGGCATTA AAAGCATTGT CTAGATGTGT   11200
TTTTTGGTCT GAAACAATCA TAGATGAGAC AAGATCAGCA TCCTCAAATC TGGCTACATC   11260
GTTTGCAAAG GCCATTGAGA ATGGCTACTC ACCTGTATTG GGATATGTAT GCTCAATCTT   11320
CAAAAATATC CAACAGTTGT ATATAGCGCT TGGAATGAAT ATAAACCCAA CTATAACCCA   11380
AAATATTAAA GATCAATATT TCAGGAATAT TCATTGGATG CAATATGCCT CCTTAATCCC   11440
TGCTAGTGTC GGAGGATTTA ATTATATGGC CATGTCAAGG TGTTTTGTCA GAAACATTGG   11500
AGATCCTACA GTCGCTGCGT TAGCCGATAT TAAAAGATTT ATAAAAGCAA ATTTGTTAGA   11560
TCGAGGTGTC CTTTACAGAA TTATGAATCA AGAACCAGGC GAGTCTTCTT TTTTAGACTG   11620
GGCCTCAGAT CCCTATTCAT GTAACTTACC ACAATCTCAA AATATAACCA CCATGATAAA   11680
GAATATAACT GCAAGAAATG TACTACAGGA CTCACCAAAC CCATTACTAT CTGGATTATT   11740
TACAAGTACA                                                          11750
```

FIGURE 1E

```
ATGATAGAAG AGGATGAGGA ATTAGCTGAG TTCCTAATGG ACAGGAGAAT AATCCTCCCA    11810
AGAGTTGCAC ATGACATTTT AGATAATTCT CTTACTGGAA TTAGGAATGC TATAGCTGGT    11870
ATGTTGGATA CAACAAAATC ACTAATTCGA GTAGGGATAA GCAGAGGAGG ATTAACCTAT    11930
AACTTATTAA GAAAGATAAG CAACTATGAT CTTGTACAAT ATGAGACACT TAGTAAAACT    11990
TTAAGACTAA TAGTCAGTGA CAAGATTAAG TATGAAGATA TGTGCTCAGT AGACCTAGCC    12050
ATATCATTAA GACAAAAAAT GTGGATGCAT TTATCAGGAG GAAGAATGAT AAATGGACTT    12110
GAAACTCCAG ATCCTTTAGA GTTACTGTCT GGAGTAATAA TAACAGGATC TGAACATTGT    12170
AGGATATGTT ATTCAACTGA AGGTGAAAGC CCATATACAT GGATGTATTT ACCAGGCAAT    12230
CTTAATATAG GATCAGCTGA GACAGGAATA GCATCATTAA GGGTCCCTTA CTTTGGATCA    12290
GTTACAGATG AGAGATCTGA AGCACAATTA GGGTATATCA AAAATCTAAG CAAACCAGCT    12350
AAGGCTGCTA TAAGAATAGC AATGATATAT ACTTGGGCAT TTGGGAATGA CGAAATATCT    12410
TGGATGGAAG CATCACAGAT TGCACAAACA CGTGCAAACT TTACATTGGA TAGCTTAAAG    12470
ATTTTGACAC CAGTGACAAC ATCAACAAAT CTATCACACA GGTTAAAAGA TACTGCTACT    12530
CAGATGAAAT TTTCTAGTAC ATCACTTATT AGAGTAAGCA GGTTCATCAC AATATCTAAT    12590
GATAATATGT CTATTAAAGA AGCAAATGAA ACTAAAGATA CAAATCTTAT TTATCAACAG    12650
GTAATGTTAA CAGGATTAAG TGTATTTGAA TATCTATTTA GGTTAGAGGA GAGTACAGGA    12710
CATAACCCTA TGGTCATGCA TCTACATATA GAGGATGGAT GTTGTATAAA AGAGAGTTAC    12770
AATGATGAGC ATATCAATCC GGAGTCTACA TTAGAGTTAA TCAAATACCC TGAGAGTAAT    12830
GAATTTATAT ATGATAAGGA CCCTTTAAAG GATATAGATC TATCAAAATT AATGGTTATA    12890
AGAGATCATT CTTATACAAT TGACATGAAT TACTGGGATG ACACAGATAT TGTACATGCA    12950
ATATCAATAT GTACTGCAGT TACAATAGCA GATACAATGT CGCAGCTAGA TCGGGATAAT    13010
CTTAAGGAGC TGGTTGTGAT TGCAAATGAT GATGATATTA ACAGTCTGAT AACTGAATTT    13070
CTGACCCTAG ATATACTAGT GTTTCTCAAA ACATTTGGAG GGTTACTCGT GAATCAATTT    13130
GCATATACCC TTTATGGATT GAAAATAGAA GGAAGGGATC CCATTTGGGA TTATATAATG    13190
AGAACATTAA AAGACACCTC ACATTCAGTA CTTAAAGTAT TATCTAATGC ACTATCTCAT    13250
CCAAAAGTGT TTAAGAGATT TTGGGATTGT GGAGTTTTGA ATCCTATTTA TGGTCCTAAT    13310
ACTGCTAGTC AAGATCAAGT TAAGCTTGCT CTCTCGATTT GCGAGTACTC CTTGGATCTA    13370
TTTATGAGAG AATGGTTGAA TGGAGCATCA CTTGAGATCT ATATCTGTGA TAGTGACATG    13430
GAAATAGCAA ATGACAGAAG ACAAGCATTT CTCTCAAGAC ATCTTGCCTT TGTGTGTTGT    13490
TTAGCAGAGA TAGCATCTTT TGGACCAAAT TTATTAAATC TAACATATCT AGAGAGACTT    13550
GATGAATTAA AACAATACTT AGATCTGAAC ATCAAAGAAG ATCCTACTCT TAAATATGTG    13610
CAAGTATCAG GACTGTTAAT TAAATCATTC CCCTCAACTG TTACGTATGT AAGGAAAACT    13670
GCGATTAAGT ATCTGAGGAT TCGTGGTATT AATCCGCCTG AAACGATTGA AGATTGGGAT    13730
CCCATAGAAG ATGAGAATAT CTTAGACAAT ATTGTTAAAA CTGTAAATGA CAATTGCAGT    13790
GATAATCAAA AGAGAAATAA AAGTAGTTAT TTCTGGGGAT TAGCTCTAAA GAATTATCAA    13850
GTCGTGAAAA TAAGATCCAT AACGAGTGAT TCTGAAGTTA ATGAAGCTTC GAATGTTACT    13910
ACACATGGAA TGACACTTCC TCAGGGAGGA AGTTATCTAT CACATCAGCT GAGGTTATTT    13970
GGAGTAAACA GTACAAGTTG TCTTAAAGCT CTTGAATTAT CACAAATCTT AATGAGGGAA    14030
GTTAAAAAAG ATAAAGATAG ACTCTTTTTA GGAGAAGGAG CAGGAGCTAT GTTAGCATGT    14090
TATGATGCTA                                                          14100
```

FIGURE 1F

```
CACTCGGTCC TGCAATAAAT TATTATAATT CTGGTTTAAA TATTACAGAT GTAATTGGTC    14160
AACGGGAATT AAAAATCTTC CCATCAGAAG TATCATTAGT AGGTAAAAAA CTAGGAAATG    14220
TAACACAGAT TCTTAATCGG GTGAGGGTGT TATTTAATGG GAATCCCAAT TCAACATGGA    14280
TAGGAAATAT GGAATGTGAG AGTTTAATAT GGAGTGAATT AAATGATAAG TCAATTGGTT    14340
TAGTACATTG TGACATGGAG GGAGCGATAG GCAAATCAGA AGAAACTGTT CTACATGAAC    14400
ATTATAGTAT TATTAGGATT ACATATTTAA TCGGGGATGA TGATGTTGTC CTAGTATCAA    14460
AAATTATACC AACTATTACT CCGAATTGGT CTAAAATACT CTATCTATAC AAGTTGTATT    14520
GGAAGGATGT AAGTGTAGTG TCCCTTAAAA CATCCAATCC TGCCTCAACA GAGCTTTATT    14580
TAATTTCAAA AGATGCTTAC TGTACTGTAA TGGAACCCAG TAATCTTGTT TTATCAAAAC    14640
TTAAAAGGAT ATCATCAATA GAAGAAAATA ATCTATTAAA GTGGATAATC TTATCAAAAA    14700
GGAAGAATAA CGAGTGGTTA CAGCATGAAA TCAAAGAAGG AGAAAGGGAT TATGGGATAA    14760
TGAGGCCATA TCATACAGCA CTGCAAATTT TTGGATTCCA AATTAACTTA AATCACTTAG    14820
CTAGAGAATT TTTATCAACT CCTGATTTAA CCAACATTAA TAATATAATT CAAAGTTTTA    14880
CAAGAACAAT TAAAGATGTT ATGTTCGAAT GGGTCAATAT CACTCATGAC AATAAAAGAC    14940
ATAAATTAGG AGGAAGATAT AATCTATTCC CGCTTAAAAA TAAGGGGAAA TTAAGATTAT    15000
TATCACGAAG ATTAGTACTA AGCTGGATAT CATTATCCTT ATCAACCAGA TTACTGACGG    15060
GCCGTTTTCC AGATGAAAAA TTTGAAAATA GGGCACAGAC CGGATATGTA TCATTGGCTG    15120
ATATTGATTT AGAATCCTTA AAGTTATTAT CAAGAAATAT TGTCAAAAAT TACAAAGAAC    15180
ACATAGGATT AATATCATAC TGGTTTTTGA CCAAAGAGGT CAAAATACTA ATGAAGCTTA    15240
TAGGAGGAGT CAAACTACTA GGAATTCCTA AACAGTACAA AGAGTTAGAG GATCGATCAT    15300
CTCAGGGTTA TGAATATGAT AATGAATTTG ATATTGATTA ATACATAAAA ACATAAAATA    15360
AAACACCTAT TCCTCACCCA TTCACTTCCA ACAAAATGAA AGTAAGAAA AACATGTAAT     15420
ATATATATAC CAAACAGAGT TTTTCTCTTG TTTGGT                              15456
```

*FIGURE 1G*

```
ACCAAACAAG AGAAGAGACT TGCTTGGGAA TATTAATTCA AATAAAAATT AACTTAGGAT      60
TAAAGAACTT TACCGAAAGG TAAGGGGAAA GAAATCCTAA GACTGTAATC ATGTTGAGTC     120
TATTCGACAC ATTCAGTGCG CGTAGGCAGG AGAAACATAAC GAAATCAGCT GGTGGGGCTG   180
TTATTCCCGG GCAAAAAAAC ACTGTGTCTA TATTTGCTCT TGGACCATCA ATAACAGATG    240
ACAATGATAA AATGACATTG GCTCTTCTCT TTTTGTCTCA TTCTTTAGAC AATGAAAAGC    300
AGCATGCGCA AAGAGCTGGA TTTTTAGTTT CTCTGTTATC AATGGCTTAT GCCAACCCAG    360
AATTATATTT AACATCAAAT GGTAGTAATG CAGATGTTAA ATATGTTATC TACATGATAG    420
AGAAAGACCC AGGAAGACAG AAATATGGTG GGTTTGTCGT CAAGACTAGA GAGATGGTTT    480
ATGAAAAGAC AACTGATTGG ATGTTCGGGA GTGATCTTGA GTATGATCAA GACAATATGT    540
TGCAAAATGG TAGAAGCACT TCTACAATCG AGGATCTTGT TCATACTTTT GGATATCCAT    600
CGTGTCTTGG AGCCCTTATA ATCCAAGTTT GGATAATACT TGTTAAGGCT ATAACCAGTA    660
TATCAGGATT GAGGAAAGGA TTCTTTACTC GGTTAGAAGC ATTTCGACAA GATGGAACAG    720
TTAAATCCAG TCTAGTGTTG AGCGGTGATG CAGTAGAACA AATTGGATCA ATTATGAGGT    780
CCCAACAGAG CTTGGTAACA CTCATGGTTG AAACACTGAT AACAATGAAC ACAGGCAGGA    840
ATGATCTGAC AACAATAGAA AAGAATATAC AGATTGTAGG AAACTACATC AGAGATGCAG    900
GTCTTGCTTC ATTTTTCAAC ACAATCAGAT ATGGCATTGA GACTAGAATG GCAGCTCTAA    960
CTCTGTCTAC CCTTAGACCG GATATCAACA GACTCAAGGC ACTGATCGAG TTATATCTAT   1020
CAAAGGGGCC ACGTGCTCCT TTTATATGCA TTTTGAGAGA TCCCGTGCAT GGTGAGTTTG   1080
CACCAGGCAA CTATCCTGCC CTCTGGAGTT ATGCGATGGG TGTAGCAGTT GTACAAAACA   1140
AGGCCATGCA ACAGTATGTA ACAGGAAGGT CTTATCTGGA TATTGAAATG TTCCAACTTG   1200
GTCAAGCAGT GGCACGTGAT GCCGAGTCGC AGATGAGTTC AATATTAGAG GATGAACTGG   1260
GGGTCACACA AGAAGCCAAG CAAAGCTTGA AGAAACACAT GAAGAACATC AGCAGTTCAG   1320
ATACAACCTT TCATAAGCCT ACAGGGGGAT CAGCCATAGA AATGGCGATA GATGAAGAAG   1380
CAGGGCAGCC TGAATCCAGA GGAGATCAGG ATCAAGGAGA TGAGCCTCGG TCATCCATAG   1440
TTCCTTATGC ATGGGCAGAC GAAACCGGGA ATGACAATCA AACTGAATCA ACTACAGAAA   1500
TTGACAGCAT CAAAACTGAA CAAAGAAACA TCAGAGACAG GCTGAACAAA AGACTCAACG   1560
AGAAAAGGAA ACAGAGTGAC CCGAGATCAA CTGACATCAC AAACAACACA AATCAAACTG   1620
AAATAGATGA TTTGTTCAGT GCATTCGGAA GCAACTAGTC ACAAAGAGAT GACCACTATC   1680
ACCAGCAACA AGTAAGAAAA ACTTAGGATT AATGGAAATT ATCCAATCCA GAGACGGAAG   1740
GACAAATCCA GAATCCAACC ACAACTCAAT CAACCAAAGA TTCATGGAAG ACAATGTTCA   1800
AAACAATCAA ATCATGGATT CTTGGGAAGA GGGATCAGGA GATAAATCAT CTGACATCTC   1860
ATCGGCCCTC GACATCATTG AATTCATACT CAGCACCGAC TCCCAAGAAA ACACGGCAGA   1920
CAGCAATGAA ATCAACACAG GAACCACAAG ACTTAGCACG ACAATCTACC AACCTGAATC   1980
CAAAACAACA GAAACAAGCA AGGAAAATAG TGGACCAGCT AACAAAAATC GACAGTTTGG   2040
GGCATCACAC GAACGTGCCA CAGAGACAAA AGATAGAAAT GTTAATCAGG AGACTGTACA   2100
GGGAGGATAT AGGAGAGGAA GCAGCCCAGA TAGTAGAACT GAGACTATGG TCACTCGAAG   2160
AATCTCCAGA AGCAGCCCAG ATCCTAACAA TGGAACCCAA ATCCAGGAAG ATATTGATTA   2220
CAATGAAGTT GGAGAGATGG ATAAGGACTC TACTAAGAGG GAAATGCGAC AATTTAAAGA   2280
TGTTCCAGTC AAGGTATCAG GAAGTGATGC CATTCCTCCA ACAAAACAAG ATGGAGACGG   2340
TGATGATGGA                                                          2350
```

*FIGURE 2A*

```
AGAGGCCTGG AATCTATCAG TACATTTGAT TCAGGATATA CCAGTATAGT GACTGCCGCA    2410
ACACTAGATG ACGAAGAAGA ACTCCTTATG AAGAACAACA GGCCAAGAAA GTATCAATCA    2470
ACACCCCAGA ACAGTGACAA GGGAATTAAA AAAGGGGTTG GAAGGCCAAA AGACACAGAC    2530
AAACAATCAT CAATATTGGA CTACGAACTC AACTTCAAAG GATCGAAGAA GAGCCAGAAA    2590
ATCCTCAAAG CCAGCACGAA TACAGGAGAA CCAACAAGAC CACAGAATGG ATCCCAGGGG    2650
AAGAGAATCA CATCCTGGAA CATCCTCAAC AGCGAGAGCG GCAATCGAAC AGAATCAACA    2710
AACCAAACCC ATCAGACATC AACCTCGGGA CAGAACCACA CAATGGGACC AAGCAGAACA    2770
ACCTCCGAAC CAAGGATCAA GACACAAAAG ACGGATGGAA AGGAAAGAGA GGACACAGAA    2830
GAGAGCACTC GATTTACAGA AAGGGCGATT ACATTATTAC AGAATCTTGG TGTAATCCAA    2890
TCTGCAGCAA AATTAGACCT ATACCAAGAC AAGAGAGTTG TGTGTGTGGC GAATGTCCTA    2950
AACAATGCAG ATACTGCATC AAAGATAGAC TTCCTAGCAG GTTTGATGAT AGGAGTGTCA    3010
ATGGATCATG ATACCAAATT AAATCAGATT CAGAACGAGA TATTAAGTTT GAAAACTGAT    3070
CTTAAAAAGA TGGATGAATC ACATAGAAGA CTAATTGAGA ATCAAAAAGA ACAATTATCA    3130
CTGATCACAT CATTAATCTC AAATCTTAAA ATTATGACAG AGAGAGGAGG AAGAAGGAC    3190
CAACCAGAAC CTAGCGGGAG GACATCCATG ATCAAGACAA AAGCAAAAGA AGAGAAAATA    3250
AAGAAAGTCA GGTTTGACCC TCTTATGGAA ACACAGGGCA TCGAGAAAAA CATCCCTGAC    3310
CTCTATAGAT CAATAGAAAA AACACCAGAA AACGACACAC AGATCAAATC AGAAATAAAC    3370
AGATTGAATG ATGAATCCAA TGCCACTAGA TTAGTACCTA GAAGAATAAG CAGTACAATG    3430
AGATCATTAA TAATAATCAT TAACAACAGC AATTTATCAT CAAAAGCAAA GCAATCATAC    3490
ATCAACGAAC TCAAGCTCTG CAAGAGTGAC GAGGAAGTGT CTGAGTTGAT GGACATGTTC    3550
AATGAGGATG TCAGCTCCCA GTAAACCGCC AACCAAGGGT CAACACCAAG AAAACCAATA    3610
GCACAAAACA GCCAATCAGA GACCACCCCA ATACACCAAA CCAATCAACA CATAACAAAG    3670
ATCTCCAGAT CATAGATGAT TAAGAAAAAC TTAGGATGAA AGGACTAATC AATCCTCCGA    3730
AACAATGAGC ATCACCAACT CCACAATCTA CACATTCCCA GAATCCTCTT TCTCCGAGAA    3790
TGGCAACATA GAGCCGTTAC CACTCAAGGT CAATGAACAG AGAAAGGCCA TACCTCATAT    3850
TAGGGTTGTC AAGATAGGAG ATCCGCCCAA ACATGGATCC AGATATCTGG ATGTCTTTTT    3910
ACTGGGCTTC TTTGAGATGG AAAGGTCAAA AGACAGGTAT GGGAGCATAA GTGATCTAGA    3970
TGATGATCCA AGTTACAAGG TTTGTGGCTC TGGATCATTG CCACTTGGGT TGGCTAGATA    4030
CACCGGAAAT GATCAGGAAC TCCTACAGGC TGCAACCAAG CTCGATATAG AAGTAAGAAG    4090
AACTGTAAAG GCTACGGAGA TGATAGTTTA CACTGTACAA AACATCAAAC CTGAACTATA    4150
TCCATGGTCC AGTAGATTAA GAAAAGGGAT GTTATTTGAC GCTAATAAGG TTGCACTTGC    4210
TCCTCAATGT CTTCCACTAG ATAGGGGAT AAAATTCAGG GTGATATTTG TGAACTGCAC    4270
AGCAATTGGA TCAATAACTC TATTCAAAAT CCCTAAGTCC ATGGCATTGT TATCATTGCC    4330
TAATACAATA TCAATAAATC TACAAGTACA TATCAAAACA GGAGTTCAGA CAGATTCCAA    4390
AGGAGTAGTT CAGATTCTAG ATGAAAAAGG TGAAAAATCA CTAAATTTCA TGGTTCATCT    4450
CGGGTTGATC AAAAGGAAGA TGGGCAGAAT GTACTCAGTT GAATATTGTA AGCAGAAGAT    4510
CGAGAAGATG AGATTATTAT TCTCATTGGG ATTAGTTGGA GGGATCAGCT TCCACGTCAA    4570
CGCAACTGGC TCTATATCAA AGACATTAGC AAGTCAATTA GCATTCAAAA GAGAAATCTG    4630
CTATCCCCTA ATGGATCTGA ATCCACACTT AAATTCAGTT ATATGGGCAT CATCAGTTGA    4690
AATTACAAGG                                                          4700
```

FIGURE 2B

```
GTAGATGCAG TTCTCCAGCC TTCATTACCT GGCGAATTCA GATACTACCC AAACATCATA      4760
GCAAAAGGGG TCGGGAAAAT CAGACAGTAA AATCAACAAC CCTGATATCC AACATTGCAA      4820
ATCAGGCTAC CCACAGGAGA AAAATCAAAA ACTTAGGATC AAAGGGATCA CCACGAACCC      4880
CGGAAAACAG CCAAACAAAC CAACACACAA ATCACAGACA AAAAGGAGAA GGCACTGCAA      4940
AGACCGAGAA AAAACAGAAC GCACACAACC AAGCAGAGAA AAGCCAAAGC CCGCCATTCA      5000
CAAACACACC AACAATCCTG CAAACAAGCA CCAAAACAGA GGTCAAAAGA CAAAGAGCAC      5060
CAGATATGAC CATCACAACC ACAATCATAG CCATATTACT AATACCCCCA TCATTTTGTC      5120
AAATAGACAT AACAAAACTG CAACGTGTAG GTGTGTTAGT CAACAATCCT AAAGGCATGA      5180
AGATTTCACA AAATTTCGAA ACGAGATACC TGATATTAAG TTTGATACCC AAAATAGAGA      5240
ATTCACACTC ATGTGGGGAT CAACAGATAA ACCAATACAA GAAGTTATTG GATAGATTGA      5300
TAATTCCTCT ATATGATGGA TTAAAATTAC AAAAAGATGT AATAGTAGTA AGTCATGAAA      5360
CCCACAACAA TACTAATCTT AGGACAAAAC GATTCTTTGG AGAGATAATT GGGACAATTG      5420
CGATAGGGAT AGCCACTTCA GCACAAATCA CCGCAGCAGT CGCTCTTGTC GAAGCTAAAC      5480
AGGCAAAGTC AGACATAGAA AAACTCAAAG AGGCTATAAG AGACACAAAC AAGGCAGTAC      5540
AATCGATTCA AAGTTCTGTA GGTAACCTAA TTGTTGCAGT TAAATCAGTT CAAGACTATG      5600
TCAACAATGA AATTATACCT TCAATCACAA GATTAGGCTG TGAAGCAGCA GGGTTACAAT      5660
TGGGAATTGC ATTGACACAA CATTACTCAG AATTAACAAA TATATTTGGT GATAATATAG      5720
GAACACTGAA AGAAAAAGGG ATAAAATTAC AAGGGATAGC ATCATTATAT CACACAAACA      5780
TAACGGAAAT ATTTACTACT TCAACAGTTG ACCAATATGA TATTTATGAC CTATTATTCA      5840
CTGAGTCAAT CAAGATGAGA GTGATAGATG TTGATTTGAG TGATTACTCA ATTACTCTTC      5900
AAGTTAGACT TCCTTTATTA ACTAAACTAT CAAATACTCA AATTTATAAA GTAGATTCTA      5960
TATCATACAA CATCCAGGGC AAAGAGTGGT ATATTCCTCT TCCCAATCAC ATCATGACAA      6020
AAGGGGCTTT TCTAGGTGGT GCTGATATTA AGAATGCAT AGAGGCATTC AGCAGTTATA      6080
TATGTCCTTC TGATCCAGGT TACATATTAA ATCACGAGAT AGAGAATTGT TTATCAGGGA      6140
ACATAACACA GTGTCCTAAG ACTGTTGTTA CATCAGATGT GGTACCACGA TACGCGTTTG      6200
TGAATGGTGG ATTAATTGCA AACTGCATAA CAACTACATG TACATGCAAT GGAATTGACA      6260
ATAGAATTAA TCAATCACCT GATCAAGGAA TTAAGATCAT AACACATAAA GAATGCCAGG      6320
TAATAGGTAT AAACGGAATG TTATTCAATA CTAATAGAGA AGGGACATTA GCAACTTATA      6380
CATTTGATGA CATCATATTA AATAACTCTG TTGCACTTAA TCCAATTGAT ATATCTATGG      6440
AACTCAACAA GGCAAAACTA GAATTAGAAG AATCGAAGGA ATGGATAAAG AAATCAAATC      6500
AAAAGTTAGA TTCCGTTGGA AGTTGGTATC AATCTAGTGC AACAATCACC ATAATCATAG      6560
TGATGATAAT AATTCTAGTT ATAATCAATA TAACAATTAT TGTAGTCATA ATCAAATTCC      6620
ATAGAATTCA GGGGAAAGAT CAAAACGACA AAAACAGTGA GCCGTATATA CTGACAAATA      6680
GACAATAAGA CTATACACGA TCAAATATAA AAGTACAAA AAACTTAGGA CAAAGTTGT      6740
TCAACACAGC AGCACCGAAT AGACCAAAAG GCAGCGCAGA GGCGACACCA AACTCAAAAA      6800
TGGAATATTG GAAACACACA AACAGCATAA ATAACACCAA CAATGAAACC GAAACAGCCA      6860
GAGGCAAACA TAGTAGCAAG GTTACAAATA TCATAATGTA CACCTTCTGG ACAATAACAT      6920
TAACAATATT ATCAGTCATT TTTATAATGA TATTGACAAA CTTAATTCAA GAGAACAATC      6980
ATAATAAATT AATGTTGCAG GAAATAAGAA AAGAATTCGC GGCAATAGAC ACCAAGATTC      7040
AGAGGACTTC                                                            7050
```

*FIGURE 2C*

```
GGATGACATT GGAACCTCAA TACAGTCAGG AATAAATACA AGACTTCTCA CAATTCAGAG  7110
TCATGTTCAA AACTATATCC CACTATCATT AACACAACAA ATGTCAGATC TCAGAAAATT  7170
TATCAATGAT CTAACAAATA AAAGAGAACA TCAAGAAGTG CCAATACAGA GAATGACTCA  7230
TGATAGAGGT ATAGAACCCC TAAATCCAAA CAAGTTCTGG AGGTGTACAT CTGGTAACCC  7290
ATCTCTAACA AGTAGTCCTA AGATAAGGTT AATACCAGGA CCAGGTTTAT TAGCAACATC  7350
TACTACAGTA AATGGCTGTA TTAGAATTCC ATCGTTAGTA ATCAATCATC TAATCTATGC  7410
TTACACCTCT AATCTTATTA CCCAGGGCTG TCAAGATATA GGGAAATCTT ACCAAGTACT  7470
ACAAATAGGG ATAATTACTA TAAATTCGGA CCTAGTACCT GATTTAAACC CCAGAGTCAC  7530
ACATACATTT AATATTGATG ATAATAGAAG ATCTTGCTCT CTGGCACTAT TGAATACAGA  7590
TGTTTATCAG TTATGCTCAA CACCAAAAGT TGATGAAAGA TCCGATTATG CATCAACAGG  7650
TATTGAGGAT ATTGTACTTG ACATTGTCAC TAATAATGGA TTAATTATAA CAACAAGGTT  7710
TACAAATAAT AATATAACTT TTGATAAACC GTATGCAGCA TTGTATCCAT CAGTGGGACC  7770
AGGAATCTAT TATAAGGATA AAGTTATATT TCTCGGATAT GGAGGTCTAG AGCATGAAGA  7830
AAACGGAGAC GTAATATGTA ATACAACTGG TTGTCCTGGC AAAACACAGA GAGACTGTAA  7890
TCAGGCTTCT TATAGCCCAT GGTTCTCAAA TAGGAGAATG GTAAACTCTA TTATTGTTGT  7950
TGATAAAGGC ATAGATGCAA CTTTTAGCTT GAGGGTGTGG ACTATTCCAA TGAGCCAAAA  8010
TTATTGGGGA TCAGAAGGAA GATTACTTTT ATTAGGTGAC AGAATATACA TATATACTAG  8070
ATCCACAAGT TGGCACAGTA AATTACAGTT AGGGGTAATT GATATTTCTG ATTATACTAA  8130
TATAAGAATA AATTGGACTT GGCATAATGT ACTATCACGG CCAGGGAATG ATGAATGTCC  8190
ATGGGGTCAT TCATGCCCAG ACGGATGTAT AACAGGAGTT TACACTGATG CATATCCGCT  8250
AAACCCATCG GGGAGTGTTG TATCATCAGT AATTCTTGAT TCACAAAAGT CTAGAGAAAA  8310
CCCAATCATT ACTTACTCAA CAGCTACAAA TAGAATAAAT GAATTAGCTA TATATAACAG  8370
AACACTTCCA GCTGCATATA CAACAACAAA TTGTATCACA CATTATGATA AAGGGTATTG  8430
TTTTCATATA GTAGAAATAA ATCACAGAAG TTTGAATACG TTCAACCTA  TGTTATTCAA  8490
AACAGAAGTT CCAAAAAACT GCAGCTAAAT TGATCATCGC ATATCGGATG CAAGATGACA  8550
TTAAAAGAGA CCACCAGACA GACAACACAG GAGACGATGC AAGATATAAA GAAATAATAA  8610
AAAACTTAGG AGAAAAGTGT GCAAGAAAAA TGGACACCGA GTCCCACAGC GGCACAACAT  8670
CTGACATTCT GTACCCTGAA TGTCACCTCA ATTCTCCTAT AGTTAAAGGA AAGATAGCAC  8730
AACTGCATAC AATAATGAGT TTGCCTCAGC CCTACGATAT GGATGATGAT TCAATACTGA  8790
TTATTACTAG ACAAAAAATT AAACTCAATA AATTAGATAA AAGACAACGG TCAATTAGGA  8850
AATTAAGATC AGTCTTAATG GAAAGAGTAA GTGATCTAGG TAAATATACC TTTATCAGAT  8910
ATCCAGAGAT GTCTAGTGAA ATGTTCCAAT TATGTATACC CGGAATTAAT AATAAAATAA  8970
ATGAATTGCT AAGTAAAGCA AGTAAAACAT ATAATCAAAT GACTGATGGA TTAAGAGATC  9030
TATGGGTTAC TATACTATCG AAGTTAGCAT CGAAAAATGA TGGAAGTAAT TATGATATCA  9090
ATGAAGATAT TAGCAATATA TCAAATGTTC ACATGACTTA TCAATCAGAC AAATGGTATA  9150
ATCCATTCAA GACATGGTTT ACTATTAAGT ATGACATGAG AAGATTACAA AAAGCCAAAA  9210
ATGAGATTAC ATTCAATAGG CATAAAGATT ATAATCTATT AGAAGACCAA AAGAATATAT  9270
TGCTGATACA TCCAGAACTC GTCTTAATAT TAGATAAACA AAATTACAAT GGGTATATAA  9330
TGACTCCTGA ATTGGTACTA ATGTATTGTG ATGTAGTTGA AGGGAGGTGG AATATAAGTT  9390
CATGTGCAAA                                                          9400
```

*FIGURE 2D*

```
ATTGGATCCT AAGTTACAAT CAATGTATTA TAAGGGTAAC AATTTATGGG AAATAATAGA    9460
TGGACTATTC TCGACCTTAG GAGAAAGAAC ATTTGACATA ATATCACTAT TAGAACCACT    9520
TGCATTATCG CTCATTCAAA CTTATGACCC GGTTAAACAG CTCAGGGGGG CTTTTTTAAA    9580
TCACGTGTTA TCAGAAATGG AATTAATATT TGCAGCTGAG TGTACAACAG AGGAAATACC    9640
TAATGTGGAT TATATAGATA AAATTTTAGA TGTGTTCAAA GAATCAACAA TAGATGAAAT    9700
AGCAGAAATT TTCTCTTTCT TCCGAACTTT TGGACACCCT CCATTAGAGG CGAGTATAGC    9760
AGCAGAGAAA GTTAGAAAGT ATATGTATAC TGAGAAATGC TTGAAATTTG ATACTATCAA    9820
TAAATGTCAT GCTATTTTTT GTACAATAAT TATAAATGGA TATAGAGAAA GACATGGTGG    9880
TCAATGGCCT CCAGTTACAT TACCTGTCCA TGCACATGAA TTTATCATAA ATGCATACGG    9940
ATCAAATTCT GCCATATCAT ATGAGAATGC TGTAGATTAT TATAAGAGCT TCATAGGAAT   10000
AAAATTTGAC AAGTTTATAG AGCCTCAATT GGATGAAGAC TTAACTATTT ATATGAAAGA   10060
TAAAGCATTA TCCCCAAAGA AATCAAACTG GGACACAGTC TATCCAGCTT CAAACCTGTT   10120
ATACCGCACT AATGTGTCTC ATGATTCACG AAGATTGGTT GAAGTATTTA TAGCAGATAG   10180
TAAATTTGAT CCCCACCAAG TATTAGATTA CGTAGAATCA GGATATTGGC TGGATGATCC   10240
TGAATTTAAT ATCTCATATA GTTAAAAGA GAAAGAAATA AAACAAGAAG GTAGACTTTT    10300
TGCAAAAATG ACATACAAGA TGAGGGCTAC ACAAGTATTA TCAGAAACAT TATTGGCGAA   10360
TAATATAGGG AAATTCTTCC AAGAGAATGG GATGGTTAAA GGAGAAATTG AATTACTCAA   10420
GAGACTAACA ACAATATCTA TGTCTGGAGT TCCGCGGTAT AATGAGGTAT ACAATAATTC   10480
AAAAAGTCAC ACAGAAGAAC TTCAAGCTTA TAATGCAATT AGCAGTTCCA ATTTATCTTC   10540
TAATCAGAAG TCAAAGAAGT TTGAATTTAA ATCTACAGAT ATATACAATG ATGGATACGA   10600
AACCGTAAGC TGCTTCTTAA CGACAGATCT TAAAAAATAT TGTTTAAATT GGAGGTATGA   10660
ATCAACAGCT TTATTCGGTG ATACTTGTAA TCAGATATTT GGGTTAAAGG AATTATTTAA   10720
TTGGCTGCAC CCTCGCCTTG AAAAGAGTAC AATATATGTT GGAGATCCTT ATTGCCCGCC   10780
ATCAGATATT GAACATTTAC CACTTGATGA CCATCCTGAT TCAGGATTTT ATGTTCATAA   10840
TCCTAAAGGA GGAATAGAAG GGTTTTGCCA AAAGTTATGG ACACTCATAT CTATCAGTGC   10900
AATACATTTA GCAGCTGTCA AAATCGGTGT AAGAGTTACT GCAATGGTTC AAGGGGATAA   10960
TCAAGCCATA GCTGTTACCA CAAGAGTACC TAATAATTAT GATTATAAAG TTAAGAAAGA   11020
GATTGTTTAT AAAGATGTGG TAAGATTTTT TGATTCCTTG AGAGAGGTGA TGGATGATCT   11080
GGGTCATGAG CTCAAACTAA ATGAAACTAT AATAAGTAGT AAAATGTTTA TATATAGCAA   11140
AAGGATATAC TATGACGGAA GAATCCTTCC TCAGGCATTA AAAGCATTGT CTAGATGTGT   11200
TTTTTGGTCT GAAACAATCA TAGATGAGAC AAGATCAGCA TCCTCAAATC TGGCTACATC   11260
GTTTGCAAAG GCCATTGAGA ATGGCTACTC ACCTGTATTG GGATATGTAT GCTCAATCTT   11320
CAAAAATATC CAACAGTTGT ATATAGCGCT TGGAATGAAT ATAAACCCAA CTATAACCCA   11380
AAATATTAAA GATCAATATT TCAGGAATAT TCATTGGATG CAATATGCCT CCTTAATCCC   11440
TGCTAGTGTC GGAGGATTTA ATTATATGGC CATGTCAAGG TGTTTTGTCA GAAACATTGG   11500
AGATCCTACA GTCGCTGCGT TAGCCGATAT TAAAAGATTT ATAAAAGCAA ATTTGTTAGA   11560
TCGAGGTGTC CTTTACAGAA TTATGAATCA AGAACCAGGC GAGTCTTCTT TTTTAGACTG   11620
GGCCTCAGAT CCCTATTCAT GTAACTTACC ACAAATCTCAA AATATAACCA CCATGATAAA   11680
GAATATAACT GCAAGAAATG TACTACAGGA CTCACCAAAC CCATTACTAT CTGGATTATT   11740
TACAAGTACA                                                          11750
```

FIGURE 2E

```
ATGATAGAAG AGGATGAGGA ATTAGCTGAG TTCCTAATGG ACAGGAGAAT AATCCTCCCA   11850
AGAGTTGCAC ATGACATTTT AGATAATTCT CTTACTGGAA TTAGGAATGC TATAGCTGGT   11870
ATGTTGGATA CAACAAAATC ACTAATTCGA GTAGGGATAA GCAGAGGAGG ATTAACCTAT   11930
AACTTATTAA GAAAGATAAG CAACTATGAT CTTGTACAAT ATGAGACACT TAGTAAAACT   11990
TTAAGACTAA TAGTCAGTGA CAAGATTAAG TATGAAGATA TGTGCTCAGT AGACCTAGCC   12050
ATATCATTAA GACAAAAAAT GTGGATGCAT TTATCAGGAG GAAGAATGAT AAATGGACTT   12110
GAAACTCCAG ATCCTTTAGA GTTACTGTCT GGAGTAATAA TAACAGGATC TGAACATTGT   12170
AGGATATGTT ATTCAACTGA AGGTGAAAGC CCATATACAT GGATGTATTT ACCAGGCAAT   12230
CTTAATATAG GATCAGCTGA GACAGGAATA GCATCATTAA GGGTCCCTTA CTTTGGATCA   12290
GTTACAGATG AGAGATCTGA AGCACAATTA GGGTATATCA AAAATCTAAG CAAACCAGCT   12350
AAGGCTGCTA TAAGAATAGC AATGATATAT ACTTGGGCAT TGGGAATGA CGAAATATCT   12410
TGGATGGAAG CATCACAGAT TGCACAAACA CGTGCAAACT TTACATTGGA TAGCTTAAAG   12470
ATTTTGACAC CAGTGACAAC ATCAACAAAT CTATCACACA GGTTAAAAGA TACTGCTACT   12530
CAGATGAAAT TTTCTAGTAC ATCACTTATT AGAGTAAGCA GGTTCATCAC AATATCTAAT   12590
GATAATATGT CTATTAAAGA AGCAAATGAA ACTAAAGATA CAAATCTTAT TTATCAACAG   12650
GTAATGTTAA CAGGATTAAG TGTATTTGAA TATCTATTTA GGTTAGAGGA GAGTACAGGA   12710
CATAACCCTA TGGTCATGCA TCTACATATA GAGGATGGAT GTTGTATAAA AGAGAGTTAC   12770
AATGATGAGC ATATCAATCC GGAGTCTACA TTAGAGTTAA TCAAATACCC TGAGAGTAAT   12830
GAATTTATAT ATGATAAGGA CCCTTTAAAG GATATAGATC TATCAAAATT AATGGTTATA   12890
AGAGATCATT CTTATACAAT TGACATGAAT TACTGGGATG ACACAGATAT TGTACATGCA   12950
ATATCAATAT GTACTGCAGT TACAATAGCA GATACAATGT CGCAGCTAGA TCGGGATAAT   13010
CTTAAGGAGC TGGTTGTGAT TGCAAATGAT GATGATATTA ACAGTCTGAT AACTGAATTT   13070
CTGACCCTAG ATATACTAGT GTTTCTCAAA ACATTTGGAG GGTTACTCGT GAATCAATTT   13130
GCATATACCC TTTATGGATT GAAAATAGAA GGAAGGGATC CCATTTGGGA TTATATAATG   13190
AGAACATTAA AAGACACCTC ACATTCAGTA CTTAAAGTAT TATCTAATGC ACTATCTCAT   13250
CCAAAAGTGT TTAAGAGATT TTGGGATTGT GGAGTTTTGA ATCCTATTTA TGGTCCTAAT   13310
ACTGCTAGTC AAGATCAAGT TAAGCTTGCT CTCTCGATTT GCGAGTACTC CTTGGATCTA   13370
TTTATGAGAG AATGGTTGAA TGGAGCATCA CTTGAGATCT ATATCTGTGA TAGTGACATG   13430
GAAATAGCAA ATGACAGAAG ACAAGCATTT CTCTCAAGAC ATCTTGCCTT TGTGTGTTGT   13490
TTAGCAGAGA TAGCATCTTT TGGACCAAAT TTATTAAATC TAACATATCT AGAGACTT    13550
GATGAATTAA AACAATACTT AGATCTGAAC ATCAAAGAAG ATCCTACTCT TAAATATGTG   13610
CAAGTATCAG GACTGTTAAT TAAATCATTC CCCTCAACTG TTACGTATGT AAGGAAAACT   13670
GCGATTAAGT ATCTGAGGAT TCGTGGTATT AATCCGCCTG AAACGATTGA AGATTGGGAT   13730
CCCATAGAAG ATGAGAATAT CTTAGACAAT ATTGTTAAAA CTGTAAATGA CAATTGCAGT   13790
GATAATCAAA AGAGAAATAA AAGTAGTTAT TTCTGGGAT TAGCTCTAAA GAATTATCAA   13850
GTCGTGAAAA TAAGATCCAT AACGAGTGAT TCTGAAGTTA ATGAAGCTTC GAATGTTACT   13910
ACACATGGAA TGACACTTCC TCAGGGAGGA AGTTATCTAT CACATCAGCT GAGGTTATTT   13970
GGAGTAAACA GTACAAGTTG TCTTAAAGCT CTTGAATTAT CACAAATCTT AATGAGGGAA   14030
GTTAAAAAAG ATAAAGATAG ACTCTTTTTA GGAGAAGGAG CAGGAGCTAT GTTAGCATGT   14090
TATGATGCTA                                                          14100
```

*FIGURE 2F*

```
CACTCGGTCC TGCAATAAAT TATTATAATT CTGGTTTAAA TATTACAGAT GTAATTGGTC    14160
AACGGGAATT AAAAATCTTC CCATCAGAAG TATCATTAGT AGGTAAAAAA CTAGGAAATG    14220
TAACACAGAT TCTTAATCGG GTGAGGGTGT TATTTAATGG GAATCCCAAT TCAACATGGA    14280
TAGGAAATAT GGAATGTGAG AGTTTAATAT GGAGTGAATT AAATGATAAG TCAATTGGTT    14340
TAGTACATTG TGACATGGAG GGAGCGATAG GCAAATCAGA AGAAACTGTT CTACATGAAC    14400
ATTATAGTAT TATTAGGATT ACATATTTAA TCGGGATGA TGATGTTGTC CTAGTATCAA     14460
AAATTATACC AACTATTACT CCGAATTGGT CTAAAATACT CTATCTATAC AAGTTGTATT    14520
GGAAGGATGT AAGTGTAGTG TCCCTTAAAA CATCCAATCC TGCCTCAACA GAGCTTTATT    14580
TAATTTCAAA AGATGCTTAC TGTACTGTAA TGGAACCCAG TAATCTTGTT TTATCAAAAC    14640
TTAAAAGGAT ATCATCAATA GAAGAAAATA ATCTATTAAA GTGGATAATC TTATCAAAAA    14700
GGAAGAATAA CGAGTGGTTA CAGCATGAAA TCAAAGAAGG AGAAAGGGAT TATGGGATAA    14760
TGAGGCCATA TCATACAGCA CTGCAAATTT TTGGATTCCA AATTAACTTA AATCACTTAG    14820
CTAGAGAATT TTTATCAACT CCTGATTTAA CCAACATTAA TAATATAATT CAAAGTTTTA    14880
CAAGAACAAT TAAAGATGTT ATGTTCGAAT GGGTCAATAT CACTCATGAC AATAAAAGAC    14940
ATAAATTAGG AGGAAGATAT AATCTATTCC CGCTTAAAAA TAAGGGGAAA TTAAGATTAT    15000
TATCACGAAG ATTAGTACTA AGCTGGATAT CATTATCCTT ATCAACCAGA TTACTGACGG    15060
GCCGTTTTCC AGATGAAAAA TTTGAAAATA GGGCACAGAC CGGATATGTA TCATTGGCTG    15120
ATATTGATTT AGAATCCTTA AAGTTATTAT CAAGAAATAT TGTCAAAAAT TACAAAGAAC    15180
ACATAGGATT AATATCATAC TGGTTTTTGA CCAAAGAGGT CAAAATACTA ATGAAGCTTA    15240
TAGGAGGAGT CAAACTACTA GGAATTCCTA AACAGTACAA AGAGTTAGAG GATCGATCAT    15300
CTCAGGGTTA TGAATATGAT AATGAATTTG ATATTGATTA ATACATAAAA ACATAAAATA    15360
AAACACCTAT TCCTCACCCA TTCACTTCCA ACAAAATGAA AGTAAGAAA AACATGTAAT     15420
ATATATATAC CAAACAGAGT TTTTCTCTTG TTTGGT                             15456
```

FIGURE 2G

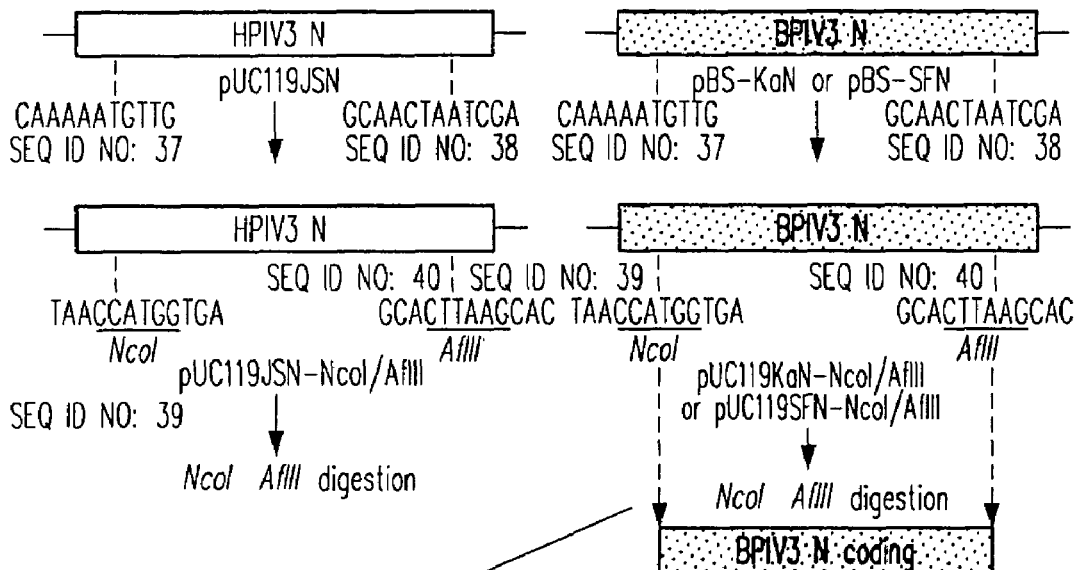
FIG. 3B
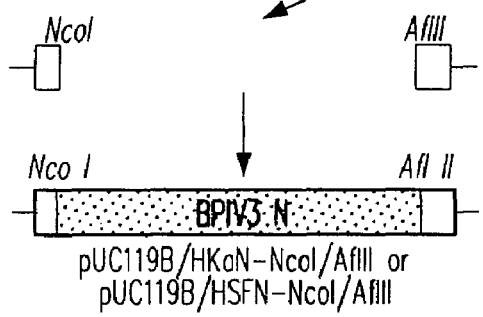
FIG. 3C
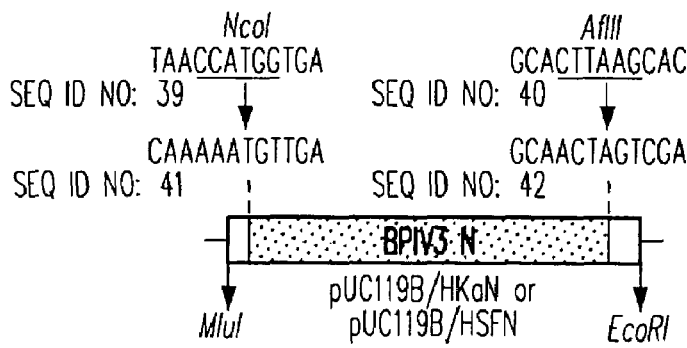

FIG. 5A

| | | |
|---|---|---|
| SEQ ID NO: 43 | rJS | GGAACTCTATAATTTCAAAA<u>ATG</u>TTGAGCCTATTTGATAC |
| SEQ ID NO: 44 | cKa | GGAACTCTATAATTTCAAAA<u>ATG</u>TTGAGTCTATTCGACAC |
| SEQ ID NO: 45 | cSF | GGAACTCTATAATTTCAAAA<u>ATG</u>TTGAGTCTATTCGACAC |
| SEQ ID NO: 46 | Ka | GAAATCCTAAGACTGTAATC<u>ATG</u>TTGAGTCTATTCGACAC |
| SEQ ID NO: 47 | SF | GAAATCCTAAGACTGTAATC<u>ATG</u>TTGAGTCTATTCGACAC |

FIG. 5B

| | | |
|---|---|---|
| SEQ ID NO: 48 | rJS | TTAACGCATTTGGAAGCAAC<u>TAA</u>TCGAATCAACATTTTAA |
| SEQ ID NO: 49 | cKa | TCAGTGCATTCGGAAGCAAC<u>TAG</u>TCGAATCAACATTTTAA |
| SEQ ID NO: 50 | cSF | TCAGTGCATTCGGAAGCAAC<u>TAG</u>TCGAATCAACATTTTAA |
| SEQ ID NO: 51 | Ka | TCAGTGCATTCGGAAGCAAC<u>TAG</u>TCACAAAGAGATGACCA |
| SEQ ID NO: 52 | SF | TCAGTGCATTCGGAAGCAAC<u>TAG</u>TCACAAAGAGATGACCA |

FIG. 13

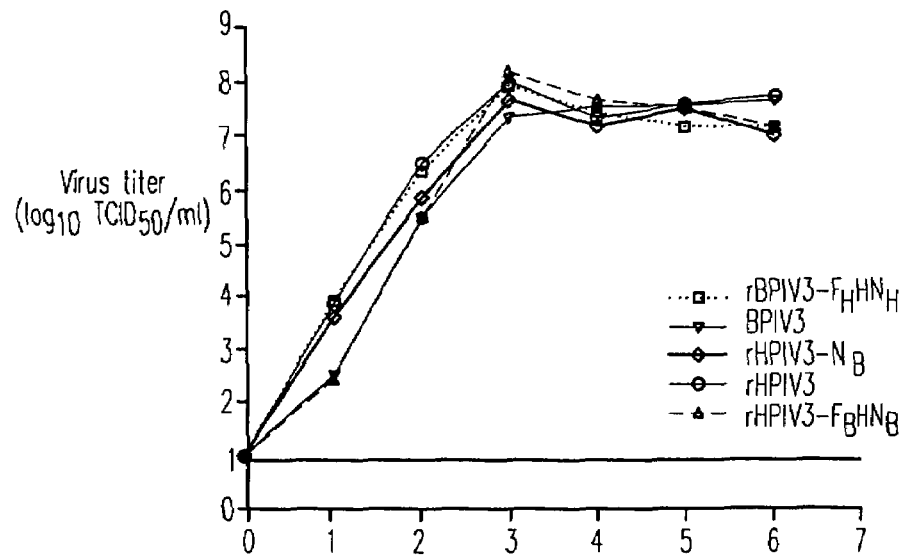

Confirmation of identity of potential BPIV3/HPIV3 chimeras by TaqI digestion
Figure 6A
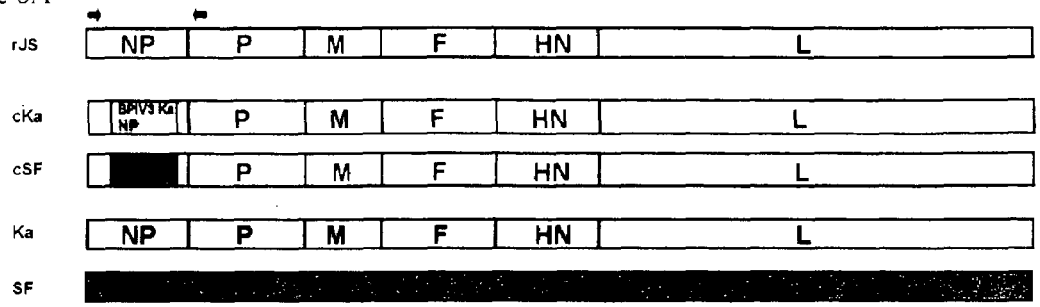
Figure 6B
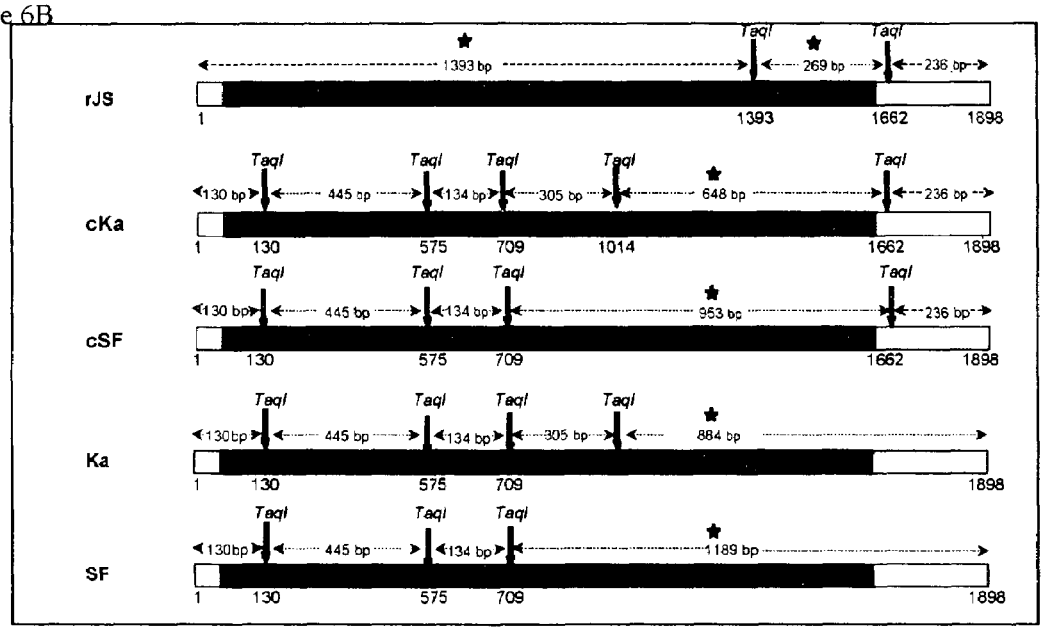
Figure 6C

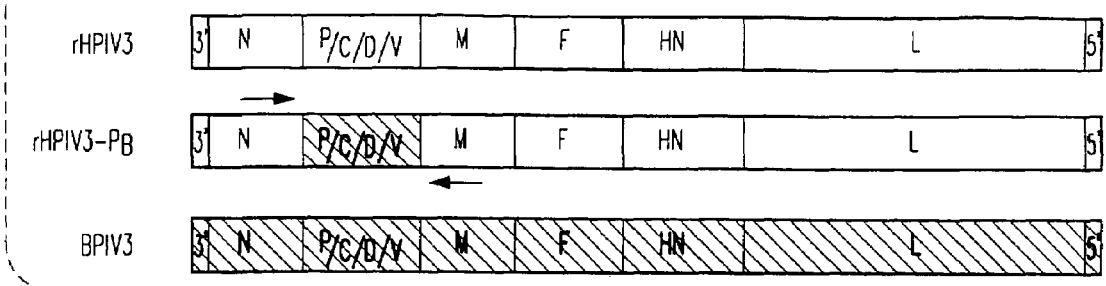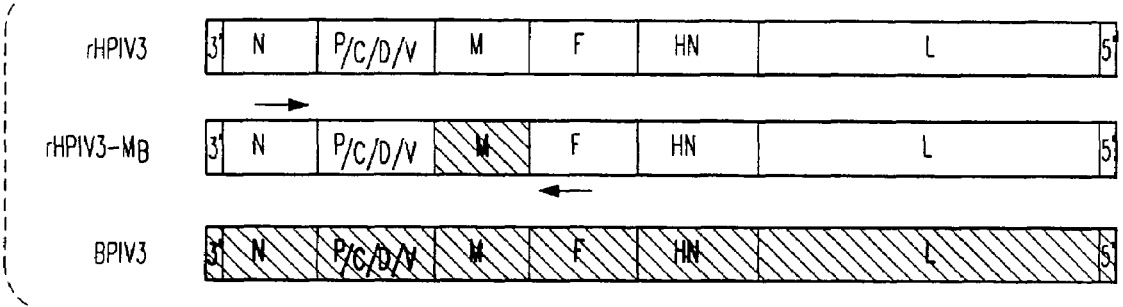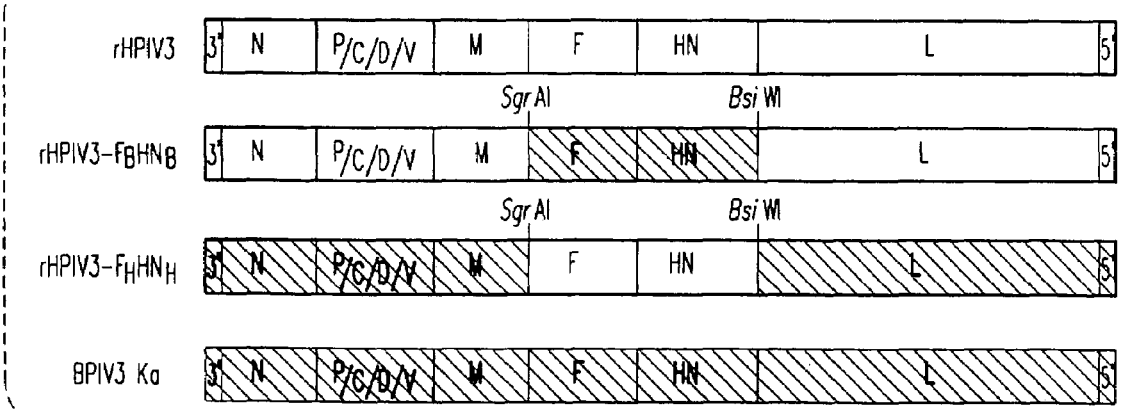

Figure 9A rHPIV3-P_B

Figure 9B

*StuI* rHPIV3-P_B

Figure 9C rPIV3-P_B : nts 1629-3784 (2156 bp), 726 bp + 1430 bp, P_B ORF, 2355(S)

rHPIV3 wt : 1629-3802, P ORF

BPIV3 : P_B ORF, 2355(S)

Figure 10A

Figure 10B rHPIV3-M_B

Figure 10C rHPIV3-M_B

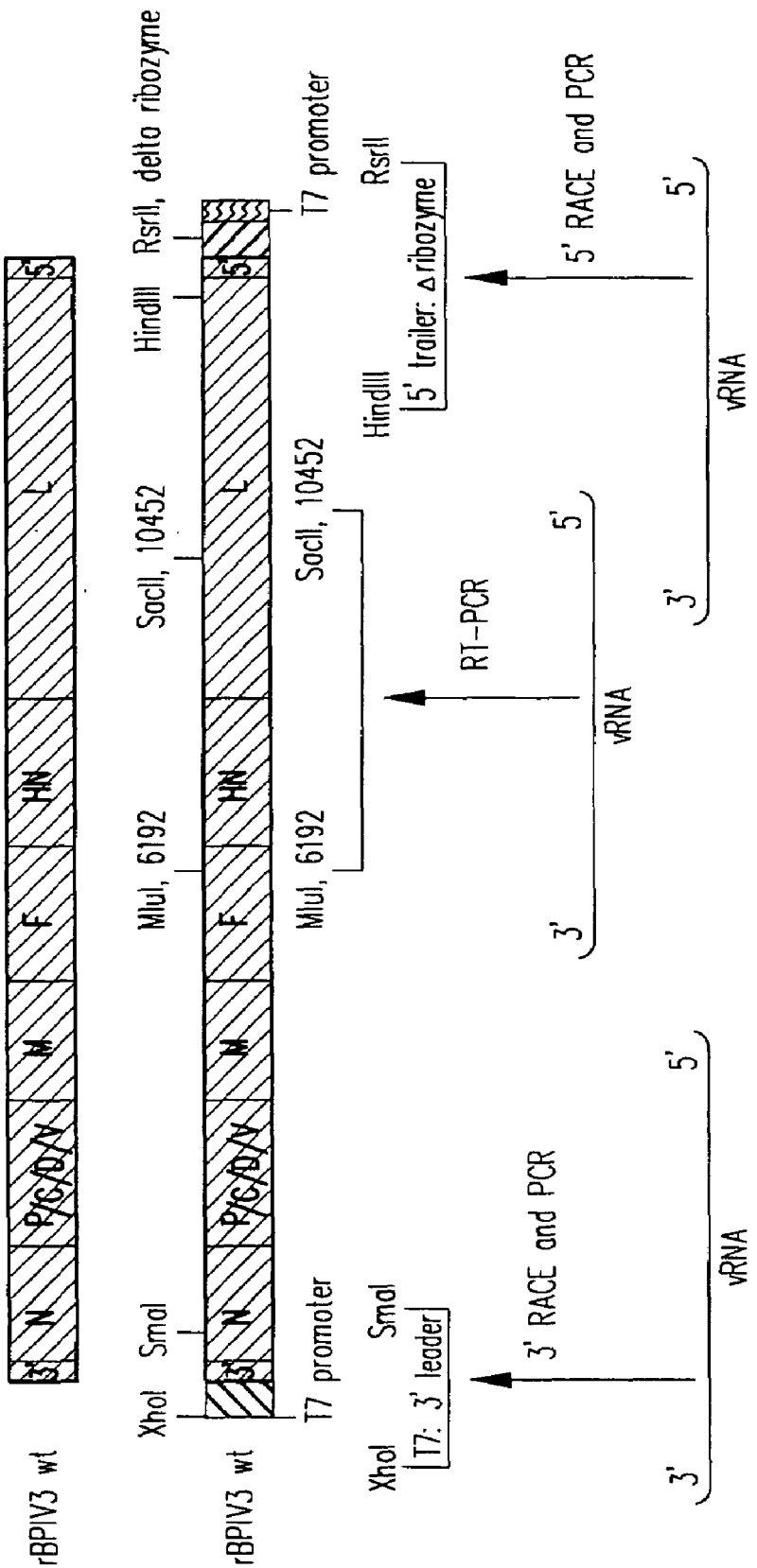
FIG. 11B Assembly of an antigenomic cDNA for BPIV3 Ka

FIG. 11C
Generation of full length cDNA clones encoding HPIV3/BPIV3 antigenic chimeric viruses

Virus titer (mean $\log_{10} TCID_{50}/ml$ ±S.E.) vs. Day after virus administation

- rHPIV3
- rHPIV3-$F_B HN_B$
- BPIV3 Ka

FIG. 14B

Virus titer (mean $\log_{10} TCID_{50}/ml$ ±S.E.) vs. Day after virus administation

- rHPIV3
- rHPIV3-$F_B HN_B$
- BPIV3 Ka

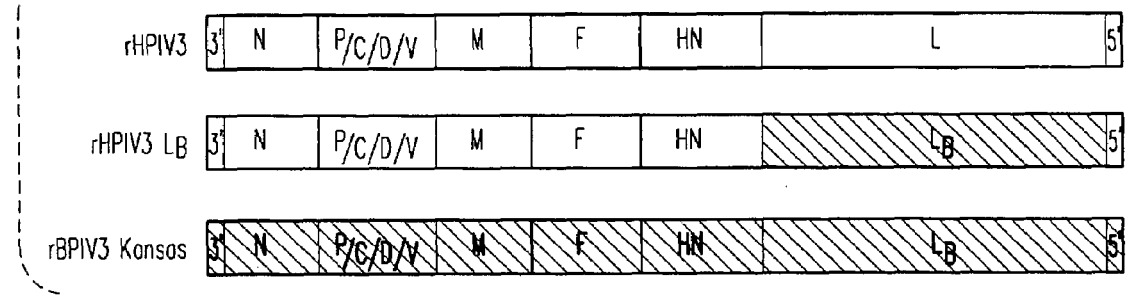

```
                       L START
SEQ ID NO: 61  rHPIV3 WT 8623  5' TAGGAGCAAAGCGTGCTCGGGAAATGGACACTGAATCTAACA 3' 8664
SEQ ID NO: 62  rHPIV3 LB 8623  5' TAGGAGCAAAGCGTGCTCGGGAAATGGACACCGAGTCCCACA 3' 8664
SEQ ID NO: 63  rBPIV3 wt 8617  5' TAGGAGAAAAGTGTGCAAGAAAAATGGACACCGAGTCCCACA 3' 8658

L STOP
SEQ ID NO: 64  rHPIV3 WT 15325 5' ATGATGAATTTGATATCGATTAAAACATAAATACAATGAAGA 3' 15366
SEQ ID NO: 65  rHPIV3 LB 15325 5' ATAATGAATTTGATATTGATTAATACGTACGTACAATGAAGA 3' 15366
SEQ ID NO: 66  rBPIV3 wt 15319 5' ATAATGAATTTGATATTGATTAATACATAAAAACATAAAATA 3' 15360
```

ATTENUATED HUMAN-BOVINE CHIMERIC PARAINFLUENZA VIRUS (PIV) VACCINES

CROSS-REFERENCES TO RELATED APPLICATIONS

The current application is a continuation of U.S. patent application Ser. No. 09/900,112, which is entitled to priority from U.S. Provisional Patent Application No. 60/215,809, filed Jul. 5, 2000 now abandoned. The current application also claims priority to, and is a continuation in part of, U.S. patent application Ser. No. 09/458,813, filed Dec. 10, 1999, and issued Jan. 1, 2008 as U.S. Pat. No. 7,314,631, which is a continuation in part of, U.S. patent application Ser. No. 09/083,793, issued Apr. 24, 2007 as U.S. Pat. No. 7,208,161, and which is entitled to priority from U.S. Provisional Patent Application No. 60/059,385, filed Sep. 19, 1997, and, U.S. Provisional Patent Application No. 60/047,575, filed May 23, 1997. The current application also claims priority to, and is a continuation in part of, U.S. patent application Ser. No. 09/459,069, filed Dec. 10, 1999, and issued Jul. 31, 2007 as U.S. Pat. No. 7,205,171, which is a continuation in part of, U.S. patent application Ser. No. 09/083,793, which is entitled to priority from U.S. Provisional Patent Application No. 60/059,385, filed Sep. 19, 1997, and U.S. Provisional Patent Application No. 60/047,575, filed May 23, 1997. The current application also claims priority to, and is a continuation in part of, U.S. patent application Ser. No. 09/586,479, filed Jun. 1, 2000 and issued Apr. 10, 2007 as U.S. Pat. No. 7,201,907 B1, which is a continuation in part of, U.S. patent application Ser. No. 09/083,793, which is entitled to priority from U.S. Provisional Patent Application No. 60/059,385, filed Sep. 19, 1997, and U.S. Provisional Patent Application No. 60/047,575, filed May 23, 1997, and U.S. Provisional Patent Application No. 60/143,134, filed Jul. 9, 1999.

BACKGROUND OF THE INVENTION

Human parainfluenza virus type 3 (HPIV3) is a common cause of serious lower respiratory tract infection in infants and children less than one year of age. It is second only to respiratory syncytial virus (RSV) as a leading cause of hospitalization for viral lower respiratory tract disease in this age group (Collins et al., in B. N. Fields Virology, p. 1205-1243, 3rd ed., vol. 1, Knipe et al., eds., Lippincott-Raven Publishers, Philadelphia, 1996; Crowe et al., Vaccine 13:415-421, 1995; Marx et al., J. Infect. Dis. 176:1423-1427, 1997, all incorporated herein by reference). Infections by this virus result in substantial morbidity in children less than 3 years of age. HPIV1 and HPIV2 are the principal etiologic agents of laryngotracheobronchitis (croup) and also can cause severe pneumonia and bronchiolitis (Collins et al., 1996, supra). In a long term study over a 20-year period, HPIV1, HPIV2, and HPIV3 were identified as etiologic agents for 6.0, 3.2, and 11.5%, respectively, of hospitalizations for respiratory tract disease accounting in total for 18% of the hospitalizations, and, for this reason, there is a need for an effective vaccine (Murphy et al., Virus Res. 11:1-15, 1988). The parainfluenza viruses have also been identified in a significant proportion of cases of virally-induced middle ear effusions in children with otitis media (Heikkinen et al., N. Engl. J. Med. 340:260-264, 1999, incorporated herein by reference). Thus, there is a need to produce a vaccine against these viruses that can prevent the serious lower respiratory tract disease and the otitis media that accompanies these HPIV infections. HPIV1, HPIV2, and HPIV3 are distinct serotypes that do not elicit significant cross-protective immunity.

Despite considerable efforts to develop effective vaccine therapies against HPIV, no approved vaccine agents have yet been achieved neither for any HPIV serotype, nor for ameliorating HPIV related illnesses. The most promising prospects to date are live attenuated vaccine viruses since these have been shown to be efficacious in non-human primates even in the presence of passively transferred antibodies, an experimental situation that simulates that present in the very young infant who possesses maternally acquired antibodies (Crowe et al., 1995, supra; and Durbin et al., J. Infect. Dis. 179:1345-1351, 1999a; each incorporated herein by reference). Two live attenuated PIV3 vaccine candidates, a temperature-sensitive (ts) derivative of the wild type PIV3 JS strain (designated PIV3cp45) and a bovine PIV3 (BPIV3) strain, are undergoing clinical evaluation (Karron et al., Pediatr. Infect. Dis. J. 15:650-654, 1996; Karron et al., 1995a, supra; Karron et al., 1995b, supra; each incorporated herein by reference). The BPIV3 vaccine candidate is attenuated, genetically stable and immunogenic in human infants and children. A second PIV3 vaccine candidate, JS cp45, is a cold-adapted mutant of the JS wildtype (wt) strain of HPIV3 (Karron et al., 1995b, supra; and Belshe et al., J. Med. Virol. 10:235-242, 1982a; each incorporated herein by reference). This live, attenuated, cold-passaged (cp) PIV3 vaccine candidate exhibits temperature-sensitive (ts), cold-adaptation (ca), and attenuation (att) phenotypes, which are stable after viral replication in vitro. The cp45 virus is protective against human PIV3 challenge in experimental animals and is attenuated, genetically stable, and immunogenic in seronegative human infants and children (Belshe et al., 1982a, supra; Belshe et al., Infect. Immun. 37:160-165, 1982b; Clements et al., J. Clin. Microbiol. 29:1175-1182, 1991; Crookshanks et al., J. Med. Virol. 13:243-249, 1984; Hall et al., Virus Res. 22:173-184, 1992; Karron et al., 1995b, supra; each incorporated herein by reference). Because these PIV3 candidate vaccine viruses are biologically derived there is no proven method for adjusting their level of attenuation as may be necessary for broad clinical application.

To facilitate development of PIV vaccine candidates, recombinant DNA technology has recently made it possible to recover infectious negative-stranded RNA viruses from cDNA (for reviews, see Conzelmann, J. Gen. Virol. 77:381-389, 1996; Palese et al., Proc. Natl. Acad. Sci. U.S.A. 93:11354-11358, 1996; each incorporated herein by reference). In this context, rescue of recombinant viruses has been reported for infectious respiratory syncytial virus (RSV), rabies virus (RaV), simian virus 5 (SV5), rinderpest virus, Newcastle disease virus (NDV), vesicular stomatitis virus (VSV), measles virus (MeV), mumps virus (MuV), and Sendai virus (SeV) from cDNA-encoded antigenomic RNA in the presence of essential viral proteins (see, e.g., Garcin et al., EMBO J. 14:6087-6094, 1995; Lawson et al., Proc. Natl. Acad. Sci. U.S.A. 92:4477-4481, 1995; Radecke et al., EMBO J. 14:5773-5784, 1995; Schnell et al., EMBO J. 13:4195-4203, 1994; Whelan et al., Proc. Natl. Acad. Sci. U.S.A. 92:8388-8392, 1995; Hoffman et al., J. Virol. 71:4272-4277, 1997; Kato et al., Genes to Cells 1:569-579, 1996, Roberts et al., Virology 247:1-6, 1998; Baron et al., J. Virol. 71:1265-1271, 1997; International Publication No. WO 97/06270; Collins et al., Proc. Natl. Acad. Sci. USA 92:11563-11567, 1995; U.S. Pat. No. 5,993,824 issued Nov. 30, 1999 (corresponding to published International Application No. WO 98/02530 and priority U.S. Provisional Application Nos. 60/047,634, filed May 23, 1997, 60/046,141, filed May 9, 1997, and 60/021,773, filed Jul. 15, 1996); U.S. patent application Ser. No. 09/291,894, filed on Apr. 13, 1999; U.S. Provisional Patent Application Ser. No. 60/129,006, filed Apr.

13, 1999; U.S. Provisional Patent Application Ser. No. 60/143,097, filed by Bucholz et al. on Jul. 9, 1999; Juhasz et al., *J. Virol.* 71:5814-5819, 1997; He et al., *Virology* 237:249-260, 1997; Peters et al., *J. Virol.* 73:5001-5009, 1999; Whitehead et al., *Virology* 247:232-239, 1998a; Whitehead et al., *J. Virol.* 72:4467-4471, 1998b; Jin et al., *Virology* 251:206-214, 1998; Bucholz et al., *J. Virol.* 73:251-259, 1999; and Whitehead et al., *J. Virol.* 73:3438-3442, 1999, and Clarke et al., *J. Virol.* 74:4831-4838, 2000; each incorporated herein by reference in its entirety for all purposes).

In more specific regard to the instant invention, a method for producing HPIV with a wt phenotype from cDNA was recently developed for recovery of infectious, recombinant HPIV3 JS strain (see, e.g., Durbin et al., *Virology* 235:323-332, 1997a; U.S. patent application Ser. No. 09/083,793, filed May 22, 1998, (corresponding to International Publication No. WO 98/53078 and priority U.S. Provisional Application Ser. No. 60/047,575, filed May 23, 1997, and Ser. No. 60/059,385, filed Sep. 19, 1997, each incorporated herein by reference). In addition, these disclosures allow for genetic manipulation of viral cDNA clones to determine the genetic basis of phenotypic changes in biological mutants, e.g., which mutations in the HPIV3 cp45 virus specify its ts, ca and att phenotypes, and which gene(s) or genome segment(s) of BPIV3 specify its attenuation phenotype. Additionally, these and related disclosures render it feasible to construct novel PIV vaccine candidates having a wide range of different mutations and to evaluate their level of attenuation, immunogenicity and phenotypic stability (see also, U.S. patent application Ser. No. 09/586,479 and its priority Provisional Patent Application Ser. No. 60/143,134, filed by Bailly et al. on Jul. 9, 1999; and U.S. patent application Ser. No. 09/350,821, filed by Durbin et al. on Jul. 9, 1999; each incorporated herein by reference).

Thus, infectious wild type recombinant PIV3 (r)PIV3, as well as a number of ts derivatives, have now been recovered from cDNA, and reverse genetics systems have been used to generate infectious virus bearing defined attenuating mutations and to study the genetic basis of attenuation of existing vaccine viruses. For example, the three amino acid substitutions found in the L gene of cp45, singularly or in combination, have been found to specify the ts and attenuation phenotypes. Additional ts and attenuating mutations are present in other regions of the PIV3 cp45. In addition a chimeric PIV1 vaccine candidate has been generated using the PIV3 cDNA rescue system by replacing the PIV3 HN and F open reading frames (ORFs) with those of PIV1 in a PIV3 full-length cDNA that contains the three attenuating mutations in L. The recombinant chimeric virus derived from this cDNA is designated rPIV3-1.cp45L (Skiadopoulos et al., *J. Virol.* 72:1762-1768, 1998; Tao et al., *J. Virol.* 72:2955-2961, 1998; Tao et al., *Vaccine* 17:1100-1108, 1999, incorporated herein by reference). rPIV3-1.cp45L was attenuated in hamsters and induced a high level of resistance to challenge with PIV1. A recombinant chimeric virus, designated rPIV3-1.cp45, has been produced that contains 12 of the 15 cp45 mutations, i.e., excluding the mutations that occur in HN and F, and is highly attenuated in the upper and lower respiratory tract of hamsters (Skiadopoulos et al., *Vaccine* 18:503-510, 1999a).

BPIV3, which is antigenically-related to HPIV3, offers an alternative approach to the development of a live attenuated virus vaccine for HPIV1, HPIV2, and HPIV3. The first vaccine used in humans, live vaccinia virus believed to be of bovine origin, was developed by Jenner almost 200 years ago for the control of smallpox. During the ensuing two centuries, vaccinia virus was successful in controlling this disease and played an essential role in the final eradication of smallpox. In this "Jennerian" approach to vaccine development, an antigenically-related animal virus is used as a vaccine for humans. Animal viruses that are well adapted to their natural host often do not replicate efficiently in humans and hence are attenuated. At present, there is a lack of a thorough understanding regarding the genetic basis for this form of host range restriction. Evolution of a virus in its mammalian or avian host results in significant divergence of nucleotide (nt) and amino acid sequences from that of the corresponding sequences in the related human virus. This divergent sequence, consisting of a large number of sequence differences, specifies the host range attenuation phenotype. Having an attenuation phenotype which is based on numerous sequence differences is a desirable property in a vaccine virus since it should contribute to the stability of the attenuation phenotype of the animal virus following its replication in humans.

The recently licensed quadrivalent rotavirus is an example of the Jennerian approach to vaccine development in which a nonhuman rotavirus strain, the rhesus rotavirus (RRV), was found to be attenuated in humans and protective against human serotype 3 to which it is antigenically highly related (Kapikian et al., *Adv. Exp. Med. Biol.* 327:59-69, 1992). Since there was a need for a multivalent vaccine that would induce resistance to each of the four major human rotavirus serotypes, the Jennerian approach was modified by constructing three reassortant viruses using conventional genetic techniques of gene reassortment in tissue culture. Each single gene reassortant virus contained 10 RRV genes plus a single human rotavirus gene that coded for the major neutralization antigen (VP7) of serotype 1, 2, or 4. The intent was to prepare single gene substitution RRV reassortants with the attenuation characteristics of this simian virus and the neutralization specificity of human rotavirus serotype 1, 2, or 4. The quadrivalent vaccine based on the host range restriction of the simian RRV in humans provided a high level of efficacy against human rotavirus infection in infants and young children (Perez-Schael et al., *N. Engl. J. Med.* 337:1181-1187, 1997). However, the vaccine virus retains mild reactogenicity in older seronegative infants lacking maternal antibody, therefore a second generation Jennerian vaccine, based on the UK strain of bovine rotavirus, is being developed to replace the RRV vaccine (Clements-Mann et al., *Vaccine* 17:2715-2725, 1999).

The Jennerian approach also is being explored to develop vaccines for parainfluenza type 1 virus and for hepatitis A virus which are attenuated and immunogenic in non-human primates (Emerson et al., *J. Infect. Dis.* 173:592-597, 1996; Hurwitz et al., *Vaccine* 15:533-540, 1997). The Jennerian approach was used for the development of a live attenuated vaccine for influenza A virus but it failed to produce a consistently attenuated vaccine for use in humans (Steinhoff et al., *J. Infect. Dis.* 163:1023-1028, 1991). As another example, reassortant viruses that contain two gene segments encoding the hemagglutinin and neuraminidase surface glycoproteins from a human influenza A virus and the six remaining gene segments from an avian influenza A virus were attenuated in humans (Clements et al., *J. Clin. Microbiol.* 27:219-222, 1989; Murphy et al., *J. Infect. Dis.* 152:225-229, 1985; and Snyder et al., *J. Clin. Microbiol.* 23:852-857, 1986). This indicated that one or more of the six gene segments of the avian virus attenuated the avian-human influenza A viruses for humans. The genetic determinants of this attenuation were mapped using reassortant viruses possessing a single gene segment from an attenuating avian influenza A virus and the remaining genes from a human strain. It was shown that the nonstructural (NS), polymerase (PB1, PB2) and M genes contributed to the attenuation phenotype of avian influenza A viruses in humans (Clements et al., *J. Clin. Microbiol.* 30:655-662, 1992).

In another study, the severe host range restriction of bovine respiratory syncytial virus (BRSV) for replication in chimpanzees was only slightly alleviated by replacement of the BRSV F and G glycoproteins with their HRSV counterparts. This indicated that F and G are involved in this host range restriction, but that one or more additional bovine RSV genes are also involved (Buchholz et al., *J. Virol.* 74:1187-1199, 2000). This illustrates that more than one gene can contribute in unpredictable ways to the host range restriction phenotype of a mammalian or avian virus in primates.

The instant invention provides a new basis for attenuating a wild type or mutant parental virus for use as a vaccine against HPIV, in which attenuation is based completely or in part on host range effects, while at least one or more of the major neutralization and protective antigenic determinant(s) of the chimeric virus is homologous to the virus against which the vaccine is directed. The HN and F proteins of BPIV3 are each approximately 80% related by amino acid sequence to their corresponding HPIV3 proteins (Suzu et al., *Nucleic Acids Res.* 15:2945-2958, 1987, incorporated herein by reference) and 25% related by antigenic analysis (Coelingh et al., *J. Virol.* 64:3833-3843, 1990; Coelingh et al., *J. Virol.* 60:90-96, 1986; van Wyke Coelingh et al., *J. Infect. Dis.* 157:655-662, 1988, each incorporated herein by reference). Previous studies indicated that two strains of BPIV3, the Kansas (Ka) strain and the Shipping Fever (SF) prototype strain, were attenuated for the upper and lower respiratory tract of rhesus monkeys, and one of these, the Ka strain, was attenuated in chimpanzees (van Wyke Coelingh et al., 1988, supra, incorporated herein by reference). Immunization of nonhuman primates with the Ka virus induced antibodies reactive with HPIV3 and induced resistance to the replication of the human virus in the upper and the lower respiratory tract of monkeys (id.). Subsequent evaluation of the Ka strain in humans indicated that the virus was satisfactorily attenuated for seronegative infants, and it retained the attenuation phenotype following replication in fully susceptible infants and children (Karron et al., 1996, supra; and Karron et al., 1995a, supra; each incorporated herein by reference). Its major advantages therefore were that it was satisfactorily attenuated for fully susceptible seronegative infants and children, and its attenuation phenotype was stable following replication in humans.

However, the level of serum hemagglutination-inhibiting antibodies reactive with HPIV3 induced in seronegative vaccinees who received $10^{5.0}$ tissue culture infectious dose$_{50}$ (TCID)$_{50}$ of the Ka strain of BPIV3 was 1:10.5, which was three-fold lower than similar vaccinees who received a live attenuated HPIV3 vaccine (Karron et al., 1995a, supra; and Karron et al., 1995b, supra; each incorporated herein by reference). This lower level of antibodies to the human virus induced by BPIV3 reflected in large part the antigenic divergence between HPIV3 and BPIV3 (Karron et al., 1996, supra; and Karron et al., 1995a, supra; each incorporated herein by reference). Studies to determine the efficacy of the Ka vaccine candidate against HPIV3 in humans have not been performed, but it is likely that this reduced level of antibodies reactive with HPIV3 will be reflected in a reduced level of protective efficacy.

Although it is clear that BPIV3 has host range genes that restrict replication in the respiratory tract of rhesus monkeys, chimpanzees and humans, it remains unknown which of the bovine proteins or noncoding sequences contribute to this host range restriction of replication. It is possible that any of the BPIV3 proteins or noncoding sequences may confer a host range phenotype. It is not possible to determine in advance which genes or genome segments will confer an attenuation phenotype. This can only be accomplished by systematic substitution of BPIV3 coding and non-coding sequences for their HPIV3 counterparts and by evaluation of the recovered HPIV3/BPIV3 chimeric viruses in seronegative rhesus monkeys or humans.

Despite the numerous advances toward development of effective vaccine agents against PIV serotypes 1, 2, and 3, there remains a clear need in the art for additional tools and methods to engineer safe and effective vaccines to alleviate the serious health problems attributable to PIV, particularly illnesses among infants and children due to infection by HPIV. Among the remaining challenges in this context is the need for additional tools to generate suitably attenuated, immunogenic and genetically stable vaccine candidates for use in diverse clinical settings. To facilitate these goals, existing methods for identifying and incorporating attenuating mutations into recombinant vaccine strains must be expanded. Furthermore, it is recognized that methods and compositions for designing vaccines against human PIV can be implemented as well to design novel vaccine candidates for veterinary use. Surprisingly, the present invention fulfills these needs and provides additional advantages as described herein below.

SUMMARY OF THE INVENTION

The present invention provides human-bovine chimeric parainfluenza viruses (PIVs) that are infectious and attenuated in humans and other mammals. In related aspects, the invention provides novel methods for designing and producing attenuated, human-bovine chimeric PIVs that are useful in various compositions to generate a desired immune response against PIV in a host susceptible to PIV infection. Included within these aspects of the invention are novel, isolated polynucleotide molecules and vectors incorporating such molecules that comprise a chimeric PIV genome or antigenome including a partial or complete human or bovine PIV "background" genome or antigenome combined or integrated with one or more heterologous gene(s) or genome segment(s) of a different PIV virus. Also provided within the invention are methods and compositions incorporating human-bovine chimeric PIV for prophylaxis and treatment of PIV infection.

The invention thus involves a method for developing live attenuated PIV vaccine candidates based on chimeras between HPIVs and BPIV3. Chimeras are constructed through a cDNA-based virus recovery system. Recombinant viruses made from cDNA replicate independently and are propagated in the same manner as if they were biologically-derived viruses. Chimeric human-bovine PIV of the invention are recombinantly engineered to incorporate nucleotide sequences from both human and bovine PIV strains to produce an infectious, chimeric virus or subviral particle. In this manner, candidate vaccine viruses are recombinantly engineered to elicit an immune response against PIV in a mammalian host susceptible to PIV infection, including humans and non-human primates. Human-bovine chimeric PIV according to the invention may elicit an immune response to a specific PIV, e.g., HPIV3, or a polyspecific response against multiple PIVs, e.g., HPIV1 and HPIV3. Additional chimeric viruses can be designed in accordance with the teachings herein which serve as vectors for antigens of non-PIV pathogens, for example respiratory syncytial virus (RSV) or measles virus.

Exemplary human-bovine chimeric PIV of the invention incorporate a chimeric PIV genome or antigenome comprising both human and bovine polynucleotide sequences, as well as a major nucleocapsid (N) protein, a nucleocapsid phosphoprotein (P), and a large polymerase protein (L). Additional PIV proteins may be included in various combinations to provide a range of infectious subviral particles, up to a complete viral particle or a viral particle containing supernumerary proteins, antigenic determinants or other additional components.

Chimeric human-bovine PIV of the invention include a partial or complete "background" PIV genome or antigenome derived from or patterned after a human or bovine PIV strain or subgroup virus combined with one or more heterologous gene(s) or genome segment(s) of a different PIV strain or subgroup virus to form the human-bovine chimeric PIV genome or antigenome. In preferred aspects of the invention, chimeric PIV incorporate a partial or complete human PIV background genome or antigenome combined with one or more heterologous gene(s) or genome segment(s) from a bovine PIV.

The partial or complete background genome or antigenome typically acts as a recipient backbone or vector into which are imported heterologous genes or genome segments of the counterpart, human or bovine PIV. Heterologous genes or genome segments from the counterpart, human or bovine PIV represent "donor" genes or polynucleotides that are combined with, or substituted within, the background genome or antigenome to yield a human-bovine chimeric PIV that exhibits novel phenotypic characteristics compared to one or both of the contributing PIVs. For example, addition or substitution of heterologous genes or genome segments within a selected recipient PIV strain may result in an increase or decrease in attenuation, growth changes, altered immunogenicity, or other desired phenotypic changes as compared with a corresponding phenotype(s) of the unmodified recipient and/or donor.

Genes and genome segments that may be selected for use as heterologous substitutions or additions within human-bovine chimeric PIV of the invention include genes or genome segments encoding a PIV N, P, C, D, V, M, F, HN and/or L protein(s) or portion(s) thereof In addition, genes and genome segments encoding non-PIV proteins, for example, an SH protein as found in mumps and SV5 viruses, may be incorporated within human-bovine PIV of the invention. Regulatory regions, such as the extragenic 3' leader or 5' trailer regions, and gene-start, gene-end, intergenic regions, or 3' or 5' non-coding regions, are also useful as heterologous substitutions or additions.

Preferred human-bovine chimeric PIV vaccine candidates of the invention bear one or more of the major antigenic determinants of HPIV3 in a background which is attenuated by the substitution or addition of one or more BPIV3 genes or genome segments. The major protective antigens of PIVs are their HN and F glycoproteins, although other proteins can also contribute to a protective immune response. In certain embodiments, the background genome or antigenome is an HPIV genome or antigenome, e.g., an HPIV3, HPIV2, or HPIV1 background genome or antigenome, to which is added or into which is substituted one or more BPIV gene(s) or genome segment(s), preferably from BPIV3. In one exemplary embodiment described below, an ORF of the N gene of a BPIV3 is substituted for that of an HPIV. Alternatively, the background genome or antigenome may be a BPIV genome or antigenome which is combined with one or more genes or genome segments encoding a HPIV3, HPIV2, or HPIV1 glycoprotein, glycoprotein domain or other antigenic determinant.

In accordance with the methods of the invention, any BPIV gene or genome segment, singly or in combination with one or more other BPIV genes, can be combined with HPIV sequences to give rise to a human-bovine chimeric PIV vaccine candidate. Any HPIV, including different strains of a particular HPIV serotype, e.g., HPIV3 will be a reasonable acceptor for attenuating BPIV gene(s). In general, the HPIV3 gene(s) or genome segment(s) selected for inclusion in a human-bovine chimeric PIV for use as a vaccine against human PIV will include one or more of the HPIV protective antigens such as the HN or F glycoproteins.

In preferred aspects of the invention, human-bovine chimeric PIVs bearing one or more bovine gene(s) or genome segment(s) exhibit a high degree of host range restriction, e.g., in the respiratory tract of mammalian models of human PIV infection such as non-human primates. The human PIV backbone is attenuated by the addition or substitution of one or more bovine gene(s) or genome segment(s), for example to a partial or complete human, e.g., HPIV3, PIV background genome or antigenome. In exemplary embodiments described herein below, the partial or complete HPIV background genome or antigenome is combined with one or more heterologous gene(s) or genome segment(s) of a N, P and/or M gene of a BPIV to form a human-bovine chimeric PIV genome or antigenome.

In related embodiments, the N gene of HPIV3, or a genome segment of N, is substituted by the BPIV3 N gene or a corresponding genome segment to yield a novel human-bovine chimeric PIV vaccine candidate. In other embodiments, one or more heterologous genes or genome segments encoding a partial or complete open reading frame (ORF) of HPIV P and/or M protein(s) is/are substituted by one or more BPIV3 counterpart gene(s) or genome segment(s). In more detailed aspects, the heterologous gene or genome segment encodes a BPIV3 M protein substituted for the counterpart M protein in a partial HPIV, e.g., HPIV3, background genome or antigenome. Exemplary recombinant viruses of this type described herein include rHPIV3-$M_B$. In other detailed aspects, the heterologous gene or genome segment encodes a BPIV3 P protein substituted for the counterpart M protein in a partial HPIV, e.g., HPIV3, background genome or antigenome. Exemplary recombinant viruses in this context described herein include rHPIV3-$P_B$. In yet additional detailed aspects, the heterologous gene or genome segment encodes a BPIV3 L protein substituted for the counterpart L protein in a partial HPIV, e.g., HPIV3, background genome or antigenome. Exemplary recombinant viruses in this context described herein include rHPIV3-$L_B$.

Preferably, the degree of host range restriction exhibited by human-bovine chimeric PIV vaccine candidates of the invention is comparable to the degree of host range restriction exhibited by the respective BPIV parent or "donor" strain. Preferably, the restriction should have a true host range phenotype, i.e., it should be specific to the host in question and should not restrict replication and vaccine preparation in vitro in a suitable cell line. In addition, human-bovine chimeric PIV bearing one or more bovine gene(s) or genome segment(s) elicit a high level of resistance in hosts susceptible to PIV infection. Thus, the invention provides a new basis for attenuating a live virus vaccine against PIV, one which is based on host range effects due to the introduction of one or more gene(s) or genome segment(s) from a heterologous PIV, e.g., between HPIV3 and BPIV3.

In related aspects of the invention, human-bovine chimeric PIV incorporates one or more heterologous gene(s) that encode an HPIV HN and/or F glycoprotein(s). Alternatively, the chimeric PIV may incorporate one or more genome segment(s) encoding an ectodomain (and alternatively a cytoplasmic domain and/or transmembrane domain), or immunogenic epitope of an HPIV HN and/or F glycoprotein(s). These immunogenic proteins, domains and epitopes are particularly useful within human-bovine chimeric PIV because they generate novel immune responses in an immunized host. In particular, the HN and F proteins, and immunogenic domains and epitopes therein, provide major protective antigens.

In certain embodiments of the invention, addition or substitution of one or more immunogenic gene(s) or genome segment(s) from a human PIV subgroup or strain to or within a bovine background, or recipient, genome or antigenome yields a recombinant, chimeric virus or subviral particle capable of generating an immune response directed against the human donor virus, including one or more specific human PIV subgroups or strains, while the bovine backbone confers an attenuated phenotype making the chimera a useful candidate for vaccine development. In one exemplary embodiment, one or more human PIV glycoprotein genes, e.g., HN and/or F, are added to or substituted within a partial or complete bovine genome or antigenome to yield an attenuated, infectious human-bovine chimera that elicits an anti-human PIV immune response in a susceptible host.

In alternate embodiments, human-bovine chimeric PIV additionally incorporate a gene or genome segment encoding an immunogenic protein, protein domain or epitope from multiple human PIV strains, for example two HN or F proteins or immunogenic portions thereof each from a different HPIV, e.g., HPIV1 or HPIV2. Alternatively, one glycoprotein or immunogenic determinant may be provided from a first HPIV, and a second glycoprotein or immunogenic determinant may be provided from a second HPIV by substitution without the addition of an extra glycoprotein- or determinant-encoding polynucleotide to the genome or antigenome. Substitution or addition of HPIV glycoproteins and antigenic determinants may also be achieved by construction of a genome or antigenome that encodes a chimeric glycoprotein in the recombinant virus or subviral particle, for example having an immunogenic epitope, antigenic region or complete ectodomain of a first HPIV fused to a cytoplasmic domain of a heterologous HPIV. For example, a heterologous genome segment encoding a glycoprotein ectodomain from a HPIV1 or HPIV2 HN or F glycoprotein may be joined with a genome segment encoding a corresponding HPIV3 HN or F glycoprotein cytoplasmic/endodomain in the background genome or antigenome.

In alternate embodiments a human-bovine chimeric PIV genome or antigenome may encode a substitute, extra, or chimeric glycoprotein or antigenic determinant thereof in the recombinant virus or subviral particle, to yield a viral recombinant having both human and bovine glycoproteins, glycoprotein domains, or immunogenic epitopes. For example, a heterologous genome segment encoding a glycoprotein ectodomain from a human PIV HN or F glycoprotein may be joined with a genome segment encoding a corresponding bovine HN or F glycoprotein cytoplasmic/endodomain in the background genome or antigenome.

Thus, according to the methods of the invention, human-bovine chimeric PIV may be constructed by substituting the heterologous gene or genome segment for a counterpart gene or genome segment in a partial PIV background genome or antigenome. Alternatively, the heterologous gene or genome segment may be added as a supernumerary gene or genome segment in combination with a complete (or partial if another gene or genome segment is deleted) PIV background genome or antigenome. For example, two human PIV HN or F genes or genome segments can be included, one each from HPIV2 and HPIV3.

Often, a heterologous gene or genome segment is added at or near an intergenic position within a partial or complete PIV background genome or antigenome. Alternatively, the gene or genome segment can be placed in other noncoding regions of the genome, for example, within the 5' or 3' noncoding regions or in other positions where noncoding nucleotides occur within the partial or complete genome or antigenome. In one aspect, noncoding regulatory regions contain cis-acting signals required for efficient replication, transcription, and translation, and therefore represent target sites for modification of these functions by introducing a heterologous gene or genome segment or other mutation as disclosed herein.

In more detailed aspects of the invention, attenuating mutations are introduced into cis-acting regulatory regions to yield, e.g., (1) a tissue specific attenuation (Gromeier et al., *J. Virol.* 73:958-964, 1999; Zimmermann et al., *J. Virol.* 71:4145-4149, 1997), (2) increased sensitivity to interferon (Zimmermann et al., 1997, supra), (3) temperature sensitivity (Whitehead et al., 1998a, supra), (4) a general restriction in level of replication (Men et al., *J. Virol.* 70:3930-3937, 1996; Muster et al., *Proc. Natl. Acad. Sci. USA* 88:5177-5181, 1991), and/or (5) host specific restriction of replication (Cahour et al., *Virology* 207:68-76, 1995). These attenuating mutations can be achieved in various ways to produce an attenuated human-bovine chimeric PIV of the invention, for example by point mutations, swaps of sequences between related viruses, or single or multiple nucleotide deletions.

In yet additional alternative methods provided herein, a heterologous gene or genome segment may be added or substituted at a position corresponding to a wild-type gene order position of a counterpart gene or genome segment within the partial or complete PIV background genome or antigenome. In other embodiments, the heterologous gene or genome segment is added or substituted at a position that is more promoter-proximal or promotor-distal compared to a wild-type gene order position of a counterpart gene or genome segment within the background genome or antigenome, to enhance or reduce expression, respectively, of the heterologous gene or genome segment.

In general aspects of the invention, bovine genes or genome segments may be added to or substituted within a human PIV background to form an attenuated, human-bovine chimeric PIV. Alternatively, the chimera may be comprised of one or more human gene(s) or genome segment(s) added to or substituted within a bovine PIV background to form an attenuated PIV vaccine candidate. In this context, a chimeric PIV genome or antigenome is formed of a partial or complete bovine PIV background genome or antigenome combined with a heterologous gene or genome segment from a human PIV. In preferred aspects, one or more bovine PIV gene(s) or genome segment(s) is substituted for a counterpart gene(s) or genome segment(s) within a human PIV background genome or antigenome. In alternate embodiments, one or more human PIV glycoprotein genes, e.g., HN and/or F or a genome segment encoding a cytoplasmic domain, transmembrane domain, ectodomain or immunogenic epitope of a human PIV glycoprotein gene is substituted for a counterpart gene or genome segment within the bovine PIV background genome or antigenome. For example, both human PIV glycoprotein genes HN and F may be substituted to replace counterpart HN and F glycoprotein genes in a bovine PIV background genome or antigenome.

In a parallel fashion, the chimeric human-bovine PIV of the invention can be readily designed as "vectors" to incorporate antigenic determinants from different pathogens, including more than one PIV strain or group (e.g., both human PIV3 and human PIV1), respiratory syncytial virus (RSV), measles and other pathogens (see, e.g., U.S. Provisional Patent Application Ser. No. 60/170,195, filed Dec. 10, 1999 by Murphy et al., incorporated herein by reference).

In more detailed aspects of the invention, human-bovine chimeric PIV are comprised of a partial or complete BPIV background genome or antigenome combined with one or more heterologous gene(s) or genome segment(s) from a human PIV. Within these aspects, one or more of the HPIV glycoprotein genes HN and F, or one or more genome segments encoding a cytoplasmic domain, transmembrane domain, ectodomain or immunogenic epitope of the HN and/or F genes, may be added to a BPIV background genome or antigenome or substituted for one or more counterpart genes or genome segments within the BPIV background genome or antigenome to yield the chimeric construct. Often, both HPIV glycoprotein genes HN and F will be substituted to replace counterpart HN and F glycoprotein genes in the BPIV background genome or antigenome, as exemplified by the recombinant chimeric virus rBPIV3-FH$_H$N$_H$ described in related U.S. patent application Ser. No. 09/586,479, filed Jun. 1, 2000 (incorporated herein by reference).

In combination with the host range phenotypic effects provided in the human-bovine chimeric PIV of the invention, it is often desirable to adjust the attenuation phenotype by introducing additional mutations that increase or decrease attenuation of the chimeric virus. Thus, in additional aspects of the invention, attenuated, human-bovine chimeric PIV are produced in which the chimeric genome or antigenome is further modified by introducing one or more attenuating mutations specifying an attenuating phenotype in the resultant virus or subviral particle. These can include mutations, for example, in RNA regulatory sequences or in encoded proteins. These attenuating mutations may be generated de novo and tested for attenuating effects according to a rational design mutagenesis strategy. Alternatively, the attenuating mutations may be identified in existing biologically derived mutant PIV and thereafter incorporated into a human-bovine chimeric PIV of the invention.

Introduction of attenuating and other desired phenotype-specifying mutations into chimeric bovine-human PIV of the invention may be achieved by transferring a heterologous gene or genome segment, e.g., a gene encoding an L protein or portion thereof, into a bovine or human PIV background genome or antigenome. Alternatively, the mutation may be present in the selected background genome or antigenome, and the introduced heterologous gene or genome segment may bear no mutations or may bear one or more different mutations. Typically, the human bovine background or "recipient" genome or antigenome is modified at one or more sites corresponding to a site of mutation in a heterologous virus (e.g., a heterologous bovine or human PIV or a non-PIV negative stranded RNA virus) to contain or encode the same or a conservatively related mutation (e.g., a conservative amino acid substitution) as that identified in the donor virus (see, PCT/US00/09695 filed Apr. 12, 2000 and its priority U.S. Provisional Patent Application Ser. No. 60/129,006, filed Apr. 13, 1999, incorporated herein by reference). In one exemplary embodiment, a bovine background or "recipient" genome or antigenome is modified at one or more sites corresponding to a site of mutation in HPIV3 JS cp45, as enumerated below, to contain or encode the same or a conservatively related mutation as that identified in the cp45 "donor."

Preferred mutant PIV strains for identifying and incorporating attenuating mutations into bovine-human chimeric PIV of the invention include cold passaged (cp), cold adapted (ca), host range restricted (hr), small plaque (sp), and/or temperature sensitive (ts) mutants, for example the JS HPIV3 cp45 mutant strain. In exemplary embodiments, one or more attenuating mutations identical or conservative to a known mutation in cp45 occur in the polymerase L protein, e.g., at a position corresponding to Tyr$_{942}$, Leu$_{992}$, or Thr$_{1558}$ of JS wild type HPIV3. Alternatively, attenuating mutations in the N protein may be selected and incorporated in a human-bovine chimeric PIV, for example which encode amino acid substitution(s) at a position corresponding to residues Val$_{96}$ or Ser$_{389}$ of JS. Alternative or additional mutations may encode amino acid substitution(s) in the C protein, e.g., at a position corresponding to Ile$_{96}$ of JS, and/or in the M protein at a position corresponding to Pro$_{199}$ (for example a Pro$_{199}$ to Thr mutation). Yet additional mutations for adjusting attenuation of a human-bovine chimeric PIV of the invention are found in the F protein, e.g., at a position corresponding to Ile$_{420}$ or Ala$_{450}$ of JS, and in the HN protein, e.g., at a position corresponding to residue Val$_{384}$ of JS.

Attenuating mutations from biologically derived PIV mutants for incorporation into human-bovine chimeric PIV of the invention also include mutations in noncoding portions of the PIV genome or antigenome, for example in a 3' leader sequence. Exemplary mutations in this context may be engineered at a position in the 3' leader of a recombinant virus at a position corresponding to nucleotide 23, 24, 28, or 45 of JS. Yet additional exemplary mutations may be engineered in the N gene start sequence, for example by changing one or more nucleotides in the N gene start sequence, e.g., at a position corresponding to nucleotide 62 of JS.

From JS cp45 and other biologically derived PIV mutants, a large "menu" of attenuating mutations is provided, each of which mutations can be combined with any other mutation(s) for adjusting the level of attenuation in a recombinant PIV bearing a genome or antigenome that is a chimera of human and bovine gene(s) or genome segment(s). For example, mutations within recombinant PIV of the invention include one or more, and preferably two or more, mutations of JS cp45. Desired human-bovine chimeric PIV of the invention selected for vaccine use often have at least two and sometimes three or more attenuating mutations to achieve a satisfactory level of attenuation for broad clinical use. Preferably, recombinant human-bovine chimeric PIV incorporate one or more attenuating mutation(s) stabilized by multiple nucleotide substitutions in a codon specifying the mutation.

Additional mutations which can be adopted or transferred to human-bovine chimeric PIV of the invention may be identified in non-PIV nonsegmented negative stranded RNA viruses and incorporated in PIV mutants of the invention. This is readily accomplished by mapping the mutation identified in a heterologous negative stranded RNA virus to a corresponding, homologous site in a recipient PIV genome or antigenome and mutating the existing sequence in the recipient to the mutant genotype (either by an identical or conservative mutation), as described in PCT/US00/09695 filed Apr. 12, 2000 and its priority U.S. Provisional Patent Application Ser. No. 60/129,006, filed Apr. 13, 1999, incorporated herein by reference.

In addition to recombinant human-bovine chimeric PIV, the invention provides related cDNA clones, vectors and particles, each of which incorporate HPIV and BPIV sequences and, optionally, one or more of the additional, phenotype-specific mutations set forth herein. These are introduced in selected combinations, e.g., into an isolated polynucleotide which is a recombinant cDNA genome or antigenome, to produce a suitably attenuated, infectious virus or subviral particle upon expression, according to the methods described herein. This process, coupled with routine phenotypic evaluation, provides human-bovine chimeric PIV having such desired characteristics as attenuation, temperature sensitivity, altered immunogenicity, cold-adaptation, small plaque size, host range restriction, genetic stability, etc. In particular, vaccine candidates are selected which are attenuated and yet are sufficiently immunogenic to elicit a protective immune response in the vaccinated mammalian host.

In yet additional aspects of the invention, human-bovine chimeric PIV, with or without additional mutations adopted, e.g., from a biologically derived attenuated mutant virus, are constructed to have additional nucleotide modification(s) to yield a desired phenotypic, structural, or functional change. Typically, the selected nucleotide modification will specify a phenotypic change, for example a change in growth characteristics, attenuation, temperature-sensitivity, cold-adaptation, plaque size, host range restriction, or immunogenicity. Structural changes in this context include introduction or ablation of restriction sites into PIV encoding cDNAs for ease of manipulation and identification.

In preferred embodiments, nucleotide changes within the genome or antigenome of a human-bovine chimeric PIV include modification of a viral gene by partial or complete deletion of the gene or reduction or ablation (knock-out) of its expression. These modifications can be introduced within the human or bovine background genome or antigenome, or may be introduced into the chimeric genome or antigenome by incorporation within the heterologous gene(s) or genome segment(s) added or substituted therein. Target genes for mutation in this context include any of the PIV genes, including the nucleocapsid protein N, phosphoprotein P, large polymerase subunit L, matrix protein M, hemagglutinin-neuraminidase protein HN, small hydrophobic SH protein, where applicable, fusion protein F, and the products of the C, D and V open reading frames (ORFs). To the extent that the recombinant virus remains viable and infectious, each of these proteins can be selectively deleted, substituted or rearranged, in whole or in part, alone or in combination with other desired modifications, to achieve novel deletion or knock out mutants. For example, one or more of the C, D, and/or V genes may be deleted in whole or in part, or its expression reduced or ablated (e.g., by introduction of a stop codon, by a mutation in an RNA editing site, by a mutation that alters the amino acid specified by an initiation codon, or by a frame shift mutation in the targeted ORF(s). In one embodiment, a mutation can be made in the editing site that prevents editing and ablates expression of proteins whose mRNA is generated by RNA editing (Kato et al., *EMBO J.* 16:578-587, 1997a and Schneider et al., *Virology* 227:314-322, 1997, each incorporated herein by reference). Alternatively, one or more of the C, D, and/or V ORF(s) can be deleted in whole or in part to alter the phenotype of the resultant recombinant clone to improve growth, attenuation, immunogenicity or other desired phenotypic characteristics (see, U.S. patent application Ser. No. 09/350,821, filed by Durbin et al. on Jul. 9, 1999, incorporated herein by reference).

Alternative nucleotide modifications in human-bovine chimeric PIV of the invention include a deletion, insertion, addition or rearrangement of a cis-acting regulatory sequence for a selected gene in the recombinant genome or antigenome. As with other such modifications described herein, these modifications can be introduced within the human or bovine background genome or antigenome, or may be introduced into the chimeric genome or antigenome by incorporation within the heterologous gene(s) or genome segment(s) added or substituted therein. In one example, a cis-acting regulatory sequence of one PIV gene is changed to correspond to a heterologous regulatory sequence, which may be a counterpart cis-acting regulatory sequence of the same gene in a different PIV, or a cis-acting regulatory sequence of a different PIV gene. For example, a gene end signal may be modified by conversion or substitution to a gene end signal of a different gene in the same PIV strain. In other embodiments, the nucleotide modification may comprise an insertion, deletion, substitution, or rearrangement of a translational start site within the recombinant genome or antigenome, e.g., to ablate an alternative translational start site for a selected form of a protein.

In addition, a variety of other genetic alterations can be produced in a human-bovine chimeric PIV genome or antigenome, alone or together with one or more attenuating mutations adopted from a biologically derived mutant PIV. For example, genes or genome segments from non-PIV sources may be inserted in whole or in part. Alternatively, the order of genes can be changed, or a PIV genome promoter replaced with its antigenome counterpart. Different or additional modifications in the recombinant genome or antigenome can be made to facilitate manipulations, such as the insertion of unique restriction sites in various intergenic or non-coding regions or elsewhere. Nontranslated gene sequences can be removed to increase capacity for inserting foreign sequences.

In yet additional aspects, polynucleotide molecules or vectors encoding the human-bovine chimeric PIV genome or antigenome can be modified to encode non-PIV sequences, e.g., a cytokine, a T-helper epitope, a restriction site marker, or a protein or immunogenic epitope of a microbial pathogen (e.g., virus, bacterium, parasite, or fungus) capable of eliciting a protective immune response in an intended host. In one such embodiment, human-bovine chimeric PIV are constructed that incorporate a gene or genome segment from a respiratory syncytial virus (RSV), for example a gene encoding an antigenic protein (e.g., an F or G protein), immunogenic domain or epitope of RSV.

In related aspects of the invention, compositions (e.g., isolated polynucleotides and vectors incorporating a PIV-encoding cDNA) and methods are provided for producing an isolated infectious human-bovine chimeric PIV. Included within these aspects of the invention are novel, isolated polynucleotide molecules and vectors incorporating such molecules that comprise a human-bovine chimeric PIV genome or antigenome. Also provided is the same or different expression vector comprising one or more isolated polynucleotide molecules encoding N, P, and L proteins. These proteins also can be expressed directly from the genome or antigenome cDNA. The vector(s) is/are preferably expressed or coexpressed in a cell or cell-free lysate, thereby producing an infectious human-bovine chimeric PIV viral particle or subviral particle.

The above methods and compositions for producing human-bovine chimeric PIV yield infectious viral or subviral particles, or derivatives thereof. A recombinant infectious virus is comparable to the authentic PIV virus particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, and L proteins is an example of a subviral particle which can initiate an infection if introduced into the cytoplasm of cells. Subviral particles provided within the invention include viral particles which lack one or more protein(s), protein segment(s), or other viral component(s) not essential for infectivity.

In other embodiments the invention provides a cell or cell-free lysate containing an expression vector which comprises an isolated polynucleotide molecule comprising a human-bovine chimeric PIV genome or antigenome as described above, and an expression vector (the same or different vector) which comprises one or more isolated polynucleotide molecules encoding the N, P, and L proteins of PIV. One or more of these proteins also can be expressed from the genome or antigenome cDNA. Upon expression the genome or antigenome and N, P and L combine to produce an infectious human-bovine chimeric PIV virus or subviral particle.

The human-bovine chimeric PIVs of the invention are useful in various compositions to generate a desired immune response against PIV in a host susceptible to PIV infection. Human-bovine chimeric PIV recombinants are capable of eliciting a protective immune response in an infected mammalian host, yet are sufficiently attenuated so as not to cause unacceptable symptoms of severe respiratory disease in the immunized host. In addition, the human-bovine chimeric PIV recombinants should replicate with sufficient efficiency in vitro to make vaccine preparation feasible. The attenuated virus or subviral particle may be present in a cell culture supernatant, isolated from the culture, or partially or completely purified. The virus may also be lyophilized, and can be combined with a variety of other components for storage or delivery to a host, as desired.

The invention further provides novel vaccines comprising a physiologically acceptable carrier and/or adjuvant and an isolated attenuated human-bovine chimeric PIV virus or subviral particle. In preferred embodiments, the vaccine is comprised of a human-bovine chimeric PIV having at least one, and preferably two or more additional mutations or other nucleotide modifications as described above to achieve a suitable balance of attenuation and immunogenicity. The vaccine can be formulated in a dose of $10^3$ to $10^7$ PFU of attenuated virus. The vaccine may comprise attenuated human-bovine chimeric PIV that elicits an immune response against a single PIV strain or against multiple PIV strains or groups. In this regard, human-bovine chimeric PIV can be combined in vaccine formulations with other PIV vaccine strains, or with other viral vaccine viruses such as RSV.

In related aspects, the invention provides a method for stimulating the immune system of an individual to elicit an immune response against PIV in a mammalian subject. The method comprises administering a formulation of an immunologically sufficient amount a human-bovine chimeric PIV in a physiologically acceptable carrier and/or adjuvant. In one embodiment, the immunogenic composition is a vaccine comprised of a human-bovine chimeric PIV having at least one, and preferably two or more attenuating mutations or other nucleotide modifications specifying a desired phenotype as described above. The vaccine can be formulated in a dose of $10^3$ to $10^7$ PFU of attenuated virus. The vaccine may comprise attenuated human-bovine chimeric PIV virus that elicits an immune response against a single PIV, against multiple PIVs, e.g., HPIV1 and HPIV3, or against one or more PIV(s) and a non-PIV pathogen such as RSV. In this context, human-bovine chimeric PIV can elicit a monospecific immune response or a polyspecific immune response against multiple PIVs, or against one or more PIV(s) and a non-PIV pathogen such as RSV. Alternatively, human-bovine chimeric PIV having different immunogenic characteristics can be combined in a vaccine mixture or administered separately in a coordinated treatment protocol to elicit more effective protection against one PIV, against multiple PIVs, or against one or more PIV(s) and a non-PIV pathogen such as RSV. Preferably the immunogenic composition is administered to the upper respiratory tract, e.g., by spray, droplet or aerosol.

BRIEF DESCRIPTION OF THE DRAWINGS

FIGS. 1A-1G set forth the complete nucleotide sequence of the bovine PIV3 Ka (SEQ ID NO: 35) strain.

FIGS. 2A-2G set forth the complete nucleotide sequence of the bovine PIV3 SF (SEQ ID NO: 36) strain.

FIG. 3 illustrates cloning of the N coding region of bovine PIV strains Ka or SF into HPIV3. In FIG. 3, panel A, (providing sequences 37-40) the BPIV3 N open reading frame (ORF) is replaced for its corresponding HPIV3 sequence in the full-length rJS antigenomic cDNA (Durbin et al., 1997a, supra). BPIV3 Ka and SF N genes were first amplified by RT-PCR using standard molecular biological techniques from virion RNA and subcloned as 1.9 kb fragments into pBluescript to give pBS-KaN or pBS-SFN, respectively. The HPIV3 rJS N gene was subcloned as a 1.9 kb MluI/EcoRI fragment into pUC 119 from a plasmid containing the 5' half of the rJS HPIV3 antigenome (Durbin et al., 1997a, supra; U.S. patent application Ser. No. 09/083,793, filed May 22, 1998, (corresponding to International Publication No. WO 98/53078 and priority U.S. Provisional Application Ser. No. 60/047,575, filed May 23, 1997, and Ser. No. 60/059,385, filed Sep. 19, 1997, each incorporated herein by reference) to give pUC119JSN. Each N gene was modified by site-directed mutagenesis to place an NcoI and AflIII site at the translational start and stop sites, respectively. The Ka and SF N genes are identical in the translational start and stop site regions and, therefore, identical mutagenesis reactions were performed on both BPIV3 N genes as depicted in FIG. 3, panel A. FIG. 3, panel B—Following AflIII/NcoI digestion, a 1.5 kb fragment from pBS-KaN or pBS-SFN representing the BPIV3 N coding region was introduced into the NcoI/AflIII window of the HPIV3 N subclone pUC119JSN-NcoI/AflIII as a replacement for its HPIV3 counterpart. FIG. 3, panel C—(provides sequences 39-42) Each chimeric subclone was then subjected to site-directed mutagenesis to restore the sequence present in HPIV3 rJS before the start codon or after the stop codon and BPIV3 coding sequence immediately after the start codon and before the stop codon. This yielded pUC119B/HKaN and pUC119B/HSFN, which were used to import the BPIV3 N gene into the HPIV3 cDNA clone as shown in FIG. 4.

In FIG. 4, panel A, the BPIV3 N ORF of Ka or SF flanked by HPIV3 sequence was subcloned as an MluI/EcoRI fragment from pUC119B/HKaN or pUC119B/HSFN and inserted into pLeft+2G (Durbin et al., 1997a, supra). The pLeft+2G plasmid contains the 5' half of the HPIV3 rJS antigenome from nt 1-7437 (genome sense) behind a T7 promoter. The location of two G residues that were inserted between T7 promoter and HPIV3 sequence to improve transcription is indicated by an asterisk. FIG. 4, panel B—An XhoI/NgoMI fragment of pRight (Durbin et al., 1997a, supra; U.S. patent application Ser. No. 09/083,793, filed May 22, 1998, (corresponding to International Publication No. WO 98/53078 and priority U.S. Provisional Application Ser. No. 60/047,575, filed May 23, 1997, and Ser. No. 60/059,385, filed Sep. 19, 1997, each incorporated herein by reference) containing the 3' end of the HPIV3 antigenome flanked by the hepatitis delta virus ribozyme and T7 terminator was cloned into the XhoI/NgoMI window of the modified pLeft plasmid resulting in plasmids pB/HPIV3KaN and pB/HPIV3SFN. Each of these chimeric constructs contains the complete positive sense sequence of the HPIV3 antigenomic RNA except for the N coding region which has been replaced by its BPIV3 Ka or SF counterpart.

FIG. 5 provides nucleotide sequences of HPIV3, BPIV3 and chimeric viruses of the invention around N start (panel A, providing sequences 43-47) and stop (panel B, providing sequences 48-52) codons. The position of the individual ORFs is described in the respective GenBank reports (#AF178654 for BPIV3 Ka, #AF178655 for BPIV3 SF and #Z11515) (each incorporated herein by reference). The sequences (positive-sense) flanking the translational start (panel A) and stop (panel B) codons (each underlined) in the N gene are shown for the parental recombinant HPIV3 JS (rJS), the parental biologically-derived BPIV3 Ka and SF viruses (Ka and SF), and the chimeric cKa and cSF viruses. Host-specific residues in the cKa and cSF virus sequences and their counterparts in rJS (before the start codon and after the stop codon) and SF or Ka (start codon through stop codon, inclusive) are in boldface type. Plaque-purified chimeric virus was amplified by RT-PCR from virion RNA and sequenced using the Taq Dye Deoxy Terminator Cycle kit (ABI, Foster City, Calif.). This confirmed that the predicted sequences were present in each chimeric virus.

FIG. 6 details the structure of the BPIV3/HPIV3 chimeric viruses of the invention, and their confirmation by TaqI digestion of RT-PCR products generated from virus RNA. In FIG. 6, panel A the genomes of the chimeric cKa and cSF viruses are shown schematically (not to scale) relative to that of HPIV3 and BPIV3 parent viruses. Ka- and SF-specific regions are indicated by light and dark shading respectively. Arrows above the rJS genome indicate the locations of primers used for RT-PCR amplification of chimeric and parent viruses for the purposes of diagnostic TaqI digestion. These primers were directed to regions conserved between HPIV3 and BPIV3 so that they could be used for the amplification of HPIV3, BPIV3 and chimeric BPIV3/HPIV3 viruses. In FIG. 6, panel B the expected sizes of TaqI digestion products for each virus are shown for a 1,898 bp PCR product containing the PIV3 N coding region and flanking sequence amplified from virion RNA using primers whose locations are shown in FIG. 6, panel A. This PCR product is illustrated at the top in FIG. 6, panel B, and the N ORF is indicated as a filled rectangle. TaqI fragments unique to each virus and which therefore serve in virus identification are indicated with an asterisk. FIG. 6, panel C provides TaqI profiles of PCR products containing the PIV3 N coding region of chimeric cKa (left) or cSF (right) are shown flanked by those of the HPIV3 and BPIV3 parent viruses. Unique TaqI fragments diagnostic of virus identity and corresponding to those identified in panel B are indicated with an asterisk. Calculated lengths (bp) of DNA gel bands are indicated.

FIG. 8, panel A provides a diagrammatic representation of the rHPIV3, rHPIV3-P$_B$, and BPIV3 genomes (not drawn to scale). The position of the BPIV3 P ORF (▩) and the PCR primers (→) used to generate an RT-PCR product spanning the P ORF are indicated relative to the rHPIV3-P$_B$ sequence.

FIG. 8, panel B provides a diagrammatic representation of the rHPIV3, rHPIV3-M$_B$, and BPIV3 genomes (not drawn to scale). The position of the BPIV3 M ORF (▩) and the PCR primers (→) used to generate an RT-PCR product spanning the M ORF are indicated relative to the rHPIV3-M$_B$ sequence.

FIG. 9, panel A presents an agarose gel electrophoresis of an RT-PCR product (2156 bp) of rHPIV3-P$_B$ (lane 1) generated with a set of HPIV3-specific primers flanking the P ORF, as indicated in FIG. 8, panel A. The absence of a PCR product of the appropriate size in the reaction lacking reverse transcriptase (−RT; lane 2) shows that viral RNA, not contaminating cDNA, served as a template. In lane 2 the unincorporated primers are evident (*). M, marker consisting of lambda phage DNA digested with HindIII and φX174 phage DNA digested with HaeIII. The position of the 2027 bp size marker is indicated. FIG. 9, panel B presents an agarose gel electrophoresis of products from a restriction enzyme digestion (StuI) of the 2156 bp rHPIV3-P$_B$ RT-PCR product from FIG. 9, panel A. Digestion of the 2156 bp fragment yields the expected (see FIG. 9, panel C) 726 bp and 1430 bp fragments demonstrating the presence of the BPIV3 P ORF in rHPIV3-P$_B$. M, marker consisting of lambda phage DNA digested with HindIII and φX174 phage DNA digested with HaeIII. The nucleotide length of several size markers are indicated in bp. FIG. 9, panel C provides a diagram (not to scale) of the indicated StuI(S) site in the RT-PCR product spanning the P ORF in rHPIV3-P$_B$ (top line), compared to the corresponding region in the genome of the rHPIV3 (middle line) and BPIV3 (bottom line) parents. The nucleotide positions of the primers and the StuI site, and the length of the resulting rHPIV3-P$_B$ digestion fragments are indicated. The position of the P ORF is shown as a rectangle (HPIV3 ▢; BPIV3 ▩).

FIG. 10, panel A presents an agarose gel electrophoresis of RT-PCR product (3445 bp) of rHPIV3-M$_B$ generated with a set HPIV3-specific primers amplifying the BPIV3 M ORF (lane 1) as indicated in FIG. 8, panel B. The absence of a PCR product of the appropriate size in the reaction lacking reverse transcriptase (−RT; lane 2) shows that viral RNA, not contaminating cDNA, served as a template. M, marker consisting of lambda phage DNA digested with HindIII and φX174 phage DNA digested with HaeIII. The nucleotide length of several size markers are indicated. FIG. 10, panel B presents an agarose gel electrophoresis of products from restriction enzyme digestions of the 3445 bp rHPIV3-M$_B$ RT-PCR product. Lane 1, the undigested 3445 bp RT-PCR product; lane 2, SpeI digestion products consisting of the expected 1825 bp and 1620 bp fragments; lane 3, EcoRV digestion products consisting of the expected 666 bp, 1396 bp, 221 bp, and 1162 bp fragments; lane 4, XbaI digestion products consisting of the expected 2354 bp, 441 bp and 650 bp fragments, demonstrating the presence of the BPIV3 M gene in rHPIV3-M$_B$. The presence of a SpeI site at nt position 3454 in rHPIV3-M$_B$ and the absence of a SpeI site at nt 1654 indicates that the RT-PCR product is indeed chimeric with the M ORF derived from BPIV3 and the flanking sequence of HPIV3 origin. A similar conclusion is supported by an examination of the EcoRV digestion. M, marker consisting of lambda phage DNA digested with HindIII and φX174 phage DNA digested with HaeIII. The nucleotide length of several size markers are indicated. FIG. 10, panel C provides diagrams (not to scale) of the indicated restriction sites in the RT-PCR product of the M ORF in rHPIV3-M$_B$ that was shown in FIG. 10, panels A and B. The first set of diagrams illustrates the SpeI (S) sites in the RT-PCR product of rHPIV3-M$_B$ (top) and the corresponding region in the genome of the rHPIV3 (middle) and BPIV3 (bottom) parents. The next set of diagrams shows the EcoRV (E) sites in the rHPIV3-M$_B$, rHPIV3, and BPIV3 segments.

The bottom set of diagrams shows the sites for the XbaI(X) sites. The nucleotide positions of the primers and restriction sites, and the length of the digestion products are indicated for rHPIV3-$M_B$. The position of the M ORF is shown as a rectangle (HPIV3 ▢; BPIV3 ▨).

FIG. 11A provides a schematic depiction of the genomes of chimeric rHPIV3-$F_BHN_B$ and rBPIV3-$F_HHN_H$ viruses, and of their parent viruses, rHPIV3 JS and BPIV3 Ka (not to scale). The F and HN genes were exchanged in a single restriction fragment between rHPIV3 and rBPIV3 using SgrAI and BsiWI sites that had been introduced in front of the M and HN gene end, respectively.

FIG. 11B depicts one of the steps in assembly of an antigenomic cDNA for BPIV3 Ka. A full length cDNA was constructed to encode the complete antigenomic sequence of BPIV3 Ka (GenBank accession #AF178654) with the exception of nt 21 and 23. The cDNA was assembled from subclones derived from reverse transcription (RT) of viral (v)RNA and polymerase chain reaction (PCR) amplification. Multiple subclones of the antigenome were sequenced, and only clones matching the consensus sequence of BPIV3 Ka (with the exception of nt 21 and nt 23, which differ from the published sequence of BPIV3 Ka, with the exception of nt 21 and 23, but appear to occur with similar frequence in the virus population) were used for assembly of the full length clone.

Figure 11C:
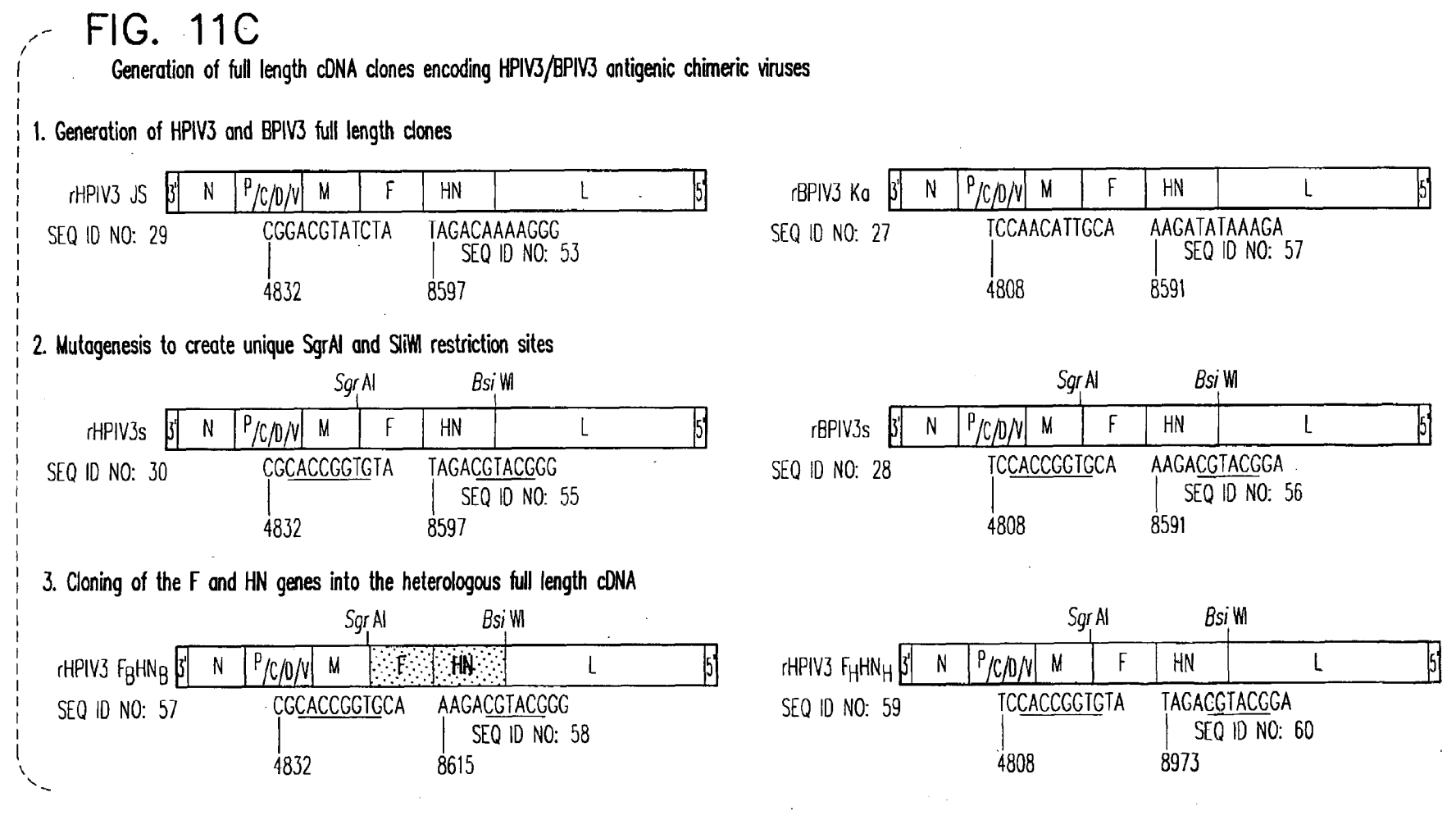

FIG. 11C (providing sequences 27-30 and 53-60) illustrates features of parental and chimeric bovine-human PIV genomes. The genomes of the chimeric rHPIV3 $F_BHN_B$ and rBPIV3 $F_H$k $HN_H$ viruses and those of their parent viruses rHPIV3 JS and BPIV3 Ka are shown schematically (not to scale). Panel 1: rPIV3JS was constructed as described elsewhere herein. Panel 2: Two unique restriction enzyme recognition sites, SgrAI and BsiWI, were introduced near the M and HN gene ends, respectively. The recombinant HPIV3 and BPIV3 viruses bearing these introduced restriction sites were designated rHPIV3s and rBPIV3s as indicated. Panel 3: Glycoprotein genes were exchanged between rHPIV3 JS and rBPIV3 Ka. The nucleotide sequence that was mutagenized is shown below each cDNA construct. The position of the first nucleotide of each sequence indicated. Restriction sites are underlined and nucleotides that differ between HPIV3 and BPIV3 and thus identify the origin of the gene inserts are depicted in bold print.

Figure 12:
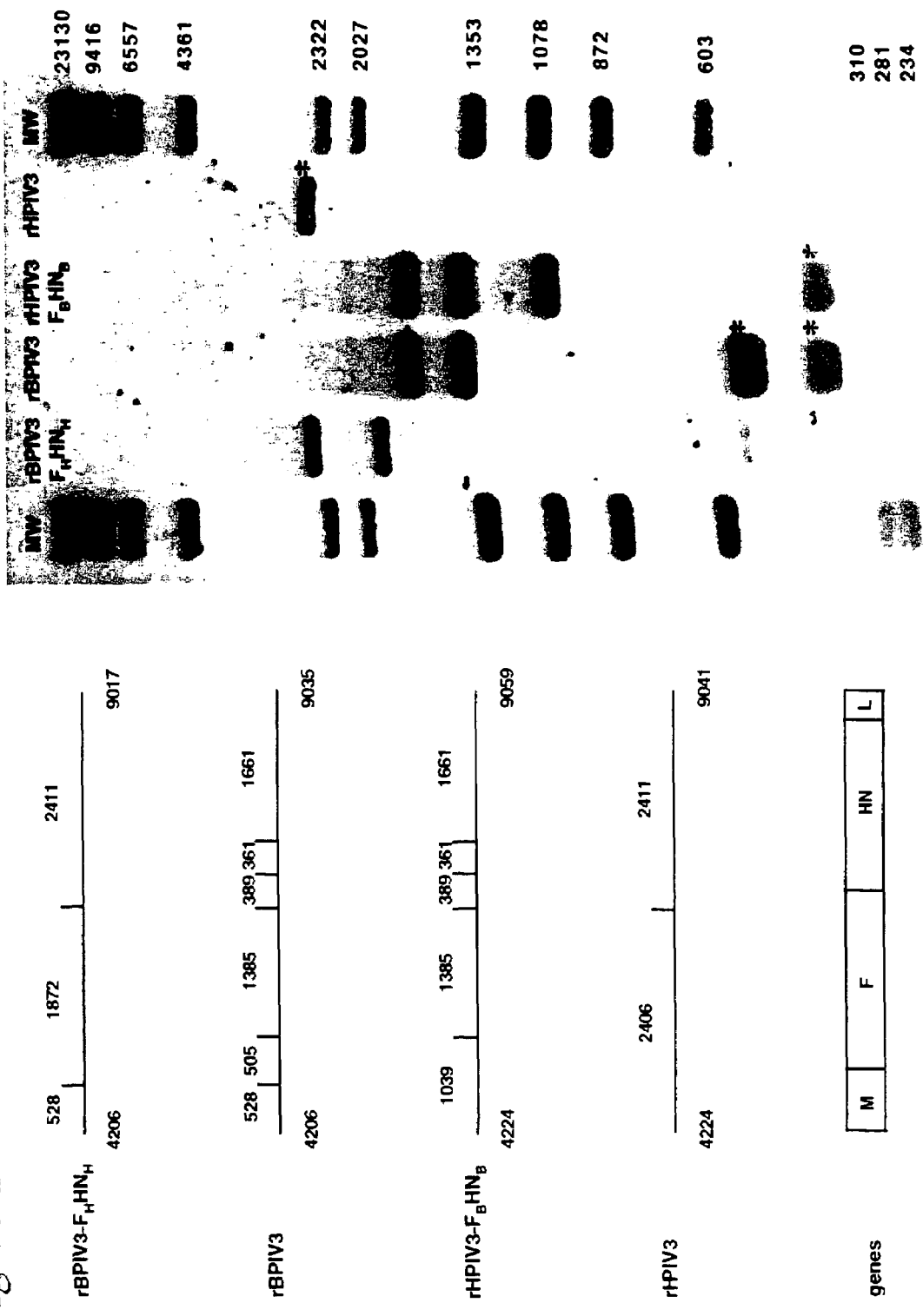

FIG. 12 provides a confirmation of the identity of recombinant viruses by RT-PCR of viral RNA and Eco RI digestion. RT-PCR products of viral RNA were prepared with a primer pair that recognized conserved regions on either side of the F and HN genes in both BPIV3 and HPIV3. Digestion with Eco RI resulted in a unique pattern of restriction fragments for each of the four viruses. In the schematic diagram on the left, horizontal lines symbolize the amplified viral sequences and vertical bars show the positions of Eco RI sites. The expected size of each restriction fragment is indicated above the line. The numbers below each line correspond to the sequence position in the antigenomic RNA of BPIV3 Ka, HPIV3 JS (GenBank accession #AF178654 and Z11575), or of the indicated chimeric derivative. On the right, a 1% agarose gel of the Eco RI digestion of PCR products is shown, confirming the identity of parental and chimeric viruses. The asterisks indicate gel bands that contain comigrating restriction fragments.

FIG. 13 depicts multicycle replication of chimeric and parental viruses in simian LLC-MK2 cells. Multicycle replication (MOI of 0.01) of the three chimeric viruses rHPIV3-$F_BHN_B$, rBPIV3-$F_HHN_H$ and rHPIV3-$N_B$ is compared with the replication of their parental viruses BPIV3 Ka and rHPIV3. The virus titers are shown as mean log 10 $TCID_{50}$/ ml±standard error of triplicate samples. The lower limit of detection of this assay is 10 $TCID_{50}$, as indicated by the dotted horizontal line.

FIG. 14 documents mean titers of chimeric and parental viruses in nasopharyngeal swabs of infected rhesus monkeys over the course of infection. Virus titers are shown as mean $TCID_{50}$/ml in LLC-MK2 cells±standard error for groups of 4 or 6 monkeys infected with the same virus. The rHPIV3 group contained two animals infected with rHPIV3s, the virus containing restriction enzyme recognition sites for the glycoprotein swap. This illustrates the same experiment as shown in Table 3. In panel A, mean titers of rHPIV3-$F_BHN_B$ are compared to rHPIV3 and BPIV3 Ka titers. In panel B, mean rBPIV3-$F_HHN_H$ titers are compared to those of BPIV3 Ka and rHPIV3, which, for the last two viruses, are the same values in panel A but are presented separately to facilitate comparison. Day 5 titers were excluded from the figures because they were much lower than day 4 and day 6 titers, most likely due to technical problems during the sample collection.

FIG. 15 provides a diagrammatic representation of the rHPIV3, rHPIV3 $L_B$ and BPIV3 genomes. The position of the BPIV3 L ORF (▭) is indicated relative to the rHPIV3 $L_B$ sequence.

FIG. 16 provides a comparison of the nucleotide sequence (sequences 61-66) of a genomic region of rHPIV3-$L_B$ flanking the translation initiation codon (ATG, in bold type) and the translation termination codon (TAA, in bold type) of the L ORF. The nucleotide sequencing of an RT-PCR fragment generated from vRNA of rHPIV3-$L_B$ around the junctions of the BPIV3 L ORF (BPIV3 GenBank accession #AF178654) and the HPIV3 (JS strain HPIV3 GenBank accession #Z11575) flanking sequences was determined using a Perkin Elmer ABI 3100 automated sequencer, and the engineered sequences for the rHPIV3 $L_B$ were confirmed to be present. The determined sequence of rHPIV3-$L_B$ is indicated in comparison to that of its two parents. The introduced BsiWI restriction enzyme recognition sequence following the L ORF stop codon in the chimera is italicized and the BPIV3 sequences are underlined.

DESCRIPTION OF THE SPECIFIC EMBODIMENTS

The present invention provides recombinant parainfluenza virus (PIV) cloned as a chimera of human and bovine PIV genomic or antigenomic sequences to yield a human-bovine chimeric PIV. The chimeric construction of human-bovine PIV yields a viral particle or subviral particle that is infectious in mammals, particularly humans, and useful for generating immunogenic compositions for clinical or veterinary use. Also provided within the invention are novel methods and compositions for designing and producing attenuated, human-bovine chimeric PIV, as well as methods and compositions for the prophylaxis and treatment of PIV infection. Human-bovine chimeric PIV and immunogenic compositions according to the invention may elicit an immune response to a specific PIV, or they may elicit a polyspecific response against multiple PIVs, e.g., multiple human PIVs such as HPIV1 and HPIV3.

Chimeric human-bovine PIV of the invention are recombinantly engineered to incorporate nucleotide sequences from both human and bovine PIV strains to produce an infectious, chimeric virus or subviral particle. In this manner, candidate vaccine viruses are recombinantly engineered to elicit an immune response against PIV in a mammalian host susceptible to PIV infection, including humans and non-human primates. Human-bovine chimeric PIV according to the invention may elicit an immune response to a specific PIV, e.g., HPIV3, or a polyspecific response against multiple PIVs, e.g., HPIV1 and HPIV3.

Exemplary human-bovine chimeric PIV of the invention incorporate a chimeric PIV genome or antigenome comprising both human and bovine polynucleotide sequences, as well as a major nucleocapsid (N) protein, a nucleocapsid phosphoprotein (P), and a large polymerase protein (L). Additional PIV proteins may be included in various combinations to provide a range of infectious subviral particles, up to a complete viral particle or a viral particle containing supernumerary proteins, antigenic determinants or other additional components.

Chimeric human-bovine PIV of the invention include a partial or complete "background" PIV genome or antigenome derived from or patterned after a human or bovine PIV strain or serotype virus combined with one or more heterologous gene(s) or genome segment(s) of a different PIV strain or serotype virus to form the human-bovine chimeric PIV genome or antigenome. In certain aspects of the invention, chimeric PIV incorporate a partial or complete human PIV (HPIV) background genome or antigenome combined with one or more heterologous gene(s) or genome segment(s) from a bovine PIV. In alternate aspects of the invention, chimeric PIV incorporate a partial or complete bovine PIV (BPIV) background genome or antigenome combined with one or more heterologous gene(s) or genome segment(s) from a human PIV.

The partial or complete background genome or antigenome typically acts as a recipient backbone or vector into which are imported heterologous genes or genome segments of the counterpart, human or bovine PIV. Heterologous genes or genome segments from the counterpart, human or bovine PIV represent "donor" genes or polynucleotides that are combined with, or substituted within, the background genome or antigenome to yield a human-bovine chimeric PIV that exhibits novel phenotypic characteristics compared to one or both of the contributing PIVs. For example, addition or substitution of heterologous genes or genome segments within a selected recipient PIV strain may result in an increase or decrease in attenuation, growth changes, altered immunogenicity, or other desired phenotypic changes as compared with a corresponding phenotype(s) of the unmodified recipient and/or donor. Genes and genome segments that may be selected for use as heterologous inserts or additions within human-bovine chimeric PIV of the invention include genes or genome segments encoding a PIV N, P, C, D, V, M, F, HN and/or L protein(s) or portion(s) thereof. Regulatory regions, such as the extragenic leader or trailer or intergenic regions, are also useful as heterologous inserts or additions.

The heterologous gene(s) or genome segment(s) may be added or substituted at a position corresponding to a wild-type gene order position of the counterpart gene(s) or genome segment(s) within the partial or complete PIV background genome or antigenome, which counterpart gene or genome segment is thereby replaced or displaced (e.g., to a more promotor-distal position). In yet additional embodiments, the heterologous gene or genome segment is added or substituted at a position that is more promoter-proximal or promotor-distal compared to a wild-type gene order position of the counterpart gene or genome segment within the background genome or antigenome, which enhances or reduces, respectively, expression of the heterologous gene or genome segment.

The introduction of heterologous immunogenic proteins, domains and epitopes to produce human-bovine chimeric PIV is particularly useful to generate novel immune responses in an immunized host. Addition or substitution of an immunogenic gene or genome segment from one, donor PIV within a recipient genome or antigenome of a different PIV can generate an immune response directed against the donor subgroup or strain, the recipient subgroup or strain, or against both the donor and recipient subgroup or strain. To achieve this purpose, human-bovine chimeric PIV may also be constructed that express a chimeric protein, e.g., an immunogenic glycoprotein having a cytoplasmic tail and/or transmembrane domain specific to one PIV fused to an ectodomain of a different PIV to provide, e.g., a human-bovine fusion protein, or a fusion protein incorporating domains from two different human PIVs. In a preferred embodiment, a human-bovine chimeric PIV genome or antigenome encodes a chimeric glycoprotein in the recombinant virus or subviral particle having both human and bovine glycoprotein domains or immunogenic epitopes. For example, a heterologous genome segment encoding a glycoprotein ectodomain from a human PIV HN or F glycoprotein may be joined with a polynucleotide sequence (i.e., a genome segment) encoding the corresponding bovine HN or F glycoprotein cytoplasmic and transmembrane domains to form the human-bovine chimeric PIV genome or antigenome.

In other embodiments, human-bovine chimeric PIV useful in a vaccine formulation can be conveniently modified to accommodate antigenic drift in circulating virus. Typically the modification will be in the HN and/or F proteins. This may involve, for example, introduction of one or more point mutations or, alternatively, may involve an entire HN or F gene, or a genome segment encoding a particular immunogenic region thereof, from one PIV strain or group is incorporated into a chimeric PIV genome or antigenome cDNA by replacement of a corresponding region in a recipient clone of a different PIV strain or group, or by adding one or more copies of the gene, such that multiple antigenic forms are represented. Progeny virus produced from the modified PIV clone can then be used in vaccination protocols against emerging PIV strains.

Replacement of a human PIV coding sequence or non-coding sequence (e.g., a promoter, gene-end, gene-start, intergenic or other cis-acting element) with a heterologous counterpart yields chimeric PIV having a variety of possible attenuating and other phenotypic effects. In particular, host range and other desired effects arise from substituting a bovine or murine PIV (MPIV) protein, protein domain, gene or genome segment imported within a human PIV background, wherein the bovine or murine gene does not function efficiently in a human cell, e.g., from incompatibility of the heterologous sequence or protein with a biologically interactive human PIV sequence or protein (i.e., a sequence or protein that ordinarily cooperates with the substituted sequence or protein for viral transcription, translation, assembly, etc.) or, more typically in a host range restriction, with a cellular protein or some other aspect of the cellular milieu which is different between the permissive and less permissive host. In exemplary embodiments, bovine PIV sequences are selected for introduction into human PIV based on known aspects of bovine and human PIV structure and function.

HPIV3 is a member of the *Respirovirus* genus of the Paramyxoviridae family in the order Mononegavirales (Collins et al., 1996, supra). A protein containing the V ORF in the P gene might also be produced (Durbin et al., *Virology* 261: 319-333, 1999, incorporated herein by reference).

HPIV3 is the best characterized of the HPIVs and represents the prototype HPIV. Its genome is a single strand of negative-sense RNA 15462 nucleotides (nt) in length (Galinski et al., *Virology* 165:499-510, 1988; and Stokes et al., *Virus Res.* 25:91-103, 1992; each incorporated herein by reference). At least eight proteins are encoded by the PIV3 genome: the nucleocapsid protein N, the phosphoprotein P, the C and D proteins of unknown functions, the matrix protein M, the fusion glycoprotein F, the hemagglutinin-neuraminidase glycoprotein HN, and the large polymerase protein L (Collins et al., 1996, supra).

The M, HN, and F proteins are envelope-associated, and the latter two are surface glycoproteins which, as is the case with each PIV, are the major neutralization and protective antigens (Collins et al., 1996, supra). The significant sequence divergence between comparable PIV HN or F proteins among the PIVs is thought to be the basis for the type specificity of the protective immunity (Collins et al., 1996, supra; Cook et al., *Amer. Jour. Hyg.* 77:150-159, 1963; Ray et al., *J. Infect. Dis.* 162:746-749, 1990; each incorporated herein by reference).

The HPIV3 genes are each transcribed as a single mRNA that encodes a single protein, with the exception of the P mRNA which contains four ORFs, namely P, C, D and V (Galinski et al., *Virology* 186:543-550, 1992; and Spriggs et al., *J. Gen. Virol.* 67:2705-2719, 1986; each incorporated herein by reference). The P and C proteins are translated from separate, overlapping ORFs in the mRNA. Whereas all paramyxoviruses encode a P protein, only members of the genus *Respirovirus* and *Morbillivirus* encode a C protein. Individual viruses vary in the number of proteins expressed from the C ORF and in its importance in replication of the virus in vitro and in vitro. Sendai virus (SeV) expresses four independently initiated proteins from the C ORF: C', C, Y1, and Y2, whose translational start sites appear in that order in the mRNA (Curran et al., *Enzyme* 44:244-249, 1990; Lamb et al., in *The Paramyxoviruses*, D. Kingsbury, ed., pp. 181-214, Plenum Press, New York, 1991; incorporated herein by reference), whereas HPIV3 and measles virus (MeV) express only a single C protein (Bellini et al., *J. Virol.* 53:908-919, 1985; Sanchez et al., *Virology* 147:177-86, 1985; and Spriggs et al., 1986, supra; each incorporated herein by reference).

The PIV3 D protein is a fusion protein of the P and D ORFs, and is expressed from the P gene by the process of co-transcriptional RNA editing in which two nontemplated G residues are added to the P mRNA at the RNA editing site (Galinski et al., 1992, supra; and Pelet et al., *EMBO J.* 10:443-448, 1991; each incorporated herein by reference). BPIV3, the only other paramyxovirus which expresses a D protein, uses RNA editing to express this protein as well as a second protein, the V protein.

Nearly all members of the genera *Respirovirus, Rubulavirus*, and *Morbillivirus* express a V protein. The one member which clearly does not is HPIV1, which lacks an intact V ORF (Matsuoka et al., *J. Virol.* 65:3406-3410, 1991, incorporated herein by reference). The V ORF is characterized by the presence of a cysteine-rich domain that is highly conserved (Cattaneo et al., *Cell* 56:759-764, 1989; Park et al., *J. Virol.* 66:7033-7039, 1992; Thomas et al., *Cell* 54:891-902, 1988; and Vidal et al., *J. Virol.* 64:239-246, 1990; each incorporated herein by reference). The V ORF is maintained in each of the HPIV3 viruses sequenced to date suggesting that this ORF is expressed and retains function for this virus (Galinski et al., *Virology* 155:46-60, 1986; Spriggs et al., 1986, supra; and Stokes et al., 1992, supra; incorporated herein by reference).

The BPIV3 V protein is expressed when one nontemplated G residue is added at the RNA editing site (Pelet et al., 1991, supra; incorporated herein by reference). However, in the case of HPIV3, two translation stop codons lie between the editing site and the V ORF, and it is not clear whether HPIV3 represents another example in which this ORF is not expressed, or whether it is expressed by some other mechanism. One possibility is that HPIV3 editing also occurs at a second, downstream site in the P gene, although this did not appear to occur in cell culture (Galinski et al., 1992, supra). Alternatively, it might be that ribosomes gain access to the V ORF by ribosomal frameshifting. This would be comparable to the situation with the P locus of MV. MV expresses C, P, and V proteins, but also expresses a novel R protein which is synthesized by frameshifting from the P ORF to the V ORF (Liston et al., *J. Virol.* 69:6742-6750, 1995, incorporated herein by reference). Genetic evidence suggests that the V ORF of HPIV3 is functional (Durbin et al., 1999, supra).

Although the means by which HPIV3 expresses its V protein is unclear, the extreme conservation of the its V ORF in different strains suggests that it is indeed expressed. The function of the V protein is not well defined, but V-minus MV and SeV recombinants have been recovered that replicate efficiently in vitro but exhibit reduced replication in vitro (Delenda, et al., *Virology* 228:55-62, 1997; Delenda et al., *Virology* 242:327-337, 1998; Kato et al., 1997a, supra; Kato et al., *J. Virol.* 71:7266-7272, 1997b; and Valsamakis et al., *J. Virol.* 72:7754-7761, 1998; each incorporated herein by reference).

The viral genome of PIV also contains extragenic leader and trailer regions, possessing all or part of the promoters required for viral replication and transcription, as well as non-coding and intergenic regions. Thus, the PIV genetic map is represented as 3' leader-N-P/C/D/V-M-F-HN-L-5' trailer. Some viruses, such as simian virus 5 and mumps virus, have a gene located between F and HN that encodes a small hydrophobic (SH) protein of unknown function. Transcription initiates at the 3' end and proceeds by a sequential stop-start mechanism that is guided by short conserved motifs found at the gene boundaries. The upstream end of each gene contains a gene-start (GS) signal, which directs initiation of its respective mRNA. The downstream terminus of each gene contains a gene-end (GE) motif which directs polyadenylation and termination. Exemplary sequences have been described for the human PIV3 strains JS (GenBank accession number Z11575, incorporated herein by reference) and Washington (Galinski M. S., in *The Paramyxoviruses*, Kingsbury, D. W., ed., pp. 537-568, Plenum Press, New York, 1991, incorporated herein by reference), and for the bovine PIV3 strain 910N (GenBank accession number D80487, incorporated herein by reference).

As used herein, "PIV gene" generally refers to a portion of the PIV genome encoding an mRNA and typically begins at the upstream end with a gene-start (GS) signal and ends at the downstream end with the gene-end (GE) signal. The term PIV gene also embraces what is referred to as a "translational open reading frame", or ORF, particularly in the case where a protein, such as C, is expressed from an additional ORF rather than from a unique mRNA. To construct human-bovine chimeric PIV of the invention, one or more PIV gene(s) or genome segment(s) may be deleted, inserted or substituted in whole or in part. This means that partial or complete deletions, insertions and substitutions may include open reading frames and/or cis-acting regulatory sequences of any one or more of the PIV genes or genome segments. By "genome segment" is meant any length of continuous nucleotides from the PIV genome, which might be part of an ORF, a gene, or an extragenic region, or a combination thereof.

The instant invention involves a method for developing live attenuated PIV vaccine candidates based on chimeras between HPIVs and BPIV3. Chimeras are constructed through a cDNA-based virus recovery system. Recombinant viruses made from cDNA replicate independently and are propagated in the same manner as if they were biologically-derived viruses. Preferred human-bovine chimeric PIV vaccine candidates of the invention bear one or more of the major antigenic determinants of one or more human PIV(s), e.g., HPIV1, HPIV2, and/or HPIV3, in a background which is attenuated by the substitution or addition of one or more BPIV genes or genome segments. The major protective antigens of PIVs are their HN and F glycoproteins, although other proteins can also contribute to a protective immune response.

Thus, the invention provides a new basis for attenuating a wild type or mutant parental virus for use as a vaccine against PIV, one which is based on host range effects due to the introduction of one or more gene(s) or genome segment(s) between HPIV and BPIV. There are numerous nucleotide and amino acid sequence differences between BPIV and HPIV, which are reflected in host range differences. For example, between HPIV3 and BPIV3 the percent amino acid identity for each of the following proteins is: N (86%), P (65%), M (93%), F (83%), HN (77%), and L (91%). The host range difference is exemplified by the highly permissive growth of HPIV3 in rhesus monkeys, compared to the restricted replication of two different strains of BPIV3 in the same animal (van Wyke Coelingh et al., 1988, supra). Although the basis of the host range differences between HPIV3 and BPIV3 remains to be determined, it is likely that they will involve more than one gene and multiple amino acid differences. The involvement of multiple genes and possibly cis-acting regulatory sequences, each involving multiple amino acid or nucleotide differences, gives a very broad basis for attenuation, one which cannot readily be altered by reversion. This is in contrast to the situation with other live attenuated HPIV3 viruses which are attenuated by one or several point mutations. In this case, reversion of any individual mutation may yield a significant reacquisition of virulence or, in a case where only a single residue specified attenuation, complete reacquisition of virulence.

In exemplary embodiments of the invention described herein below, the background genome or antigenome is an HPIV3 genome or antigenome, and the heterologous gene or genome segment is a N ORF derived from, alternatively, a Ka or SF strain of BPIV3 (which are 99% related in amino acid sequence). The N ORF of the HPIV3 background antigenome is substituted by the counterpart BPIV3 N ORF—yielding a novel recombinant human-bovine chimeric PIV cDNA clone. Replacement of the HPIV3 N ORF with that of BPIV3 Ka or SF results in a protein with approximately 70 amino acid differences (depending on the strain involved) from that of HPIV3 N. N is one of the more conserved proteins, and substitution of other proteins such as P, singly or in combination, would result in many more amino acid differences. The involvement of multiple genes and genome segments each conferring multiple amino acid or nucleotide differences provides a broad basis for attenuation which is highly stable to reversion.

This mode of attenuation contrasts sharply to HPIV vaccine candidates that are attenuated by one or more point mutations, where reversion of an individual mutation may yield a significant or complete reacquisition of virulence. In addition, several known attenuating point mutations in HPIV typically yield a temperature sensitive phenotype. One problem with attenuation associated with temperature sensitivity is that the virus can be overly restricted for replication in the lower respiratory tract while being under attenuated in the upper respiratory tract. This is because there is a temperature gradient within the respiratory tract, with temperature being higher (and more restrictive) in the lower respiratory tract and lower (less restrictive) in the upper respiratory tract. The ability of an attenuated virus to replicate in the upper respiratory tract can result in complications including congestion, rhinitis, fever and otitis media, whereas overattenuation in the lower respiratory tract can reduce immunogenicity. Thus, attenuation achieved solely by temperature sensitive mutations may not be ideal. In contrast, host range mutations present in human-bovine chimeric PIV of the invention will not in most cases confer temperature sensitivity. Therefore, the novel method of PIV attenuation provided by the invention will be more stable genetically and phenotypically and less likely to be associated with residual virulence in the upper respiratory tract compared to other known PIV vaccine candidates.

Surprisingly, both the Ka and SF HPIV3/BPIV3 chimeric recombinants were viable, since the N gene of Ka or SF strain BPIV3 differs in 70 of 515 amino acid residues, respectively, from that of the JS strain of HPIV3. It was therefore unexpected that a bovine N protein with this level of amino acid sequence divergence could efficiently interact with the HPIV3 RNA, or with other HPIV3 proteins that constitute the functional replicase/transcriptase. Equally surprising was the finding that the Ka and SF chimeric viruses replicated as efficiently in cell culture as either HPIV3 or BPIV3 parent indicating that the chimeric recombinants did not exhibit gene incompatibilities that restricted replication in vitro. This property of efficient replication in vitro is important since it permits efficient manufacture of this biological.

Also surprising is the observation, based on the studies herein below, that the Ka and the SF HPIV3/BPIV3 chimeric recombinants (termed cKa and cSF), bearing only one bovine gene, are nearly equivalent to their BPIV3 parents in the degree of host range restriction in the respiratory tract of the rhesus monkey. In particular, the cKa and cSF viruses exhibited approximately a 60-fold or 30-fold reduction, respectively, in replication in the upper respiratory tract of rhesus monkeys compared to replication of HPIV3. Based on this finding, it is expected that other BPIV3 genes will also confer desired levels of host range restriction within human-bovine chimeric PIV of the invention. Thus, according to the methods herein, a list of attenuating determinants will be readily identified in heterologous genes and genome segments of both HPIV and BPIV that will confer, in appropriate combination, an optimal level of host range restriction and immunogenicity on human-bovine chimeric PIV selected for vaccine use. In preferred vaccine recombinants, attenuation marked by replication in the lower and/or upper respiratory tract in an accepted animal model for PIV replication in humans, e.g., hamsters or rhesus monkeys, may be reduced by at least about two-fold, more often about 5-fold, 10-fold, or 20-fold, and preferably 50-100-fold and up to 1,000-fold or greater overall (e.g., as measured between 3-8 days following infection) compared to growth of the corresponding wild-type or mutant parental PIV strain.

Confirming the unexpected nature and advantages provided by the human-bovine chimeric PIV of the invention, both the cKa and cSF induced a high level of protection against HPIV3 challenge in the respiratory tract of rhesus monkeys, despite the exceptional degree of restriction of replication exhibited by these viruses in this model for human PIV infection and protection. In particular, previous infection with either chimeric virus induced a high level of resistance to replication of the rJS challenge virus in both the upper and lower respiratory tract. Infection of monkeys with cKa elicited a high degree of protection as indicated by an approximate 300-fold reduction of replication of wild type HPIV3 (rJS) in the upper respiratory tract, and an approximate 1000- fold reduction in the lower tract compared to uninoculated control monkeys. Monkeys infected with cSF manifested a 2000-fold reduction of replication of rJS in the upper respiratory tract, and a 1000-fold reduction in the lower tract compared to uninoculated control monkeys. The levels of protection elicited by cKa or cSF were comparable to those seen in monkeys previously infected with either the bovine or the human PIV parent. Thus, infection with human-bovine chimeric PIV of the invention provides a high level of protection in the upper and lower respiratory tract of monkeys, and both chimeric viruses represent promising vaccine candidates. In other preferred vaccine recombinants, the immunogenic activity of human-bovine chimeric PIV will be balanced against the level of attenuation to achieve useful vaccine candidates, and will typically be marked by a reduction of replication of challenge virus, e.g., rJS in the lower and/or upper respiratory tract by about 50-100-fold, 100-500-fold, preferably about 500-2,000-fold and up to 3,000-fold or greater overall (e.g., as measured between 3-8 days post-challenge). Thus, the recombinant vaccine viruses of the invention maintain immunogenicity while exhibiting concomitant reductions in replication and growth. This surprising assemblage of phenotypic traits is highly desired for vaccine development.

The observation that the N gene from two independent strains of BPIV3 confers an attenuation phenotype on HPIV3 for the rhesus monkey indicates that this is likely a property shared by N genes of other BPIV strains. Accordingly, within the methods of the invention any BPIV gene or genome segment, singly or in combination with one or more other BPIV gene(s) or genome segment(s), can be combined with HPIV sequences to produce an attenuated HPIV3/BPIV3 chimeric recombinant virus suitable for use as a vaccine virus. In preferred embodiments, all HPIVs, including HPIV1, HPIV2, HPIV3 and variant strains thereof, are useful recipients for attenuating BPIV gene(s) and/or genome segment(s). In general, the HPIV genes selected for inclusion in a HPIV3/BPIV3 chimeric virus will include one or more of the protective antigens, such as the HN or F glycoproteins.

In preferred aspects of the invention, human-bovine chimeric PIVs bearing one or more bovine gene(s) or genome segment(s) exhibit a high degree of host range restriction, e.g., in the respiratory tract of mammalian models of human PIV infection such as non-human primates. The human PIV backbone is attenuated by the addition or substitution of one or more bovine gene(s) or genome segment(s), for example to a partial or complete human, e.g., HPIV3, PIV background genome or antigenome. In exemplary embodiments described herein below, the partial or complete HPIV background genome or antigenome is combined with one or more heterologous gene(s) or genome segment(s) of a N, P and/or M gene of a BPIV to form a human-bovine chimeric PIV genome or antigenome.

In other exemplary embodiments of the invention described herein below, the background genome or antigenome is an HPIV3 genome or antigenome and the heterologous gene or genome segment is a gene or genome segment of a BPIV3 M or P gene. In one specific example, the M ORF of a HPIV3 background antigenome is substituted by a counterpart BPIV3 M ORF—yielding a novel recombinant human-bovine chimeric PIV cDNA clone designated rHPIV3M$_B$. In another example, the P ORF of a HPIV3 background antigenome is substituted by a counterpart BPIV3 P ORF—yielding a novel recombinant human-bovine chimeric PIV cDNA clone designated rHPIV3M$_P$. Replacement of the HPIV3 M and P ORFs with those of BPIV3 also results in proteins substantial amino acid differences from that of the substituted HPIV3 M and P proteins, conferring multiple amino acid or nucleotide differences provides a broad basis for attenuation which is highly stable to reversion. The rHPIV3-P$_B$ and rHPIV3-M$_B$ recombinants each viable and replicated efficiently in tissue culture. Thus, the heterologous BPIV3 M and P proteins are shown to be sufficiently compatible with the remaining HPIV3 proteins to allow efficient growth in vitro, a property that is highly desired for vaccine production.

In view of these findings, the invention also provides human-bovine chimeric PIV which have one or more substituted genome segment(s) from BPIV3 N, P and/or M gene(s) substituted or added within a partial or complete HPIV3 genome or antigenome. For example, the ORFs for the C, D, and V proteins, as well as the sequence for the RNA editing site, are all contained within the sequence containing the P ORF. Therefore transfer of only a genome segment within the P ORF can selectively transfer one or a plurality of these genetic elements without transferring the entire P ORF.

Alternative human-bovine chimeric PIV of the invention will contain protective antigenic determinants of HPIV1 or HPIV2. This may be achieved, for example, by expression of an HN and/or F gene of HPIV1 or HPIV2 as an extra gene(s) in an attenuated HPIV3/BPIV3 chimeric recombinant. Alternatively, it is possible to use a HPIV3/HPIV1 or a HPIV3/HPIV2 antigenic chimeric virus, in which the HPIV1 or HPIV2 HN and/or F genes replace their PIV3 counterpart(s) (Skiadopoulos et al., 1999a, supra; Tao et al., 1999, supra; and U.S. patent application Ser. No. 09/083,793, filed May 22, 1998; each incorporated herein by reference), as a recipient or background virus for one or more heterologous, attenuating bovine gene(s) or genome segment(s), for example a Ka or SF N gene or genome segment. Such antigenic chimeric viruses will be attenuated by the bovine N gene, but will induce immunity to the HPIV1 or HPIV2 virus. In this context, a chimeric PIV1 vaccine candidate has been generated using the PIV3 cDNA rescue system by replacing the PIV3 HN and F open reading frames (ORFs) with those of PIV1 in a PIV3 full-length cDNA that contains the three attenuating mutations in L. The recombinant chimeric virus derived from this cDNA is designated rPIV3-1.cp45L (Skiadopoulos et al., 1998, supra; Tao et al., 1998, supra; Tao et al., 1999, supra). rPIV3-1.cp45L was attenuated in hamsters and induced a high level of resistance to challenge with PIV1. A recombinant chimeric virus, designated rPIV3-1.cp45, has also been produced that contains 12 of the 15 cp45 mutations, i.e., excluding the mutations in HN and F, and is highly attenuated in the upper and lower respiratory tract of hamsters (Skiadopoulos et al., 1999a, supra).

Still other HPIV/BPIV chimeric recombinants will incorporate two or more BPIV genes or genome segments, in any combination, up to and including all of the BPIV genome other than selected genes or antigenic determinants selected from HN or F gene(s) and genome segment(s), which could come from a human HPIV1, HPIV2, or HPIV3 virus. Yet additional embodiments of the invention are directed to human-bovine chimeric PIV incorporating attenuating genes from other animal PIVs, such as murine PIV1, the canine SV5 PIV2 virus, or another avian or mammalian PIV in combination with a HPIV backbone, alternatively including a chimeric HPIV backbone, from HPIV1, HPIV2, and/or HPIV3.

In other detailed aspects of the invention, human-bovine chimeric PIV are employed as vectors for protective antigens of heterologous pathogens, including other PIVs and non-PIV viruses and non-viral pathogens. Within these aspects, the bovine-human chimeric genome or antigenome comprises a partial or complete PIV "vector genome or antigenome" combined with one or more heterologous genes or genome segments encoding one or more antigenic determinants of one or more heterologous pathogens (see, e.g., U.S. Provisional Patent Application Ser. No. 60/170,195, filed Dec. 10, 1999 by Murphy et al., incorporated herein by reference). The heterologous pathogen in this context may be a heterologous PIV and the heterologous gene(s) or genome segment(s) can be selected to encodes one or more PIV N, P, C, D, V, M, F, SH, where applicable, HN and/or L protein(s), as well as protein domains, fragments, and immunogenic regions or epitopes. PIV vector vaccines thus constructed may elicit a polyspecific immune response and may be administered simultaneously or in a coordinate administration protocol with other vaccine agents.

In exemplary embodiments of the invention, human-bovine chimeric PIV may comprise a vector genome or antigenome that is a partial or complete HPIV genome or antigenome, which is combined with or is modified to incorporate one or more heterologous genes or genome segments encoding antigenic determinant(s) of one or more heterologous PIV(s), including heterologous HPIVs selected from HPIV1, HPIV2, or HPIV3. In more detailed aspects, the vector genome or antigenome is a partial or complete HPIV3 genome or antigenome and the heterologous gene(s) or genome segment(s) encoding the antigenic determinant(s) is/are of one or more heterologous HPIV(s). Typically, the chimeric genome or antigenome incorporates one or more gene(s) or genome segment(s) of a BPIV that specifies attenuation.

In exemplary aspects of the invention, the bovine-human chimeric PIV incorporates one or more HPIV1 or HPIV2 genes or genome segments that encode(s) one or more HN and/or F glycoproteins or antigenic domains, fragments or epitopes thereof within a partial or complete HPIV3 vector genome or antigenome. In more detailed aspects, both HPIV1 genes encoding HN and F glycoproteins are substituted for counterpart HPIV3 HN and F genes to form a chimeric HPIV3-1 vector genome or antigenome. Such recombinant constructs can be used to produce vaccine virus directly, or can be further modified by addition or incorporation of one or more genes or gene segments encoding one or more antigenic determinants. Such constructs for the production of vaccine viruses typically incorporate one or more heterologous gene(s) or genome segment(s) of a BPIV that specifies attenuation, for example an open reading frame (ORF) encoding an attenuating BPIV protein, such as N. Certain human-bovine chimeric PIV of the invention may be employed as vectors for generating specific vaccines to HPIV2, for example wherein a transcription unit comprising an open reading frame (ORF) of an HPIV2 HN gene is added to or incorporated within a chimeric HPIV3-1 vector genome or antigenome and the chimeric construct is attenuated by incorporation of a BPIV gene or genome segment.

Within related aspects of the invention, the vector genome or antigenome is a partial or complete BPIV genome or antigenome, and the heterologous genes or genome segments encoding the antigenic determinant(s) is/are of one or more HPIV(s). Typically, the determinant(s) is/are selected from HPIV1, HPIV2 or HPIV3 HN and F glycoproteins, but antigenic domains, fragments and epitopes of these and other antigenic proteins are also useful. In certain embodiments, one or more genes or genome segments encoding one or more antigenic determinant(s) of HPIV2 is/are added to or substituted within the partial or complete BPIV vector genome or antigenome. Alternatively, a plurality of heterologous genes or genome segments encoding antigenic determinants of multiple HPIVs may be added to or incorporated within the partial or complete BPIV vector genome or antigenome.

In yet additional aspects of the invention, human-bovine chimeric PIV are provided as vectors for a range of non-PIV pathogens (see, e.g., U.S. Provisional Patent Application Ser. No. 60/170,195, filed Dec. 10, 1999 by Murphy et al., incorporated herein by reference). The vector genome or antigenome for use within these aspects of the invention may comprise a partial or complete BPIV or HPIV genome or antigenome, and the heterologous pathogen may be selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses.

For example, a HPIV or BPIV vector genome or antigenome for constructing bovine-human chimeric PIV of the invention may incorporate heterologous antigenic determinant(s) selected from the measles virus HA and F proteins, or antigenic domains, fragments and epitopes thereof. In exemplary embodiments, a transcription unit comprising an open reading frame (ORF) of a measles virus HA gene is added to or incorporated within a BPIV or HPIV3 vector genome or antigenome.

Alternatively bovine-human chimeric PIV of the invention may used as vectors to incorporate heterologous antigenic determinant(s) from respiratory syncytial virus (RSV), for example by incorporating one or more genes or genome segments that encode(s) RSV F and/or G glycoprotein or immunogenic domain(s) or epitope(s) thereof. In this context, the cloning of RSV cDNA and other disclosure useful within the invention is provided in U.S. patent application Ser. No. 08/720,132, filed Sep. 27, 1996 (corresponding to priority U.S. Provisional Patent Application No. 60/007,083, filed Sep. 27, 1995); U.S. patent application Ser. No. 09/444,067, filed Nov. 19, 1999 (corresponding to priority U.S. Provisional Patent Application No. 60/046,141, filed May 9, 1997 and U.S. Provisional Patent Application No. 60/047,634, filed May 23, 1997); U.S. Pat. No. 5,993,824 issued Nov. 30, 1999 (corresponding to International Publication No. WO 98/02530 and priority U.S. Provisional Patent Application No. 60/021,773, filed Jul. 15, 1996); U.S. patent application Ser. No. 09/291,894, filed on Apr. 13, 1999; U.S. Provisional Patent Application Ser. No. 60/129,006, filed on Apr. 13, 1999; U.S. Patent Application entitled PRODUCTION OF ATTENUATED, HUMAN-BOVINE CHIMERIC RESPIRATORY SYNCYTIAL VIRUS VACCINES, filed by Buchholz et al. on Jun. 23, 2000 and identified by its priority U.S. Provisional Application Ser. No. 60/143,132; Collins, et al., 1995, supra; Bukreyev, et al., J. Virol. 70:6634-6641, 1996; Juhasz et al., 1997, supra; Durbin et al., 1997a, supra; He et al., 1997, supra; Baron et al., 1997, supra; Whitehead et al., 1998a, supra; Whitehead et al., 1998b, supra; Jin et al., 1998, supra; and Whitehead et al., 1999, supra; and Bukreyev et al., Proc. Natl. Acad. Sci. USA 96:2367-2372, 1999, each incorporated herein by reference in its entirety for all purposes).

According to this aspect of the invention, human-bovine chimeric PIV are provided which incorporate at least one antigenic determinant from a heterologous PIV or non-PIV pathogen. For example, one or more individual gene(s) or genome segment(s) of HPIV3 may be replaced with counterpart gene(s) or genome segment(s) from human RSV, or an RSV gene or genome segment can be inserted or added as an supernumerary gene. Alternatively, a selected, heterologous genome segment, e.g. encoding a cytoplasmic tail, transmembrane domain or ectodomain of an RSV glycoprotein, is substituted for a counterpart genome segment in, e.g., the same gene in HPIV3 or within a different gene in HPIV3, or added within a non-coding sequence of the HPIV3 genome or antigenome to yield a chimeric PIV-RSV glycoprotein. In one embodiment, a genome segment from an F gene of human RSV is substituted for a counterpart HPIV3 genome segment to yield constructs encoding chimeric proteins, e.g. fusion proteins having a cytoplasmic tail and/or transmembrane domain of PIV fused to an ectodomain of RSV to yield a novel attenuated virus, and/or a multivalent vaccine immunogenic against both PIV and RSV.

As noted above, it is often desirable to adjust the attenuation phenotype in human-bovine chimeric PIV of the invention by introducing additional mutations that increase or decrease attenuation or otherwise alter the phenotype of the chimeric virus. Detailed descriptions of the materials and methods for producing recombinant PIV from cDNA, and for making and testing the full range of mutations and nucleotide modifications set forth herein as supplemental aspects of the present invention, provided in, e.g., Durbin et al., 1997a, supra; U.S. patent application Ser. No. 09/083,793, filed May 22, 1998, (corresponding to International Publication No. WO 98/53078 and priority U.S. Provisional Application Ser. No. 60/047,575, filed May 23, 1997, and Ser. No. 60/059,385, filed Sep. 19, 1997, each incorporated herein by reference). In particular, these documents describe methods and procedures for mutagenizing, isolating and characterizing PIV to obtain attenuated mutant strains (e.g., temperature sensitive (ts), cold passaged (cp) cold-adapted (ca), small plaque (sp) and host-range restricted (hr) mutant strains) and for identifying the genetic changes that specify the attenuated phenotype. In conjunction with these methods, the foregoing documents detail procedures for determining replication, immunogenicity, genetic stability and protective efficacy of biologically derived and recombinantly produced attenuated human PIV in accepted model systems, including murine and non-human primate model systems. In addition, these documents describe general methods for developing and testing immunogenic compositions, including monovalent and bivalent vaccines, for prophylaxis and treatment of PIV infection. Methods for producing infectious recombinant PIV by construction and expression of cDNA encoding a PIV genome or antigenome coexpressed with essential PIV proteins are also described in the above-incorporated documents, which include description of the following exemplary plasmids that may be employed to produce infectious PIV viral clones: p3/7(131) (ATCC 97990); p3/7(131)2G (ATCC 97889); and p218(131) (ATCC 97991); each deposited under the terms of the Budapest Treaty with the American Type Culture Collection (ATCC) of 10801 University Boulevard, Manassas, Va. 20110-2209, U.S.A., and granted the above identified accession numbers.

Also disclosed in the above-incorporated references are methods for constructing and evaluating infectious recombinant PIV that are modified to incorporate phenotype-specific mutations identified in biologically-derived PIV and non-PIV mutants, e.g., cold passaged (cp), cold adapted (ca), host range restricted (hr), small plaque (sp), and/or temperature sensitive (ts) mutants, for example the JS HPIV3 cp45 mutant strain. Other mutations may be attenuating without an auxiliary marker phenotype. Mutations identified in these mutants can be readily adopted in human-bovine chimeric PIV. In exemplary embodiments, one or more attenuating mutations occur in the polymerase L protein, e.g., at a position corresponding to $Tyr_{942}$, $Leu_{992}$, or $Thr_{1558}$ of JS wild type HPIV3. Preferably, these mutations are incorporated in human-bovine chimeric PIV of the invention by an identical, or conservative, amino acid substitution as identified in the biological mutant. Thus, PIV recombinants may incorporate a mutation wherein $Tyr_{942}$ is replaced by His, $Leu_{992}$ is replaced by Phe, and/or $Thr_{1558}$ is replaced by Ile. Substitutions that are conservative to these replacement amino acids are also useful to achieve a desired mutant phenotype.

Other exemplary mutations adopted from a biologically derived PIV mutant include one or more mutations in the N protein, including specific mutations at a position corresponding to residues $Val_{96}$ or $Ser_{389}$ of JS. In more detailed aspects, these mutations are represented as $Val_{96}$ to Ala or $Ser_{389}$ to Ala or substitutions that are conservative thereto. Also useful within recombinant PIV of the invention are amino acid substitution in the C protein, e.g., a mutation at a position corresponding to $Ile_{96}$ of JS, preferably represented by an identical or conservative substitution of $Ile_{96}$ to Thr. Further exemplary mutations adopted from biologically derived PIV mutants include one or more mutations in the F protein, including mutations adopted from JS cp45 at a position corresponding to residues $Ile_{420}$ or $Ala_{450}$ of JS, preferably represented by acid substitutions $Ile_{420}$ to Val or $Ala_{450}$ to Thr or substitutions conservative thereto. Other human-bovine chimeric PIV within the invention adopt one or more amino acid substitutions in the HN protein, as exemplified herein below by a recombinant PIV adopting a mutation at a position corresponding to residue $Val_{384}$ of JS, preferably represented by the substitution $Val_{384}$ to Ala.

Yet additional examples within this aspect of the invention include human-bovine chimeric PIV which incorporate one or more mutations in noncoding portions of the PIV genome or antigenome, for example in a 3' leader sequence. Exemplary mutations in this context may be engineered at a position in the 3' leader of a recombinant virus at a position corresponding to nucleotide 23, 24, 28, or 45 of JS. Yet additional exemplary mutations may be engineered in the N gene start sequence, for example by changing one or more nucleotides in the N gene start sequence, e.g., at a position corresponding to nucleotide 62 of JS. In more detailed aspects human-bovine chimeric PIV incorporate a T to C change at nucleotide 23, a C to T change at nucleotide 24, a G to T change at nucleotide 28, and/or a T to A change at nucleotide 45. Additional mutations in extragenic sequences are exemplified by a A to T change in N gene start sequence at a position corresponding to nucleotide 62 of JS.

These foregoing exemplary mutations which can be engineered in a human-bovine chimeric PIV of the invention have been successfully engineered and recovered in recombinant PIV—as represented by the recombinant PIV clones designated rcp45, rcp45 L, rcp45 F, rcp45 M, rcp45 HN, rcp45 C, rcp45 F, rcp45 3'N, 3'NL, and rcp45 3'NCMFHN (Durbin et al., 1997a, supra; Skiadopoulos et al., 1998, supra; Skiadopoulos et al., J. Virol. 73:1374-1381, 1999b; U.S. patent application Ser. No. 09/083,793, filed May 22, 1998, (corresponding to International Publication No. WO 98/53078 and priority U.S. Provisional Application Ser. No. 60/047,575, filed May 23, 1997, and Ser. No. 60/059,385, filed Sep. 19, 1997, each incorporated herein by reference). In addition, the above-incorporated references describe construction of chimeric PIV recombinants, e.g., having the HN and F genes of HPIV1 substituted into a partial HPIV3 background genome or antigenome, which is further modified to bear one or more of the attenuating mutations identified in HPIV3 JS cp45. One such chimeric recombinant incorporates all of the attenuating mutations identified in the L gene of cp45. It has since been shown that all of the cp45 mutations outside of the heterologous (HPIV1) HN and F genes can be incorporated in a HPIV3-1 recombinant to yield an attenuated, chimeric vaccine candidate.

From JS cp45 and other biologically derived PIV mutants, a large "menu" of attenuating mutations is provided, each of which can be combined with any other mutation(s) for adjusting the level of attenuation, immunogenicity and genetic stability in a recombinant PIV bearing C, D, and/or V deletion or knock out mutation(s). In this context, many recombinant PIVs of the invention will include one or more, and preferably two or more, mutations from biologically derived PIV mutants, e.g., any one or combination of mutations identified in JS cp45. Preferred PIV recombinants within the invention will incorporate a plurality and up to a full complement of the mutations present in JS cp45 or other biologically derived mutant PIV strains. Preferably, these mutations are stabilized against reversion in human-bovine chimeric PIV by multiple nucleotide substitutions in a codon specifying each mutation.

Additional mutations that may be incorporated in human-bovine chimeric PIV of the invention are mutations, e.g., attenuating mutations, identified in heterologous PIV or more distantly related nonsegmented negative stranded RNA viruses. In particular, attenuating and other desired mutations identified in one negative stranded RNA virus may be "transferred", e.g., introduced by mutagenesis in a corresponding position, within the genome or antigenome of the human-bovine chimeric PIV. Briefly, desired mutations in one heterologous negative stranded RNA virus are transferred to the PIV recipient (e.g., bovine or human PIV, respectively). This involves mapping the mutation in the heterologous virus, thus identifying by sequence alignment the corresponding site in the recipient RSV, and mutating the native sequence in the PIV recipient to the mutant genotype (either by an identical or conservative mutation), as described in PCT/US00/09695 filed Apr. 12, 2000 and its priority U.S. Provisional Patent Application Ser. No. 60/129,006, filed Apr. 13, 1999, incorporated herein by reference). As this disclosure teaches, it is preferable to modify the recipient genome or antigenome to encode an alteration at the subject site of mutation that corresponds conservatively to the alteration identified in the heterologous mutant virus. For example, if an amino acid substitution marks a site of mutation in the mutant virus compared to the corresponding wild-type sequence, then a similar substitution should be engineered at the corresponding residue(s) in the recombinant virus. Preferably the substitution will involve an identical or conservative amino acid to the substitute residue present in the mutant viral protein. However, it is also possible to alter the native amino acid residue at the site of mutation non-conservatively with respect to the substitute residue in the mutant protein (e.g., by using any other amino acid to disrupt or impair the function of the wild-type residue).

Negative stranded RNA viruses from which exemplary mutations are identified and transferred into human-bovine chimeric PIV of the invention include other PIVs (e.g., HPIV1, HPIV2, HPIV3, HPIV4A, HPIV4B and BPIV), RSV, Sendai virus (SeV), Newcastle disease virus (NDV), simian virus 5 (SV5), measles virus (MeV), rinderpest virus, canine distemper virus (CDV), rabies virus (RaV) and vesicular stomatitis virus (VSV), among others.

A variety of exemplary mutations for use within the invention are disclosed in the above-incorporated reference, including but not limited to an amino acid substitution of phenylalanine at position 521 of the RSV L protein corresponding to and therefore transferable to a substitution of phenylalanine (or a conservatively related amino acid) at position 456 of the HPIV3 L protein. In the case of mutations marked by deletions or insertions, these can be introduced as corresponding deletions or insertions into the recombinant virus, either within the background genome or antigenome or within the heterologous gene or genome segment incorporated therein. However the particular size and amino acid sequence of the deleted or inserted protein fragment can vary.

Yet additional human-bovine PIV vaccine candidates within the invention can be achieved by modifying the chimeric PIV genome or antigenome to encode an analogous mutation to an attenuating mutation identified in Sendai virus (SeV). In one example, the attenuating mutation comprises an amino acid substitution of phenylalanine at position 170 of the C protein of SeV. The PIV genome or antigenome is modified to encode an alteration of a conserved residue that corresponds conservatively to the alteration marking the attenuating mutation in the heterologous, SeV mutant. In one embodiment, the mutation is incorporated within a recombinant HPIV3 protein and comprises an amino acid substitution of phenylalanine at position 164 of the C protein of HPIV3.

Various target proteins are amenable to introduction of attenuating mutations from one negative stranded RNA virus at a corresponding site within chimeric human-bovine PIV of the invention. Throughout the order Mononegavirales, five target proteins are strictly conserved and show moderate to high degrees of sequence identity for specific regions or domains. In particular, all known members of the order share a homologous constellation of five proteins: a nucleocapsid protein (N), a nucleocapsid phosphoprotein (P), a nonglycosylated matrix (M) protein, at least one surface glycoprotein (HN, F, H, or G) and a large polymerase (L) protein. These proteins all represent useful targets for incorporating attenuating mutations by altering one or more conserved residues in a protein of the recombinant virus at a site corresponding to the site of an attenuating mutation identified in the heterologous, mutant virus.

In this context, the methods for transferring heterologous mutations into chimeric human-bovine PIV of the invention are based on identification of an attenuating mutation in a first negative stranded RNA virus. The mutation, identified in terms of mutant versus wild-type sequence at the subject amino acid position(s) marking the site of the mutation, provides an index for sequence comparison against a homologous protein in the chimeric virus (either in the background genome or antigenome or in the heterologous gene or gene segment added or substituted therein) that is the target for recombinant attenuation. The attenuating mutation may be previously known or may be identified by mutagenic and reverse genetics techniques applied to generate and characterize biologically-derived mutant virus. Alternatively, attenuating mutations of interest may be generated and characterized de novo, e.g., by site directed mutagenesis and conventional screening methods.

Each attenuating mutation identified in a negative stranded RNA virus provides an index for sequence comparison against a homologous protein in one or more heterologous negative stranded virus(es). In this context, existing sequence alignments may be analyzed, or conventional sequence alignment methods may be employed to yield sequence comparisons for analysis, to identify corresponding protein regions and amino acid positions between the protein bearing the attenuating mutation and a homologous protein of a different virus that is the target recombinant virus for attenuation. Where one or more residues marking the attenuating mutation have been altered from a "wild-type" identity that is conserved at the corresponding amino acid position(s) in the target, human-bovine chimeric virus protein, the genome or antigenome of the target virus is recombinantly modified to encode an amino acid deletion, substitution, or insertion to alter the conserved residue(s) in the target virus protein and thereby confer an analogous, attenuated phenotype on the recombinant virus.

Within this rational design method for constructing attenuated recombinant negative stranded viruses, the wild-type identity of residue(s) at amino acid positions marking an attenuating mutation in one negative stranded RNA virus may be conserved strictly, or by conservative substitution, at the corresponding amino acid position(s) in the target, human-bovine chimeric virus protein. Thus, the corresponding residue(s) in the target virus protein may be identical, or may be conservatively related in terms of amino acid side-group structure and function, to the wild-type residue(s) found to be altered by the attenuating mutation in the heterologous, mutant virus. In either case, analogous attenuation in the recombinant virus may be achieved according to the methods of the invention by modifying the recombinant genome or antigenome of the target virus to encode the amino acid deletion, substitution, or insertion to alter the conserved residue(s).

In this context, it is preferable to modify the genome or antigenome to encode an alteration of the conserved residue(s) that corresponds conservatively to the alteration marking the attenuating mutation in the heterologous, mutant virus. For example, if an amino acid substitution marks a site of mutation in the mutant virus compared to the corresponding wild-type sequence, then a substitution should be engineered at the corresponding residue(s) in the recombinant virus. Preferably the substitution will be identical or conservative to the substitute residue present in the mutant viral protein. However, it is also possible to alter the native amino acid residue at the site of mutation non-conservatively with respect to the substitute residue in the mutant protein (e.g., by using any other amino acid to disrupt or impair the identity and function of the wild-type residue). In the case of mutations marked by deletions or insertions, these can transferred as corresponding deletions or insertions into the recombinant virus, however the particular size and amino acid sequence of the deleted or inserted protein fragment can vary.

Within alternative aspects of the invention, mutations thus transferred from heterologous mutant negative stranded viruses may confer a variety of phenotypes within human-bovine chimeric PIV of the invention, in addition to or associated with the desired, an attenuated phenotype. Thus, exemplary mutations incorporated within recombinant proteins of the virus may confer temperature sensitive (ts), cold-adapted (ca), small plaque (sp), or host range restricted (hr) phenotypes, or a change in growth or immunogenicity, in addition to or associated with the attenuated phenotype.

Attenuating mutations in biologically derived PIV and other nonsegmented negative stranded RNA viruses for incorporation within human-bovine chimeric PIV may occur naturally or may be introduced into wild-type PIV strains by well known mutagenesis procedures. For example, incompletely attenuated parental PIV strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture, as described in the above incorporated references.

By "biologically derived PIV" is meant any PIV not produced by recombinant means. Thus, biologically derived PIV include all naturally occurring PIV, including, e.g., naturally occurring PIV having a wild-type genomic sequence and PIV having allelic or mutant genomic variations from a reference wild-type RSV sequence, e.g., PIV having a mutation specifying an attenuated phenotype. Likewise, biologically derived PIV include PIV mutants derived from a parental PIV by, inter alia, artificial mutagenesis and selection procedures.

As noted above, production of a sufficiently attenuated biologically derived PIV mutant can be accomplished by several known methods. One such procedure involves subjecting a partially attenuated virus to passage in cell culture at progressively lower, attenuating temperatures. For example, partially attenuated mutants are produced by passage in cell cultures at suboptimal temperatures. Thus, a cp mutant or other partially attenuated PIV strain is adapted to efficient growth at a lower temperature by passage in culture. This selection of mutant PIV during cold-passage substantially reduces any residual virulence in the derivative strains as compared to the partially attenuated parent.

Alternatively, specific mutations can be introduced into biologically derived PIV by subjecting a partially attenuated parent virus to chemical mutagenesis, e.g., to introduce ts mutations or, in the case of viruses which are already ts, additional ts mutations sufficient to confer increased attenuation and/or stability of the ts phenotype of the attenuated derivative. Means for the introduction of ts mutations into PIV include replication of the virus in the presence of a mutagen such as 5-fluorouridine according to generally known procedures. Other chemical mutagens can also be used. Attenuation can result from a ts mutation in almost any PIV gene, although a particularly amenable target for this purpose has been found to be the polymerase (L) gene.

The level of temperature sensitivity of replication in exemplary attenuated PIV for use within the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of PIV correlate with the mutant's shutoff temperature.

The JS cp45 HPIV3 mutant has been found to be relatively stable genetically, highly immunogenic, and satisfactorily attenuated. Nucleotide sequence analysis of this biologically derived and recombinant viruses incorporating various individual and combined mutations found therein, indicates that each level of increased attenuation is associated with specific nucleotide and amino acid substitutions. The above-incorporated references also disclose how to routinely distinguish between silent incidental mutations and those responsible for phenotype differences by introducing the mutations, separately and in various combinations, into the genome or antigenome of infectious PIV clones. This process coupled with evaluation of phenotype characteristics of parental and derivative virus identifies mutations responsible for such desired characteristics as attenuation, temperature sensitivity, cold-adaptation, small plaque size, host range restriction, etc.

Mutations thus identified are compiled into a "menu" and are then introduced as desired, singly or in combination, to adjust a human-bovine chimeric PIV to an appropriate level of attenuation, immunogenicity, genetic resistance to reversion from an attenuated phenotype, etc., as desired. In accordance with the foregoing description, the ability to produce infectious PIV from cDNA permits introduction of specific engineered changes within human-bovine chimeric PIV. In particular, infectious, recombinant PIVs are employed for identification of specific mutation(s) in biologically derived, attenuated PIV strains, for example mutations which specify ts, ca, att and other phenotypes. Desired mutations are thus identified and introduced into recombinant, human-bovine chimeric PIV vaccine strains. The capability of producing virus from cDNA allows for routine incorporation of these mutations, individually or in various selected combinations, into a full-length cDNA clone, whereafter the phenotypes of rescued recombinant viruses containing the introduced mutations can be readily determined.

By identifying and incorporating specific, biologically derived mutations associated with desired phenotypes, e.g., a cp or ts phenotype, into infectious PIV clones, the invention provides for other, site-specific modifications at, or within close proximity to, the identified mutation. Whereas most attenuating mutations produced in biologically derived PIV are single nucleotide changes, other "site specific" mutations can also be incorporated by recombinant techniques into biologically derived or recombinant PIV. As used herein, site-specific mutations include insertions, substitutions, deletions or rearrangements of from 1 to 3, up to about 5-15 or more altered nucleotides (e.g., altered from a wild-type PIV sequence, from a sequence of a selected mutant PIV strain, or from a parent recombinant PIV clone subjected to mutagenesis). Such site-specific mutations may be incorporated at, or within the region of, a selected, biologically derived point mutation. Alternatively, the mutations can be introduced in various other contexts within a PIV clone, for example at or near a cis-acting regulatory sequence or nucleotide sequence encoding a protein active site, binding site, immunogenic epitope, etc. Site-specific PIV mutants typically retain a desired attenuating phenotype, but may additionally exhibit altered phenotypic characteristics unrelated to attenuation, e.g., enhanced or broadened immunogenicity, and/or improved growth. Further examples of desired, site-specific mutants include recombinant PIV designed to incorporate additional, stabilizing nucleotide mutations in a codon specifying an attenuating point mutation. Where possible, two or more nucleotide substitutions are introduced at codons that specify attenuating amino acid changes in a parent mutant or recombinant PIV clone, yielding a biologically derived or recombinant PIV having genetic resistance to reversion from an attenuated phenotype. In other embodiments, site-specific nucleotide substitutions, additions, deletions or rearrangements are introduced upstream (N-terminal direction) or downstream (C-terminal direction), e.g., from 1 to 3, 5-10 and up to 15 nucleotides or more 5' or 3', relative to a targeted nucleotide position, e.g., to construct or ablate an existing cis-acting regulatory element.

In addition to single and multiple point mutations and site-specific mutations, changes to the human-bovine chimeric PIV disclosed herein include deletions, insertions, substitutions or rearrangements of one or more gene(s) or genome segment(s). Particularly useful are deletions involving one or more gene(s) or genome segment(s), which deletions have been shown to yield additional desired phenotypic effects for adjusting the characteristics of human-bovine chimeric PIV within the invention. Thus, U.S. patent application Ser. No. 09/350,821, filed by Durbin et al. on Jul. 9, 1999) describes methods and compositions whereby expression of one or more HPIV genes, exemplified by the C, D, and/or V ORFs, is reduced or ablated by modifying the PIV genome or antigenome to incorporate a mutation that alters the coding assignment of an initiation codon or mutation(s) that introduce one or one or more stop codon(s). Alternatively, one or more of the C, D, and/or V ORFs can be deleted in whole or in part to render the corresponding protein(s) partially or entirely non-functional or to disrupt protein expression altogether. Recombinant PIV having such mutations in C, D, and/or V, or other non-essential gene(s), possess highly desirable phenotypic characteristics for vaccine development. For example, these modifications may specify one or more desired phenotypic changes including (i) altered growth properties in cell culture, (ii) attenuation in the upper and/or lower respiratory tract of mammals, (iii) a change in viral plaque size, (iv) a change in cytopathic effect, and (v) a change in immunogenicity. One such exemplary "knock out" mutant lacking C ORF expression, designated rC-KO, was able to induce a protective immune response against wild type HPIV3 challenge in a non-human primate model despite its beneficial attenuation phenotype.

Thus, in more detailed aspects of the instant invention, human-bovine chimeric PIV incorporate deletion or knock out mutations in a C, D, and/or V ORF(s) which alters or ablates expression of the selected gene(s) or genome segment(s). This can be achieved, e.g., by introducing a frame shift mutation or termination codon within a selected coding sequence, altering translational start sites, changing the position of a gene or introducing an upstream start codon to alter its rate of expression, changing GS and/or GE transcription signals to alter phenotype, or modifying an RNA editing site (e.g., growth, temperature restrictions on transcription, etc.). In more detailed aspects of the invention, human-bovine chimeric PIVs are provided in which expression of one or more gene(s), e.g., a C, D, and/or V ORF(s), is ablated at the translational or transcriptional level without deletion of the gene or of a segment thereof, by, e.g., introducing multiple translational termination codons into a translational open reading frame (ORF), altering an initiation codon, or modifying an editing site. These forms of knock-out virus will often exhibit reduced growth rates and small plaque sizes in tissue culture. Thus, these methods provide yet additional, novel types of attenuating mutations which ablate expression of a viral gene that is not one of the major viral protective antigens. In this context, knock-out virus phenotypes produced without deletion of a gene or genome segment can be alternatively produced by deletion mutagenesis, as described, to effectively preclude correcting mutations that may restore synthesis of a target protein. Several other gene knock-outs for the C, D, and/or V ORF(s) deletion and knock out mutants can be made using alternate designs and methods that are well known in the art (as described, for example, in (Kretschmer et al., *Virology* 216:309-316, 1996; Radecke et al., *Virology* 217:418-421, 1996; and Kato et al., 1987a, supra; and Schneider et al., 1997, supra; each incorporated herein by reference).

These and other nucleotide modifications in human-bovine chimeric PIV may alter small numbers of bases (e.g., from 15-30 bases, up to 35-50 bases or more), large blocks of nucleotides (e.g., 50-100, 100-300, 300-500, 500-1,000 bases), or nearly complete or complete genes (e.g., 1,000-1, 500 nucleotides, 1,500-2,500 nucleotides, 2,500-5,000, nucleotides, 5,000-6,5000 nucleotides or more) in the donor or recipient genome or antigenome, depending upon the nature of the change (i.e., a small number of bases may be changed to insert or ablate an immunogenic epitope or change a small genome segment, whereas large block(s) of bases are involved when genes or large genome segments are added, substituted, deleted or rearranged.

In related aspects, the invention provides for supplementation of mutations adopted into a recombinant PIV clone from biologically derived PIV, e.g., cp and ts mutations, with additional types of mutations involving the same or different genes in a further modified PIV clone. Each of the PIV genes can be selectively altered in terms of expression levels, or can be added, deleted, substituted or rearranged, in whole or in part, alone or in combination with other desired modifications, to yield a human-bovine chimeric PIV exhibiting novel vaccine characteristics. Thus, in addition to or in combination with attenuating mutations adopted from biologically derived PIV mutants, the present invention also provides a range of additional methods for attenuating or otherwise modifying the phenotype of human-bovine chimeric PIV based on recombinant engineering of infectious PIV clones. A variety of alterations can be produced in an isolated polynucleotide sequence encoding a targeted gene or genome segment, including a donor or recipient gene or genome segment in a chimeric PIV genome or antigenome for incorporation into infectious clones. More specifically, to achieve desired structural and phenotypic changes in recombinant PIV, the invention allows for introduction of modifications which delete, substitute, introduce, or rearrange a selected nucleotide or plurality of nucleotides from a parent genome or antigenome, as well as mutations which delete, substitute, introduce or rearrange whole gene(s) or genome segment(s), within a human-bovine chimeric PIV clone.

Thus provided are modifications in the human-bovine chimeric PIV which simply alter or ablate expression of a selected gene, e.g., by introducing a termination codon within a selected PIV coding sequence or altering its translational start site or RNA editing site, changing the position of a PIV gene relative to an operably linked promoter, introducing an upstream start codon to alter rates of expression, modifying (e.g., by changing position, altering an existing sequence, or substituting an existing sequence with a heterologous sequence) GS and/or GE transcription signals to alter phenotype (e.g., growth, temperature restrictions on transcription, etc.), and various other deletions, substitutions, additions and rearrangements that specify quantitative or qualitative changes in viral replication, transcription of selected gene(s), or translation of selected RNA(s). In this context, any PIV gene or genome segment which is not essential for growth can be ablated or otherwise modified in a recombinant PIV to yield desired effects on virulence, pathogenesis, immunogenicity and other phenotypic characters. As for coding sequences, noncoding, leader, trailer and intergenic regions can be similarly deleted, substituted or modified and their phenotypic effects readily analyzed, e.g., by the use of minireplicons and recombinant PIV.

In addition, a variety of other genetic alterations can be produced in a PIV genome or antigenome for incorporation into human-bovine chimeric PIV, alone or together with one or more attenuating mutations adopted from a biologically derived mutant PIV, e.g., to adjust growth, attenuation, immunogenicity, genetic stability or provide other advantageous structural and/or phenotypic effects. These additional types of mutations are also disclosed in the foregoing incorporated references and can be readily engineered into human-bovine chimeric PIV of the invention. For example, restriction site markers are routinely introduced within the human-bovine chimeric PIV antigenome or genome to facilitate cDNA construction and manipulation.

In addition to these changes, the order of genes in a human-bovine chimeric PIV can be changed, a PIV genome promoter replaced with its antigenome counterpart, portions of genes removed or substituted, and even entire genes deleted. Different or additional modifications in the sequence can be made to facilitate manipulations, such as the insertion of unique restriction sites in various intergenic regions or elsewhere. Nontranslated gene sequences can be removed to increase capacity for inserting foreign sequences.

Other mutations for incorporation into human-bovine chimeric PIV of the invention include mutations directed toward cis-acting signals, which can be identified, e.g., by mutational analysis of PIV minigenomes. For example, insertional and deletional analysis of the leader and trailer and flanking sequences identifies viral promoters and transcription signals and provides a series of mutations associated with varying degrees of reduction of RNA replication or transcription. Saturation mutagenesis (whereby each position in turn is modified to each of the nucleotide alternatives) of these cis-acting signals also has identified many mutations which affect RNA replication or transcription. Any of these mutations can be inserted into a human-bovine chimeric PIV antigenome or genome as described herein. Evaluation and manipulation of trans-acting proteins and cis-acting RNA sequences using the complete antigenome cDNA is assisted by the use of PIV minigenomes as described in the above-incorporated references.

Additional mutations within the human-bovine chimeric PIV involve replacement of the 3' end of genome with its counterpart from antigenome, which is associated with changes in RNA replication and transcription. In one exemplary embodiment, the level of expression of specific PIV proteins, such as the protective HN and/or F antigens, can be increased by substituting the natural sequences with ones which have been made synthetically and designed to be consistent with efficient translation. In this context, it has been shown that codon usage can be a major factor in the level of translation of mammalian viral proteins (Hans et al., *Current Biol.* 6:315-324, 1996, incorporated herein by reference). Optimization by recombinant methods of the codon usage of the mRNAs encoding the HN and F proteins of PIV, which are the major protective antigens, will provide improved expression for these genes.

In another exemplary embodiment, a sequence surrounding a translational start site (preferably including a nucleotide in the −3 position) of a selected PIV gene is modified, alone or in combination with introduction of an upstream start codon, to modulate PIV gene expression by specifying up- or down-regulation of translation (Kozak et al., *J. Mol. Biol.* 196:947-950, 1987, incorporated herein by reference). Alternatively, or in combination with other PIV modifications disclosed herein, gene expression of a human-bovine chimeric PIV can be modulated by altering a transcriptional GS or GE signal of any selected gene(s) of the virus. In alternative embodiments, levels of gene expression in the human-bovine chimeric PIV are modified at the level of transcription.

In one aspect of the invention, the position of a selected gene in the PIV gene map can be changed to a more promoter-proximal or promotor-distal position, whereby the gene will be expressed more or less efficiently, respectively (see, U.S. Provisional Patent Application Ser. No. 60/213,708 entitled RESPIRATORY SYNCYTIAL VIRUS VACCINES EXPRESSING PROTECTIVE ANTIGENS FROM PROMOTER-PROXIMAL GENES, filed by Krempl et al. on Jun. 23, 2000, incorporated herein by reference). According to this aspect, modulation of expression for specific genes can be achieved yielding reductions or increases of gene expression from two-fold, more typically four-fold, up to ten-fold or more compared to wild-type levels often attended by a commensurate decrease in expression levels for reciprocally, positionally substituted genes. These and other transpositioning changes yield novel human-bovine chimeric PIV having attenuated phenotypes, for example due to decreased expression of selected viral proteins involved in RNA replication, or having other desirable properties such as increased antigen expression. In one embodiment, one or more of the PIV N, P, M, HN and/or F gene(s), or genome segment(s), is/are shifted to a more promoter-proximal or promoter-distal location in the chimeric genome or antigenome (e.g., by inserting, deleting or rearranging one or more polynucleotides in the background genome or antigenome, which may or may not involve the heterologous gene or genome segment as a "displacement polynucleotide") compared to the wild type position(s) of the subject gene(s) or genome segment(s) within the recombinant or background genome or antigenome.

Infectious human-bovine chimeric PIV clones of the invention can also be engineered according to the methods and compositions disclosed herein to enhance immunogenicity and induce a level of protection greater than that provided by infection with a wild-type PIV or a parent PIV. For example, an immunogenic epitope from a heterologous PIV strain or type, or from a non-PIV source such as RSV, can be added to a recombinant clone by appropriate nucleotide changes in the polynucleotide sequence encoding the genome or antigenome. Alternatively, mutant PIV of the invention can be engineered to add or ablate (e.g., by amino acid insertion, substitution or deletion) immunogenic proteins, protein domains, or forms of specific proteins associated with desirable or undesirable immunological reactions.

Within the methods of the invention, additional genes or genome segments may be inserted into or proximate to the human-bovine chimeric PIV genome or antigenome. These genes may be under common control with recipient genes, or may be under the control of an independent set of transcription signals. Genes of interest include the PIV genes identified above, as well as non-PIV genes. Non-PIV genes of interest include those encoding cytokines (e.g., IL-2 through IL-18, especially IL-2, IL-6 and IL-12, IL-18, etc.). Gamma-interferon, and proteins rich in T helper cell epitopes. These additional proteins can be expressed either as a separate protein, or as a supernumerary copy of an existing PIV proteins, such as HN or F. This provides the ability to modify and improve the immune responses against PIV both quantitatively and qualitatively.

Deletions, insertions, substitutions and other mutations involving changes of whole viral genes or genome segments within a human-bovine chimeric PIV yield highly stable vaccine candidates, which are particularly important in the case of immunosuppressed individuals. Many of these changes will result in attenuation of resultant vaccine strains, whereas others will specify different types of desired phenotypic changes. For example, accessory (i.e., not essential for in vitro growth) genes are excellent candidates to encode proteins that specifically interfere with host immunity (see, e.g., Kato et al., 1997a, supra). Ablation of such genes in vaccine viruses is expected to reduce virulence and pathogenesis and/or improve immunogenicity.

In another aspect of the invention, compositions (e.g., isolated polynucleotides and vectors incorporating human-bovine chimeric PIV-encoding cDNA) are provided for producing an isolated infectious PIV. Using these compositions and methods, infectious PIV are generated from a PIV genome or antigenome, a nucleocapsid (N) protein, a nucleocapsid phosphoprotein (P), and a large (L) polymerase protein. In related aspects of the invention, compositions and methods are provided for introducing the aforementioned structural and phenotypic changes into a recombinant PIV to yield infectious, attenuated vaccine viruses.

Introduction of the foregoing defined mutations into an infectious, human-bovine chimeric PIV clone can be achieved by a variety of well known methods. By "infectious clone" with regard to DNA is meant cDNA or its product, synthetic or otherwise, which can be transcribed into genomic or antigenomic RNA capable of serving as template to produce the genome of an infectious virus or subviral particle.

Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA as described herein has the advantage that each region can be manipulated separately (smaller cDNAs are easier to manipulate than large ones) and then readily assembled into a complete cDNA. Thus, the complete antigenome or genome cDNA, or any subfragment thereof can be used as template for oligonucleotide-directed mutagenesis. This can be through the intermediate of a single-stranded phagemid form, such as using the Muta-gene® kit of Bio-Rad Laboratories (Richmond, Calif.) or a method using a double-stranded plasmid directly as template such as the Chameleon mutagenesis kit of Stratagene (La Jolla, Calif.), or by the polymerase chain reaction employing either an oligonucleotide primer or template which contains the mutation(s) of interest. A mutated subfragment can then be assembled into the complete antigenome or genome cDNA. A variety of other mutagenesis techniques are known and available for use in producing the mutations of interest in the PIV antigenome or genome cDNA. Mutations can vary from single nucleotide changes to replacement of large cDNA pieces containing one or more genes or genome regions.

Thus, in one illustrative embodiment mutations are introduced by using the Muta-gene phagemid in vitro mutagenesis kit available from Bio-Rad. In brief, cDNA encoding a portion of a PIV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome fragment is then amplified and the mutated piece is then reintroduced into the full-length genome or antigenome clone.

Infectious PIV of the invention are produced by intracellular or cell-free coexpression of one or more isolated polynucleotide molecules that encode a PIV genome or antigenome RNA, together with one or more polynucleotides encoding viral proteins necessary to generate a transcribing, replicating nucleocapsid. Among the viral proteins useful for coexpression to yield infectious PIV are the major nucleocapsid protein (N) protein, nucleocapsid phosphoprotein (P), large (L) polymerase protein, fusion protein (F), hemagglutinin-neuraminidase glycoprotein (HN), and matrix (M) protein. Also useful in this context are products of the C, D and V ORFs of PIV.

cDNAs encoding a PIV genome or antigenome are constructed for intracellular or in vitro coexpression with the necessary viral proteins to form infectious PIV. By "PIV antigenome" is meant an isolated positive-sense polynucleotide molecule which serves as a template for synthesis of progeny PIV genome. Preferably a cDNA is constructed which is a positive-sense version of the PIV genome corresponding to the replicative intermediate RNA, or antigenome, so as to minimize the possibility of hybridizing with positive-sense transcripts of complementing sequences encoding proteins necessary to generate a transcribing, replicating nucleocapsid.

In some embodiments of the invention the genome or antigenome of a recombinant PIV (rPIV) need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule. In other embodiments, the PIV genome or antigenome encodes all functions necessary for viral growth, replication, and infection without the participation of a helper virus or viral function provided by a plasmid or helper cell line.

By "recombinant PIV" is meant a PIV or PIV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in PIV gene expression, for example, a promoter, a structural or coding sequence which is transcribed into PIV RNA, and appropriate transcription initiation and termination sequences.

To produce infectious PIV from a cDNA-expressed PIV genome or antigenome, the genome or antigenome is coexpressed with those PIV N, P and L proteins necessary to (i) produce a nucleocapsid capable of RNA replication, and (ii) render progeny nucleocapsids competent for both RNA replication and transcription. Transcription by the genome nucleocapsid provides the other PIV proteins and initiates a productive infection. Alternatively, additional PIV proteins needed for a productive infection can be supplied by coexpression.

Synthesis of PIV antigenome or genome together with the above-mentioned viral proteins can also be achieved in vitro (cell-free), e.g., using a combined transcription-translation reaction, followed by transfection into cells. Alternatively, antigenome or genome RNA can be synthesized in vitro and transfected into cells expressing PIV proteins.

In certain embodiments of the invention, complementing sequences encoding proteins necessary to generate a transcribing, replicating PIV nucleocapsid are provided by one or more helper viruses. Such helper viruses can be wild type or mutant. Preferably, the helper virus can be distinguished phenotypically from the virus encoded by the PIV cDNA. For example, it is desirable to provide monoclonal antibodies which react immunologically with the helper virus but not the virus encoded by the PIV cDNA. Such antibodies can be neutralizing antibodies. In some embodiments, the antibodies can be used in affinity chromatography to separate the helper virus from the recombinant virus. To aid the procurement of such antibodies, mutations can be introduced into the PIV cDNA to provide antigenic diversity from the helper virus, such as in the HN or F glycoprotein genes.

In alternate embodiments of the invention, the N, P, L and other desired PIV proteins are encoded by one or more nonviral expression vectors, which can be the same or separate from that which encodes the genome or antigenome. Additional proteins may be included as desired, each encoded by its own vector or by a vector encoding one or more of the N, P, L and other desired PIV proteins, or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., *Virology* 210:202-205, 1995, incorporated herein by reference in its entirety). The viral proteins, and/or T7 RNA polymerase, can also be provided by transformed mammalian cells or by transfection of preformed mRNA or protein.

A PIV antigenome may be constructed for use in the present invention by, e.g., assembling cloned cDNA segments, representing in aggregate the complete antigenome, by polymerase chain reaction or the like (PCR; described in, e.g., U.S. Pat. Nos. 4,683,195 and 4,683,202, and *PCR Protocols: A Guide to Methods and Applications*, Innis et al., eds., Academic Press, San Diego, 1990; each incorporated herein by reference in its entirety) of reverse-transcribed copies of PIV mRNA or genome RNA. For example, a first construct is generated which comprises cDNAs containing the left hand end of the antigenome, spanning from an appropriate promoter (e.g., T7 RNA polymerase promoter) and assembled in an appropriate expression vector, such as a plasmid, cosmid, phage, or DNA virus vector. The vector may be modified by mutagenesis and/or insertion of synthetic polylinker containing unique restriction sites designed to facilitate assembly. For ease of preparation the N, P, L and other desired PIV proteins can be assembled in one or more separate vectors. The right hand end of the antigenome plasmid may contain additional sequences as desired, such as a flanking ribozyme and tandem T7 transcriptional terminators. The ribozyme can be hammerhead type (e.g., Grosfeld et al., *J. Virol.* 69:5677-5686, 1995), which would yield a 3' end containing a single nonviral nucleotide, or can be any of the other suitable ribozymes such as that of hepatitis delta virus (Perrotta et al., *Nature* 350:434-436, 1991), incorporated herein by reference in its entirety) which would yield a 3' end free of non-PIV nucleotides. The left- and right-hand ends are then joined via a common restriction site.

A variety of nucleotide insertions, deletions and rearrangements can be made in the PIV genome or antigenome during or after construction of the cDNA. For example, specific desired nucleotide sequences can be synthesized and inserted at appropriate regions in the cDNA using convenient restriction enzyme sites. Alternatively, such techniques as site-specific mutagenesis, alanine scanning, PCR mutagenesis, or other such techniques well known in the art can be used to introduce mutations into the cDNA.

Alternative means to construct cDNA encoding the genome or antigenome include reverse transcription-PCR using improved PCR conditions (e.g., as described in Cheng et al., *Proc. Natl. Acad. Sci. USA* 91:5695-5699, 1994, incorporated herein by reference) to reduce the number of subunit cDNA components to as few as one or two pieces. In other embodiments different promoters can be used (e.g., T3, SP6) or different ribozymes (e.g., that of hepatitis delta virus. Different DNA vectors (e.g., cosmids) can be used for propagation to better accommodate the larger size genome or antigenome.

Isolated polynucleotides (e.g., cDNA) encoding the genome or antigenome may be inserted into appropriate host cells by transfection, electroporation, mechanical insertion, transduction or the like, into cells which are capable of supporting a productive PIV infection, e.g., HEp-2, FRhL-DBS2, LLC-MK2, MRC-5, and Vero cells. Transfection of isolated polynucleotide sequences may be introduced into cultured cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841-845, 1982), DEAE-dextran mediated transfection (Ausubel et al., ed., *Current Protocols in Molecular Biology*, John Wiley and Sons, Inc., New York, 1987), cationic lipid-mediated transfection (Hawley-Nelson et al., *Focus* 15:73-79, 1993) or a commercially available transfection regent, e.g., LipofectACE® (Life Technologies, Gaithersburg, Md.) or the like (each of the foregoing references are incorporated herein by reference in its entirety).

As noted above, in some embodiments of the invention the N, P, L and other desired PIV proteins are encoded by one or more helper viruses which is phenotypically distinguishable from that which encodes the genome or antigenome. The N, P, L and other desired PIV proteins can also be encoded by one or more expression vectors which can be the same or separate from that which encodes the genome or antigenome, and various combinations thereof. Additional proteins may be included as desired, encoded by its own vector or by a vector encoding one or more of the N, P, L and other desired PIV proteins, or the complete genome or antigenome.

By providing infectious clones of PIV the invention permits a wide range of alterations to be recombinantly produced within the PIV genome (or antigenome), yielding defined mutations which specify desired phenotypic changes. By "infectious clone" is meant cDNA or its product, synthetic or otherwise, RNA capable of being directly incorporated into infectious virions which can be transcribed into genomic or antigenomic RNA capable of serving as a template to produce the genome of infectious viral or subviral particles. As noted above, defined mutations can be introduced by a variety of conventional techniques (e.g., site-directed mutagenesis) into a cDNA copy of the genome or antigenome. The use of genomic or antigenomic cDNA subfragments to assemble a complete genome or antigenome cDNA as described herein has the advantage that each region can be manipulated separately, where small cDNA subjects provide for better ease of manipulation than large cDNA subjects, and then readily assembled into a complete cDNA. Thus, the complete antigenome or genome cDNA, or a selected subfragment thereof, can be used as a template for oligonucleotide-directed mutagenesis. This can be through the intermediate of a single-stranded phagemid form, such as using the MUTA-gene® kit of Bio-Rad Laboratories (Richmond, Calif.), or a method using the double-stranded plasmid directly as a template such as the Chameleon® mutagenesis kit of Strategene (La Jolla, Calif.), or by the polymerase chain reaction employing either an oligonucleotide primer or a template which contains the mutation(s) of interest. A mutated subfragment can then be assembled into the complete antigenome or genome cDNA. A variety of other mutagenesis techniques are known and can be routinely adapted for use in producing the mutations of interest in a PIV antigenome or genome cDNA of the invention.

Thus, in one illustrative embodiment mutations are introduced by using the MUTA-gene® phagemid in vitro mutagenesis kit available from Bio-Rad Laboratories. In brief, cDNA encoding an PIV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome is then amplified.

Mutations can vary from single nucleotide changes to the introduction, deletion or replacement of large cDNA segments containing one or more genes or genome segments. Genome segments can correspond to structural and/or functional domains, e.g., cytoplasmic, transmembrane or ectodomains of proteins, active sites such as sites that mediate binding or other biochemical interactions with different proteins, epitopic sites, e.g., sites that stimulate antibody binding and/or humoral or cell mediated immune responses, etc. Useful genome segments in this regard range from about 15-35 nucleotides in the case of genome segments encoding small functional domains of proteins, e.g., epitopic sites, to about 50, 75, 100, 200-500, and 500-1,500 or more nucleotides.

The ability to introduce defined mutations into infectious PIV has many applications, including the manipulation of PIV pathogenic and immunogenic mechanisms. For example, the functions of PIV proteins, including the N, P, M, F, HN, and L proteins and C, D and V ORF products, can be manipulated by introducing mutations which ablate or reduce the level of protein expression, or which yield mutant protein. Various genome RNA structural features, such as promoters, intergenic regions, and transcription signals, can also be routinely manipulated within the methods and compositions of the invention. The effects of trans-acting proteins and cis-acting RNA sequences can be readily determined, for example, using a complete antigenome cDNA in parallel assays employing PIV minigenomes (Dimock et al., *J. Virol.* 67:2772-2778, 1993, incorporated herein by reference in its entirety), whose rescue-dependent status is useful in characterizing those mutants that may be too inhibitory to be recovered in replication-independent infectious virus.

Certain substitutions, insertions, deletions or rearrangements of genes or genome segments within recombinant PIV of the invention (e.g., substitutions of a genome segment encoding a selected protein or protein region, for instance a cytoplasmic tail, transmembrane domain or ectodomain, an epitopic site or region, a binding site or region, an active site or region containing an active site, etc.) are made in structural or functional relation to an existing, "counterpart" gene or genome segment from the same or different PIV or other source. Such modifications yield novel recombinants having desired phenotypic changes compared to wild-type or parental PIV or other viral strains. For example, recombinants of this type may express a chimeric protein having a cytoplasmic tail and/or transmembrane domain of one PIV fused to an ectodomain of another PIV. Other exemplary recombinants of this type express duplicate protein regions, such as duplicate immunogenic regions.

As used herein, "counterpart" genes, genome segments, proteins or protein regions, are typically from heterologous sources (e.g., from different PIV genes, or representing the same (i.e., homologous or allelic) gene or genome segment in different PIV types or strains). Typical counterparts selected in this context share gross structural features, e.g., each counterpart may encode a comparable protein or protein structural domain, such as a cytoplasmic domain, transmembrane domain, ectodomain, binding site or region, epitopic site or region, etc. Counterpart domains and their encoding genome segments embrace an assemblage of species having a range of size and sequence variations defined by a common biological activity among the domain or genome segment variants.

Counterpart genes and genome segments, as well as other polynucleotides disclosed herein for producing recombinant PIV within the invention, often share substantial sequence identity with a selected polynucleotide "reference sequence," e.g., with another selected counterpart sequence. As used herein, a "reference sequence" is a defined sequence used as a basis for sequence comparison, for example, a segment of a full-length cDNA or gene, or a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences.

Optimal alignment of sequences for aligning a comparison window may be conducted by the local homology algorithm of Smith & Waterman (*Adv. Appl. Math.* 2:482, 1981; incorporated herein by reference), by the homology alignment algorithm of Needleman & Wunsch, (*J. Mol. Biol*, 48:443, 1970; incorporated herein by reference), by the search for similarity method of Pearson & Lipman, (*Proc. Natl. Acad. Sci. USA* 85:2444, 1988; incorporated herein by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

In addition to these polynucleotide sequence relationships, proteins and protein regions encoded by recombinant PIV of the invention are also typically selected to have conservative relationships, i.e. to have substantial sequence identity or sequence similarity, with selected reference polypeptides. As applied to polypeptides, the term "sequence identity" means peptides share identical amino acids at corresponding positions. The term "sequence similarity" means peptides have identical or similar amino acids (i.e., conservative substitutions) at corresponding positions. The term "substantial sequence identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). The term "substantial similarity" means that two peptide sequences share corresponding percentages of sequence similarity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Abbreviations for the twenty naturally occurring amino acids used herein follow conventional usage (*Immunology—A Synthesis,* 2nd ed., E. S. Golub & D. R. Gren, eds., Sinauer Associates, Sunderland, Mass., 1991, incorporated herein by reference). Stereoisomers (e.g., D-amino acids) of the twenty conventional amino acids, unnatural amino acids such as α, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). Moreover, amino acids may be modified by glycosylation, phosphorylation and the like.

To select candidate vaccine viruses according to the invention, the criteria of viability, attenuation and immunogenicity are determined according to well known methods. Viruses which will be most desired in vaccines of the invention must maintain viability, have a stable attenuation phenotype, exhibit replication in an immunized host (albeit at lower levels), and effectively elicit production of an immune response in a vaccinee sufficient to confer protection against serious disease caused by subsequent infection from wild-type virus. The recombinant PIV of the invention are not only viable and more appropriately attenuated than previous vaccine candidates, but are more stable genetically in vitro—retaining the ability to stimulate a protective immune response and in some instances to expand the protection afforded by multiple modifications, e.g., induce protection against different viral strains or subgroups, or protection by a different immunologic basis, e.g., secretory versus serum immunoglobulins, cellular immunity, and the like.

Recombinant PIV of the invention can be tested in various well known and generally accepted in vitro and in vitro models to confirm adequate attenuation, resistance to phenotypic reversion, and immunogenicity for vaccine use. In in vitro assays, the modified virus (e.g., a multiply attenuated, biologically derived or recombinant PIV) is tested, e.g., for temperature sensitivity of virus replication, i.e. ts phenotype, and for the small plaque or other desired phenotype. Modified viruses are further tested in animal models of PIV infection. A variety of animal models have been described and are summarized in various references incorporated herein. PIV model systems, including rodents and non-human primates, for evaluating attenuation and immunogenic activity of PIV vaccine candidates are widely accepted in the art, and the data obtained therefrom correlate well with PIV infection, attenuation and immunogenicity in humans.

In accordance with the foregoing description, the invention also provides isolated, infectious recombinant PIV viral compositions for vaccine use. The attenuated virus which is a component of a vaccine is in an isolated and typically purified form. By isolated is meant to refer to PIV which is in other than a native environment of a wild-type virus, such as the nasopharynx of an infected individual. More generally, isolated is meant to include the attenuated virus as a component of a cell culture or other artificial medium where it can be propagated and characterized in a controlled setting. For example, attenuated PIV of the invention may be produced by an infected cell culture, separated from the cell culture and added to a stabilizer.

For vaccine use, recombinant PIV produced according to the present invention can be used directly in vaccine formulations, or lyophilized, as desired, using lyophilization protocols well known to the artisan. Lyophilized virus will typically be maintained at about 4° C. When ready for use the lyophilized virus is reconstituted in a stabilizing solution, e.g., saline or comprising SPG, $Mg^{++}$ and HEPES, with or without adjuvant, as further described below.

PIV vaccines of the invention contain as an active ingredient an immunogenically effective amount of PIV produced as described herein. The modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, MPL™ (3-o-deacylated monophosphoryl lipid A; RIBI ImmunoChem Research, Inc., Hamilton, Mont.) and IL-12 (Genetics Institute, Cambridge Mass.), among many other suitable adjuvants well known in the art.

Upon immunization with a PIV composition as described herein, via aerosol, droplet, oral, topical or other route, the immune system of the host responds to the vaccine by producing antibodies specific for PIV virus proteins, e.g., F and HN glycoproteins. As a result of the vaccination with an immunogenically effective amount of PIV produced as described herein, the host becomes at least partially or completely immune to PIV infection, or resistant to developing moderate or severe PIV infection, particularly of the lower respiratory tract.

The host to which the vaccines are administered can be any mammal which is susceptible to infection by PIV or a closely related virus and which host is capable of generating a protective immune response to the antigens of the vaccinizing strain. Accordingly, the invention provides methods for creating vaccines for a variety of human and veterinary uses.

The vaccine compositions containing the PIV of the invention are administered to a host susceptible to or otherwise at risk for PIV infection to enhance the host's own immune response capabilities. Such an amount is defined to be a "immunogenically effective dose." In this use, the precise amount of PIV to be administered within an effective dose will depend on the host's state of health and weight, the mode of administration, the nature of the formulation, etc., but will generally range from about $10^3$ to about $10^7$ plaque forming units (PFU) or more of virus per host, more commonly from about $10^4$ to $10^6$ PFU virus per host. In any event, the vaccine formulations should provide a quantity of modified PIV of the invention sufficient to effectively protect the host patient against serious or life-threatening PIV infection.

The PIV produced in accordance with the present invention can be combined with viruses of other PIV serotypes or strains to achieve protection against multiple PIV serotypes or strains. Alternatively, protection against multiple PIV serotypes or strains can be achieved by combining protective epitopes of multiple serotypes or strains engineered into one virus, as described herein. Typically when different viruses are administered they will be in admixture and administered simultaneously, but they may also be administered separately. Immunization with one strain may protect against different strains of the same or different serotype.

In some instances it may be desirable to combine the PIV vaccines of the invention with vaccines which induce protective responses to other agents, particularly other childhood viruses. In another aspect of the invention the PIV can be employed as a vector for protective antigens of other pathogens, such as respiratory syncytial virus (RSV) or measles virus, by incorporating the sequences encoding those protective antigens into the PIV genome or antigenome which is used to produce infectious PIV, as described herein (see, e.g., U.S. Provisional Patent Application Ser. No. 60/170,195, filed Dec. 10, 1999 by Murphy et al., incorporated herein by reference).

In all subjects, the precise amount of recombinant PIV vaccine administered, and the timing and repetition of administration, will be determined based on the patient's state of health and weight, the mode of administration, the nature of the formulation, etc. Dosages will generally range from about $10^3$ to about $10^7$ plaque forming units (PFU) or more of virus per patient, more commonly from about $10^4$ to $10^6$ PFU virus per patient. In any event, the vaccine formulations should provide a quantity of attenuated PIV sufficient to effectively stimulate or induce an anti-PIV immune response, e.g., as can be determined by complement fixation, plaque neutralization, and/or enzyme-linked immunosorbent assay, among other methods. In this regard, individuals are also monitored for signs and symptoms of upper respiratory illness. As with administration to rhesus monkeys, the attenuated virus of the vaccine grows in the nasopharynx of vaccinees at levels approximately 10-fold or more lower than wild-type virus, or approximately 10-fold or more lower when compared to levels of incompletely attenuated PIV.

In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) PIV infection. Similarly, adults who are particularly susceptible to repeated or serious PIV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered PIV strain expressing a cytokine or an additional protein rich in T cell epitopes may be particularly advantageous for adults rather than for infants.

PIV vaccines produced in accordance with the present invention can be combined with viruses expressing antigens of another subgroup or strain of PIV to achieve protection against multiple PIV subgroups or strains. Alternatively, the vaccine virus may incorporate protective epitopes of multiple PIV strains or subgroups engineered into one PIV clone, as described herein.

The PIV vaccines of the invention elicit production of an immune response that is protective against serious lower respiratory tract disease, such as pneumonia and bronchiolitis when the individual is subsequently infected with wild-type PIV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there are detectable levels of host-engendered serum and secretory antibodies which are capable of neutralizing homologous (of the same subgroup) wild-type virus in vitro and in vitro. In many instances the host antibodies will also neutralize wild-type virus of a different, non-vaccine subgroup.

Preferred PIV vaccine candidates of the invention exhibit a very substantial diminution of virulence when compared to wild-type virus that is circulating naturally in humans. The virus is sufficiently attenuated so that symptoms of infection will not occur in most immunized individuals. In some instances the attenuated virus may still be capable of dissemination to unvaccinated individuals. However, its virulence is sufficiently abrogated such that severe lower respiratory tract infections in the vaccinated or incidental host do not occur.

The level of attenuation of PIV vaccine candidates may be determined by, for example, quantifying the amount of virus present in the respiratory tract of an immunized host and comparing the amount to that produced by wild-type PIV or other attenuated PIV which have been evaluated as candidate vaccine strains. For example, the attenuated virus of the invention will have a greater degree of restriction of replication in the upper respiratory tract of a highly susceptible host, such as a chimpanzee or rhesus monkey, compared to the levels of replication of wild-type virus, e.g., 10- to 1000-fold less. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of PIV in the nasopharynx of an infected host are well known in the literature.

Levels of induced immunity provided by the vaccines of the invention can also be monitored by measuring amounts of neutralizing secretory and serum antibodies. Based on these measurements, vaccine dosages can be adjusted or vaccinations repeated as necessary to maintain desired levels of protection. Further, different vaccine viruses may be advantageous for different recipient groups. For example, an engineered PIV strain expressing an additional protein rich in T cell epitopes may be particularly advantageous for adults rather than for infants.

In yet another aspect of the invention the PIV is employed as a vector for transient gene therapy of the respiratory tract. According to this embodiment the recombinant PIV genome or antigenome incorporates a sequence which is capable of encoding a gene product of interest. The gene product of interest is under control of the same or a different promoter from that which controls PIV expression. The infectious PIV produced by coexpressing the recombinant PIV genome or antigenome with the N, P, L and other desired PIV proteins, and containing a sequence encoding the gene product of interest, is administered to a patient. Administration is typically by aerosol, nebulizer, or other topical application to the respiratory tract of the patient being treated. Recombinant PIV is administered in an amount sufficient to result in the expression of therapeutic or prophylactic levels of the desired gene product. Representative gene products which may be administered within this method are preferably suitable for transient expression, including, for example, interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

The following examples are provided by way of illustration, not limitation.

Example I

Construction of cDNAs Encoding a Chimeric HPIV3/BPIV3 Antigenome and Recovery of Infectious Virus The following three examples document studies to identify which of the proteins of BPIV3 contribute to its host range restriction in primates. To illustrate these methods, the N protein of the wild type HPIV3 virus was replaced with its counterpart from BPIV3. This exchange was accomplished using a reverse genetics system for recovery of infectious PIV from cDNA as described above. The studies were initiated with the N gene of BPIV3 because this protein possesses an intermediate level of amino acid sequence difference from its HPIV3 counterpart compared to other HPIV3 and BPIV3 proteins (see Example I).

A chimeric recombinant virus was constructed in which the N ORF of the JS strain of HPIV3 was replaced by that of either the Ka or SF strain of BPIV3. These chimeric viruses possess the HN and F glycoproteins of the HPIV3 parent and will induce a high level of immunity to HPIV3 in primates. Both chimeric viruses were successfully recovered. Both grew to high titer in cell culture and both were found to be attenuated in rhesus monkeys. Thus, the N protein was identified as an exemplary protein that contributes to the host range phenotype of BPIV3. Immunization of rhesus monkeys with either the Ka or SF chimeric recombinant virus induced a high level of resistance to the replication of HPIV3 used as a wild type challenge.

The present invention, therefore, establishes the usefulness of reverse genetics methods to generate chimeric human-bovine PIV virus that combines the host range attenuation properties of BPIV3 and the immunogenicity of the HPIV3 HN and F protective antigens. Immunization of humans with such a chimeric recombinant will redress the problem of suboptimal immunogenicity of the BPIV3 vaccine previously observed in humans.

The complete consensus nucleotide sequence for each of the Ka or SF BPIV3 strains was determined from RT-PCR products generated from virion RNA. These sequences are set forth in FIGS. 1A-1G, and FIGS. 2A-2G, respectively. The full length cDNA encoding a complete 15456 nucleotide (nt) antigenomic RNA of BPIV3 Ka is set forth in FIGS. 1A-1G herein (see also GenBank accession #AF178654). It was noted during construction of one exemplary cDNA used within the present examples that the nucleotide sequence departed from the published GenBank sequence by two, non-material nucleotide differences—that may be attributed to sequencing error or other factors. The former cDNA contains a sequence beginning at nucleotide 18, ACT<u>GG</u>TT, (SEQ ID NO: 1) whereas the corresponding published sequence (Gen-Bank accession #AF178654; FIGS. 1A-1G) reads ACT<u>T</u>G <u>C</u>T (SEQ ID NO: 2) (differing nucleotides at positions 21 and 23 are underscored).

To construct consensus nucleotide sequences for the Ka and SF BPIV3 strains, virion RNA was subjected to reverse transcription using the Superscript II Preamplification System (Life Technologies, Gaithersburg, Md.) and 200 ng of random hexamer primers. PCR was carried out on the first strand product using the Advantage cDNA PCR kit (Clontech Laboratories, Palo Alto, Calif.). Ka and SF genomes were each amplified by PCR in 3 or 4 overlapping fragments using primers homologous to regions of RNA conserved among previously-published paramyxovirus sequences. Each primer pair was constructed to include matching restriction enzyme sites (not represented in the sequence targeted for amplification).

A separate random library was generated for each amplicon by digesting a set of PCR products with the appropriate restriction enzyme, followed by gel-purification, ligation of the products into tandem arrays and sonication. A random library was generated from this pool of sheared cDNA sequences by cloning a subset (approx. 500 bp fragments) into M13. The nucleotide sequences of cDNA inserts were determined by automated DNA sequencing using the Taq DYE Deoxy Terminator cycle sequencing kit (ABI, Foster City, Calif.). A continuous sequence (contig) was assembled for each of the original large RT-PCR fragments with sufficient redundancy that each nucleotide position genomic sequences of Ka and SF were converted to cDNA using the system for Rapid Amplification of cDNA Ends (Life Technologies, Gaithersburg, Md.) and sequenced by automated sequencing.

These sequences are set forth in FIGS. 1A-1G (Ka) (SEQ ID NO: 35) and FIGS. 2A-2G (SF) (SEQ ID NO: 36), respectively. Analysis of these sequences revealed that the percent amino acid identity between HPIV3 and BPIV3 for each of the following proteins is: N (86%), P (65%), M (93%), F (83%), HN (77%), and L (91%). Thus sequence divergence was found distributed over many genes. The deduced amino acid sequence of the N genes of these two viruses is presented in Seq. ID No 3 (Ka) and Seq. ID No 4 (SF). In the example below, the N ORF of the Ka or SF virus was initially selected for replacement of the corresponding gene in the HPIV3 virus because the N gene represents a gene with an intermediate level of sequence divergence among the six HPIV3 and BPIV3 proteins. In this study the N ORF, but not the 3' or 5', noncoding N gene sequences, was exchanged, which permitted assignment of the observed attenuation phenotype of cKa and cSF to the protein encoded by the N gene.

Human-bovine chimeric full-length PIV3 genomes were constructed by introducing the BPIV3 Ka or SF N coding region as a replacement for its HPIV3 counterpart into the rJS cDNA p3/7(131)2G which encodes a complete copy of HPIV3 positive-sense antigenomic RNA (see, e.g., Durbin et al., 1997a, supra; Hoffman et al., 1997, supra; Skiadopoulos et al., 1998, supra; U.S. patent application Ser. No. 09/083, 793, filed May 22, 1998, (corresponding to International Publication No. WO 98/53078 and priority U.S. Provisional Application Ser. No. 60/047,575, filed May 23, 1997, and Ser. No. 60/059,385, filed Sep. 19, 1997, each incorporated herein by reference). BPIV3 and HPIV3 N coding regions with flanking sequences were first subcloned and further modified to permit an exchange of just the N ORF. pUC119JSN bearing the HPIV3 N gene and the plasmids with a BPIV3 N Ka or SF gene (pBSKaN and PBSSFN) were subjected to mutagenesis using the method of Kunkel (*Proc. Natl. Acad. Sci. USA* 82:488-492, 1985, incorporated herein by reference) to introduce NcoI and AflIII restriction enzyme recognition sites at translational start and stop sites, respectively (FIG. 3, panel A).

Figure 4A:
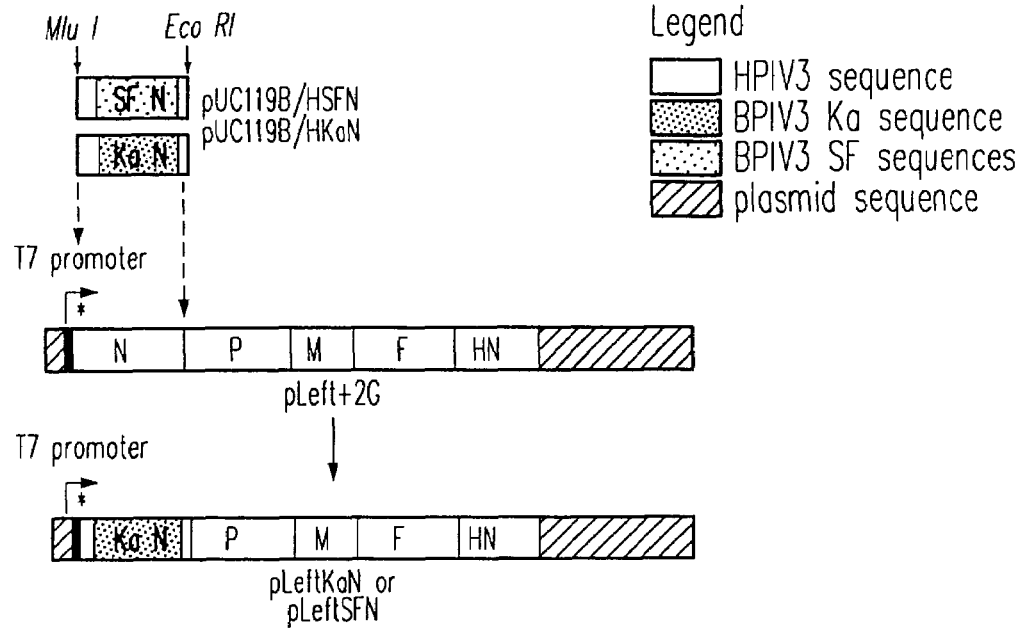
FIG. 4 illustrates insertion of the HPIV3/BPIV3 (strain Ka or SF) chimeric N gene into the HPIV3 antigenomic cDNA.
Figure 4B:
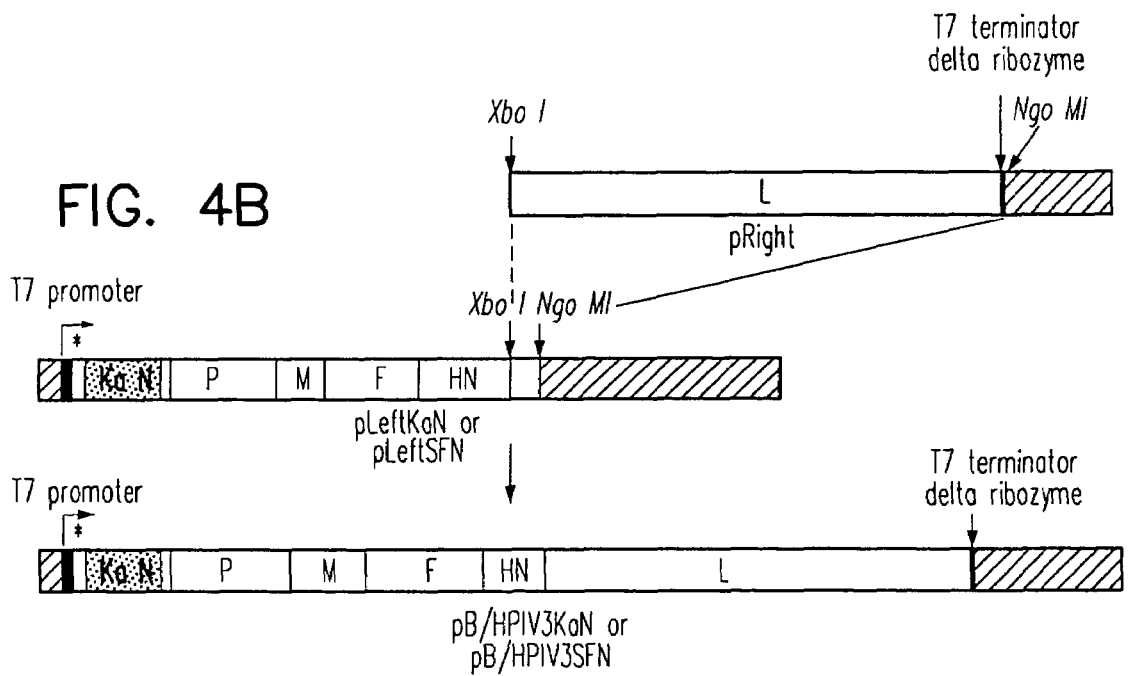

Following NcoI/AflIII digestion of pUC119KaN-NcoI/ AflIII, the BPIV3 N coding region was introduced as an NcoI/ AflIII fragment into pUC119JSN-NcoI/AflIII as a replacement for the HPIV3 N coding region (FIG. 3, panel B). The chimeric N genes, which contain the HPIV3 3' and 5', noncoding sequences and the BPIV3 ORF, were modified by site-directed mutagenesis to restore the original HPIV3 noncoding sequence and BPIV3 coding sequence. This chimeric N gene was then introduced into the 5' half of the rJS antigenome, pLeft, in exchange for its corresponding HPIV3 sequence (FIG. 4, panels A and B) using existing Mlu I and EcoRI sites present in the human sequence. In each case parallel reactions were carried out for the SF N ORF. The chimeric pLeft plasmid was combined with the XhoI/NgoMl fragment from pRight containing the 3' half of the rJS antigenome flanked by the delta ribozyme and the T7 terminator at its 3' end (FIG. 4). The resulting chimeric PIV3 plasmids comprising a human PIV3 background genome or antigenome incorporating a BPIV3 N protein, designated pB/HPIV3NKa or pB/HPIV3NSF, contained the full-length rJS antigenome in which the N ORF encoded the BPIV3 Ka or SF N protein.

Chimeric antigenomic HPIV3/BPIV3 cDNAs were transfected individually into HEp-2 cells grown to near-confluence in 6-well plates along with two previously-described support plasmids, pTM(P) and pTM(L), Lipofectace (Life Technologies, Gaithersburg, Md.), and a modified vaccinia virus recombinant that expresses bacteriophage T7 RNA polymerase (MVA-T7) as previously described (Durbin et al., *Virology* 234:74-83, 1997b). An N support plasmid used in previous work was omitted because the antigenomic plasmid expressed sufficient levels of the N protein. The cultures were maintained for 3.5 days at 32° C. after which supernatants were harvested, passaged in LLC-MK2 cells and plaque-purified 3 times in LLC-MK2 cells. The identities of the chimeric viruses incorporating a human PIV3 background genome or antigenome and a BPIV3 N protein (designated as rHPIV3-$N_B$ chimeric recombinants or, more specifically, as "cKa" and "cSF" chimeric viruses recovered from the transfections were confirmed by sequencing RT-PCR products containing the regions of start and stop codons from virion RNA isolated after amplification of triply plaque-purified virus (FIG. 5). This amplified product and the corresponding amplified HPIV3 rJS and BPIV3 Ka or SF sequences were also subjected to TaqI digestion to confirm the chimeric identity of cKa and cSF viruses (FIG. 6). TaqI digestion profiles were distinct for the 3 parental and 2 chimeric viruses and each parental profile included TaqI fragments of unique size, allowing the contribution of sequence of rJS, Ka and SF parents to the chimeric viruses to be verified. The recovered cKa and cSF chimeric recombinants each contained the expected sequences as designed.

Example II

Replication of HPIV3/BPIV3 Chimeric Viruses in Cell Culture

Figure 7A:
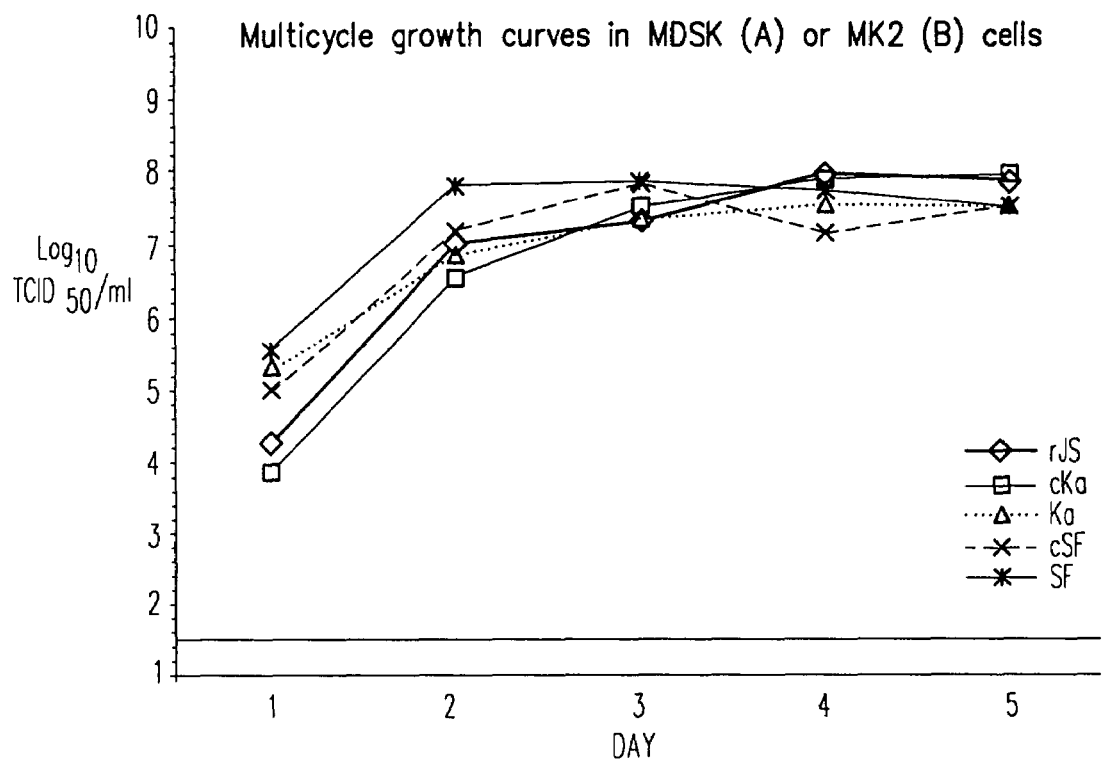
FIG. 7 provides multicycle growth curves of parental and chimeric viruses in MDBK (panel A) or LLC-MK2 (panel B) cells. Monolayers of bovine MDBK (panel A) or simian LLC-MK2 (panel B) cells in wells (9.6 cm$^2$ each) of a 6 well plate were infected individually at a multiplicity of infection of 0.01 with the indicated parental or chimeric virus. Three replicate infections were performed for each virus. Samples were taken at the indicated time points, stored at −70° C., and titered by TCID$_{50}$ assay in parallel. Growth curves are constructed using the average of 3 replicate samples at each time point. The lower limit of virus detectability was $10^{1.5}$ TCID$_{50}$/ml, which is indicated by a dotted line.
Figure 7B:
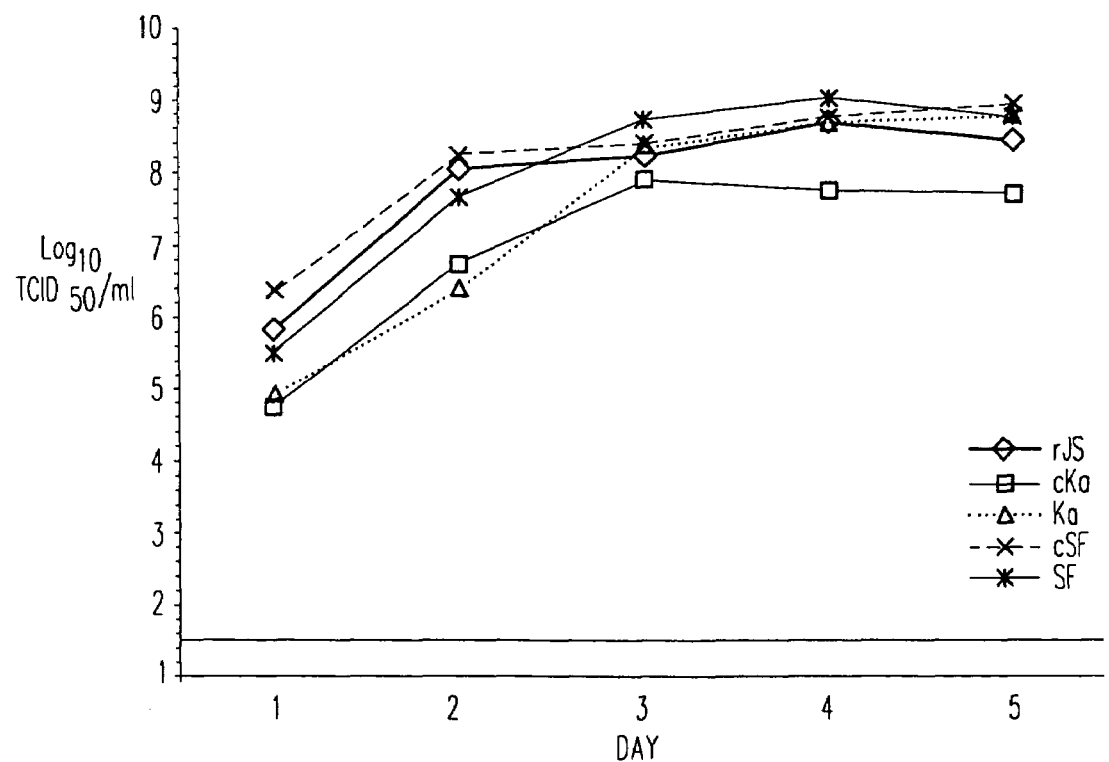

Efficient replication of live attenuated virus vaccines in tissue culture cells is a feature of human-bovine chimeric PIV of the invention that permits efficient manufacture of the recombinant vaccine materials. The multicycle replication of rJS parent, cKa, Ka parent, cSF, and SF parent in a bovine cell line (MDBK) and in a simian cell line (LLC-MK2) was determined by infecting cells with virus at a multiplicity of infection of 0.01 and harvesting samples (in triplicate) over a five day period of time (FIG. 7) as previously described (Tao et al., 1998, supra, incorporated herein by reference). The chimeric viruses replicated efficiently in both cell lines like their human or bovine parent viruses without significant delay in replication or a significant reduction in the titer of virus achieved. In each case, the chimeric viruses replicated to over $10^{7.0}$ $TCID_{50}$ ml which is well above the $10^{4.0}$ or $10^{5.0}$ dose of live attenuated human or bovine PIV vaccines currently being used in human clinical trials (Karron et al., 1996, supra; Karron et al., 1995a, supra; and Karron et al., 1995b, supra).

Example III

Evaluation of Attenuation and Protective Efficacy of the HPIV3/BPIV3 Chimeric Viruses in Rhesus Monkeys Both the SF and Ka BPIV3s are attenuated for the upper and the lower respiratory tract of the rhesus monkey (van Wyke Coelingh et al., 1988, supra). This attenuation phenotype correlates with attenuation in humans (Karron et al., 1995a, supra) as indicated by the fact that Ka is highly restricted in replication in the upper respiratory tract of fully susceptible seronegative infants and children. The absence of cough, croup, bronchiolitis, or pneumonia in the BPIV3-infected vaccinees suggests that the Ka BPIV3 virus is attenuated for the lower respiratory tract as well. Therefore, the rhesus monkey is widely accepted as a reasonably correlative model to evaluate attenuation of candidate PIV vaccine viruses and their efficacy against challenge with wild type PIV.

The rJS, cKa, Ka parent, cSF, and SF parent were administered intranasally and intratracheally at a dose of $10^{5.0}$ $TCID_{50}$ per site to rhesus monkeys. Replication was monitored using previously described procedures for obtaining samples from the upper (nasopharyngeal swab specimens) and lower (tracheal lavage specimens) respiratory tract and for titering the virus in LLC-MK2 cells (Hall et al., 1992, supra). The cKa and cSF recombinants were significantly attenuated for the upper respiratory tract (Table 1) exhibiting, respectively, a 63-fold or a 32-fold reduction in mean peak virus titer compared to that of the rJS HPIV3 parent. Both cKa and cSF were also attenuated for the lower respiratory tract, but this difference was only statistically significant for cSF. The low level of replication of rJS in the lower respiratory tract made it difficult to demonstrate in a statistically-significant fashion further restriction of replication due to an attenuation phenotype at this site.

TABLE 1

Replication of chimeric rB-HPIV3 viruses is restricted in replication relative to HPIV3 in the upper and lower respiratory tracts of rhesus monkeys.

| Immunizing virus[1] | No. of animals | Virus Replication | | | | | |
|---|---|---|---|---|---|---|---|
| | | Mean titers $Log_{10}TCID_{50}$/ml ± standard error [Duncan grouping][2] | | | | Mean peak titers $Log_{10}TCID_{50}$/ml ± standard error [Duncan grouping] | |
| | | Nasopharynx | | Trachea | | | |
| | | day 6 | day 7 | day 4 | day 6 | Nasopharynx | Trachea |
| rJS | 4 | 5.3 ± 0.59[A] | 3.9 ± 0.36[A] | 1.7 ± 0.45[A] | 1.7 ± 0.29[A] | 5.3 ± 0.59[A] | 2.5 ± 50.51[A] |
| cKa | 4 | 3.0 ± 0.58[B] | 2.9 ± 0.42[AB] | 1.5 ± 0.40[A] | 1.0 ± 0.19[A] | 3.5 ± 0.54[B] | 1.5 ± 0.18[AB] |
| Ka | 4 | 2.0 ± 0.27[B] | 2.4 ± 0.30[B] | 1.3 ± 0.26[A] | 1.3 ± 0.21[A] | 2.5 ± 0.30[B] | 1.6 ± 0.15[AB] |
| cSF | 4 | 3.3 ± 0.40[B] | 3.7 ± 0.57[A] | 1.1 ± 0.25[A] | 1.1 ± 0.24[A] | 3.8 ± 0.46[B] | 1.4 ± 0.26[B] |
| SF | 4 | 2.8 ± 0.48[B] | 2.6 ± 0.40[AB] | 1.6 ± 0.46[A] | 1.5 ± 0.40[A] | 3.3 ± 0.28[B] | 1.8 ± 0.41[AB] |

[1]Monkeys were inoculated intranasally and intratracheally with $Log_{10}TCID_{50}$/ml in 1 ml at each site.
[2]Mean viral titers in each column were assigned to statistically similar groups (designated with a letter) using a Duncan Multiple Range test ($\alpha = 0.05$). Mean titers in each column with different letters are statistically different.

The level of replication of each chimeric virus, cKa and cSF, was not significantly different from its bovine parent in the upper or the lower respiratory tract, although the chimeric viruses each replicated somewhat better than their BPIV3 parents in the upper respiratory tract. Thus, the acquisition of the N gene of either the Ka or SF BPIV3 by rJS HPIV3 attenuated the human virus for rhesus monkeys to a level approximately equivalent to that of the BPIV parent. Since the HPIV3/BPIV3 chimeric recombinants replicated efficiently in tissue culture cells in vitro, it is clear that the phenotype of host range restricted replication manifested by the two bovine parental viruses was transferred to HPIV3 by the N ORF. The observation that the level of replication of cKa and cSF is slightly greater than that of their BPIV parents in the upper respiratory tract suggests that additional bovine genes will contribute to the host range attenuation phenotype at this site.

Uninoculated monkeys and monkeys that were previously infected with a human or bovine PIV3 parental virus, or with the cKa or cSF chimeric virus, were challenged 42 days after the initial inoculation with $10^{6.0}$ TCID$_{50}$ of rJS intranasally and intratracheally in a 1 ml inoculum at each site. The nasopharynx and the trachea were sampled as described previously on the days indicated in Table 2. The titer of virus present at each site was determined for each monkey on LLC-MK2 cell monolayers, and the titers presented are mean peak titers (Hall et al., 1992, supra). Previous infection with either chimeric virus induced a high level of resistance to replication of the rJS challenge virus in both the upper and lower respiratory tract. Monkeys previously infected with cKa manifested a 300-fold reduction of replication of wild type HPIV3 (rJS) in the upper respiratory tract and a 1000-fold reduction in the lower tract compared to uninoculated control monkeys. Monkeys previously infected with cSF manifested a 2000-fold reduction of replication of rJS in the upper respiratory tract and a 1000-fold reduction in the lower tract compared to uninoculated control monkeys. The level of reduction of replication of rJS challenge virus in monkeys previously-inoculated with cKa or cSF was comparable to that of monkeys previously infected with either the bovine or the human PIV parent. Thus, infection with either HPIV3/BPIV3 chimeric virus provided a high level of protection in the upper and lower respiratory tract of monkeys, and both chimeric viruses represent promising vaccine candidates.

TABLE 2

Rhesus monkeys previously-infected with HPIV3/BPIV3 chimeric viruses manifest a high level of resistance to replication of HPIV3 challenge virus.

| Initial infection with | Number of animals | Replication of rJS challenge virus in | |
|---|---|---|---|
| | | Nasopharynx[1] Mean peak titer[3] (Log$_{10}$TCID$_{50}$/ml ± SE) [Duncan Grouping] | Trachea[2] Mean peak titer[3] (Log$_{10}$TCID$_{50}$/ml ± SE) [Duncan Grouping] |
| None | 4 | 5.1 ± 0.22[A] | 4.6 ± 0.26[A] |
| rJS | 4 | 2.2 ± 0.18[BC] | 1.6 ± 0.06[B] |
| cKa | 4 | 2.6 ± 0.57[BC] | 1.5 ± 0[B] |
| Ka | 4 | 3.0 ± 0.4[B] | 1.6 ± 0.12[B] |
| cSF | 4 | 1.8 ± 0.16[C] | 1.6 ± 0.11[B] |
| SF | 4 | 2.6 ± 0.57[BC] | 1.5 ± 0[B] |

Note:
Monkeys were challenged with rJS intranasally and intratracheally ($10^6$TCID$_{50}$ in 1 ml at each site)
[1]Nasopharyngeal swab samples were collected on days 3, 4, 5, 6, 7 and 8 post-challenge
[2]Trachaeal lavage samples were collected on days 4, 6 and 8 post-challenge
[3]The titer (TCID$_{50}$/ml) of virus present in each specimen was determined using LLC-MK2 cells, and the mean peak titers for four animals were determined and expressed as log$_{10}$TCID$_{50}$/ml ± Standard Error (SE). Mean peak viral titers in each column were assigned to statistically similar groups (designated with a letter) using a Duncan Multiple Range test ($\alpha = 0.05$). Mean titers in each column with different letters are statistically different.

Serum collected from monkeys on days 0 and 28 was tested by HAI assay using HPIV3 (JS strain) and BPIV3 (Ka strain) as antigen as previously described (Coelingh et al., J. Infect. Dis. 157:655-662, 1988). Although cKa-N and cSF-N were highly attenuated in the upper and lower respiratory tract of rhesus monkeys relative to rJS, each chimeric virus induced a hemagglutination-inhibiting (HAI) antibody response to HPIV3 that was 2.5 to 5-fold greater in magnitude than that induced by immunization with its respective BPIV3 patent. This likely is due to the presence of HPIV3 HN protein in the chimeric viruses. Furthermore, the HPIV3-specific HAI-responses induced by the chimeric viruses were statistically indistinguishable from that induced by immunization with rJS. An additional unexpected result demonstrated herein is that, following challenge of the monkeys with HPIV3, the level of HAI antibody in monkeys initially immunized with cKa-N or cSF-N was significantly greater than levels observed in animals immunized with rJS, Ka or SF.

Example IV

Construction and Analysis of Human-Bovine Chimeric PIVs Having a P or M Open Reading Frame of Bovine PIV3 Substituted into a Human PIV Background As noted above, certain aspects of the invention are directed to chimeric viruses that are attenuated by one or more host-range attenuating genetic elements of BPIV3, wherein the chimeric virus retains the immunogenicity of a human PIV, for example HPIV1, HPIV2 or HPIV3. The major neutralization and protective antigens of HPIVs are the F and HN glycoproteins. Hence, certain human-bovine chimeric constructs for developing live-attenuated HPIV vaccine viruses will contain one or more of the HPIV3 F and HN glycoprotein genes, or one or more genome segments encoding an immunogenic domain, region or epitope of HN and/or F, in a backbone in which one or more genes or genome segments (e.g., from N, P, C, V, D, M, and/or L) are derived from BPIV3. The subject genes or genome segments may encode proteins or selected protein domains or immunogenic fragments. Alternatively, additional BPIV genetic elements, including cis-acting promoter and transcription signals in the leader, trailer, gene-start, gene-end, editing, and intergenic regions, can be used to confer an attenuation phenotype on the resulting chimeric vaccine candidate.

Figures 10A, 10B, 10C:
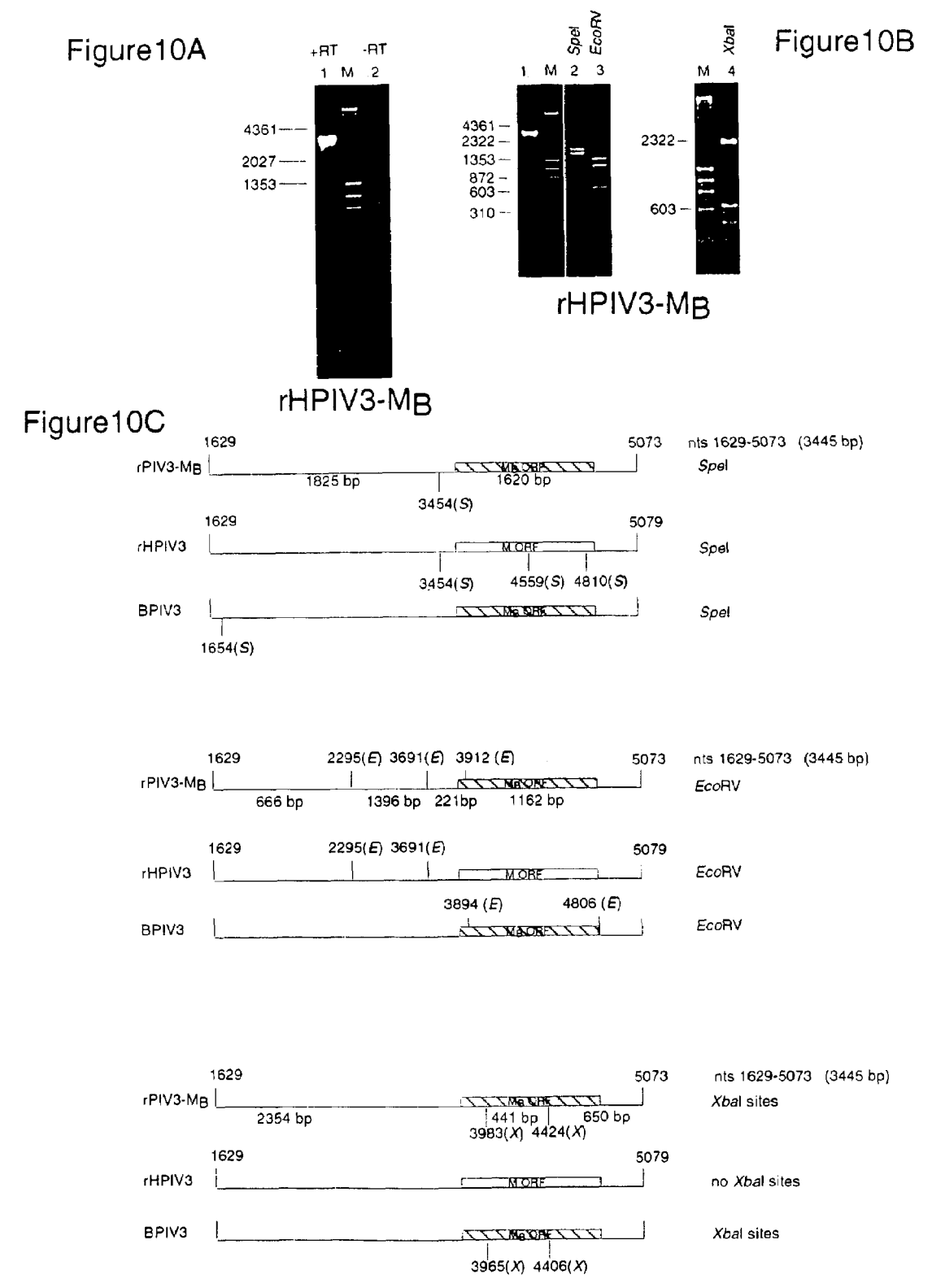

In the present example, two chimeric viruses (rHPIV3-P$_B$) and (rHPIV3-M$_B$) are constructed bearing the P or M ORF, respectively, of the wild type Kansas/15626/84 strain of BPIV3 (see FIGS. 8-10). Notably, the ORFs for the C, D, and V proteins, as well as the sequence for the RNA editing site, are contained within the sequence containing the P ORF. Therefore transfer of the P ORF also transfers these genetic elements. In more specific detail, rHPIV3 cDNA plasmids bearing the P or M ORF of BPIV3 were assembled by first introducing unique restriction sites near the start and stop codons of the human P or M ORF and its bovine counterpart using site-directed mutagenesis. The P or M ORF of HPIV3 was then exchanged with that of its BPIV3 counterpart using molecular cloning techniques as described herein and in Bailly et al., J. Virol. 74:3188-3195, 2000; Durbin et al., Virology 235:323-332, 1997a; Durbin et al., Virology 234:74-83, 1997b; Durbin et al., Virology 261:319-330, 1999, each incorporated herein by reference. The sequence upstream of the exchanged ORF was subsequently mutagenized back to the wt HPIV3 sequence, and an appropriate restriction enzyme fragment bearing the exchanged ORF was assembled into a full-length rHPIV3 cDNA plasmid to yield an infectious full-length chimeric rHPIV3 cDNA.

The P ORF of HPIV3 in pUC(M-B) (Skiadopoulos et al., J. Virol. 73:1374-1381, 1999) was first modified. pUC(M-B) is a subclone of the full-length HPIV3 cDNA plasmid p3/7(131) 2G. This plasmid contains nt 1-3903 of the complete HPIV3 antigenomic RNA sequence (HPIV3 JS strain; GenBank accession #Z11575). pUC(M-B) was modified by site-directed mutagenesis using the Clontech site-directed mutagenesis kit as described previously (Skiadopoulos et al., J. Virol. 73:1374-1381, 1999, incorporated herein by reference) to introduce an NcoI restriction site near the P ORF translation initiation codon (TGATGG (SEQ ID NO: 3) to CCATGG (SEQ ID NO: 4); HPIV3 nts 1782-1787) and an NheI restriction site after the translation termination codon of the P ORF (TCCAAC (SEQ ID NO: 5) to GCTAGC (SEQ ID NO: 6); HPIV3 nts 3596-3601). Similarly, the bovine PIV3 P ORF in pUC(DF) (see above, including incorporated references, for description of bovine plasmids) was engineered at the analogous P ORF translation start and stop positions to introduce NcoI (TCATGG (SEQ ID NO: 7) to CCATGG (SEQ ID NO: 4); BPIV3 nts 1782-1787; BPIV3 Kansas strain; GenBank accession #AF178654) and NheI (GCCAAC (SEQ ID NO: 8) to GCTAGC (SEQ ID NO: 9); BPIV3 nts 3578-3583) restriction sites, respectively. Because the BPIV3 P ORF is 21 nt shorter than that of HPIV3, the 3 nt that immediately follow the BPIV3 P ORF were included to bring the difference to 18 nt, which complies with the rule of six. (Durbin et al., *Virology* 234:74-83, 1997b, incorporated herein by reference).

The specific sequence at the P ORF translation start and stop is given in Table 3. This table provides a nucleotide sequence comparison of the genomic region of rHPIV3-$P_B$ flanking the translation initiation codon (ATG, in bold type) and the translation termination codon (TAG or TAA, in bold type) of the P ORF. The nucleotide sequencing of the 2156 bp RT-PCR fragment generated from vRNA of rHPIV3-$P_B$ around the junctions of the BPIV3 P ORF and the HPIV3 flanking sequences was determined using a Perkin Elmer ABI 310 sequencer, and the engineered sequences for the rHPIV3-$P_B$ were confirmed to be present. The determined sequence of rHPIV3-$P_B$ is indicated in comparison to that of its two parents. The introduced NheI restriction enzyme recognition sequence following the P ORF stop codon in the chimera is italicized and the BPIV3 sequences are underlined.

TABLE 3

| | | | | |
|---|---|---|---|---|
| P START | | | | |
| | | | | SEQ ID NO.: 10 |
| HPIV3 WT | 1765 | 5'CTCAATCAATAGAGAGTTGATGGAAAGCGATGCT 3' | 1798 | |
| | | | | SEQ ID NO.: 11 |
| rHPIV3-$P_B$ | 1765 | 5'CTCAATCAATAGAGAGTTGATGGAAGACAATGTT 3' | 1798 | |
| | | | | SEQ ID NO.: 12 |
| BPIV3 WT | 1765 | 5'CTCAATCAACCAAAGATTCATGGAAGACAATGTT 3' | 1798 | |
| P STOP | | | | |
| | | | | SEQ ID NO.: 13 |
| HPIV3 WT | 3577 | 5'TGTCAACAATTGCCAATGATCCAACAAAGAAACGACACCGAA 3' | 3618 | |
| | | | | SEQ ID NO.: 14 |
| rHPIV3-$P_B$ | 3556 | 5'GGATGTCAGCTCCCAGTAAACC*GCTAGC*AAAGAAACGACACC 3' | 3597 | |
| | | | | SEQ ID NO.: 15 |
| BPIV3 WT | 3556 | 5'GGATGTCAGCTCCCAGTAAACCGCCAACCAAGGGTCAACACC 3' | 3597 | |

The human PIV3 P ORF present in the NcoI to NheI fragment in the modified pUC(M-B) was exchanged with that of the modified BPIV3 P ORF in pUC(DF). After the exchange of the P ORF the sequence immediately preceding the translation initiation site was changed by site-directed mutagenesis to restore the original HPIV3 sequence (CCATGG (SEQ ID NO: 4) to TGATGG (SEQ ID NO:3); HPIV3 nts 1782-1787). The introduced restriction site after the P ORF translation stop was not modified.

The 5' and 3' portions of M ORF of HPIV3 are present in pUC(M-B) and in pUC(B-BII) (Skiadopoulos et al., *J. Virol.* 73:1374-1381, 1999), respectively. pUC(M-B) and pUC(B-BII) are subclones of p3/7(131)2G that contain HPIV3 nts 1-3903 and 3903-5261, respectively. pUC(M-B) was modified by site directed mutagenesis to introduce an SphI restriction site near the M ORF translation initiation codon (AAATGA (SEQ ID NO: 16) to GCATGC (SEQ ID NO: 17); HPIV3 nts 3751-3756). pUC(B-BII) was modified to contain an NheI restriction site after the translation termination codon (AATCTC (SEQ ID NO: 18) to GCTAGC (SEQ ID NO: 9); HPIV3 nts 4816-4821).

| | | | | |
|---|---|---|---|---|
| BPIV3 WT | 3712 | 5'GGACTAATCAATCCTCCGAAACAATGAGCATCACCAACTC 3' | 3751 | |
| M STOP | | | | |
| | | | | SEQ ID NO: 24 |
| HPIV3 WT | 4798 | 5'TCAAACAATGGAACTAGTAATCTCTATTTTAGTCCGG 3' | 4834 | |
| | | | | SEQ ID NO: 25 |
| rPIV3-$M_B$ | 4792 | 5'GGAAAATCAGACAGTAAA*GCTAGC*TATTTTAGTCCGG 3' | 4828 | |
| | | | | SEQ ID NO: 26 |
| BPIV3 WT | 4774 | 5'GGAAAATCAGACAGTAAAATCAACAACCCTGATATCC 3' | 4810 | |

Chimeric virus was recovered by transfection of HEp-2 cells with each individual chimeric full-length cDNA, the pTM(N), pTM(PnoC) and pTM(L) support plasmids, and with MVA-T7 infection as described previously (Durbin et al., *Virology* 235:323-332, 1997a; Durbin et al., *Virology* 234:74-83, 1997b; Durbin et al., *Virology* 261:319-330, 1999; Skiadopoulos et al., *J. Virol.* 73:1374-1381, 1999). Supernatants were harvested four days after transfection and were passaged twice in LLC-MK2 cell cultures to generate virus suspensions which were subsequently cloned biologically by three rounds of plaque isolation on LLC-MK2 cell monolayers. The biologically cloned viruses were then amplified on LLC-MK2 monolayers to generate a sufficient volume of virus for further characterization.

rHPIV3-$P_B$ and rHPIV3-$M_B$ replicated efficiently in tissue culture. rHPIV3-$P_B$ replicated to an average titer of $10^{7.8}$ TCID$_{50}$/ml and rHPIV3-$M_B$ replicated to an average titer of $10^{8.0}$ TCID$_{50}$/ml, compared to $10^{8.2}$ TCID$_{50}$/ml, for rHPIV3 wt. Thus, both rHPIV3-$P_B$ and rHPIV3-$M_B$ were viable and exhibited efficient replication in vitro. As was the case with rHPIV3-$N_B$, there had been no way to predict that either heterologous introduced BPIV3 M or P protein would be sufficiently compatible with the other HPIV3 proteins to allow efficient growth in vitro, a property that is highly desired for vaccine production.

The identity of rHPIV3-$P_B$ and rHPIV3-$M_B$ was confirmed by isolation of the viral RNA (vRNA) and generation of specific RT-PCR fragments containing the BPIV3 ORF flanked by HPIV3 sequence using previously described techniques (Skiadopoulos et al., *J. Virol.* 72:1762-1768, 1998; Skiadopoulos et al., *J. Virol.* 73:1374-1381, 1999), with PCR primers flanking the BPIV3 P or BPIV3 M ORF (FIG. 8, panels A and B, FIG. 9, panels A-C, and FIG. 10, panels A-C). Sense (HPIV3 nts 1629-1661) and antisense primers (HPIV3 nts 3802-3763) were used to generate the 2156 bp fragment containing the BPIV3 P ORF in rHPIV3-$P_B$ (FIG. 8). Sense (HPIV3 nts 1629-1661) and antisense primers (HPIV3 nts 5079-5041) were used to generate the 3445 bp fragment containing the BPIV3 M ORF in rHPIV3-$M_B$ (FIG. 10). Digestion of RT-PCR products with restriction enzymes that were specific in either the human or the bovine PIV3 portion of the chimera, respectively (FIGS. 9 and 10) as well as partial DNA sequencing at the ORF junction of RT-PCR products (Tables 3 and 4), using the Perkin Elmer ABI sequencing kit and an ABI 310 automated sequencer, confirmed that the cloned rHPIV3-$P_B$ and rHPIV3-$M_B$ viruses were recombinant chimeric viruses that contained the BPIV3 P or M ORF, respectively, in an HPIV3 background.

The foregoing example focuses on exchanging protein-coding sequences of BPIV into an HPIV background genome or antigenome bearing one or more HPIV antigenic determinants to elicit a host immune response against one or more HPIVs. In the preceding examples, a chimeric virus was generated in which the N open reading frame (ORF) of rHPIV3 was replaced with that of BPIV3, and the resulting chimeric virus, rHPIV3-$N_B$, replicated efficiently in vitro but was attenuated for the respiratory tract of rhesus monkeys. Despite the attenuation phenotype specified by the host-range attenuating elements of the BPIV3 N protein, the rHPIV3-$N_B$ chimera induced high titers of antibody in rhesus monkeys to HPIV3 and protected them against wild type HPIV3 challenge. The unrestricted nature of the replication phenotype of rHPIV3-$N_B$ in vitro is a highly desirable, because it makes it possible to efficiently produce recombinant virus for vaccine use. Thus, surprisingly, the BPIV3 N protein has been demonstrated herein to be sufficiently compatible with human PIV3 internal proteins to permit efficient growth in vitro, while at the same time it is shown that replacement of this single ORF confers a host range restriction phenotype in vitro.

Additional results herein demonstrate that chimeric rHPIV3 in which the P or M ORF of HPIV3 was replaced by that of BPIV3 Kansas is attenuated in the respiratory tract of rhesus monkeys. The basis of the host range restriction of replication of BPIV3 for the respiratory tract of rhesus monkeys was examined by the generation and characterization of human-bovine chimeric PIV3s in which the HPIV3 P, or M ORF was replaced by that of its BPIV3 counterpart. The replication of chimeric rHPIV3 $P_B$, and rHPIV3 $M_B$ viruses in the upper and lower respiratory tract of rhesus monkeys was compared to that of their wild type rHPIV3 and BPIV3 Kansas parent viruses. Each virus was administered intranasally and intratracheally at a dose of $10^{5.0}$ TCID$_{50}$ per site. The mean peak titer at each site was quantified for each virus by plaque titration in LLC-MK2 cells (e.g., as described by Bailly et al., *J. Virol.* 74:3188-3195, 2000; Hall et al., *Virus Res.* 22:173-184, 1992; and Schmidt et al., *J. Virol.* 74:8922-9, 2000, each incorporated herein by reference), and the results are presented in Table 5. The rHPIV3 NB, rHPIV3 PB, and rHPIV3 MB chimeric viruses were each restricted in replication in the upper respiratory tract compared to the level of replication of rHPIV3 (Table 5), demonstrating that each bovine ORF can specify an attenuation phenotype when transferred to rHPIV3. In the lower respiratory tract, only rBPIV3 $N_B$ and rHPIV3 $P_B$ were attenuated and replicated to levels slightly lower than those of the highly attenuated BPIV3 Ka virus. The availability of human-bovine chimeric PIV3 candidate vaccines bearing the HPIV3 F and HN glycoproteins described here with a range of attenuation of replication will be advantageous for selecting candidate vaccines with the appropriate level of attenuation in humans.

TABLE 5

Replication of chimeric recombinant PIV3s in the respiratory tract of rhesus monkeys

| Group No. | Immunizing virus[a] | Number of animals[b] | Mean peak virus titer[c,d] (log$_{10}$TCID$_{50}$/ml ± S.E.) | |
|---|---|---|---|---|
| | | | NP swab[e] | Tracheal lavage[f] |
| 1 | rHPIV3 wt | 8 | 4.7 ± 0.4A | 3.3 ± 0.4 |
| 2 | rHPIV3 $M_B$ | 4 | 3.0 ± 0.6A | 3.4 ± 0.6 |
| 3 | rHPIV3 $N_B$ | 8 | 2.6 ± 0.6B | 2.0 ± 0.4 |
| 4 | rHPIV3 $P_B$ | 6 | 1.2 ± 0.2B | 1.5 ± 0.3 |
| 5 | BPIV3 Ka | 8 | 2.4 ± 0.3B | 1.9 ± 0.2 |

[a]Monkeys were inoculated intranasally and intratracheally with $10^5$ TCID$_{50}$ of virus in a 1 ml inoculum at each site.
[b]Groups 1 and 5 contain animals from previous rhesus studies (Bailley et al., J Virol. 74:3188-3195, 2000, and Schmidt et al., J Virol 74:8922-9, 2000). Group 5 contains 2 new animals from the present study. Group 1 contains 4 animals from the present study.
[c]Mean of the peak virus titers for each animal in its group irrespective of sampling day. S.E.—standard error.
[d]Virus titrations were performed on LLC-MK2 cells at 32° C. The limit of detection of virus titer was 10 TCID$_{50}$/ml.
[e]Nasopharyngeal swab samples were collected on days 1 to 10 post-infection.
[f]Trachael lavage samples were collected on days 2, 4, 6, 8 and 10 post-infection. rHPIV3 $N_B$, rHPIV3 $P_B$, and rHPIV3 $M_B$ induce a high level of resistance of rhesus monkeys to wild type HPIV3 challenge. Although rHPIV3 $N_B$, rHPIV3 $P_B$, and rHPIV3 $M_B$ were attenuated in the upper or lower respiratory tract of rhesus monkeys relative to rHIPV3, each chimeris virus induced a hemagglutination-inhibiting (HAI) antibody response to HPIV3 that was 8-fold or greater in magnitude than that induced by immunization with the BPIV3 parent and was almost as immunogenic as rHIPV3. This indicates that, as intended ny design of the chimeras, the presence of the HPIV3 HN and F glycoprotein gene in each chimeric virus resulted in the induction of an antibody response that resembled that of the HPIV3 parent and not that of the BPIV3 parent.

To evaluate the protective efficacy of the recombinant chimeric PIV3s, rhesus monkeys previously immunized with the parent viruses or with rHPIV3 $N_B$, rHPIV3 $P_B$, or rHPIV3 $M_B$ were challenged intranasally and intratracheally with $10^6$ TCID$_{50}$ of the biologically derived JS strain of HPIV3 virus on day 28 or 31 post-immunization. The animals immunized with the recombinant or biologically derived PIV3s were protected against challenge with HPIV3 (Table 6) as indicated by a 100-fold or greater reduction in replication of challenge virus in both the upper and the lower respiratory tract of the animals immunized with rHPIV3 $N_B$, rHPIV3 $P_B$, or rHPIV3 $M_B$ compared to that of control animals. These data confirm that, despite their reduced growth in rhesus monkeys relative to rHPIV3 wt, the rHPIV3 $N_B$, rHPIV3 $P_B$, or rHPIV3 $M_B$ chimeric viruses induce protective immunity to HPIV3 infection that was comparable to that induced by rHPIV3.

viruses, and it was not known whether such viruses would be restricted in replication in vitro, or attenuated and immunogenic in vivo.

Example V

Construction and Characterization of Chimeric HPIV3/BPIV3 Vaccine Candidates Having Heterologous Fusion and Hemagglutinin-Neuraminidase Glycoproteins In the preceding examples, the basis of host range restriction of replication of BPIV3 for the respiratory tract of primates was examined by the generation and characterization of a recombinant human PIV3 (rHPIV3) in which the N, M

TABLE 6

Serum antibody response to immunization with chimeric human-bovine viruses and efficacy against challenge with wt HPIV3

| Group No. | Immunizing virus[a] | Number of animals[b] | Serum HAI antibody titer (mean recip. log$_2$ ± S.E.) for HPIV3 on day 28-31[c] | Mean peak virus titer[d] following HPIV3 challenge (log$_{10}$TCID$_{50}$/ml ± S.E.) | | Serum HAI antibody titer (mean recip. log$_2$ ± S.E.) for HPIV3 on day 28-31 after challenges |
|---|---|---|---|---|---|---|
| | | | | NP swab | Trachael lavage | |
| 1 | rHPIV3 | 8 | 8.4 ± 0.5 | 1.4 ± 0.3 | 1.1 ± 0.2 | 11.5 ± 0.2 |
| 2 | rHPIV3M$_B$ | 4 | 7.8 ± 0.9 | 1.4 ± 0.9 | 1.2 ± 0.4 | 11.0 ± 0.4 |
| 3 | rHPIV3N$_B$ | 8 | 7.5 ± 0.4 | 2.1 ± 0.4 | 1.2 ± 0.2 | 11.5 ± 0.3 |
| 4 | rHPIV3P$_B$ | 6 | 7.2 ± 0.6 | 2.4 ± 0.5 | 2.2 ± 0.6 | 10.5 ± 0.4 |
| 5 | BPIV3 Ka | 8 | 4.4 ± 0.5 | 2.9 ± 0.2 | 2.0 ± 0.5 | 9.8 ± 0.6 |
| 6 | control[f] | 10 | <2.0 ± 0.0 | 4.8 ± 0.2 | 4.3 ± 0.2 | 11.1 ± 0.4 |

[a]Monkeys were inoculated intranasally and intratracheally with 10$^5$TCID$_{50}$ of virus in a 1 ml inoculum at each site.
[b]The groups with 8 or 10 animals contain animals each from previous rhesus studies (Bailley et al., J Virol. 74:3188-3195, 2000, and Schmidt et al., J Virol. 74:8922-9, 2000).
[c]In the present study, sera were collected from monkeys on day 31 post immunization and animals were then challenged with HPIV3. In the two previous studies, monkeys were sampled and challenged on day 28 post immunization. Antibody titers reported were performed in the same assay. Serum HAI tier is expressed as the mean reciprocal log$_2$ ± standard error.
[d]Virus titrations were performed on LLC-MK2 cells at 32° C. The limit of detection of virus titer was 10TCID$_{50}$/ml. Nasopharyngeal swab and Trachael lavage samples were collected on days 2, 4, 6, 8 and 10 post-challenge. The tiers on day 0 were < 10 TCID50/ml.
e. With the exception of the groups that received rHPIV3 $M_B$ or rHPIV3 $P_B$ (groups 2 and 4), the data presented includes historical data from studies reported previously (Bailley et al., J Virol. 74:3188-3195, 2000, and Schmidt et al., J Virol. 74:8922-9, 2000).
[f]The control group consisted of animals that were not immunized, or that had received 10$^5$ pfu of respiratory syncytial virus (2 new animals in the present study).

The results set forth in the present example demonstrate that replacement of other HPIV3 proteins with BPIV3 counterparts also yields viable viruses for use within the invention. In particular, the M and P proteins of BPIV3 and HPIV3, which are 93% and 65% related, respectively, are shown to be useful elements for incorporation into human-bovine chimeric PIV of the invention. Previously, it was unknown whether these proteins could be exchanged with their HPIV3 counterparts and yield viable BPIV3/HPIV3 recombinant and P open reading frames (ORFs) were replaced by that of their BPIV3 counterparts. The resulting chimeric viruses efficiently replicated in vitro but were restricted in replication in the upper respiratory tract of rhesus monkeys, identifying these proteins as independent determinants of the host range restriction of BPIV3 in rhesus monkeys (see also, Bailly et al., J. Virol. 74:3188-3195, 2000, incorporated herein by reference).

In the present example, the contribution of the fusion (F) and hemagglutinin-neuraminidase (HN) glycoprotein genes of bovine parainfluenza virus type 3 (BPIV3) to its restricted replication in the respiratory tract of non-human primates was examined by generating and characterizing two reciprocal chimeric BPIV3/HPIV3 viruses. A chimeric HPIV3 containing heterologous, BPIV3 F and HN glycoprotein genes in place of its own, and the reciprocal recombinant comprising a BPIV3 "backbone" bearing the HPIV3 F and HN genes substituted for the counterpart BPIV3 glycoprotein genes, were generated to assess the effect of glycoprotein substitution on replication of HPIV3 and BPIV3 in the upper and lower respiratory tract of rhesus monkeys. Thus, in one chimeric virus, the F and HN genes of HPIV3 were replaced with their BPIV3 counterparts, resulting in a chimeric recombinant designated rHPIV3-$F_B HN_B$. The reciprocal chimeric recombinant PIV3 (rBPIV3-$F_H HN_H$) was constructed by replacing the F and HN genes of a recombinant BPIV3 (rBPIV3) with their HPIV3 counterparts. In the latter virus, the introduction of the HPIV3 F and HN ORFs into the BPIV3 backbone combines the antigenic determinants of HPIV3 with the backbone of BPIV3 and thus provides and improved vaccine candidate compared with parental BPIV3. The F and HN genes were exchanged as pairs in view of the proposed requirement for homologous HN and F proteins for parainfluenza viruses for full functional activity (Deng et al., *Virology* 209:457-469, 1995; and Tanabayashi et al., *J. Virol.* 70:6112-6118, 1996; each incorporated herein by reference).

The foregoing chimeric viruses were readily recovered and exhibited kinetics of replication in simian LLC-MK2 cells that were comparable to those of their parent viruses, suggesting that the heterologous glycoproteins were compatible with the PIV3 internal proteins. The distinctive features of cytopathology of BPIV3 versus HPIV3 cosegregated with their respective F and HN genes. HPIV3 bearing the BPIV3 F and HN genes was attenuated for replication in rhesus monkeys to a level similar to that of its BPIV3 parent virus, indicating that the glycoprotein genes of BPIV3 are major determinants of its host range restriction of replication in rhesus monkeys. BPIV3 bearing the HPIV3 F and HN genes (rBPIV3-$F_H HN_H$) replicated in rhesus monkeys to a level intermediate between that of HPIV3 and BPIV3.

These results indicate that the F and HN genes make a significant contribution to the overall attenuation of BPIV3. Furthermore, they demonstrate that BPIV3 sequences outside the F and HN region also contribute to the attenuation phenotype in primates. This latter finding is consistent with the demonstration in the preceding example that the nucleoprotein coding sequence of BPIV3 is a determinant of its attenuation for primates. Despite its restricted replication in the respiratory tract of rhesus monkeys, rBPIV3-$F_H HN_H$ conferred a level of protection against challenge with wild type HPIV3 that was indistinguishable from that conferred by previous infection with wild type HPIV3. From these and related findings, the usefulness of rBPIV3-$F_H HN_H$ as a vaccine candidate against HPIV3 is readily apparent.

Viruses and Cells

HEp-2 and simian LLC-MK2 monolayer cell cultures were maintained in MEM medium (Life Technologies, Gaithersburg, Md.) supplemented with 5% fetal bovine serum (Summit Biotechnology, Ft. Collins, Colo.), 50 ug/ml gentamicin sulfate, and 4 mM glutamine (Life Technologies, Gaithersburg, Md.).

The wild type BPIV3 strain Kansas/15626/84 (Clone 5-2-4, Lot BPI3-1) (BPIV3 Ka), the HPIV3 JS wild type, its recombinant version (rHPIV3), and the rHPIV3 virus containing the BPIV3 Ka N ORF in place of the HPIV3-N ORF (rHPIV3-$N_B$) are each described above (see also, Clements et al., 1991, supra; Karron et al., 1995a, supra; Bailly et al., 2000, supra; and Durbin et al., 1997, supra). PIVs were propagated at 32° C. in LLC-MK2 cells (ATCC CCL-7), as previously described (Hall et al., 1992, supra). The modified vaccinia strain Ankara (MVA) recombinant virus that expresses bacteriophage T7 RNA polymerase is described by Wyatt et al. (1995, supra).

Construction of Antigenomic cDNAs Encoding Recombinant BPIV3/HPIV3 Viruses.

a) Construction of cDNA to Recover rBPIV3

A full length cDNA was constructed to encode the complete 15456 nucleotide (nt) antigenomic RNA of BPIV3 Ka, as described above. The cDNA was assembled from 4 subclones derived from reverse transcription (RT) of viral RNA using the SuperScript II Pre-amplification System (Life Technologies, Gaithersburg, Md.) and polymerase chain reaction (PCR) amplification with a High Fidelity PCR kit (Clontech Laboratories, Palo Alto, Calif.). The RT-PCR products were cloned into modified pUC19 plasmids (New England Biolabs, Beverly, Mass.) using the following naturally occurring internal restriction enzyme recognition sites: Sma I (BPIV3 Ka sequence position nt186), Pst I (nt 2896), Mlu I (nt 6192), Sac II (nt 10452) and Bsp LU11 (nt 15412). Multiple subclones of the antigenomic cDNA were sequenced using a Perkin Elmer ABI 310 sequencer with dRhodamine Terminator Cycle Sequencing (Perkin Elmer Applied Biosystems, Warrington, UK), and only those matching the consensus sequence of BPIV3 Ka were used for assembly of the full length clone. The 3' and 5' ends of BPIV3 Ka were cloned and the assembly of the full length cDNA took place in the previously described p(Right) vector (Durbin et al., 1997, supra), which we modified to contain a new polylinker with restriction enzyme recognition sites for Xho I, Sma I, Mlu I, Sac II, Eco RI, Hind III and RsrII. The full length cDNA clone pBPIV3(184) contained the following elements in 3' to 5' order: a T7 promoter followed by 2 non-viral guanosine residues, the complete antigenomic sequence of BPIV3 Ka, a hepatitis delta virus ribozyme and a T7 polymerase transcription terminator (Bailly et al., 2000, supra; and Durbin et al., 1997a, supra).

b) Construction of rHPIV3-$F_B HN_B$ and rBPIV3-$F_H HN_H$

Unique restriction enzyme recognition sites were introduced into the BPIV3 antigenomic cDNA and into the previously described HPIV3 antigenomic cDNA p3/7(131)2G (Durbin et al., 1997a, supra) to facilitate the exchange of the F and HN genes between BPIV3 and HPIV3 cDNAs. Using the transformer site-directed mutagenesis protocol from Clontech (Clontech Laboratories, Palo Alto, Calif.), SgrAI restriction sites were introduced in the downstream non-coding region of the M gene at position 4811 of the rBPIV3 sequence and position 4835 of the rHPIV3 JS sequence (GenBank accession #Z11575). The nucleotide number given for the position of restriction enzyme recognition sites indicates the nucleotide after which the enzyme cuts, not the first nucleotide of the restriction enzyme recognition site. The sequence was changed from TCCAACATTGCA (SEQ. ID. NO. 27) to TCCACCGGTGCA (SEQ. ID. NO. 28) in rBPIV3 and from CGGACGTATCTA (SEQ. ID. NO. 29) to CGCACCGGTGTA (SEQ. ID. NO. 30) in rHPIV3 (recognition sites underlined). BsiWI restriction sites were introduced in the downstream non-coding region of the HN gene at nt 8595 of the rBPIV3 sequence and at nt 8601 of the rHPIV3 JS sequence. The sequence was changed from GATATAAAGA (SEQ. ID. NO. 31) to GACGTACGGA (SEQ. ID. NO. 32) in rBPIV3 to give pBPIVs(107) and from GACAAAAGGG (SEQ. ID. NO. 33) to GACGTACGGG (SEQ. ID. NO. 34) in rHPIV3 to give pHPIVs(106). The F and HN genes were exchanged between pBPIVs(107) and pHPIV3s(106) by digestion of each with SgrAI and BsiWI, gel purification of the fragments, and assembly of the appropriate fragments into the two full length cDNAs. The HPIV3 backbone bearing the BPIV3 F and HN genes, designated pHPIV(215), encoded 15480 nts of viral sequence, of which nts 4835 to 8619 came from BPIV3, and it was used to derive rHPIV3-$F_B HN_B$ (FIGS. 11A-11C). The BPIV3 backbone bearing the HPIV3 F and HN genes, designated pBPIV(215), encoded 15438 nts of viral sequence, of which nts 4811 to 8577 came from HPIV3, and it was used to derive rBPIV3-$F_H HN_H$ (FIGS. 11A-11C).

BPIV3 Support Plasmids for Recovery of Virus from cDNA.

Support plasmids encoding the BPIV3 Ka N, P and L genes were assembled in modified pUC19 vectors and then cloned into the previously described pTM vector (Durbin et al., 1997a, supra). In order to place the individual genes immediately downstream of the T7 promoter in the pTM vector, an Nco I site was introduced at the start codon of the N, P and L open reading frames (ORFs) using site-directed mutagenesis. The Nco I restriction site and a naturally occurring restriction site downstream of each ORF (Spe I for N, HincII for P and Bsp LU11I for L) was used for cloning into pTM. After cloning, the Nco I site in pTM(N) was mutagenized back to the original sequence to restore the correct amino acid assignment in the second codon. In pTM(P) and pTM(L) the amino acid sequence encoded by the ORF was not altered by the introduction of Nco I sites.

Transfection.

HEp-2 cells (approximately $1.5 \times 10^6$ cells per well of a six-well plate) were grown to 90% confluence and transfected with 0.2 µg each of the BPIV3 support plasmids pTM(N) and pTM(P), and 0.1 µg of pTM(L), along with 5 µg of the full length antigenomic cDNA and 12 µl LipofectACE (Life Technologies, Gaithersburg, Md.). Each transfection mixture also contained $1.5 \times 10^7$ plaque forming units (PFU) of MVA-T7, as previously described (Durbin et al., 1997, supra). The cultures were incubated at 32° C. for 12 hrs before the medium was replaced with MEM (Life Technologies, Gaithersburg, Md.) containing 10% fetal bovine serum. The supernatants were harvested after incubation at 32° C. for an additional three days, and were passaged onto LLC-MK2 cell monolayers in 25 cm² flasks and incubated for 5 days at 32° C. Virus present in the supernatant was plaque-purified three times prior to amplification and characterization.

Molecular Characterization of Recovered Chimeric Recombinants.

The presence of the heterologous F and HN genes in the bovine or human PIV3 backbone was confirmed in plaque-purified recombinant viruses by RT-PCR of viral RNA isolated from infected cells or supernatant, which was performed using a primer pair that recognizes conserved sequences in rBPIV3 and rHPIV3. This yielded similarly sized fragments (nts 4206-9035 in rBPIV3, nts 4224-9041 in rHPIV3, nts 4206-9017 in rBPIV3-$F_H HN_H$, and nts 4224-9059 in rHPIV3-$F_B HN_B$) which were then digested with Eco RI and analyzed by electrophoresis on a 1% agarose gel. The nucleotide sequence flanking the introduced SgrAI and BsiWI restriction sites in each virus was confirmed by sequencing the respective RT-PCR product.

Replication of HPIV3/BPIV3 Chimeric Viruses in Cell Culture.

The multicycle growth kinetics of BPIV3 Ka, rHPIV3-$F_B HN_B$, rBPIV3-$F_H HN_H$, rHPIV3-$N_B$ and rHPIV3 in LLC-MK2 cells were determined by infecting cells in triplicate at a multiplicity of infection (MOI) of 0.01 and harvesting samples at 24 hr intervals over a six day period, as previously described (Tao et al., 1998, supra). Samples were flash-frozen and titered in a single assay on LLC-MK2 cell monolayers in 96 well plates at 32° C., as described (Durbin et al., *Virology* 261:319-330, 1999b, incorporated herein by reference).

Primate Model Studies.

Rhesus monkeys seronegative for PIV3 as determined by hemagglutination-inhibition (HAI) assay (van Wyke Coelingh et al., 1988, supra) were inoculated intranasally and intratracheally in groups of 2 or 4 animals with $10^5$ tissue culture infectious dose$_{50}$ (TCID$_{50}$) per ml of BPIV3 Ka, rHPIV3-$F_B HN_B$, rBPIV3-$F_H HN_H$, rHPIV3-$N_B$ or rHPIV3. Nasopharyngeal swabs were collected daily on days 1 to 11 and on day 13. Tracheal lavage samples were collected on days 2, 4, 6, 8, and 10 post-infection. Individual samples were flash-frozen and stored at -70° C. until all samples were available for titration. Virus in the specimens was titered on LLC-MK2 cell monolayers in 24 and 96 well plates as previously described (Durbin et al., 1999b, supra). Sera collected from monkeys on days 0 and 28 was tested by HAI assay using HPIV3 JS and BPIV3 Ka as antigens, as previously described (van Wyke Coelingh et al., 1988, supra). On day 28 post inoculation, the monkeys were challenged intranasally and intratracheally with $10^6$ TCID$_{50}$ per site of HPIV3 JS. Nasopharyngeal swab samples were collected on days 3, 4, 5, 6, 7 and 8, and tracheal lavage samples on days 4, 6 and 8 post challenge. Samples were titered in a single assay as described above. Serum was collected on day 28 post challenge.

Recovery of rBPIV3 and BPIV3HPIV3 Chimeric Viruses (rHPIV3-$F_B HN_B$ and rBPIV3-$F_H HN_H$) from cDNA.

A complete BPIV3 antigenomic cDNA, designated pBPIV (184), was constructed to encode the consensus sequence of BPIV3 Ka. This BPIV3 antigenomic cDNA was further modified by the introduction of unique SgrAI and BsiWI sites into the downstream noncoding region of the M and HN genes, respectively. The same restriction sites were introduced into the downstream noncoding region of the M and HN genes of a previously described complete HPIV3 antigenomic cDNA, p3/7(131)2G (Durbin et al., 1997a, supra). The F and HN glycoprotein genes of HPIV3 and BPIV3 were swapped by exchanging this SgrAI-BsiWI restriction fragment. A direct exchange of entire genes was anticipated to be well-tolerated because of the high level of sequence conservation between the cis-acting signals of BPIV3 and HPIV3. The HPIV3 antigenomic cDNA bearing the BPIV3 F and HN genes was designated pHPIV(215), and the BPIV3 antigenomic cDNA bearing the HPIV3 F and HN genes was designated pBPIV(215).

The antigenomic cDNAs pBPIV(184), pHPIV(215), pBPIV(215) and p3/7(131)2G were separately transfected into HEp-2 cells along with the three BPIV3 support plasmids pTM(N), pTM(P) and pTM(L), and the cells were simultaneously infected with recombinant MVA expressing the T7 RNA polymerase. To confirm that the recovered viruses indeed were the expected rBPIV3, rHPIV3-$F_B HN_B$, rBPIV3-$F_H HN_H$ and rHPIV3 viruses, intracellular RNA or RNA from supernatant from each cloned virus was analyzed by RT-PCR using a primer pair that recognized identical sequences in HPIV3 JS and BPIV3 Ka. The primer pair amplified a 4.8 kb fragment of DNA corresponding to the downstream end of the M gene, the F and HN genes, and the upstream end of the L gene (nts 4206-9035 in rBPIV3, nts 4224-9041 in rHPIV3, nts 4206-9017 in rBPIV3-$F_H HN_H$, and nts 4224-9059 in rHPIV3-$F_B HN_B$). The generation of each PCR product was dependent upon the inclusion of reverse transcriptase, indicating that each was derived from viral RNA and not from contaminating cDNA. The PCR products were then digested with Eco R1, which would be predicted to yield a different, unique restriction enzyme digest pattern for each of the four viruses (FIG. 12). In each case, the predicted pattern was observed, confirming the identity of the backbone and the inserted F and HN genes. In addition, nucleotide sequencing was performed on the RT-PCR products to confirm the presence of the introduced restriction sites and flanking sequences.

The cytopathic effect (CPE) caused by rBPIV3-$F_H HN_H$ in LLC-MK2 cells was indistinguishable from that of HPIV3 JS (condensed, rounded-up cells and small syncytia) but different from BPIV3 (large multicellular syncytia), whereas the CPE caused by rHPIV3-$F_B HN_B$ was identical to that caused by the BPIV3. This indicates that the cytopathology of the chimeric PIVs cosegregated with the parental origin of the F and HN genes.

BPIV3/HPIV3 Chimeric Viruses Replicate Efficiently in Cell Culture.

The growth kinetics of rHPIV3-$F_B HN_B$ and rBPIV3-$F_H HN_H$ were compared with that of their parental viruses by infecting LLC-MK2 monolayers at an MOI of 0.01 and monitoring the production of infectious virus. The kinetics and magnitude of replication of the two chimeric viruses were comparable to those of their HPIV3 or BPIV3 parental viruses (FIG. 13). This suggested that BPIV3 and HPIV3 glycoproteins were compatible with the heterologous PIV3 internal proteins. This is an important property because it will be possible to efficiently prepare vaccine virus.

The F and HN Genes of the BPIV3/HPIV3 Chimeric Viruses are Determinants of the Host Range Restriction of Replication of BPIV3 Ka in the Respiratory Tract of Rhesus Monkeys.

rHPIV3-$F_B HN_B$ and rBPIV3-$F_H HN_H$ were evaluated for their ability to replicate in the upper and lower respiratory tract of rhesus monkeys. In particular, the effects of introduction of the BPIV3 F and HN genes into HPIV3 on attenuation of replication in rhesus monkeys was demonstrated, as described above for the BPIV3 N protein (see also, Bailly et al., 2000, supra). In addition, the effects of introduction of the HPIV3 F and HN genes into BPIV3 on replication in rhesus monkeys was determined. If the predominant attenuating mutations of BPIV3 were in genes other than the F and HN, then one would expect little overall effect of the HPIV3-BPIV3 glycoprotein exchange on replication of BPIV3 in rhesus monkeys.

Each chimeric virus was administered intranasally and intratracheally to rhesus monkeys at a dose of $10^5$ $TCID_{50}$ per site. The level of replication of the chimeric viruses was compared to that of the rHPIV3 and BPIV3 parental viruses and to that of rHPIV3-$N_B$ (Table 7). Since the rHPIV3 parental virus replicated to a low to moderate level in the lower respiratory tract, meaningful comparisons between groups could only be made for replication in the upper respiratory tract. The level of replication of rHPIV3-$F_B HN_B$ was similar to that of its BPIV3 parent and substantially lower than that of its HPIV3 parent (Table 3; FIG. 14, panel A). This showed that the BPIV3 glycoprotein genes contained one or more major determinants of the host range attenuation phenotype of BPIV3 for rhesus monkeys. The magnitude and pattern of replication of rHPIV3-$F_B HN_B$ and rHPIV3-$N_B$ were very similar, indicating that each of the two bovine genetic elements, namely the N gene versus the F and HN genes, attenuate HPIV3 to a similar extent.

TABLE 7

The F and HN glycoprotein genes of BPIV3 contribute to its restricted replication in the respiratory tract of rhesus monkeys.

| Immunizing virus[1] | Number of animals[2] | Mean peak virus titer[3] ($log_{10}TCID_{50}$/ml ± S.E.) [Duncan Grouping][4] | | Serum HAI antibody titer (mean recip. $log_2$ ± S.E.) for | Serum HAI antibody titer (mean recip. $log_2$ ± S.E.) for |
|---|---|---|---|---|---|
| | | NP swab[5] | Tracheal lavage[6] | HPIV3 on day 28[7] | BPIV3 on day 28[7] |
| rHPIV3 | 6 | 4.7 ± 0.54 [A] | 2.4 ± 0.37 [A] | 9.5 ± 0.72 [A] | 6.8 ± 1.03 [B] |
| rBPIV3-$F_H HN_H$ | 4 | 3.1 ± 0.58 [B] | 1.6 ± 0.05 [A] | 6.8 ± 0.63 [BC] | 3.8 ± 0.63 [C] |
| rHPIV3-$N_B$ | 6 | 3.0 ± 0.60 [B] | 1.4 ± 0.19 [A] | 8.2 ± 0.48 [AB] | 6.5 ± 0.62 [B] |
| rHPIV3-$F_B HN_B$ | 4 | 2.9 ± 0.28 [B] | 2.0 ± 0.24 [A] | 4.5 ± 0.29 [D] | 9.5 ± 0.65 [A] |
| BPIV3 Ka | 6 | 2.6 ± 0.26 [B] | 1.6 ± 0.10 [A] | 5.5 ± 0.62 [CD] | 9.2 ± 0.60 [A] |

[1]Monkeys were inoculated intranasally and intratracheally with $10^5 TCID_{50}$ of virus in a 1 ml inoculum at each site.
[2]The groups with 6 animals contain 4 animals each from a previous rhesus study (Bailly et al., 2000, supra).
[3]Mean of the peak virus titers for each animal in its group irrespective of sampling day. S.E. = standard error.
[4]Virus titrations were performed on LLC-MK2 cells at 32° C. The limit of detectability of virus titer was 10 $TCID_{50}$/ml. Mean viral titers were compared using a Duncan Multiple Range test ($\alpha$= 0.05). Within each column, mean titers with different letters are statistically different. Titers indicated with two letters are not significantly different from those indicated with either letter.
[5]Nasopharyngeal swab samples were collected on days 1 to 11 and on day 13.
[6]Trachael lavage samples were collected on days 2, 4, 6, 8 and 10 post-infection.
[7]The titers on day 0 were <2.0. Day 28 was the day of challenge with wild type HPIV3.
** Two of the animals in the fHPIV3 group were infected with rHPIV3s, the virus containing two restriction enzyme recognition sites for the glycoprotein swap.

The rBPIV3-$F_H HN_H$ chimeric virus replicated significantly less well than rHPIV3 (Table 5), and it grouped with BPIV3 in a Duncan multiple range test. However, inspection of its pattern of replication in FIG. 14, panel B suggested that rBPIV3-$F_H HN_H$ replicated to a level intermediate between that of its HPIV3 and BPIV3 parents. The interpretation that rBPIV3-$F_H HN_H$ replicates to a level intermediate between that of its parents is supported by Friedman's test of consistency of ranks (Sprent, P., "A Generalization Of The Sign Test," *Applied Nonparametric Statistical Methods, pp.* 123-126, Chapman and Hall, London, 1989, incorporated herein by reference), which indicated that the median titers of HPIV3, rBPIV3-F$_H$HN$_H$, and BPIV3 between day 3 and day 8 post infection are significantly different (d.f. 2.8; p<0.05). The observation that the introduction of the HPIV3 F and HN proteins resulted in an increase in the replication of BPIV3 in rhesus monkeys indicates (i) that F and HN contain one or more determinants of host range restriction and (ii) that one or more genetic elements of BPIV3 that lie outside of the F and HN genes, e.g. the N protein, attenuate the virus for rhesus monkeys. This confirms that the genetic basis for host range restriction can involve multiple genes.

The Chimeric BPIV3 Bearing HPIV3 Glycoprotein Genes Induces Serum HAI Antibody to HPIV3 and a High Level of Resistance to Wt HPIV3 Challenge.

rBPIV3-F$_H$HN$_H$ has important features that make it a candidate live attenuated virus vaccine against HPIV3, including attenuating genes from BPIV3 and the antigenic specificity of HPIV3, i.e. the F and HN glycoproteins, which are the major protective antigens. Therefore, its immunogenicity and protective efficacy against challenge with HPIV3 were documented. Rhesus monkeys were immunized by infection with BPIV3 Ka, rHPIV3-F$_B$HN$_B$, rBPIV3-F$_H$HN$_H$, rHPIV3-N$_B$, or rHPIV3. They were challenged 28 days later with HPIV3 JS wild type virus. Serum samples were taken prior to the initial infection on day 0 and prior to the challenge. BPIV3 and rHPIV3-F$_B$HN$_B$ induced serum HAI antibodies that reacted more efficiently with BPIV3 than HPIV3, whereas the converse was the case for HPIV3 and rBPIV3-F$_H$HN$_H$. Thus, the origin of the glycoprotein genes in each virus determined whether the HAI antibody response was directed predominantly against HPIV3 or against BPIV3. The replication of challenge HPIV3 virus was significantly reduced in the upper and lower respiratory tract of previously immunized monkeys (Table 8). Although the level of protective efficacy against HPIV3 was not significantly different among the different viruses, viruses bearing HPIV3 F and HN were consistently more protective in the upper respiratory tract than were viruses bearing BPIV3 F and HN. This is in accordance with the higher level of HPIV3-specific serum HAI antibodies induced by viruses bearing HPIV3 F and HN.

Based on the foregoing examples, the invention provides for importation of BPIV genes into a virulent HPIV backbone and visa versa to yield novel, human-bovine chimeric PIV vaccine candidates. In exemplary chimeric recombinants disclosed in the present example, rBPIV3-F$_H$HN$_H$ and its rHPIV3-F$_B$HN$_B$ counterpart, replicated in vitro as well as the respective parental viruses. It was also confirmed that the F and HN exchange between the BPIV3 and HPIV3 is compatible since the considerably more divergent HPIV1 F and HN proteins were highly functional in a HPIV3 background (Tao et al., *J. Virol.* 72:2955-2961, 1998), which was evinced by the undiminished capacity of the chimeric viruses for replication in vitro. rBPIV3-F$_H$HN$_H$ replicated in the upper respiratory tract of rhesus monkeys to a level intermediate between that of its HPIV3 and BPIV3 parents indicating that the BPIV3 F and HN genes make an independent contribution to the overall attenuation of BPIV3 for primates. The overall attenuation of BPIV3 virus thus is the sum of two or more genetic elements, one of which is the set of F and HN genes and others are indicated to be N, M, and P.

Although BPIV3 itself is being evaluated as a vaccine virus for HPIV3 (Karron et al., *Pediatr. Infect. Dis. J.* 15:650-654, 1996; and Karron et al., *J. Infect. Dis.* 171:1107-1114, 1995), it is only 25% related antigenically to HPIV3 (Coelingh et al., *J. Infect. Dis.* 157:655-662, 1988). Thus, the immunogenicity of BPIV3 against HPIV3 will be improved if it is modified according to the present invention to express the protective F and HN antigens of HPIV3. rBPIV3-F$_H$HN$_H$ represents such a virus, and, in the present example, immunization of rhesus monkeys with rBPIV3-F$_H$HN$_H$ induced a higher level of antibody to HPIV3 than did immunization with BPIV3. Furthermore, rBPIV3-F$_H$HN$_H$ conferred a level of protection against replication of HPIV3 challenge in the upper and lower respiratory tract that was statistically indistinguishable from that conferred by a previous infection with rHPIV3. Similarly, rHPIV3-NB, which is attenuated by the BPIV3 N protein but possesses HPIV3 protective antigens, also induced a high level of resistance to HPIV3 challenge. Despite replicating to

TABLE 8

Immunization of rhesus monkeys with BPIV3/HPIV3 chimeric recombinant virus induces resistance to challenge with wild type HPIV3

| Immunizing virus[1] | Number of animals[2] | Mean peak virus titer[3] ($\log_{10}$TCID$_{50}$/ml ± S.E.) [Duncan Grouping][4] | | Serum HAI antibody titer (mean recip. log$_2$ ± S.E.) for HPIV3 on the day of challenge | Serum HAI antibody titer (mean recip. log$_2$ ± S.E.) for HPIV3 28 days after challenge |
|---|---|---|---|---|---|
| | | Nasopharyngeal swab[5] | Tracheal lavage[6] | | |
| none | 4 | 4.5 ± 0.33 [A] | 4.5 ± 0.19 [A] | <2 | 12.0 ± 0.58 [A] |
| rHPIV3 | 6 | 2.3 ± 0.14 [B] | 1.2 ± 0.20 [B] | 9.5 ± 0.72 [A] | 11.7 ± 0.21 [A] |
| rBPIV3-F$_H$HN$_H$ | 4 | 2.5 ± 0.25 [B] | 1.0 ± 0.48 [B] | 6.8 ± 0.63 [BC] | 10.5 ± 0.29 [AB] |
| rHPIV3-N$_B$ | 6 | 2.3 ± 0.41 [B] | 1.4 ± 0.08 [B] | 8.2 ± 0.48 [AB] | 11.5 ± 0.22 [A] |
| rHPIV3-F$_B$HN$_B$ | 4 | 3.0 ± 0.14 [B] | 1.0 ± 0.0 [B] | 4.5 ± 0.29 [D] | 9.5 ± 0.87 [B] |
| BPIV3 Ka | 6 | 2.9 ± 0.26 [B] | 1.3 ± 0.20 [B] | 5.5 ± 0.62 [CD] | 9.3 ± 0.76 [B] |

[1]Each previously immunized monkey and non-immunized controls were challenged with 10$^6$TCID$_{50}$ of HPIV3 JS in a 1 ml inoculum at each site 28 days after immunization.
[2]The groups with 6 animals contain 4 animals each from a previous rhesus study (Bailly et al., 2000, supra).
[3]Mean of the peak virus titers for each animal in its group irrespective of sampling day.
[4]Virus titrations were performed on LLC-MK2 cells. The limit of detectability of virus titer was 10 TCID$_{50}$/ml. Mean viral titers were compared using a Duncan Multiple Range test ($\alpha$ = 0.05). Within each column, mean titers with different letters are statistically different. Titers indicated with two letters are not significantly different from those indicated with either letter. The group of unimmunized animals were not included in the Duncan analysis at the day of challenge.
[5]Nasopharyngeal swab samples were collected on days 3 to 8 post challenge.
[6]Trachael lavage samples were collected on days 4, 6 and 8 post challenge.
** Two animals in the rHPIV3 group were infected with rHPIV3s.

similar levels in rhesus monkeys, rHPIV3-N$_B$ induced higher levels of antibodies to HPIV3 than rBPIV3-F$_H$HN$_H$.

rBPIV3-F$_H$HN$_H$ replicates to higher levels in rhesus monkeys than BPIV3, although it is significantly attenuated compared to HPIV3. Since the level of replication of BPIV3 in humans is low (Karron et al., *J. Infect. Dis.* 171:1107-1114, 1995), this increase is expected to be well tolerated among vaccinees. Alternatively, additional methods to attenuate human-bovine chimeric viruses of the invention are disclosed herein to ensure that the vaccine viruses replicate only to moderate levels, for example in human infants, to prevent unacceptable respiratory tract illness among vaccinees. Within other aspects of the invention, the slight increase in replication of rBPIV3-F$_H$HN$_H$ in primates offers an opportunity to use rBPIV3-F$_H$HN$_H$ as a vector for heterologous viral antigens such as glycoproteins of other PIVs (e.g., HPIV1 and HPIV2), the RSV F and G glycoproteins, and the measles HA glycoprotein, which can be incorporated as added or substituted gene(s) or genome segment(s) into the attenuated HPIV3 vaccine candidate. In various alternative embodiments disclosed herein, the slight increase in replication of rBPIV3-F$_H$HN$_H$ in monkeys over that of BPIV3 can be offset by the addition of foreign viral protective antigens, e.g., RSV glycoproteins, whose addition provides a selected level of attenuation. The data presented here further defined the basis for the host range restriction of BPIV3 for primates and identify rBPIV3-F$_H$HN$_H$ as a potential vaccine candidate against HPIV3 and as a vector for heterologous viral antigens.

Example VI

Replacement of the Human PIV3 L Open Reading Frame (ORF) with that of the Bovine PIV3 L ORF The Kansas strain of bovine parainfluenza type 3 (BPIV3) is restricted for replication in the respiratory tract of humans and non-human primates and is currently being evaluated as a live-attenuated vaccine candidate to protect human infants from the severe lower respiratory tract disease caused by HPIV3 infection (Karron et al., 1996; Karron et al., 1995). In the preceding examples the N, P and M ORFs of BPIV3 were shown to confer attenuation of replication in the respiratory tract of rhesus monkeys when substituted for the corresponding human ORF in rHPIV3. In addition to possessing an attenuation phenotype, rHPIV3 N$_B$, rHPIV3 P$_B$, or rHPIV3 M$_B$ chimeras, which contained the human PIV3 F and HN glycoproteins, were immunogenic and protective against HPIV3 challenge. To examine the contribution of the L ORF to the attenuation phenotype of BPIV3, a chimeric HPIV3 was constructed bearing the L ORF of BPIV3 in place of the human PIV3 L ORF (FIG. 15).

A full-length antigenomic HPIV3 cDNA plasmid bearing the L ORF of BPIV3 (BPIV3 nts 8640-15341; GenBank accession #AF178654) in place of the human PIV3 L ORF (HPIV3 nts 8646-15347; GenBank accession #Z11575) was assembled by introducing unique restriction sites near the start and stop codons of the human L ORF and its bovine counterpart using site directed mutagenesis. The L ORF of HPIV3 was then exchanged with that of its bovine counterpart using standard molecular cloning techniques. The sequence immediately before and after the translation start codon of the exchanged ORF was subsequently mutagenized back to human or bovine PIV3 sequence, respectively. An appropriate restriction enzyme fragment bearing the exchanged L ORF was then assembled into a full-length HPIV3 cDNA plasmid to yield an infectious full length chimeric antigenomic HPIV3 cDNA using techniques described previously (see, e.g., Durbin et al., *Virology* 235:323-332, 1997; Skiadopoulos et al., *Virology* 260:125-135, 1999b, each incorporated herein by reference).

Chimeric virus was recovered by transfection of HEp-2 cells with the chimeric full-length cDNA, with the pTM(N), pTM(PnoC) and pTM(L) support plasmids, and with the recombinant vaccinia virus MVA-T7, as described previously (see, e.g., Durbin et al., *Virology* 235:323-332, 1997; Skiadopoulos et al., *Virology* 260:125-135, 1999b, each incorporated herein by reference). Supernatant fluid from the transfected culture was harvested four days after transfection and was passaged twice in LLC-MK2 cell cultures to generate a virus suspension which was subsequently biologically cloned by plaque to plaque passage on LLC-MK2 monolayers. The biologically cloned viruses were then amplified on LLC-MK2 monolayers to generate working virus suspensions. rHPIV3 L$_B$ replicated efficiently in tissue culture, growing to a mean titer of $10^{6.2}$ (TCID$_{50}$/ml). The identity of rHPIV3 L$_B$ was confirmed by isolation of the viral RNA (vRNA) which was used to amplify specific fragments by RT-PCR (see, e.g., Skiadopoulos et al., *Virology* 260:125-135, 1999b; Skiadopoulos et al., Virology 272:225-234, 2000, each incorporated herein by reference). Partial DNA sequencing of the RT-PCR products confirmed that rHPIV3 L$_B$ was a recombinant chimeric HPIV3 that contained the bovine PIV3 L ORF (FIG. 16) as designed.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation.

What is claimed is:

1. A chimeric, infectious human-bovine chimeric parainfluenza virus (PIV) comprising a major nucleocapsid (N) protein, a nucleocapsid phosphoprotein (P), a large polymerase protein (L), and a partial or complete PIV background genome or antigenome of a human PIV3 (HPIV3) combined with a M gene or genome segment(s) thereof of a bovine PIV to form a human-bovine chimeric PIV genome or antigenome.

2. The chimeric PIV of claim 1, wherein said partial or complete PIV background genome or antigenome further comprises one or more heterologous gene(s) or genome segment(s) that encodes one or more PIV N, P, C, D, V, F, HN and/or L protein(s) or fragment(s) thereof.

3. The chimeric PIV of claim 1, wherein said one or more heterologous gene(s) or genome segment(s) encodes a complete open reading frame (ORF) of one or more PIV N, P, C, D, V, F, HN and/or L protein(s).

4. The chimeric PIV of claim 1, wherein said one or more heterologous gene(s) or genome segment(s) includes a heterologous regulatory element comprising an extragenic 3' leader or 5' trailer region, a gene-start signal, gene-end signal, RNA editing site, encapsidation signal, intergenic region, or 3' or 5' non-coding region.

5. The chimeric PIV of claim 1, wherein said background genome or antigenome incorporates a heterologous genome segment integrated with the background genome or anti genome to form a chimeric gene.

6. The chimeric PIV of claim 1, wherein a heterologous gene or genome segment is added adjacent to or within a noncoding region of the partial or complete PIV background genome or antigenome.

7. The chimeric PIV of claim 1, wherein a heterologous gene or genome segment is added or substituted at a position corresponding to a wild-type gene order position of a counterpart gene or genome segment within the partial or complete PIV background genome or antigenome.

8. The chimeric PIV of claim 1, wherein a heterologous gene or genome segment is added or substituted at a position that is more promoter-proximal or promoter-distal compared to a wild-type gene order position of a counterpart gene or genome segment within the partial or complete PIV background genome or antigenome.

9. The chimeric PIV of claim 2, wherein said one or more heterologous gene(s) or genome segment(s) encodes a complete open reading frame (ORF) of one or more PIV N, P or L protein(s).

10. The chimeric PIV of claim 2, wherein a bovine PIV3 N, L, or P open reading frame (ORF) is substituted for a human PIV N, L, or P ORF.

11. The chimeric PIV of claim 1, wherein the chimeric genome or anti genome is further modified by addition or substitution of one or more additional heterologous gene(s) or genome segment(s) from a bovine PIV within the partial or complete bovine background genome or anti genome to increase genetic stability or alter attenuation, reactogenicity or growth in culture of the chimeric virus.

12. The chimeric PIV of claim 1, wherein the genome or antigenome further incorporates at least one and up to a full complement of attenuating mutations specifying an amino acid substitution in the L protein at a position corresponding to $Tyr_{942}$, $Leu_{992}$, or $Thr1_{558}$ of JS; in the N protein at a position corresponding to residues $Val_{96}$ or $Ser_{389}$ of JS, in the C protein at a position corresponding to $Ile_{96}$ of JS, in the M protein at a position corresponding to residues $Pro_{199}$ of JS, in the F protein at a position corresponding to residues $Ile_{420}$ or $Ala_{450}$ of is, in the HN protein at a position corresponding to residue $Val_{384}$ of JS, a nucleotide substitution a 3' leader sequence of the chimeric virus at a position corresponding to nucleotide 23, 24, 28, or 45 of JS, and/or a mutation in an N gene start sequence at a position corresponding to nucleotide 62 of JS.

13. The chimeric PIV of claim 12, wherein the genome or antigenome includes at least one attenuating mutation stabilized by multiple nucleotide changes in a codon specifying the mutation.

14. The chimeric PIV of claim 1, wherein the genome or antigenome comprises an additional nucleotide modification specifying a phenotypic change selected from a change in growth characteristics, attenuation, temperature-sensitivity, cold-adaptation, plaque size, host-range restriction, or a change in immunogenicity.

15. The chimeric PIV of claim 14, wherein the additional nucleotide modification alters one or more of the PIV N, P, C, D, V, F, HN and/or L genes and/or a 3' leader, 5' trailer RNA editing site, encapsidation signal, and/or an intergenic region.

16. The chimeric PIV of claim 15, wherein one or more genes of the chimeric virus is deleted in whole or in part or expression of the genes is reduced or ablated by a mutation in an RNA editing site, by a frameshift mutation, by a mutation that alters an amino acid specified by an initiation codon, or by introduction of one or more stop codons in an open reading frame (ORF) of the gene.

17. The chimeric PIV of claim 14, wherein a modification is introduced in the chimeric genome or anti genome comprising a partial or complete deletion of one or more C, D and/or V ORF(s) or one or more nucleotide change(s) that reduces or ablates expression of said one or more C, D and/or V ORF(s).

18. The chimeric PIV of claim 1, wherein the chimeric genome or antigenome is modified to encode a non-PIV molecule selected from a cytokine, a T-cell helper epitope, a restriction site marker, or a protein of a microbial pathogen capable of eliciting a protective immune response in a mammalian host.

19. The chimeric PIV of claim 1, wherein the bovine-human chimeric genome or antigenome comprises a partial or complete PIV vector genome or antigenome combined with one or more heterologous genes or genome segments encoding one or more antigenic determinants of one or more heterologous pathogens.

20. The chimeric PIV of claim 1, wherein one or more HP1V1 or HP1V2 gene(s) or genome segment(s) encoding one or more HN and/or F glycoprotein(s) or antigenic domain(s), fragment(s) or epitope(s) thereof is/are added to or incorporated within the partial or complete HP1V3 vector genome or antigenome.

21. The chimeric PIV of claim 20, wherein both HPIV1 genes encoding HN and F glycoproteins are substituted for counterpart HPIV3 HN and F genes and the vector genome or anti genome is further modified by addition or incorporation of one or more gene(s) or gene segment(s) encoding one or more antigenic determinant(s) of HPIV2.

22. The chimeric PIV of claim 21, wherein a transcription unit comprising an open reading frame (ORF) of an HPIV2 HN gene is added to or incorporated within the chimeric vector genome or antigenome.

23. The chimeric PIV of claim 19, wherein a plurality of antigenic determinants of multiple HPIVs are added to or incorporated within the partial or complete vector genome or antigenome.

24. The chimeric PIV of claim 19, wherein the vector genome or antigenome is a partial or complete HPIV genome or antigenome and the heterologous pathogen is selected from measles virus, subgroup A and subgroup B respiratory syncytial viruses, mumps virus, human papillomaviruses, type 1 and type 2 human immunodeficiency viruses, herpes simplex viruses, cytomegalovirus, rabies virus, Epstein-Barr virus, filoviruses, bunyaviruses, flaviviruses, alphaviruses and influenza viruses.

25. The chimeric PIV of claim 24, wherein said one or more heterologous antigenic determinant(s) is/are selected from measles virus HA and F proteins, subgroup A or subgroup B respiratory syncytial virus F, G, SH and M2 proteins, mumps virus HN and F proteins, human papillomavirus L 1 protein, type 1 or type 2 human immunodeficiency virus gp 160 protein, herpes simplex virus and cytomegalovirus gB, gC, gD, gE, gG, gR, gI, gJ, gK, gL, and gM proteins, rabies virus G protein, Epstein-Barr Virus gp350 protein; filovirus G protein, bunyavirus G protein, Flavivirus B and NS 1 proteins, and alphavirus E protein, and antigenic domains, fragments and epitopes thereof.

26. The chimeric PIV of claim 25, wherein the heterologous pathogen is measles virus and the heterologous antigenic determinant(s) is/are selected from the measles virus HA and F proteins and antigenic domains, fragments and epitopes thereof.

27. The chimeric PIV of claim 26, wherein a transcription unit comprising an open reading frame (ORF) of a measles virus HA gene is added to or incorporated within the vector genome or antigenome.

28. The chimeric PIV of claim 25, which incorporates a gene or genome segment from respiratory syncytial virus (RSV).

29. The chimeric PIV of claim 28, wherein the gene or genome segment encodes a RSV F and/or G glycoprotein or immunogenic domain(s) or epitope(s) thereof.

30. An immunogenic composition to elicit an immune response against PIV comprising an immunogenically sufficient amount of the chimeric PIV of claim 1 in a physiologically acceptable carrier.

31. The immunogenic composition of claim 30, formulated in a dose of $10^3$ to $10^7$ PFU.

32. The immunogenic composition of claim 30, formulated for administration to the upper respiratory tract by spray, droplet or aerosol.

33. The immunogenic composition of claim 30, wherein the chimeric PIV elicits an immune response against one or more virus(es) selected from HPIV1, HPIV2 and HPIV3.

34. The immunogenic composition of claim 33, wherein the chimeric PIV elicits an immune response against HPIV3 and another virus selected from HPIV1 and HPIV2.

35. An immunogenic composition to elicit an immune response against PIV comprising an immunogenically sufficient amount of the chimeric PIV of claim 14 in a physiologically acceptable carrier.

36. An immunogenic composition to elicit an immune response against PIV comprising an immunogenically sufficient amount of the chimeric PIV of claim 20 in a physiologically acceptable carrier.

* * * * *

UNITED STATES PATENT AND TRADEMARK OFFICE
CERTIFICATE OF CORRECTION

PATENT NO. : 7,622,123 B2
APPLICATION NO. : 10/982223
DATED : November 24, 2009
INVENTOR(S) : Skiadopoulos et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 366 days.

Signed and Sealed this

Twenty-sixth Day of October, 2010

David J. Kappos
*Director of the United States Patent and Trademark Office*

SEQUENCE LISTING

<160> NUMBER OF SEQ ID NOS: 66

<210> SEQ ID NO 1
<211> LENGTH: 7
<212> TYPE: DNA
<213> ORGANISM: Artificial Sequence
<220> FEATURE:
<223> OTHER INFORMATION: Parainfluenza Virus

<400> SEQUENCE: 1

-continued

```
actggtt                                                              7

<210> SEQ ID NO 2
<211> LENGTH: 7
<212> TYPE: DNA
<213> ORGANISM: Artificial Sequence
<220> FEATURE:
<223> OTHER INFORMATION: Parainfluenza Virus

<400> SEQUENCE: 2 acttgct                                                              7

<210> SEQ ID NO 3
<211> LENGTH: 6
<212> TYPE: DNA
<213> ORGANISM: Artificial Sequence
<220> FEATURE:
<223> OTHER INFORMATION: Parainfluenza Virus

<400> SEQUENCE: 3 tgatgg                                                               6

<210> SEQ ID NO 4
<211> LENGTH: 6
<212> TYPE: DNA
<213> ORGANISM: Artificial Sequence
<220> FEATURE:
<223> OTHER INFORMATION: Parainfluenza Virus

<400> SEQUENCE: 4 ccatgg                                                               6

<210> SEQ ID NO 5
<211> LENGTH: 6
<212> TYPE: DNA
<213> ORGANISM: Artificial Sequence
<220> FEATURE:
<223> OTHER INFORMATION: Parainfluenza Virus

<400> SEQUENCE: 5 tccaac                                                               6

<210> SEQ ID NO 6
<211> LENGTH: 6
<212> TYPE: DNA
<213> ORGANISM: Artificial Sequence
<220> FEATURE:
<223> OTHER INFORMATION: Parainfluenza Virus

<400> SEQUENCE: 6 gctagc                                                               6

<210> SEQ ID NO 7
<211> LENGTH: 6
<212> TYPE: DNA
<213> ORGANISM: Artificial Sequence
<220> FEATURE:
<223> OTHER INFORMATION: Parainfluenza Virus

<400> SEQUENCE: 7 tcatgg                                                               6

<210> SEQ ID NO 8
<211> LENGTH: 6
<212> TYPE: DNA
<213> ORGANISM: Artificial Sequence
```

```
<220> FEATURE:
<223> OTHER INFORMATION: Parainfluenza Virus

<400> SEQUENCE: 8 gccaac                                                                    6

<210> SEQ ID NO 9
<211> LENGTH: 6
<212> TYPE: DNA
<213> ORGANISM: Artificial Sequence
<220> FEATURE:
<223> OTHER INFORMATION: Parainfluenza Virus

<400> SEQUENCE: 9 gctagc                                                                    6

<210> SEQ ID NO 10
<211> LENGTH: 34
<212> TYPE: DNA
<213> ORGANISM: Artificial Sequence
<220> FEATURE:
<223> OTHER INFORMATION: Parainfluenza Virus

<400> SEQUENCE: 10
ctcaatcaat agagagttga tggaaagcga tgct                                    34

<210> SEQ ID NO 11
<211> LENGTH: 34
<212> TYPE: DNA
<213> ORGANISM: Artificial Sequence
<220> FEATURE:
<223> OTHER INFORMATION: Parainfluenza Virus

<400> SEQUENCE: 11
ctcaatcaat agagagttga tggaagacaa tgtt                                    34

<210> SEQ ID NO 12
<211> LENGTH: 34
<212> TYPE: DNA
<213> ORGANISM: Artificial Sequence
<220> FEATURE:
<223> OTHER INFORMATION: Parainfluenza Virus

<400> SEQUENCE: 12
ctcaatcaac caaagattca tggaagacaa tgtt                                    34

<210> SEQ ID NO 13
<211> LENGTH: 42
<212> TYPE: DNA
<213> ORGANISM: Artificial Sequence
<220> FEATURE:
<223> OTHER INFORMATION: Parainfluenza Virus

<400> SEQUENCE: 13
tgtcaacaat tgccaatgat ccaacaaaga aacgacaccg aa                            42

<210> SEQ ID NO 14
<211> LENGTH: 42
<212> TYPE: DNA
<213> ORGANISM: Artificial Sequence
<220> FEATURE:
<223> OTHER INFORMATION: Parainfluenza Virus

<400> SEQUENCE: 14
ggatgtcagc tcccagtaaa ccgctagcaa agaaacgaca cc                            42
```

```
<210> SEQ ID NO 15
<211> LENGTH: 42
<212> TYPE: DNA
<213> ORGANISM: Artificial Sequence
<220> FEATURE:
<223> OTHER INFORMATION: Parainfluenza Virus

<400> SEQUENCE: 15
ggatgtcagc tcccagtaaa ccgccaacca agggtcaaca cc                           42

<210> SEQ ID NO 16
<211> LENGTH: 6
<212> TYPE: DNA
<213> ORGANISM: Artificial Sequence
<220> FEATURE:
<223> OTHER INFORMATION: Parainfluenza Virus

<400> SEQUENCE: 16 aaatga                                                                    6

<210> SEQ ID NO 17
<211> LENGTH: 6
<212> TYPE: DNA
<213> ORGANISM: Artificial Sequence
<220> FEATURE:
<223> OTHER INFORMATION: Parainfluenza Virus

<400> SEQUENCE: 17 gcatgc                                                                    6

<210> SEQ ID NO 18
<211> LENGTH: 6
<212> TYPE: DNA
<213> ORGANISM: Artificial Sequence
<220> FEATURE:
<223> OTHER INFORMATION: Parainfluenza Virus

<400> SEQUENCE: 18 aatctc                                                                    6

<210> SEQ ID NO 19
<211> LENGTH: 6
<212> TYPE: DNA
<213> ORGANISM: Artificial Sequence
<220> FEATURE:
<223> OTHER INFORMATION: Parainfluenza Virus

<400> SEQUENCE: 19 caatga                                                                    6

<210> SEQ ID NO 20
<211> LENGTH: 6
<212> TYPE: DNA
<213> ORGANISM: Artificial Sequence
<220> FEATURE:
<223> OTHER INFORMATION: Parainfluenza Virus

<400> SEQUENCE: 20 atcaac                                                                    6

<210> SEQ ID NO 21
<211> LENGTH: 40
<212> TYPE: DNA
<213> ORGANISM: Artificial Sequence
<220> FEATURE:
<223> OTHER INFORMATION: Parainfluenza Virus
```

-continued

<400> SEQUENCE: 21
gaataaatta atccttgtcc aaaatgagta taactaactc                    40

<210> SEQ ID NO 22
<211> LENGTH: 40
<212> TYPE: DNA
<213> ORGANISM: Artificial Sequence
<220> FEATURE:
<223> OTHER INFORMATION: Parainfluenza Virus

<400> SEQUENCE: 22
gaataaatta atccttgtcc aaaatgagca tcaccaactc                    40

<210> SEQ ID NO 23
<211> LENGTH: 40
<212> TYPE: DNA
<213> ORGANISM: Artificial Sequence
<220> FEATURE:
<223> OTHER INFORMATION: Parainfluenza Virus

<400> SEQUENCE: 23
ggactaatca atcctccgaa acaatgagca tcaccaactc                    40

<210> SEQ ID NO 24
<211> LENGTH: 37
<212> TYPE: DNA
<213> ORGANISM: Artificial Sequence
<220> FEATURE:
<223> OTHER INFORMATION: Parainfluenza Virus

<400> SEQUENCE: 24
tcaaacaatg gaactagtaa tctctatttt agtccgg                       37

<210> SEQ ID NO 25
<211> LENGTH: 37
<212> TYPE: DNA
<213> ORGANISM: Artificial Sequence
<220> FEATURE:
<223> OTHER INFORMATION: Parainfluenza Virus

<400> SEQUENCE: 25
ggaaaatcag acagtaaagc tagctatttt agtccgg                       37

<210> SEQ ID NO 26
<211> LENGTH: 37
<212> TYPE: DNA
<213> ORGANISM: Artificial Sequence
<220> FEATURE:
<223> OTHER INFORMATION: Parainfluenza Virus

<400> SEQUENCE: 26
ggaaaatcag acagtaaaat caacaaccct gatatcc                       37

<210> SEQ ID NO 27
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 27
tccaacattg ca                                                  12

<210> SEQ ID NO 28

```
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 28
tccaccggtg ca                                                               12

<210> SEQ ID NO 29
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 29
cggacgtatc ta                                                               12

<210> SEQ ID NO 30
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 30
cgcaccggtg ta                                                               12

<210> SEQ ID NO 31
<211> LENGTH: 10
<212> TYPE: DNA
<213> ORGANISM: Artificial Sequence
<220> FEATURE:
<223> OTHER INFORMATION: Parainfluenza Virus

<400> SEQUENCE: 31
gatataaaga                                                                  10

<210> SEQ ID NO 32
<211> LENGTH: 10
<212> TYPE: DNA
<213> ORGANISM: Artificial Sequence
<220> FEATURE:
<223> OTHER INFORMATION: Parainfluenza Virus

<400> SEQUENCE: 32
gacgtacgga                                                                  10

<210> SEQ ID NO 33
<211> LENGTH: 10
<212> TYPE: DNA
<213> ORGANISM: Artificial Sequence
<220> FEATURE:
<223> OTHER INFORMATION: Parainfluenza Virus

<400> SEQUENCE: 33
gacaaaaggg                                                                  10

<210> SEQ ID NO 34
<211> LENGTH: 10
<212> TYPE: DNA
<213> ORGANISM: Artificial Sequence
<220> FEATURE:
<223> OTHER INFORMATION: Parainfluenza Virus

<400> SEQUENCE: 34
```

```
<210> SEQ ID NO 35
<211> LENGTH: 15456
<212> TYPE: DNA
<213> ORGANISM: Artificial Sequence
<220> FEATURE:
<223> OTHER INFORMATION: Parainfluenza Virus

<400> SEQUENCE: 35
```

| | | | | | |
|---|---|---|---|---|---|
| accaaacaag | agaagagact | tgcttgggaa | tattaattca | aataaaaatt | aacttaggat | 60 |
| taaagaactt | taccgaaagg | taaggggaaa | gaaatcctaa | gactgtaatc | atgttgagtc | 120 |
| tattcgacac | attcagtgcg | cgtaggcagg | agaacataac | gaaatcagct | ggtggggctg | 180 |
| ttattcccgg | gcaaaaaaac | actgtgtcta | tatttgctct | tggaccatca | ataacagatg | 240 |
| acaatgataa | aatgacattg | gctcttctct | ttttgtctca | ttctttagac | aatgaaaagc | 300 |
| agcatgcgca | aagagctgga | tttttagttt | ctctgttatc | aatggcttat | gccaacccag | 360 |
| aattatattt | aacatcaaat | ggtagtaatg | cagatgttaa | atatgttatc | tacatgatag | 420 |
| agaaagaccc | aggaagacag | aaatatggtg | ggtttgtcgt | caagactaga | gagatggttt | 480 |
| atgaaaagac | aactgattgg | atgttcggga | gtgatcttga | gtatgatcaa | gacaatatgt | 540 |
| tgcaaaatgg | tagaagcact | tctacaatcg | aggatcttgt | tcatacttt | ggatatccat | 600 |
| cgtgtcttgg | agcccttata | atccaagttt | ggataatact | tgttaaggct | ataaccagta | 660 |
| tatcaggatt | gaggaaagga | ttctttactc | ggttagaagc | atttcgacaa | gatgaacag | 720 |
| ttaaatccag | tctagtgttg | agcggtgatg | cagtagaaca | aattggatca | attatgaggt | 780 |
| cccaacagag | cttggtaaca | ctcatggttg | aaacactgat | aacaatgaac | acaggcagga | 840 |
| atgatctgac | aacaatagaa | aagaatatac | agattgtagg | aaactacatc | agagatgcag | 900 |
| gtcttgcttc | atttttcaac | acaatcagat | atggcattga | gactagaatg | gcagctctaa | 960 |
| ctctgtctac | ccttagaccg | gatatcaaca | gactcaaggc | actgatcgag | ttatatctat | 1020 |
| caaaggggcc | acgtgctcct | tttatatgca | ttttgagaga | tcccgtgcat | ggtgagtttg | 1080 |
| caccaggcaa | ctatcctgcc | ctctggagtt | atgcgatggg | tgtagcagtt | gtacaaaaca | 1140 |
| aggccatgca | acagtatgta | acaggaaggt | cttatctgga | tattgaaatg | ttccaacttg | 1200 |
| gtcaagcagt | ggcacgtgat | gccgagtcgc | agatgagttc | aatattagag | gatgaactgg | 1260 |
| gggtcacaca | agaagccaag | caaagcttga | agaaacacat | gaagaacatc | agcagttcag | 1320 |
| atacaacctt | tcataagcct | acaggggat | cagccataga | aatggcgata | gatgaagaag | 1380 |
| cagggcagcc | tgaatccaga | ggagatcagg | atcaaggaga | tgagcctcgg | tcatccatag | 1440 |
| ttccttatgc | atgggcagac | gaaaccggga | atgacaatca | aactgaatca | actacagaaa | 1500 |
| ttgacagcat | caaaactgaa | caagaaaca | tcagagacag | gctgaacaaa | agactcaacg | 1560 |
| agaaaaggaa | acagagtgac | ccgagatcaa | ctgacatcac | aaacaacaca | aatcaaactg | 1620 |
| aaatagatga | tttgttcagt | gcattcggaa | gcaactagtc | acaaagagat | gaccactatc | 1680 |
| accagcaaca | agtaagaaaa | acttaggatt | aatggaaatt | atccaatcca | gagacggaag | 1740 |
| gacaaatcca | gaatccaacc | acaactcaat | caaccaaaga | ttcatggaag | acaatgttca | 1800 |
| aaacaatcaa | atcatggatt | cttgggaaga | gggatcagga | gataaatcat | ctgacatctc | 1860 |
| atcggccctc | gacatcattg | aattcatact | cagcaccgac | tcccaagaga | acacggcaga | 1920 |
| cagcaatgaa | atcaacacag | gaaccacaag | acttagcacg | acaatctacc | aacctgaatc | 1980 |

```
caaaacaaca gaaacaagca aggaaaatag tggaccagct aacaaaaatc gacagtttgg    2040
ggcatcacac gaacgtgcca cagagacaaa agatagaaat gttaatcagg agactgtaca    2100
gggaggatat aggagaggaa gcagcccaga tagtagaact gagactatgg tcactcgaag    2160
aatctccaga agcagcccag atcctaacaa tggaacccaa atccaggaag atattgatta    2220
caatgaagtt ggagagatgg ataaggactc tactaagagg gaaatgcgac aatttaaaga    2280
tgttccagtc aaggtatcag gaagtgatgc cattcctcca acaaaacaag atggagacgg    2340
tgatgatgga agaggcctgg aatctatcag tacatttgat tcaggatata ccagtatagt    2400
gactgccgca acactagatg acgaagaaga actccttatg aagaacaaca ggccaagaaa    2460
gtatcaatca acacccaga acagtgacaa gggaattaaa aaggggttg aaggccaaa     2520 agacacagac aaacaatcat caatattgga ctacgaactc aacttcaaag gatcgaagaa    2580
gagccagaaa atcctcaaag ccagcacgaa tacaggagaa ccaacaagac cacagaatgg    2640
atcccagggg aagagaatca catcctggaa catcctcaac agcgagagcg gcaatcgaac    2700
agaatcaaca aaccaaaccc atcagacatc aacctcggga cagaaccaca caatgggacc    2760
aagcagaaca acctccgaac caaggatcaa gacacaaaag acggatggaa aggaaagaga    2820
ggacacagaa gagagcactc gatttacaga aagggcgatt acattattac agaatcttgg    2880
tgtaatccaa tctgcagcaa aattagacct ataccaagac aagagagttg tgtgtgtggc    2940
gaatgtccta aacaatgcag atactgcatc aaagatagac ttcctagcag gtttgatgat    3000
aggagtgtca atggatcatg ataccaaatt aaatcagatt cagaacgaga tattaagttt    3060
gaaaactgat cttaaaaaga tggatgaatc acatagaaga ctaattgaga atcaaaaaga    3120
acaattatca ctgatcacat cattaatctc aaatcttaaa attatgacag agagaggagg    3180
gaagaaggac caaccagaac ctagcgggag gacatccatg atcaagacaa agcaaaagaa    3240
agagaaaata aagaaagtca ggtttgaccc tcttatggaa acacagggca tcgagaaaaa    3300
catccctgac ctctatagat caatagagaa acaccagaa aacgacacac agatcaaatc     3360
agaaataaac agattgaatg atgaatccaa tgccactaga ttagtaccta agaagaataag    3420 cagtacaatg agatcattaa taataatcat taacaacagc aatttatcat caaaagcaaa    3480
gcaatcatac atcaacgaac tcaagctctg caagagtgac gaggaagtgt ctgagttgat    3540
ggacatgttc aatgaggatg tcagctccca gtaaaccgcc aaccaagggt caacaccaag    3600
aaaaccaata gcacaaaaca gccaatcaga gaccaccca atacaccaaa ccaatcaaca     3660
cataacaaag atctccagat catagatgat taagaaaaac ttaggatgaa aggactaatc    3720
aatcctccga acaatgagc atcaccaact ccacaatcta cacattccca gaatcctctt     3780
tctccgagaa tggcaacata gagccgttac cactcaaggt caatgaacag agaaaggcca    3840
tacctcatat tagggttgtc aagataggag atccgcccaa acatggatcc agatatctgg    3900
atgtcttttt actgggcttc tttgagatgg aaaggtcaaa agacaggtat gggagcataa    3960
gtgatctaga tgatgatcca agttacaagg tttgtggctt ggatcattgc cacttgggtt    4020
tggctagata caccggaaat gatcaggaac tcctacaggc tgcaaccaag ctcgatatag    4080
aagtaagaag aactgtaaag gctacggaga tgatagttta cactgtacaa aacatcaaac    4140
ctgaactata tccatggtcc agtagattaa gaaaagggat gttatttgac gctaataagg    4200
ttgcacttgc tcctcaatgt cttccactag atagagggat aaaattcagg gtgatatttg    4260
tgaactgcac agcaattgga tcaataactc tattcaaaat ccctaagtcc atggcattgt    4320
tatcattgcc taatacaata tcaataaatc tacaagtaca tatcaaaaca ggagttcaga    4380
```

```
cagattccaa aggagtagtt cagattctag atgaaaaagg tgaaaaatca ctaaatttca   4440
tggttcatct cgggttgatc aaaaggaaga tgggcagaat gtactcagtt gaatattgta   4500
agcagaagat cgagaagatg agattattat tctcattggg attagttgga gggatcagct   4560
tccacgtcaa cgcaactggc tctatatcaa agacattagc aagtcaatta gcattcaaaa   4620
gagaaatctg ctatcccta atggatctga atccacactt aaattcagtt atatgggcat    4680
catcagttga aattacaagg gtagatgcag ttctccagcc ttcattacct ggcgaattca   4740
gatactaccc aaacatcata gcaaaagggg tcgggaaaat cagacagtaa atcaacaac    4800 cctgatatcc aacattgcaa atcaggctac ccacaggaga aaaatcaaaa acttaggatc   4860
aaagggatca ccacgaaccc cggaaaacag ccaaacaaac caacacacaa atcacagaca   4920 aaaggagaa ggcactgcaa agaccgagaa aaaacagaac gcacacaacc aagcagagaa    4980
aagccaaagc ccgccattca caaacacacc aacaatcctg caaacaagca ccaaaacaga   5040
ggtcaaaaga caaagagcac cagatatgac catcacaacc acaatcatag ccatattact   5100
aataccccca tcattttgtc aaatagacat aacaaaactg caacgtgtag gtgtgttagt   5160
caacaatcct aaaggcatga agatttcaca aaatttcgaa acgagatacc tgatattaag   5220
tttgataccc aaaatagaga attcacactc atgtggggat caacagataa accaatacaa   5280
gaagttattg gatagattga taattcctct atatgatgga ttaaaattac aaaaagatgt   5340
aatagtagta agtcatgaaa cccacaacaa tactaatctt aggacaaaac gattctttgg   5400
agagataatt gggacaattg cgatagggat agccacttca gcacaaatca ccgcagcagt   5460
cgctcttgtc gaagctaaac aggcaaagtc agacatagaa aaactcaaag aggctataag   5520
agacacaaac aaggcagtac aatcgattca aagttctgta ggtaacctaa ttgttgcagt   5580
taaatcagtt caagactatg tcaacaatga aattatacct tcaatcacaa gattaggctg   5640
tgaagcagca gggttacaat gggaattgc attgacacaa cattactcag aattaacaaa    5700
tatatttggt gataatatag gaacactgaa agaaaaaggg ataaaattac aagggatagc   5760
atcattatat cacacaaaca taacggaaat atttactact tcaacagttg accaatatga   5820 tattatgac ctattattca ctgagtcaat caagatgaga gtgatagatg ttgatttgag    5880
tgattactca attactcttc aagttagact tcctttatta actaaactat caaatactca   5940
aatttataaa gtagattcta tatcatacaa catccagggc aaagagtggt atattcctct   6000
tcccaatcac atcatgacaa aaggggcttt tctaggtggt gctgatatta agaatgcat    6060 agaggcattc agcagttata tatgtccttc tgatccaggt tacatattaa atcacgagat   6120
agagaattgt ttatcaggga acataacaca gtgtcctaag actgttgtta catcagatgt   6180
ggtaccacga tacgcgtttg tgaatggtgg attaattgca aactgcataa caactacatg   6240
tacatgcaat ggaattgaca atagaattaa tcaatcacct gatcaaggaa ttaagatcat   6300
aacacataaa gaatgccagg taataggtat aaacggaatg ttattcaata ctaatagaga   6360
agggacatta gcaacttata catttgatga catcatatta ataactctg ttgcacttaa    6420 tccaattgat atatctatgg aactcaacaa ggcaaaacta gaattagaag aatcgaagga   6480
atggataaag aaatcaaatc aaagttaga ttccgttgga agttggtatc aatctagtgc    6540
aacaatcacc ataatcatag tgatgataat aattctagtt ataatcaata taacaattat   6600
tgtagtcata atcaaattcc atagaattca ggggaaagat caaaacgaca aaacagtga    6660 gccgtatata ctgacaaata gacaataaga ctatacacga tcaaatataa aaagtacaaa   6720
```

```
aaacttagga caaagttgt tcaacacagc agcaccgaat agaccaaaag gcagcgcaga    6780
ggcgacacca aactcaaaaa tggaatattg gaaacacaca aacagcataa ataacaccaa    6840
caatgaaacc gaaacagcca gaggcaaaca tagtagcaag gttacaaata tcataatgta    6900
caccttctgg acaataacat taacaatatt atcagtcatt tttataatga tattgacaaa    6960
cttaattcaa gagaacaatc ataataaatt aatgttgcag gaaataagaa aagaattcgc    7020
ggcaatagac accaagattc agaggacttc ggatgacatt ggaacctcaa tacagtcagg    7080
aataaataca agacttctca caattcagag tcatgttcaa aactatatcc cactatcatt    7140
aacacaacaa atgtcagatc tcagaaaatt tatcaatgat ctaacaaata aaagagaaca    7200
tcaagaagtg ccaatacaga gaatgactca tgatagaggt atagaacccc taaatccaaa    7260
caagttctgg aggtgtacat ctggtaaccc atctctaaca agtagtccta agataaggtt    7320
aataccagga ccaggtttat tagcaacatc tactacagta aatggctgta ttagaattcc    7380
atcgttagta atcaatcatc taatctatgc ttacacctct aatcttatta cccagggctg    7440
tcaagatata gggaaatctt accaagtact acaaataggg ataattacta taaattcgga    7500
cctagtacct gatttaaacc ccagagtcac acatacattt aatattgatg ataatagaag    7560
atcttgctct ctggcactat tgaatacaga tgtttatcag ttatgctcaa caccaaaagt    7620
tgatgaaaga tccgattatg catcaacagg tattgaggat attgtacttg acattgtcac    7680
taataatgga ttaattataa caacaaggtt tacaaataat aatataactt tgataaaacc    7740
gtatgcagca ttgtatccat cagtgggacc aggaatctat tataaggata aagttatatt    7800
tctcggatat ggaggtctag agcatgaaga aaacggagac gtaatatgta atacaactgg    7860
ttgtcctggc aaaacacaga gagactgtaa tcaggcttct tatagcccat ggttctcaaa    7920
taggagaatg gtaaactcta ttattgttgt tgataaaggc atagatgcaa ctttttagctt    7980 gagggtgtgg actattccaa tgagccaaaa ttattgggga tcagaaggaa gattactttt    8040
attaggtgac agaatataca tatatactag atccacaagt tggcacagta aattacagtt    8100 agggggtaatt gatatttctg attatactaa tataagaata aattggactt ggcataatgt    8160
actatcacgg ccagggaatg atgaatgtcc atggggtcat tcatgcccag acggatgtat    8220
aacaggagtt tacactgatg catatccgct aaacccatcg gggagtgttg tatcatcagt    8280
aattcttgat tcacaaaagt ctagagaaaa cccaatcatt acttactcaa cagctacaaa    8340
tagaataaat gaattagcta tatataacag aacacttcca gctgcatata caacaacaaa    8400
ttgtatcaca cattatgata aagggtattg ttttcatata gtagaaataa atcacagaag    8460
tttgaatacg tttcaaccta tgttattcaa aacagaagtt ccaaaaaact gcagctaaat    8520
tgatcatcgc atatcggatg caagatgaca ttaaaagaga ccaccagaca gacaacacag    8580
gagacgatgc aagatataaa gaaataataa aaaacttagg agaaaagtgt gcaagaaaaa    8640
tggacaccga gtcccacagc ggcacaacat ctgacattct gtaccctgaa tgtcacctca    8700
attctcctat agttaaagga aagatagcac aactgcatac aataatgagt ttgcctcagc    8760
cctacgatat ggatgatgat tcaatactga ttattactag acaaaaaatt aaactcaata    8820
aattagataa aagacaacgg tcaattagga aattaagatc agtcttaatg gaaagagtaa    8880 gtgatcctagg taaatatacc tttatcagat atccagagat gtctagtgaa atgttccaat    8940 tatgtataccc cggaattaat aataaaataa atgaattgct aagtaaagca agtaaaacat    9000
ataatcaaat gactgatgga ttaagagatc tatgggttac tatactatcg aagttagcat    9060
cgaaaaatga tggaagtaat tatgatatca atgaagatat tagcaatata tcaaatgttc    9120
```

```
acatgactta tcaatcagac aaatggtata atccattcaa gacatggttt actattaagt    9180
atgacatgag aagattacaa aaagccaaaa atgagattac attcaatagg cataaagatt    9240
ataatctatt agaagaccaa aagaatatat tgctgataca tccagaactc gtcttaatat    9300
tagataaaca aaattacaat gggtatataa tgactcctga attggtacta atgtattgtg    9360
atgtagttga agggaggtgg aatataagtt catgtgcaaa attggatcct aagttacaat    9420
caatgtatta aagggtaac aatttatggg aaataataga tggactattc tcgaccttag    9480
gagaaagaac atttgacata atatcactat tagaaccact tgcattatcg ctcattcaaa    9540
cttatgaccc ggttaaacag ctcagggggg cttttttaaa tcacgtgtta tcagaaatgg    9600
aattaatatt tgcagctgag tgtacaacag aggaaatacc taatgtggat tatatagata    9660
aaattttaga tgtgttcaaa gaatcaacaa tagatgaaat agcagaaatt ttctctttct    9720
tccgaacttt tggacaccct ccattagagg cgagtatagc agcagagaaa gttagaaagt    9780
atatgtatac tgagaaatgc ttgaaatttg atactatcaa taaatgtcat gctattttt    9840 gtacaataat tataaatgga tatagagaaa gacatggtgg tcaatggcct ccagttacat    9900
tacctgtcca tgcacatgaa tttatcataa atgcatacgg atcaaattct gccatatcat    9960
atgagaatgc tgtagattat tataagagct tcataggaat aaaatttgac aagtttatag   10020
agcctcaatt ggatgaagac ttaactattt atatgaaaga taaagcatta tccccaaaga   10080
aatcaaactg ggacacagtc tatccagctt caaacctgtt ataccgcact aatgtgtctc   10140
atgattcacg aagattggtt gaagtattta tagcagatag taaatttgat ccccaccaag   10200
tattagatta cgtagaatca ggatattggc tggatgatcc tgaatttaat atctcatata   10260
gtttaaaaga gaaagaaata aaacaagaag gtagactttt tgcaaaaatg acatacaaga   10320
tgagggctac acaagtatta tcagaaacat tattggcgaa taatataggg aaattcttcc   10380
aagagaatgg gatggttaaa ggagaaattg aattactcaa gagactaaca acaatatcta   10440
tgtctggagt tccgcggtat aatgaggtat acaataattc aaaaagtcac acagaagaac   10500
ttcaagctta taatgcaatt agcagttcca atttatcttc taatcagaag tcaaagaagt   10560
ttgaatttaa atctacagat atatacaatg atggatacga aaccgtaagc tgcttcttaa   10620
cgacagatct taaaaatat tgtttaaatt ggaggtatga atcaacagct ttattcggtg   10680
atacttgtaa tcagatattt gggttaaagg aattatttaa ttggctgcac cctcgccttg   10740
aaaagagtac aatatatgtt ggagatcctt attgcccgcc atcagatatt gaacatttac   10800
cacttgatga ccatcctgat tcaggatttt atgttcataa tcctaaagga ggaatagaag   10860
ggttttgcca aaagttatgg acactcatat ctatcagtgc aatacattta gcagctgtca   10920
aaatcggtgt aagagttact gcaatggttc aagggggataa tcaagccata gctgttacca   10980
caagagtacc taataattat gattataaag ttaagaaaga gattgtttat aaagatgtgg   11040
taagattttt tgattccttg agagaggtga tggatgatct gggtcatgag ctcaaactaa   11100
atgaaactat aataagtagt aaaatgttta tatatagcaa aaggatatac tatgacggaa   11160
gaatccttcc tcaggcatta aaagcattgt ctagatgtgt tttttggtct gaaacaatca   11220
tagatgagac aagatcagca tcctcaaatc tggctcatc gtttgcaaag gccattgaga   11280
atggctactc acctgtattg ggatatgtat gctcaatctt caaaaatatc caacagttgt   11340
atatagcgct tggaatgaat ataaacccaa ctataaccca aaatattaaa gatcaatatt   11400
tcaggaatat tcattggatg caatatgcct ccttaatccc tgctagtgtc ggaggattta   11460
```

```
attatatggc catgtcaagg tgttttgtca gaaacattgg agatcctaca gtcgctgcgt    11520
tagccgatat taaaagattt ataaaagcaa atttgttaga tcgaggtgtc ctttacagaa    11580
ttatgaatca agaaccaggc gagtcttctt ttttagactg ggcctcagat ccctattcat    11640
gtaacttacc acaatctcaa aatataacca ccatgataaa gaatataact gcaagaaatg    11700
tactacagga ctcaccaaac ccattactat ctggattatt tacaagtaca atgatagaag    11760
aggatgagga attagctgag ttcctaatgg acaggagaat aatcctccca agagttgcac    11820
atgacatttt agataattct cttactggaa ttaggaatgc tatagctggt atgttggata    11880
caacaaaatc actaattcga gtagggataa gcagaggagg attaacctat aacttattaa    11940
gaaagataag caactatgat cttgtacaat atgagacact tagtaaaact ttaagactaa    12000
tagtcagtga caagattaag tatgaagata tgtgctcagt agacctagcc atatcattaa    12060
gacaaaaaat gtggatgcat ttatcaggag gaagaatgat aaatggactt gaaactccag    12120
atcctttaga gttactgtct ggagtaataa taacaggatc tgaacattgt aggatatgtt    12180
attcaactga aggtgaaagc ccatatacat ggatgtattt accaggcaat cttaatatag    12240
gatcagctga gacaggaata gcatcattaa gggtcccttta cttttggatca gttacagatg    12300 agagatctga agcacaatta gggtatatca aaaatctaag caaaccagct aaggctgcta    12360
taagaatagc aatgatatat acttgggcat ttgggaatga cgaaatatct tggatggaag    12420
catcacagat tgcacaaaca cgtgcaaact ttacattgga tagcttaaag attttgacac    12480
cagtgacaac atcaacaaat ctatcacaca ggttaaaaga tactgctact cagatgaaat    12540
tttctagtac atcacttatt agagtaagca ggttcatcac aatatctaat gataatatgt    12600
ctattaaaga agcaaatgaa actaaagata caaatcttat ttatcaacag gtaatgttaa    12660
caggattaag tgtatttgaa tatctatttta ggttagagga gagtacagga cataaccta    12720 tggtcatgca tctacatata gaggatggat gttgtataaa agagagttac aatgatgagc    12780
atatcaatcc ggagtctaca ttagagttaa tcaaatacc tgagagtaat gaatttatat    12840
atgataagga ccctttaaag gatatagatc tatcaaaatt aatggttata agagatcatt    12900
cttatacaat tgacatgaat tactgggatg acacagatat tgtacatgca atatcaatat    12960
gtactgcagt tacaatagca gatacaatgt cgcagctaga tcgggataat cttaaggagc    13020
tggttgtgat tgcaaatgat gatgatatta acagtctgat aactgaattt ctgacccta    13080 atatactagt gtttctcaaa acatttggag ggttactcgt gaatcaattt gcatatacc    13140 tttatggatt gaaaatagaa ggaagggatc ccatttggga ttatataatg agaacattaa    13200
aagacacctc acattcagta cttaaagtat tatctaatgc actatctcat ccaaaagtgt    13260
ttaagagatt ttgggattgt ggagttttga atccctattta tggtcctaat actgctagtc    13320
aagatcaagt taagcttgct ctctcgattt gcgagtactc cttggatcta tttatgagag    13380
aatggttgaa tggagcatca cttgagatct atatctgtga tagtgacatg gaaatagcaa    13440
atgacagaag acaagcattt ctctcaagac atcttgcctt tgtgtgttgt ttagcagaga    13500
tagcatcttt tggaccaaat ttattaaatc taacatatct agagagactt gatgaattaa    13560
aacaatactt agatctgaac atcaaagaag atcctactct taaatatgtg caagtatcag    13620
gactgttaat taaatcattc ccctcaactg ttacgtatgt aaggaaaact gcgattaagt    13680
atctgaggat tcgtggtatt aatccgcctg aaacgattga agattgggat cccatagaag    13740
atgagaatat cttagacaat attgttaaaa ctgtaaatga caattgcagt gataatcaaa    13800
agagaaataa aagtagttat ttctgggggat tagctctaaa gaattatcaa gtcgtgaaaa    13860
```

```
taagatccat aacgagtgat tctgaagtta atgaagcttc gaatgttact acacatggaa    13920
tgacacttcc tcagggagga agttatctat cacatcagct gaggttattt ggagtaaaca    13980
gtacaagttg tcttaaagct cttgaattat cacaaatctt aatgagggaa gttaaaaaag    14040
ataaagatag actcttttta ggagaaggag caggagctat gttagcatgt tatgatgcta    14100
cactcggtcc tgcaataaat tattataatt ctggtttaaa tattacagac gtaattggtc    14160
aacgggaatt aaaaatcttc ccatcagaag tatcattagt aggtaaaaaa ctaggaaatg    14220
taacacagat tcttaatcgg gtgagggtgt tatttaatgg gaatcccaat tcaacatgga    14280
taggaaatat ggaatgtgag agtttaatat ggagtgaatt aaatgataag tcaattggtt    14340
tagtacattg tgacatggag ggagcgatag gcaaatcaga agaaactgtt ctacatgaac    14400
attatagtat tattaggatt acatatttaa tcggggatga tgatgttgtc ctagtatcaa    14460
aaattatacc aactattact ccgaattggt ctaaaatact ctatctatac aagttgtatt    14520
ggaaggatgt aagtgtagtg tcccttaaaa catccaatcc tgcctcaaca gagctttatt    14580
taatttcaaa agatgcttac tgtactgtaa tggaacccag taatcttgtt ttatcaaaac    14640
ttaaaaggat atcatcaata gaagaaaata atctattaaa gtggataatc ttatcaaaaa    14700
ggaagaataa cgagtggtta cagcatgaaa tcaagaagg agaaagggat tatgggataa    14760
tgaggccata tcatacagca ctgcaaattt ttggattcca aattaactta aatcacttag    14820
ctagagaatt tttatcaact cctgatttaa ccaacattaa taatataatt caaagttta    14880 caagaacaat taaagatgtt atgttcgaat gggtcaatat cactcatgac aataaaagac    14940
ataaattagg aggaagatat aatctattcc cgcttaaaaa taaggggaaa ttaagattat    15000
tatcacgaag attagtacta agctggatat cattatcctt atcaaccaga ttactgacgg    15060
gccgttttcc agatgaaaaa tttgaaaata gggcacagac cggatatgta tcattggctg    15120
atattgattt agaatcctta aagttattat caagaaatat tgtcaaaaat acaaagaac    15180 acataggatt aatatcatac tggttttga ccaaagaggt caaaatacta atgaagctta    15240
taggaggagt caaactacta ggaattccta acagtacaa agagttagag gatcgatcat    15300
ctcagggtta tgaatatgat aatgaatttg atattgatta atacataaaa acataaaata    15360
aaacacctat tcctcaccca ttcacttcca acaaaatgaa aagtaagaaa acatgtaat    15420 atatatatac caaacagagt ttttctcttg tttggt                             15456
```

<210> SEQ ID NO 36
<211> LENGTH: 15456
<212> TYPE: DNA
<213> ORGANISM: Artificial Sequence
<220> FEATURE:
<223> OTHER INFORMATION: Parainfluenza Virus

<400> SEQUENCE: 36

```
accaaacaag agaagagact tgcttgggaa tattaattca ataaaaatt aacttaggat      60 taaagaactt taccgaaagg taagggaaa gaaatcctaa gactgtaatc atgttgagtc     120
tattcgacac attcagtgcg cgtaggcagg agaacataac aaaatcagct ggtggggctg    180
ttattcccgg gcaaaaaaac actgtgtcta tatttgctct tggaccatca ataacagatg    240
acaatgacaa aatgacattg gctcttctct ttttgtctca ttctttagac aatgaaaagc    300
agcatgcgca aagagctgga ttttttagtt tctctgttat caatggctta tgccaacccag   360 aattatattt aacatcaaat ggtagtaatg cagatgttaa atatgtcatc tacatgatag    420
```

-continued

```
agaaagaccc aggaagacag aaatatggtg ggtttgtcgt caagactaga gagatggttt    480
atgaaaagac aactgactgg atgtttggga gtgatcttga gtatgatcaa gacaatatgt    540
tgcaaaatgg tagaagcact tctacaatcg aggatcttgt tcatactttt ggatatccat    600
cgtgtcttgg agcccttata atccaggttt ggataatact tgttaaggct ataaccagta    660
tatcaggatt gaggaaagga ttctttactc ggttagaagc atttcgacaa gatggaacag    720
ttaaatccag tctagtgttg agcggtgatg cagtagaaca aattggatca attatgaggt    780
cccaacagag cttggtaaca ctcatggttg aaacactgat aacaatgaac acaggcagga    840
atgacctgac aacaatagaa aagaatatac agattgtagg aaactacatc agagatgcag    900
gtcttgcttc atttttcaac acaatcagat atggcattga actagaatg gcagctctaa     960 ctctgtctac ccttagaccg gacatcaaca gactcaaggc actgatagag ctatatctat   1020
caaaggggcc acgtgctcct tttatatgca ttttgagaga tcctgtgcat ggtgagtttg   1080
caccaggcaa ctatcctgcc ctctggagtt atgcgatggg tgtagcagtt gtacaaaaca   1140
aggccatgca acagtatgta acaggaaggt cctatctgga tattgaaatg ttccaactgg   1200
gtcaagcagt ggcacgtgac gccgagtcgc agatgagttc aatattagag gatgaactgg   1260
gggtcacaca agaagccaag caaagcttga agaaacacat gaagaacatc agcagttcag   1320
atacaacctt ctataagcct acaggggat cagccataga aatggcaata gatgaggaag    1380
cagagcagcc cgaatccaga ggagaccaag accaaggaga tgaacctcgg tcatccatag   1440
ttccttatgc atgggcagac gaaaccggga atgacaacca aactgaatca accacagaaa   1500
ttgacagcat caaaactgaa caaagaaaca tcagagacag gctgaacaaa agactcaacg   1560 agaaaggaa acagagtaac ccgggatcaa ctgacatcac aaacaacaca aatcaaactg    1620
aaatagatga tttattcagt gcattcggaa gcaactagtc acaaagagat gaccaccatc   1680
atcagcaaca agtaagaaaa acttaggatt aatggaaatt atccaatccg agacgggaag   1740
gacaaatcca gaatccaacc acaactcaat caaccaaaga ttcatggaag acaatgttca   1800
aaacaatcaa atcatggatt cttgggaaga gggatcagga gataaatcat ctgacatctc   1860
atcggccctc gacatcattg aattcatact caacaccgac tcccaagaga acacggcaga   1920
acttagcacg acaatctacc aacttgagtc caaaacaaca gaaacaagca cagcaatgaa   1980
atcaacacag gagccacaag aggaaaatag tggaccagct aacaaaaatc gacagtttgg   2040
ggcatcacac gaacgtgcca cagagacaaa agatagaaat gttaatcaga agactgtaca   2100
gggaggatat aggagaggaa gcagcccaga tagtagaact gagactatgg tcactcgagg   2160
aatctccaga agcagcccag atcctaacaa tggaacccaa atccaggaag atattgatta   2220
caatgaagtt ggagagatgg ataaggactc tactaagagg gaaatgcgac aatttaaaga   2280
tgttccagtc aaggtatcag gaagtgatgc cattcctcca acaaaacaag atggagacgg   2340
tgatgatgga agaggcctgg aatctatcag tacatctgat tcaggatata ccagtatagt   2400
gactgccgca acactagatg acgaagaaga actccttatg aagaacaaca ggccaagaaa   2460
gtatcaatca acaccccaga acagtgacaa gggaattaaa aaagggagtg aaggccaaa    2520 agacacagac aaacaatcac caatattgga ctacgaactc aactccaaag atcgaagaa    2580 gagccagaaa atcctcaaag ccagcacgaa tacaggagaa ccaacaagat cacagagtgg   2640
atcccagggg aagagaatca gatcctggaa catcctcaac agcgagagcg gcaatcgagc   2700
agaatcaaca aaccaaaccc atcagacatc aatctcggga cagaaccaca caatgggacc   2760
aagcagaaca acctcagaac caaggaccaa gacacaaaag acggatggaa aggaaagaga   2820
```

```
ggacacagaa gagagcactc gatttacaga aagggcgatt acattattac agaatcttgg    2880
tgtaatccaa tctgcagcaa aattagacct ataccaagac aagagagttg tgtgtgtggc    2940
gaatgtccta aacaatgcag atactgcatc aaagatagac ttcctagcag gtttgatgat    3000
aggagtgtca atggatcatg atgtcaaatt aaatcagatt cagaacgaga tattaagttt    3060
aaaaactgat cttaagaaga tggatgaatc acatagaaga ctaattgaga atcaaaaaga    3120
acaattatca ctgatcacat cattaatctc aaatcttaaa atcatgacag agagaggagg    3180
gaagaaggac caaccagaac ctagcgggag gacatccatg atcaagacaa aggcaaaaga    3240
agagagaata aagaaagtca ggtttgaccc tcttatggaa acacagggca tcgagaaaaa    3300
catccctgac ctctacagat caatagagaa acaccagaa aacgacacac agatcaaatc     3360
agaaataaac agattgaatg atgaatccaa tgccactaga ttagtaccta aagaataag     3420 cagtacaatg agatcactaa taataatcat caacaacagc aatttatcat caaaagcaaa    3480
gcaatcatac atcaacgaac tcaagctctg caagagtgat gaggaagtgt ctgacttgat    3540
ggacatgttc aatgaggatg tcagctccca gtaaaccgcc aaccaagggt caacaccaag    3600
aaaaccaaca gcacaaaaca gccaataaga gaccatccca acacaccgaa ccaatcaaca    3660
cataacaaag atctttagat catagatgac taagaaaaac ttaggatgaa aggactgatc    3720
aatcctccaa aacaatgagc atcaccagct ccacaatcta cacattccca gaatcctctt    3780
tctccgagaa tggcaacata gagccgttac cactcaaggt caatgaacag agaaaggcca    3840
tacctcatat tagggttgtc aagataggag atccgcccaa acatggatcc agatatctgg    3900
atgtcttttt actgggcttc tttgaaatgg aaaggtcaaa agacaggtat gggagcataa    3960
gtgatctaga tgatgatcca agttacaagg tttgtggctc tggatcattg ccacttgggt    4020
tggctagata cactggaaat gatcaggaac tcctacaggc tgcaaccaag ctcgatatag    4080
aagtaagaag aactgtaaag gctacggaga tgatagttta cactgtgcaa aacatcaaac    4140
ctgaactata tccatggtcc agtagattaa gaaagggat gttatttgac gctaacaagg     4200
ttgcacttgc tcctcaatgt cttccactag atagagggat aaaattcagg gtgatatttg    4260
tgaactgcac agcaattgga tcaataactc tattcaaaat ccccaagtcc atggcattgt    4320
tatcattgcc taatacaata tcaataaatc tacaagtaca tatcaaaaca ggaattcaga    4380
cagattccaa aggagtagtt cagattctag atgaaaaagg tgaaaaatca ctaaatttca    4440
tggttcatct cggggttgatc aaaaggaaga tgggtagaat gtactcagtt gaatattgta    4500
agcagaagat tgagaagatg agattattat tctcattggg attagttgga gggatcagct    4560
tccacgtcaa cgcaactggc tctatatcaa agacattagc aagtcaatta gcatttaaaa    4620
gagaaatctg ctatccccta atggatctga atccacactt aaatttagtt atatgggcat    4680
catcagttga aattcaaaga gtagatgcaa ttctccagcc ttcattacct ggcgaattca    4740
gatactaccc gcaaaagggg tcgggaaaat cagacagtaa aaccaacaac cctgacatcc    4800
aacactgcaa atcaggctac ccacaggaga aaaatcaaaa acttaggatc aaagggatca    4860
ccacaaaccc cgggaaacag ccaaaccaac caacacacaa atcacagaca aaaaggaaaa    4920
ggcactgcaa agaccgagaa aaacatcata caagcagaac gcacacaacc aagcagagga    4980
aagccaaagc ccgccattca caaacacacc aacaatccta caaacaagca ccaaaataga    5040
ggtcaaaaga caaagagcat cagatatgac catcacaacc ataatcatag ccatactact    5100 aatacccta tcattctgtc aaatagacat aacaaaactg caacgtgtag gtgtattagt     5160
```

```
caacaatccc aaaggcatga aaatttcaca aaattttgaa acgagatacc tgatattaag   5220
tctgataccc aaaatagaga attcacactc atgtggggat caacagataa accaatacaa   5280
gaagttattg gatagattga taattcctct atatgatgga ttaaaattac aaaaagatgt   5340
aatagtagta agtcatgaaa cccataataa tactaatctt aggacaaaac gattctttgg   5400
agagataatt gggacaattg cgatagggat agccacctca gcgcaaatca ccgcagcagt   5460
cgctcttgtc gaagctaaac aggcaaggtc agacatagaa aaactcaaag aagctataag   5520
agacacaaac aaggcagtac aatcgattca aagttctgta ggtaacctaa ttgttgcagt   5580
taaatcagtt caagactatg tcaacaatga aattgtacct tcaatcacaa gattaggctg   5640
tgaagcagca gggttacaat tgggaattgc actgacacaa cattactcag aattaacaaa   5700
tatatttggt gataatatag gaacactgaa agaaaaaggg ataaaattac agggatagc   5760 atcgttatat catacaaaca taacagaaat atttactact tcaacagttg accaatatga   5820
tatttatgac ctattattca ctgaatcaat caagatgaga gtgatagatg ttgatttgag   5880
tgattactca attactcttc aagttagact tcctttatta actaaactat caaatactca   5940
gatttataaa gtagattcta tatcatacaa catccagggc aaagagtggt atattcctct   6000
tcccaatcac atcatgacaa aaggggcttt tctaggtggt gctgatatta agaatgcat   6060 agaggcattc agcagttata tatgtccttc tgatccaggt tatatattaa atcacgagat   6120
agagaattgt ttatcaggga acataacaca gtgtcctaag actgttgtta catcagatgt   6180
ggtaccacga tacgcgtttg tgaatggtgg attaattgca aactgcataa caactacatg   6240
tacatgcaat ggaattgaca atagaattaa tcaatcacct gatcaaggaa ttaagatcat   6300
aacacataaa gaatgccagg taataggtat aaacggaatg ttattcaata ctaatagaga   6360
agggacatta gcaacttata catttgatga cattatatta ataactctg ttgcacttaa   6420 tccaattgat atatctatgg aacttaacaa ggcaaaacta gaattagaag aatcgaagga   6480
atggataaag aaatcaaatc aaaagttaga ttccgttgga agttggtatc aatctagtgc   6540
aacaatcacc ataatcatag tgatgataat aattctatt ataatcaata taacaattat   6600
tgtagtcata atcaaattct atagaattaa gggggaaaat caaaacgaca aaaacagtga   6660
gccgtatata ctgacaaaata gacaataaga ctatacacga tcaaatatag aaagtacaaa   6720
aaacttagga acaaagttgt tcaacacagc agcagcgaac agacccaaag gcagcgcaga   6780
ggcgacaccg aacccaaaaa tggaatattg gaaacacaca aacagcacaa aaaacaccaa   6840
caatgaaacc gaaacaacca gaggcaaaca cagtagcaag gttacaaata tcataatgta   6900
caccttctgg acaataacat caacaatatt attagtcatt tttataatga tattgacaaa   6960
cttaattcaa gagaacaatc ataataaatt aatgttgcag gaaataagaa aagaattcgc   7020
ggcaatagac accaagattc agaggacctc ggatgacatt ggaacctcaa tacagtcagg   7080
aataaataca agacttctca caattcagag tcatgttcaa aactatatcc cactatcact   7140
aacacaacaa atgtcagatc tcagaaaatt tatcaatgat ctaacaaata aaagagaaca   7200
tcaagaagtg ccaatacaga gaatgactca tgatagaggt atagaacccc taatccaga   7260 caagttctgg aggtgtacat ctggtaaccc atctctaaca agtagtccta agataaggtt   7320
aataccaggc ccaggtttat tagcaacatc tactacagta aatggctgta ttagaatccc   7380
atcgttagca atcaatcatt taatctacgc ttacacctct aatcttatca cccagggctg   7440
tcaaaatata gggaaatctt accaagtact acaaataggg ataattacta aaattcgga   7500 cctagtacct gatttaaatc ccagagtcac acatacattt aatattgatg ataataggaa   7560
```

```
atcttgctct ctggcactat tgaatacaga tgtttatcag ttatgctcaa caccaaaagt      7620
tgatgagaga tccgattatg catcaacagg tattgaggat attgtacttg acattgtcac      7680
taataatgga ttaattataa caacaaggtt tacaaataat aatataactt ttgataaacc      7740
gtatgcagca ttgtatccat cagtaggacc aggaatctat tataagggta aagttatatt      7800
tctcggatat ggaggtctag agcatgaaga aaacggagac gtaatatgta atacaactgg      7860
ttgtcctggc aaaacacaga gagactgtaa tcaggcttct tatagcccat ggttctcaaa      7920
taggagaatg gtaaactcta ttattgttgt tgataaaggc atagatgcaa cttttagctt      7980
gagggtgtgg actattccaa tgagccaaaa ttattgggga tcagaaggaa gattacttt      8040 attaggtgac agaatataca tatatactag atccacaagt tggcacagta aattacagtt      8100 agggtaatt gatatttctg attataataa tataagaata aattggactt ggcataatgt      8160
actatcacgg ccaggaaatg atgaatgtcc atggggtcat tcatgcccag acggatgtat      8220
aacaggagtt tacactgatg catatccgct aaacccatcg gggagtgttg tatcatcagt      8280
aattcttgac tcacaaaagt ctagagaaaa cccaatcatt acctactcaa cagctacaaa      8340
tagaataaat gaattagcta tatataacag aacacttcca gctgcatata caacaacaaa      8400
ttgtatcaca cattatgata aagggtattg ttttcatata gtagaaataa atcacagaag      8460
tttgaatacg tttcaaccta tgttattcaa aacagaagtt ccaaaaaact gcagctaaat      8520
tgatcatcgc atatcggatg ccagatgaca ttaaaagaga ccaccagaca gacaacacag      8580
gagatgatgc aagatataaa ggaataataa aaaacttagg agaaaagtgt gcaagaaaaa      8640
tggacactga atcccacagc ggcacaaacat ctgacattct gtaccctgaa tgtcacctca      8700
attctcctat agttaaagga aaaatagcac aactgcatac aataatgagt ttgccccaac      8760
cctacgatat ggatgatgat tcaatactga ttattactag acaaaaaatc aaactcaata      8820
aattagataa aagacaacgg tcaattagga aattaagatc agtcttaatg gaaagagtaa      8880
atgatcttgg taaatacacc tttatcagat atccagaaat gtctagtgaa atgttccaat      8940
tatgtatacc cggaattaat aataaaataa atgaattgct aagtaaagca agtaaaacat      9000
ataatcaaat gactgatgga ttaagagatc tatgggttac tgtactatcg aagttagcat      9060
cgaaaaatga tggaagtaat tatgatatca atgaagatat tagcaatata tcaaatgttc      9120
acatgactta ccaatcagac aaatggtata atccattcaa gacatggttt actattaagt      9180
atgacatgag gagattacaa aaagccaaaa atgagattac attcaatagg cataaagatt      9240
ataatctatt agaagaccaa aagaatatat tgctgataca tccagaactc gtcttaatat      9300
tagataaaca aaattacaat gggtatataa tgactcctga attggtacta atgtattgtg      9360
atgtagttga agggaggtgg aatataagtt catgtgcaaa attggatcct aaattacaat      9420
caatgtatta taaaggtaac aatttatggg aaataataga tggactattc ctgaccttag      9480
gagaaagaac atttgacata atatcactat tagaaccgct tgcattatcg ctcattcaaa      9540
ctcatgaccc ggttaaacag ctcagagggg cttttttaaa tcacgtgtta tcagaaatgg      9600
aatcaatatt cgcagctgag tgtacaacag aggaaatacc taatgtggat tatatagata      9660
aaattttaga tgtattcaaa gaatcaacaa tagatgaaat agcagaaatt ttctctttct      9720
tccgaacttt tggacacccct ccattagagg cgagtatagc agcagagaaa gttagaaagt      9780
atatgtacac tgagaaatgt ttgaaatttg atactatcaa taaatgtcat gctattttt       9840 gtacaataat tataaatgga tatagagaaa gacatggtgg tcaatggcct ccagttacat      9900
```

```
tacctattca tgcacatgaa tttatcataa atgcgtacgg atcaaattct gccatatcat    9960
atgaaaatgc tgtagattat tataagagct tcataggaat aaaatttgac aagtttatag   10020
agcctcaatt ggatgaagac ttaactattt atatgaaaga taaagcatta tccccaaaga   10080
aatctaactg ggacacagtc tatccagctt caaacctgtt ataccgcact aatgtgtctc   10140
atgattcacg aagattggtt gaagtattta tagcagatag taaatttgat ccccaccaag   10200
tattagatta cgtagaatca ggatattggc tagatgatcc tgaatttaat atctcatata   10260
gtttaaaaga gaaagaaata aaacaagaag gtagactttt tgcaaaaatg acatacaaga   10320
tgagagctac acaagtatta tcagaaacat tattggcgaa taatataggg aaattcttcc   10380
aagagaatgg gatggttaaa ggagaaattg aattactcaa gagactgaca acaatatcta   10440
tgtctggggt tccgcggtat aatgaggtat acaataattc aaaaagtcac acagaggaac   10500
ttcaagctta taatgcaatt agcagttcca atttatcttc taatcagaag tcaaagaagt   10560
ttgaatttaa atcaacagat atatacaatg atggatacga accgtaagc tgcttcttaa   10620
cgacagatct taaaaaatat tgtttaaatt ggaggtatga atcaacagct ttattcggtg   10680
atacttgtaa tcagatattt gggttaaagg aattatttaa ttggctgcac cctcgccttg   10740
aaaagagtac aatatatgtt ggagatcctt attgcccgcc atcagatatt gaacatttac   10800
cacttgatga ccatcctgat tcaggatttt atgttcataa tcctaaagga ggaatagaag   10860
ggttttgcca aaagttatgg acactcatat ctatcagtgc catacattta gcagctgtca   10920
aaatcggtgt aagagttact gcaatggttc aaggggataa tcaagccata gctgttacca   10980
ccagagtacc taataattat gattataagg ttaagaaaga gattgtttat aaagatgtgg   11040
taagattttt tgattctttg agagaggtta tggatgatct gggtcatgag ctcaaactaa   11100
atgaaactat aataagtagt aaaatgttta tatatagcaa aaggatatac tatgacggaa   11160
gaatccttcc tcaggcgtta aaagcattgt ctagatgtgt tttttggtct gaaacaatca   11220
tagatgagac aagatcagca tcctcaaatc tggcgacatc gtttgcaaag gccattgaga   11280
atggctactc acctgtattg ggatatgtat gctcaatctt caaaaatatc caacagttgt   11340
atatagcact tggaatgaat ataaatccaa ctataaccca aaatattaaa gatcaatatt   11400
tcaggaatat tcattggatg caatatgcat ctctaatccc tgctagtgtc ggaggattta   11460
attatatggc catgtcaagg tgttttgtca gaaacattgg agatcctaca gtcgctgcat   11520
tagctgatat taaagatttt ataaaagcaa atttgttaga tcgaggtgtc ctttacagaa   11580
ttatgaatca ggaaccaggc gagtcctcct ttttagactg ggcttcagac ccctattcat   11640
gtaacttacc acaatctcaa aatataacca ccatgataaa gaatataact gcaagaaatg   11700
tactacagga ctcaccaaac ccattactat ctggattatt tacaagtaca atgatagaag   11760
aggatgagga attagctgag ttcctaatgg acaggagaat aattctccca agggttgcgc   11820
atgacatttt agataattct cttactggaa ttaggaatgc tatagctggt atgttggata   11880
caacaaaatc actaattcga gtagggataa acagaggagg attaacctat aacttattaa   11940
gaaagataag caactatgat cttgtacaat atgagacact tagtaaaact ttaagactaa   12000
tagtcagtga caagattaag tatgaagata tgtgctcagt agaccctagcc atatcattaa   12060
gacaaaaaat gtggatgcat ttatcaggag gaagaatgat aaatggactt gaaactccag   12120
atcctttaga gttactgtct ggagtaataa taacaggatc tgagcattgt aggatatgtt   12180
attcaactga aggtgaaagc ccatatacat ggatgtattt accaggcaat cttaatatag   12240
gatcagctga aacaggaata gcatcattaa gggtccctta ctttggatca gttacggatg   12300
```

```
agagatctga agcacaattg gggtatatca aaaatctaag caaaccagct aaggctgcta    12360
taagaatagc aatgatatat acttgggcat ttgggaatga cgaaatatct tggatggaag    12420
catcacagat tgcacaaaca cgtgcgaact ttacattaga tagcttaaag attttgacac    12480
cagtgacaac atcaacaaat ctatcacata ggttaaaaga tactgctact cagatgaaat    12540
tttctagtac atcacttatt agagtaagca ggttcatcac aatatctaat gataatatgt    12600
ctattaaaga ggcaaatgaa actaaagata caaatcttat ttatcaacag gtaatgttaa    12660
cagggttaag tgtatttgaa tatctatttta ggttagagga gagtacagga cataacccta    12720
tggtcatgca tctacatata gaggatggat gttgtatcaa agagagttac aatgatgagc    12780
atatcaatcc ggagtctaca ttagagttaa ttaaataccc tgagagtaat gaatttatat    12840
atgataagga cccttttaaag gatatagatc tatcaaaatt aatggttata agagatcatt    12900
cttatacaat tgcatgaat tactgggacg acacagatat tgtacatgca atatcaatat    12960
gtactgcagt tacaatagca gatacaatgt cgcagctaga tcgggaataa cttaaggagc    13020
tggttgtaat tgcaaatgat gatgatatta acagtctgat aactgaattt ctgaccctag    13080
atatactagt gtttctcaaa acatttggag ggttactcgt gaatcaattt gcatataccc    13140
tttatggatt gaaaatagaa ggaagggatc ccatttggga ttatataatg agaacattaa    13200
aagacacctc acattcagta cttaaagtat tatctaatgc actatctcat ccaaaagtgt    13260
tttaagagat ttgggattgt ggagttttga atcctatttta tggtcctaat actgctagtc    13320
aggaccaagt taagcttgct ctctcaattt gcgagtactc cttggatcta tttatgagag    13380
aatggctgaa tggagcatca cttgagatct atatctgtga tagtgacatg gaaatagcaa    13440
atgatagaag acaagcattt ctctcaagac accttgcctt tgtgtgttgt ttagcagaga    13500
tagcatcttt tggaccaaat ttattaaatc taacatatct agagagactt gacgaattaa    13560
aacaatactt ggatctgaac atcaaagaag atcctactct taaatatgtg caagtatcag    13620
gactgttaat taaatcattc ccctcaactg ttacgtatgt gaggaaaact gcgattaagt    13680
atctgaggat tcgtggcatt aatccgcctg aaacgattga agattgggat cccatagaag    13740
atgagaatat cttagacaat attgttaaaa ctgtaaatga caattgcagt gataatcaaa    13800
agagaaataa aagtagttat ttctgggat tagctctaaa gaattatcaa gtcgtaaaaa    13860
taagatccat aacgagtgat tctgaagtta atgaagcttc gaatgttact acacatggaa    13920
tgacacttcc tcagggagga agttatctat cacatcagct gaggttattt ggagtaaaca    13980
gtacaagttg tctgaaagct cttgaattgt cacaaatttt aatgagggaa gttaaaaaag    14040
ataaagatag actcttttta ggagaaggag caggagctat gttagcatgt tatgatgcta    14100
cactcggtcc tgcaataaat tattacaatt ctggtttaaa tattacagat gtaattggtc    14160
aacgggaatt aaaaatcttc ccatcagaag tatcattagt aggtaaaaaa ctaggaaatg    14220
taacacagat tcttaatcgg gtgagggtgt tatttaatgg gaatcccaat tcaacatgga    14280
taggaaatat ggaatgtgag agtttaatat ggagtgaatt aaatgataag tcaattggtt    14340
tagtacattg tgacatggag ggagcaatag gcaaatcaga agaaactgtt ttacatgaac    14400
attatagtat tattaggatt acatatttaa ttggggatga tgatgttgtt ctagtatcaa    14460
aaattatacc aactattact ccgaattggt ctaaaatact ctatctatac aggttgtatt    14520
ggaaggatgt gagtgtagtg tcccttaaaa catccaatcc tgcctcaaca gagctttatt    14580
taatttcaaa ggatgcttac tgtactgtaa tggaacccag taatcttgtt ttatcaaaac    14640
```

-continued

```
ttaaaggat atcatcagta gaagaaaata atctattaaa atggataatc ttatcaaaaa    14700
ggaagaacaa cgaatggtta cagcatgaaa tcaaagaagg agaaagggat tatgggataa    14760
tgaggccata tcatacagca ctgcaaattt ttggattcca aattaactta aatcacttag    14820
ctaaagaatt tttatcaact cctgatttaa ccaacattaa taatataatt caagttttta    14880
caagaacaat taaagatgtt atgttcgaat gggtcaatat cactcatgac aataaaagac    14940
ataaattagg aggaagatat aatctattcc cgcttaaaaa taaggggaag ttaagattac    15000
tatcacgaag attagtacta agctggatat cattatcttt atcaaccaga ttactgacag    15060
gccgtttccc agatgaaaaa tttgaaaata gggcacagac cggatatgta tcattggctg    15120
atactgattt agaatcttta aagttattat caagaaatat tgtcaaaagt tacaaagaac    15180
acataggatt aatatcatac tggtttttaa ccaaagagg caaatacta atgaaactta    15240 taggggagt caaactacta ggaattccca acagtacaa agagttagag gatcgatcat    15300
ttcagggtta tgaatatgat aatgaatttg atattgatta atacataaaa acaaaaaata    15360
aaacacctaa tcctctccca ttcacttcca acaaatgaa aagtaagaaa aacatataat    15420
atacatatac caaacagagt ttttctcttg tttggt                             15456
```

<210> SEQ ID NO 37
<211> LENGTH: 11
<212> TYPE: DNA
<213> ORGANISM: Artificial Sequence
<220> FEATURE:
<223> OTHER INFORMATION: Parainfluenza Virus

<400> SEQUENCE: 37
caaaaatgtt g                                                              11

<210> SEQ ID NO 38
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 38
gcaactaatc ga                                                             12

<210> SEQ ID NO 39
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 39
taaccatggt ga                                                             12

<210> SEQ ID NO 40
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 40
gcacttaagc ac                                                             12

<210> SEQ ID NO 41
<211> LENGTH: 12

```
<212> TYPE: DNA
<213> ORGANISM: Artificial Sequence
<220> FEATURE:
<223> OTHER INFORMATION: Parainfluenza Virus

<400> SEQUENCE: 41
caaaaatgtt ga                                                            12

<210> SEQ ID NO 42
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 42
gcaactagtc ga                                                            12

<210> SEQ ID NO 43
<211> LENGTH: 40
<212> TYPE: DNA
<213> ORGANISM: Artificial Sequence
<220> FEATURE:
<223> OTHER INFORMATION: Parainfluenza Virus

<400> SEQUENCE: 43
ggaactctat aatttcaaaa atgttgagcc tatttgatac                              40

<210> SEQ ID NO 44
<211> LENGTH: 40
<212> TYPE: DNA
<213> ORGANISM: Artificial Sequence
<220> FEATURE:
<223> OTHER INFORMATION: Parainfluenza Virus

<400> SEQUENCE: 44
ggaactctat aatttcaaaa atgttgagtc tattcgacac                              40

<210> SEQ ID NO 45
<211> LENGTH: 40
<212> TYPE: DNA
<213> ORGANISM: Artificial Sequence
<220> FEATURE:
<223> OTHER INFORMATION: Parainfluenza Virus

<400> SEQUENCE: 45
ggaactctat aatttcaaaa atgttgagtc tattcgacac                              40

<210> SEQ ID NO 46
<211> LENGTH: 40
<212> TYPE: DNA
<213> ORGANISM: Artificial Sequence
<220> FEATURE:
<223> OTHER INFORMATION: Parainfluenza Virus

<400> SEQUENCE: 46
gaaatcctaa gactgtaatc atgttgagtc tattcgacac                              40

<210> SEQ ID NO 47
<211> LENGTH: 40
<212> TYPE: DNA
<213> ORGANISM: Artificial Sequence
<220> FEATURE:
<223> OTHER INFORMATION: Parainfluenza Virus

<400> SEQUENCE: 47
```

-continued

```
gaaatcctaa gactgtaatc atgttgagtc tattcgacac                                40
```

<210> SEQ ID NO 48
<211> LENGTH: 40
<212> TYPE: DNA
<213> ORGANISM: Artificial Sequence
<220> FEATURE:
<223> OTHER INFORMATION: Parainfluenza Virus

<400> SEQUENCE: 48

```
ttaacgcatt tggaagcaac taatcgaatc aacattttaa                                40
```

<210> SEQ ID NO 49
<211> LENGTH: 40
<212> TYPE: DNA
<213> ORGANISM: Artificial Sequence
<220> FEATURE:
<223> OTHER INFORMATION: Parainfluenza Virus

<400> SEQUENCE: 49

```
tcagtgcatt cggaagcaac tagtcgaatc aacattttaa                                40
```

<210> SEQ ID NO 50
<211> LENGTH: 40
<212> TYPE: DNA
<213> ORGANISM: Artificial Sequence
<220> FEATURE:
<223> OTHER INFORMATION: Parainfluenza Virus

<400> SEQUENCE: 50

```
tcagtgcatt cggaagcaac tagtcgaatc aacattttaa                                40
```

<210> SEQ ID NO 51
<211> LENGTH: 40
<212> TYPE: DNA
<213> ORGANISM: Artificial Sequence
<220> FEATURE:
<223> OTHER INFORMATION: Parainfluenza Virus

<400> SEQUENCE: 51

```
tcagtgcatt cggaagcaac tagtcacaaa gagatgacca                                40
```

<210> SEQ ID NO 52
<211> LENGTH: 40
<212> TYPE: DNA
<213> ORGANISM: Artificial Sequence
<220> FEATURE:
<223> OTHER INFORMATION: Parainfluenza Virus

<400> SEQUENCE: 52

```
tcagtgcatt cggaagcaac tagtcacaaa gagatgacca                                40
```

<210> SEQ ID NO 53
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 53

```
tagacaaaag gg                                                              12
```

<210> SEQ ID NO 54
<211> LENGTH: 12
<212> TYPE: DNA
<213> ORGANISM: Artificial Sequence

```
<220> FEATURE:
<223> OTHER INFORMATION: Parainfluenza Virus

<400> SEQUENCE: 54
aagatataaa ga                                                              12

<210> SEQ ID NO 55
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 55
tagacgtacg gg                                                              12

<210> SEQ ID NO 56
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 56
aagacgtacg ga                                                              12

<210> SEQ ID NO 57
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 57
cgcaccggtg ca                                                              12

<210> SEQ ID NO 58
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 58
aagacgtacg gg                                                              12

<210> SEQ ID NO 59
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 59
tccaccggtg ta                                                              12

<210> SEQ ID NO 60
<211> LENGTH: 12
<212> TYPE: DNA
<213> ORGANISM: Artificial Sequence
<220> FEATURE:
<223> OTHER INFORMATION: Parainfluenza Virus

<400> SEQUENCE: 60
tagacgtacg ga                                                              12
```

```
<210> SEQ ID NO 61
<211> LENGTH: 42
<212> TYPE: DNA
<213> ORGANISM: Artificial Sequence
<220> FEATURE:
<223> OTHER INFORMATION: Parainfluenza Virus

<400> SEQUENCE: 61
taggagcaaa gcgtgctcgg gaaatggaca ctgaatctaa ca        42

<210> SEQ ID NO 62
<211> LENGTH: 42
<212> TYPE: DNA
<213> ORGANISM: Artificial Sequence
<220> FEATURE:
<223> OTHER INFORMATION: Parainfluenza Virus

<400> SEQUENCE: 62
taggagcaaa gcgtgctcgg gaaatggaca ccgagtccca ca        42

<210> SEQ ID NO 63
<211> LENGTH: 42
<212> TYPE: DNA
<213> ORGANISM: Artificial Sequence
<220> FEATURE:
<223> OTHER INFORMATION: Parainfluenza Virus

<400> SEQUENCE: 63
taggagaaaa gtgtgcaaga aaaatggaca ccgagtccca ca        42

<210> SEQ ID NO 64
<211> LENGTH: 42
<212> TYPE: DNA
<213> ORGANISM: Artificial Sequence
<220> FEATURE:
<223> OTHER INFORMATION: Parainfluenza Virus

<400> SEQUENCE: 64
atgatgaatt tgatatcgat taaaacataa atacaatgaa ga        42

<210> SEQ ID NO 65
<211> LENGTH: 42
<212> TYPE: DNA
<213> ORGANISM: Artificial Sequence
<220> FEATURE:
<223> OTHER INFORMATION: Parainfluenza Virus

<400> SEQUENCE: 65
ataatgaatt tgatattgat taatacgtac gtacaatgaa ga        42

<210> SEQ ID NO 66
<211> LENGTH: 42
<212> TYPE: DNA
<213> ORGANISM: Artificial Sequence
<220> FEATURE:
<223> OTHER INFORMATION: Parainfluenza Virus

<400> SEQUENCE: 66
ataatgaatt tgatattgat taatacataa aaacataaaa ta        42
```